United States Patent [19]
Hill

[11] Patent Number: 6,124,931
[45] Date of Patent: *Sep. 26, 2000

[54] APPARATUS AND METHODS FOR MEASURING INTRINSIC OPTICAL PROPERTIES OF A GAS

[75] Inventor: Henry Allen Hill, Tucson, Ariz.

[73] Assignee: Zygo Corporation, Middlefield, Conn.

[ * ] Notice: This patent is subject to a terminal disclaimer.

[21] Appl. No.: 09/232,515

[22] Filed: Jan. 16, 1999

Related U.S. Application Data

[63] Continuation-in-part of application No. 09/176,442, Oct. 21, 1998, which is a continuation-in-part of application No. 08/942,848, Oct. 2, 1997.
[60] Provisional application No. 60/075,595, Feb. 23, 1998.
[51] Int. Cl.[7] .................................................. G01B 9/82
[52] U.S. Cl. .......................... 356/361; 356/349; 356/358; 356/351
[58] Field of Search .................................... 356/345, 349, 356/351, 361, 358

[56] References Cited

U.S. PATENT DOCUMENTS

| | | |
|---|---|---|
| 3,647,302 | 3/1972 | Zipin et al. . |
| 4,215,938 | 8/1980 | Farrand et al. . |
| 4,685,803 | 8/1987 | Sommargren . |
| 4,733,967 | 3/1988 | Sommargren . |
| 4,813,783 | 3/1989 | Torge . |
| 4,948,254 | 8/1990 | Ishida . |
| 5,218,426 | 6/1993 | Hall et al. . |
| 5,404,222 | 4/1995 | Lis . |
| 5,483,343 | 1/1996 | Iwamato et al. . |
| 5,537,209 | 7/1996 | Lis . |
| 5,663,793 | 9/1997 | de Groot . |

FOREIGN PATENT DOCUMENTS

| | | |
|---|---|---|
| 0 094 836 | 11/1983 | European Pat. Off. . |
| WO 91/03729 | 3/1991 | WIPO . |

OTHER PUBLICATIONS

Erikson, Kent E., *Long–Path Interferometry through an Uncontrolled Atmosphere*, Journal of the Optical Society of America, vol. 52, No. 7 (Jul. 1962), pp. 781–787.

Bender, Peter L. and Owens, James C., *Correction Of Optical Distance Measurements for the Fluctuating Atmospheric Index of Refraction*, Journal of Geophysical Research, vol. 70, No. 10 (May 15, 1965), pp. 2461–2462.

Edlen, Bengt, *The Refractive Index of Air*, Metrologia, vol. 2, No. 2 (1966), pp 71–80.

(List continued on next page.)

*Primary Examiner*—Robert H. Kim
*Assistant Examiner*—Andrew H. Lee
*Attorney, Agent, or Firm*—Francis J. Caufield

[57] ABSTRACT

Interferometric apparatus and method for measuring and monitoring intrinsic optical properties of a gas, especially the reciprocal dispersive power of the gas, so that information about the gas properties can be used in downstream applications, such as interferometric distance measuring instruments, to increase accuracy by correcting for refractive index of the gas and especially environmental and air turbulence effects in the measurement path. The apparatus comprises a concentric measurement cell having an inner chamber containing a vacuum surrounded by an outer occupied by the gas. Wavelength selective mirrors are arranged at each end of the measurement cell and operate in conjunction with plane mirror interferometers to change the phase of orthogonally polarized components of light beams of different wavelength introduced in the measurement cell from opposite ends of the cell. Preferably, the polarized components are frequency-shifted to facilitate the generation of heterodyne and superheterodyne signals which contain information about the intrinsic optical properties of the gas. The heterodyne and superheterodyne signals are electronically analyzed by a general purpose computer programmed for that purpose or from a specially programmed microprocessor.

119 Claims, 45 Drawing Sheets

OTHER PUBLICATIONS

Earnshaw, K. B. and Hernandez, E. Norman, *Two–Laser Optical Distance–Measuring Instrument That Corrects For The Atmospheric Index Of Refraction*, Applied Optics, vol. 11, No. 4 (Apr. 1972), pp. 749–754.

Hernandez, E. N. and Earhshaw, K. B. *Field Tests of a Two–Laser (4416A and 6328A) Optical Distance–Measuring Instrument Correcting for the Atmospheric Index of Refraction*, Journal of Geophysical Research, vol. 77, No. 35, (Dec. 10,1972), pp. 6994–6998.

Slater, L. E. and Huggett, G. R., *A Multiwavelength Distance–Measuring Instrument for Geophysical Experiments*, Journal of Geophysical Research, vol. 81, No. 35 (Dec. 10, 1976), pp. 6299–6306.

Berg, Eduard and Carter, Jerry A., *Distance Corrections for Single–and Dual–Color Lasers by Ray Tracing*, Journal of Geophysical Research, vol. 85, No. B11, (Nov. 10, 1980), pp. 6513–6520.

Jones, Frank E., *The Refractivity of Air*, Jorunal of Research of the National Bureau of STandards, vol. 86, No. 1, (Jan.–Feb. 1981), pp 27–32.

Matsumoto, Hirokazu and Tsukahara, Koichi, *Effects of the atmospheric phase fluctuation on long–distance measurement*, Applied Optics, vol. 23, No. 19, (Oct. 1, 1984), pp 3388–3394.

Gibson, G. N.; Heyman, J., Lugten, J., Fitelson, W., and Townes, C. H., *Optical path length fluctuations in the atmosphere*, App. Optics, vol. 23, No. 23, (Dec. 1, 1984), pp 4383–4389.

Estler, W. Tyler, *High–accuracy displacement interferometry in air*, Applied Optics, vol. 24, (Mar. 15, 1985), pp. 808–815.

Dobroff, Norman, *Residual errors in laser interferometry form air turbulence and nonlinearity*, Applied Optics, vol. 16, No. 13, (Jul. 1, 1987), pp. 2676–2682.

Ishida, Akira, *Two–Wavelength Displacement–Measuring Interferometer Using Second–Harmonic Light to Eliminate Air–Turbulence–Induced Errors*, Japanese Journal of Applied Physics, vol. 28(3), (Mar. 1989), pp. L473–L475.

Birch, K. P. and Downs, M. J., *Error sources in the determination of the refractive index of air*, Applied Optics, vol. 28, No. 5, (Mar. 1, 1989), pp. 825–826.

Howe, Uwe and Kerl, Klaus, *Interferometric measurements of the dipole polarizability [alpha] of molecules between 300K and 1100K*, Molercular Physics, vol. 69 (1990), pp. 803–817.

Zhu, Yucong; Matsumoto, Hirokazu; and O'ishi, Tadanao, *Long–arm two–color interferometer for measuring the change of air refractive index*, SPIE, vol. 1319, Optics in Complex Systems (1990), pp 538–539.

Achtermann, H. J. and Magnus, G., *Refractivity virial coefficients of gaseous* $CH_4$, $C_2H_4$, $C_2H_6$, $CO_2$, $SF_6$, $H_2$, $N_2$, $He$, *and* $Ar$, J. Chem. Phys., 94(8), (Apr. 15, 1991), pp. 5669–5684.

Beers, J. and Doiron, T., *Verification of Revised Water Vapour Correction to the Index of Refraction of Air*, Metrologia, 29 (1992), PP. 315–316.

Bobroff, Norman, *Recent advances in displacement measuring interferometry*, Measurement Science and Technology, vol. 4, No. 9 (Sep. 1993), pp. 907–926.

Lis, Steven A., *An Air Turbulence Compensated Interferometer For IC Manufacturing*, SPIE, Conf. 2440 (Feb. 24, 1995).

APPARATUS AND METHODS FOR MEASURING INTRINSIC OPTICAL PROPERTIES OF A GAS

CROSS REFERENCE TO RELATED APPLICATIONS

This application is a continuation-in-part of commonly owned U.S. patent application Ser. No. 09/176,442 entitled "INTERFEROMETRIC METHOD AND APPARATUS FOR MEASURING INTRINSIC OPTICAL PROPERTIES OF A GAS" and filed on Oct. 21, 1998 which, in turn, is a continuation-in-part U.S. patent application Ser. No. 08/942,848 filed on Oct. 2, 1997 in the name of Henry Allen Hill for "APPARATUS AND METHODS FOR MEASURING INTRINSIC OPTICAL PROPERTIES OF A GAS" and also claims priority from U.S. Provisional patent application Ser. No. 60/075,595 entitled "APPARATUS AND METHODS FOR MEASURING INTRINSIC OPTICAL PROPERTIES OF A GAS" filed on Feb. 23, 1998.

FIELD OF INVENTION

The present invention generally relates to a method and apparatus for measuring and monitoring the intrinsic optical properties of a gas. More particularly, the invention relates to interferometric measurement of the reciprocal dispersive power of a gas and to optical apparatus which is useful for high accuracy displacement metrology in the presence of an uncontrolled turbulent gas.

Background and Prior Art

Interferometric techniques have broad applicability to a variety of tasks requiring precision measurement. The precise measurement of length, displacement, geometric features, surface structure, and vibration have been common applications where these techniques have played important roles, which continue to grow and evolve because of the ever increasing demands for greater precision. However, as with other metrologies, practicalities often intrude to make it difficult to achieve what may be theoretically possible.

One dominant factor which limits the absolute accuracy of interferometric displacement metrology is the uncertainty in the refractive index of the ambient air, see W. T. Estler, "High-Accuracy Displacement Interferometry in Air," Appl. Opt., 24, 808–815 (1985); C. L. Farrand, V. F. Foster, and W. H. Grace, U.S. Pat. No. 4,215,938 issued Aug. 15, 1980; N. Bobroff, "Residual Errors in Laser Interferometry from Air Turbulence and Non-Linearity," Appl. Opt. 26(13), 2676–2682 (1987); and N. Bobroff, "Recent Advances in Displacement Measuring Interferometry," Measurement Science & Tech. 4(9), 907–926 (1993).

As noted in the aforementioned cited references, interferometric displacement measurements in air are subject to environmental uncertainties, particularly to changes in air pressure, temperature, and humidity; air composition; and to the effects of turbulence in the air. Such factors alter the wavelength of the light used to measure the displacement. Under normal conditions the refractive index of air is approximately 1.0003 with a variation of the order of $1 \times 10^{-5}$ to $1 \times 10^{-4}$. In many applications the refractive index of air must be known with a relative precision of less than 0.1 ppm (parts per million) to 0.003 ppm, these two relative precisions corresponding to a displacement measurement accuracy of 100 nm and 3 nm, respectively, for a one meter interferometric displacement measurement.

One way to detect refractive index fluctuations is to measure changes in pressure and temperature along a measurement path and calculate the effect on refractive index of the path. Mathematical equations for effecting this calculation are disclosed in an article entitled "The Refractivity Of Air" by F. E. Jones, J. Res. NBS 86(1), 27–32 (1981). An implementation of the technique is described in the cited article by Estler. Unfortunately, this technique provides only approximate values, is cumbersome, and corrects only for slow, global fluctuations in air density.

One prior-art technique of the type described in the preceding paragraph for correcting the environmental uncertainties is based on using individual sensors to measure the barometric pressure, temperature, and humidity, and then using these measurements to correct the measured displacement. The commercially available Automatic Compensator, Model 5510 Opt 010, from Hewlett-Packard uses this technique. This technique has been only partly satisfactory due to the errors in the sensors and due to the errors arising from variations in the composition of the air, e.g., the percentage $CO_2$ content and presence of industrial gases, i.e. Freon and solvents are ignored in the technique.

Another type of technique for correcting for the effects of air is based on a measurement of the refractivity of the air. A procedure of this type will hereinafter be referred to as a refractivity technique. One of the more serious limitations encountered with a refractivity technique with regard to use in high precision distance measuring interferometry arises at a fundamental level. The refractivity of a gas is directly proportional to the density of the gas that is dependent in first order on environmental conditions such as temperature and pressure. Thus, to relate the value of a refractivity measured at the site of a refractivity measuring apparatus to a second site, e.g. the measuring path of a distance measuring interferometer, the environmental conditions at the latter site relative to the environmental conditions at the former site must be known with a relative precision of less than 300 ppm to 10 ppm, the required relative precision for the refractive index at the latter site being less than 0.1 ppm to 0.003 ppm in accordance with relative precisions previously cited. This serious limitation in regard to use in high precision distance measuring interferometry will in general be present with all techniques classified as refractivity techniques.

A prior-art refractivity technique for correcting for environmental uncertainties is based on the C. L. Farrand, V. F. Foster, and W. H. Grace U.S. Pat., ibid.. This technique incorporates a rigid enclosure, the length of which must be accurately known, independent of environmental conditions and constant in time. The change in optical path length of this enclosure is measured as remotely controlled valves allow the enclosure to be evacuated and refilled with ambient air. The refractivity of the air in the enclosure is proportional to the measured change in optical path length. This technique has been only partly satisfactory due to the fact that the characteristics of the air in the enclosure do not adequately represent those of the air in the measurement path, thusly systematic errors are introduced. It has been found that even with a perforated enclosure, serious systematic differences exist between the characteristics of the air inside of and external to the enclosure in addition to the limitations of the refractivity technique previously cited.

Other prior-art refractivity techniques which incorporate a fixed length optical reference path are found in commonly owned U.S. Pat. No. 4,685,803 issued Aug. 11, 1987 and U.S. Pat. No. 4,733,967 issued Mar. 29, 1988, to G. E. Sommargren. The principal advantages of the inventions disclosed in the two-cited Sommargren patents are that the length of the measurement path need not be known with extreme accuracy, small variations in the measurement path length during the measurement are tolerable, and the air around the refractive index cell can truly represent the ambient environment. However, the two cited Sommargren patents measure the refractivity of a gas and therefore encounter the cited limitations of the refractivity technique with regard to use in high precision distance measuring interferometry.

Perhaps the most difficult measurement related to the effects of environmental conditions on the refractive index of air is the measurement of index fluctuations over a measurement path of unknown or variable length, with uncontrolled temperature and pressure. Such circumstances arise frequently in geophysical and meteorological surveying, for which the atmosphere is obviously uncontrolled and the refractive index is changing dramatically because of variations in air density and composition. The problem is described in an article entitled "Effects Of The Atmospheric Phase Fluctuation On Long-Distance Measurement" by H. Matsumoto and K. Tsukahara, *Appl. Opt.* 23(19), 3388–3394 (1984) and in an article entitled "Optical Path Length Fluctuation In The Atmosphere" by G. N. Gibson, J. Heyman, J. Lugten, W. Fitelson, and C. H. Townes, *Appl. Opt.* 23(23), 4383–4389 (1984).

Another example situation with respect to uncontrolled atmosphere and changing refractive index is high-precision distance measuring interferometry, such as is employed in micro-lithographic fabrication of integrated circuits. See for example the two cited articles by N. Bobroff. The correction for index fluctuations due to air turbulence is typically on the order of 0.1 ppm in magnitude, and the residual errors due to index fluctuations resulting in part from air turbulence in the corrected measured path length must be with a relative precision less than or of the order of 0.003 ppm in high accuracy displacement interferometry, a relative precision corresponding to a displacement measurement accuracy of 3 nm for a one meter interferometric displacement measurement. This high level of precision involves frequency-stabilized laser sources and high-resolution phase detection.

One direct way to detect index fluctuations over a path is taught in U.S. Pat. No. 5,218,426 issued Jun. 8, 1993 to J. L. Hall, P. J. Martin, M. L. Eickhoff, and M. P. Winters and entitled "Highly Accurate In-Situ Determination of the Refractivity of an Ambient Atmosphere". The system of Hall et al. includes use of a refractometer exposed to an ambient atmosphere and having light directed thereto to form an optical interference fringe pattern having a dependence upon the refractivity of the ambient atmosphere. The fringe pattern is measured as a function of angle either by sequentially scanning a collimated input beam in angle while detecting the transmitted light, or by imaging (onto a multi-element detector) the angular exit space of the interferometer illuminated with a diverging input beam. The measuring path of the apparatus of Hall et. al. is substantially a combination of two right circular cones whereas the measuring path of a distance measuring interferometer is substantially comprised of a set of right circular cylinders. As a consequence, the apparatus of Hall et al. is not suited to measuring fluctuations in the optical path length of distance measuring interferometers due to atmospheric turbulence.

Another more direct way to detect index fluctuations over a path is by multiple-wavelength distance measurement. The basic principle may be understood as follows. Interferometers and laser radar measure the optical path length between a reference and an object, most often in open air. The optical path length is the integrated product of the refractive index and the physical path traversed by the measurement beam. In that the refractive index varies with wavelength, but the physical path is independent of wavelength, it is generally possible to separate the physical path length from the contributions of the refractive index, provided that the instrument employs at least two wavelengths. The variation of index with wavelength is known in the art as dispersion, accordingly this technique will be referred to hereinafter as the dispersion technique.

The dispersion technique measures the difference in optical path at two different wavelengths and then uses properties of the refractive index to compute the effects of the refractive index on a path length from the measured difference in optical path at two different wavelengths. The dispersion technique encounters two serious limitations. The more basic limitation arises from the fact that the dispersion technique is by definition a technique that uses properties of the first derivative with respect to wavelength of the refractive index. The second limitation arises from the fact that the properties of the refractive index must be available to the required accuracy.

The first derivative character of the dispersion technique increases the relative precision at which interferometric phase measurements must be made relative to distance measuring interferometers by more than one to two orders of magnitude. The first derivative character of the dispersion technique also increases the relative precision to which properties of the refractive index must be known relative to refractivity techniques by more than one to two orders of magnitude. The information available on the refractive index is not known with sufficient relative precision for certain applications of the refractivity technique and consequently is not known with sufficient relative precision for even fewer applications of the dispersion technique.

The dispersion technique for refractive index measurement has a long history, and predates the introduction of the laser. An article entitled "Long-Path Interferometry Through An Uncontrolled Atmosphere" by K. E. Erickson, *J. Opt. Soc. Am.* 52(7), 781–787 (1962) describes the basic principles and provides an analysis of the feasibility of the technique for geophysical measurements. Additional theoretical proposals are found in an article entitled "Correction Of Optical Distance Measurements for the Fluctuating Atmospheric Index of Refraction" by P. L. Bender and J. C. Owens, *J. Geo. Res.* 70(10), 2461–2462 (1965).

Commercial distance-measuring laser radar based on the dispersion technique for index compensation appeared in the 1970's. An article entitled "Two-Laser Optical Distance-Measuring Instrument That Corrects For The Atmospheric Index Of Refraction" by K. B. Earnshaw and E. N. Hernandez, *Appl. Opt.* 11(4), 749–754 (1972), discloses an instrument employing microwave-modulated HeNe and HeCd lasers for operation over a 5 to 10 km measurement path. Further details of this instrument are found in an article entitled "Field Tests of a Two-Laser (4416A And 6328A) Optical Distance-Measuring Instrument Correcting for the Atmospheric Index of Refraction" by E. N. Hernandez and K. B. Earnshaw, *J. Geo. Res.* 77(35), 6994–6998 (1972). A further example of an application of the dispersion technique is discussed in an article entitled "Distance Corrections for Single- and Dual-Color Lasers by Ray Tracing" by E. Berg and J. A. Carter, *J. Geo. Res.* 85(B11), 6513–6520 (1980).

Although instrumentation for geophysical measurements typically employs intensity-modulation laser radar, it is understood in the art that optical interference phase detection is more advantageous for shorter distances. In U.S. Pat. No. 3,647,302 issued to R. B. Zipin and J. T. Zalusky, March 1972, entitled "Apparatus For And Method Of Obtaining Precision Dimensional Measurements," there is disclosed an interferometric displacement-measuring system employing multiple wavelengths to compensate for variations in ambient conditions such as temperature, pressure, and humidity. The instrument is specifically designed for operation with a movable object, that is, with a variable physical path length. In that the technique of Zipin et al. employs three different wavelengths and assumes knowledge of the wavelength dependent refractive index to correct for changes in environmental conditions along a measurement path, the technique of Zipin et al. is not a dispersion technique. The dispersion technique being described as a technique which uses properties of the first derivative of the refractive index with respect to wavelength, the technique of Zipin et al. may be described as a technique which uses properties of the second derivative of the refractive index with respect to wavelength and accordingly, will hereinafter be referred to a second derivative refractive index technique.

An example of an application of the second derivative refractive index technique in geophysical experiments is found in an article entitled "Multi-Wavelength Distance-Measuring Instrument For Geophysical Experiments" by L. E. Slater and G. R. Huggett, *J. Geo. Res.* 81(35), 6299–6306 (1976).

The second derivative refractive index technique encounters two serious limitations. The more basic limitation arises from the fact that the second derivative refractive index technique is by definition a technique that uses properties of the second derivative with respect to wavelength of the refractive index. The second limitation arises from the fact that the properties of the refractive index must be available to the required relative precision. The second derivative character of the second derivative refractive index technique increases the relative precision at which interferometric phase measurements must be made relative to dispersion techniques by more than one to two orders of magnitude. The second derivative character of the second derivative refractive index technique also increases the relative precision to which properties of the refractive index must be known relative to dispersion techniques by more than one to two orders of magnitude. The information available on the refractive index is not known with sufficient relative precision for certain applications of the refractivity technique, to fewer applications of the dispersion technique, and consequently to yet an even smaller set of applications of the second derivative refractive index technique.

A detailed example of a system employing a dispersion technique with the basic limitations previously cited is described by Y. Zhu, H. Matsumoto, and T. O'ishi in an article entitled "Long-Arm Two-Color Interferometer For Measuring The Change Of Air Refractive Index," *SPIE*, 1319, optics in complex systems, 538–539 (1990). The system of Zhu et al. employs a 1064 nm wavelength YAG laser and an 632 nm HeNe laser together with quadrature phase detection. Substantially the same instrument is described in Japanese in an earlier article by Zhu et al. entitled "Measurement Of Atmospheric Phase And Intensity Turbulence For Long-Path Distance Interferometer," Proc. 3$^{rd}$ meeting on lightwave sensing technology, *Appl. Phys. Soc. of Jpn.* 39 (1989).

A recent attempt at high-precision interferometry for microlithography using a dispersion technique is represented by U.S. Pat. No. 4,948,254 issued to A. Ishida, Aug. 1990. A similar device is described by Ishida in an article entitled "Two Wavelength Displacement-Measuring Interferometer Using Second-Harmonic Light To Eliminate Air-Turbulence-Induced Errors," *Jpn. J. Appl. Phys.* 28(3), L473–475 (1989). In the article, a displacement-measuring interferometer is disclosed which reduces errors caused by fluctuations in the refractive index by means of two-wavelength dispersion detection. An Ar$^+$ laser source provides both wavelengths simultaneously by means of a frequency-doubling crystal known in the art as BBO. The use of a BBO doubling crystal results in two wavelengths that are fundamentally phase-locked, thus greatly improving the stability and accuracy of the dispersion measurement. In addition to the basic limitations of the dispersion technique previously cited, the phase detection and signal processing means are not suitable for dynamic measurements, in which the motion of the object results in rapid variations in phase that are difficult to detect accurately.

In U.S. Pat. No. 5,404,222 entitled "Interferometric Measuring System With Air Turbulence Compensation," issued to S. A. Lis, April 1995, there is disclosed a two-wavelength interferometer employing the dispersion technique for detecting and compensating index fluctuations. A similar device is described by Lis in an article entitled "An Air Turbulence Compensated Interferometer For IC Manufacturing," *SPIE* 2440 (1995). Improvement on U.S. Pat. No. 5,404,222 by S. A. Lis is disclosed in U.S. Pat. No. 5,537,209 issued July 1996. The principle innovation of this system with respect to that taught by Ishida in *Jpn. J. Appl. Phys.* (ibid.) is the addition of a second BBO doubling crystal to improve the precision of the phase detection means. The additional BBO crystal makes it possible to optically interfere two beams having wavelengths that are exactly a factor of two different. The resultant interference signal has a phase that is directly dependent on the dispersion but is substantially independent of stage motion. However, the cited patents of Lis are all based on the dispersion technique and therefore have the basic limitations of the dispersion technique previously cited.

The relative precision of any dispersion technique depends directly on the accuracy to which both the dispersion and the reciprocal dispersive power of the gas in the measurement path is known, the reciprocal dispersive power being defined as the ratio of the refractivity of a gas measured at a first wavelength to the dispersion of the refractivity of the gas between a second and third wavelengths. The first wavelength is preferably the same wavelength as used in an associated distance measuring interferometer. The second or third wavelengths used in the measurement of the dispersion may be the same as the first wavelength used in the measurement of the refractivity. The reciprocal dispersive power is used to compute the refractivity of a gas in the measuring path of for example a distance measuring interferometer from measured values of the dispersion of the gas in the measuring path of the distance measuring interferometer.

The reciprocal dispersive power depends on the three wavelengths for which a specific reciprocal dispersive power is defined as well as on the composition of the gas. The principle advantage of the dispersion technique is that the reciprocal dispersive power is independent of environmental conditions such as temperature and pressure for environmental conditions normally encountered in high-precision distance-measuring interferometers. However, in many situations the composition of the gas may be unknown, the gas composition may vary in time in an unknown way, and the dispersion of the refractivity and/or the refractivity of the gas constituents is not available or not known to the accuracy required for a given application. Either lack of the knowledge of the gas composition or of the reciprocal dispersive power to the necessary relative precision can pose serious limitations on the utility of the dispersion technique.

With respect to the latter point regarding availability of refractivities and corresponding reciprocal dispersive powers, consider the accuracy to which the reciprocal dispersive power is known for the example of water vapor. The widely used equations for the refractivity of water vapor found in the work of B. Edlen entitled "The Refractive Index of Air," *Metrologia* 2(2), 71–80 (1966) or the improved results reported by K. P. Birch and M. J. Downs, *Appl. Opt.* 28(5), 825–826 (1989) may be used to compute the reciprocal dispersive power for water vapor. The Birch and Downs findings have been verified by J. Beers and T. Doiron, *Metrologia* 29, 315–316 (1992). The relative precision to which the reciprocal dispersive power can be computed using either of these two cited sources for the refractivity of water vapor is of the order of 0.1%, the first, second, and third wavelengths used in the computing the reciprocal dispersive power being in the visible part of the spectrum, the first and second wavelengths being equal, and the second and third wavelengths being in the ratio of 2:1, respectively. The situation respect to $CO_2$ is only better by approximately a factor of 3.

It is evident from the examples given in the preceding paragraph that current knowledge of the refractivity of water vapor and $CO_2$ are not accurate enough to make absolute length measurements using dispersion interferometry in ambient air to the relative precision of approximately 0.003 ppm. They may also not be known accurate enough for atmospheric turbulence compensation for the more turbulent environments. The situation with respect to contaminant gases vis-a-vis respective reciprocal dispersive powers may present an even more serious problem in the use of dispersion interferometry [cf. N. Bobroff, *Meas. Sci. Technol.* 4, 907–926, (1993)].

It is clear from the foregoing, that the prior art does not provide a practical, high-speed, high-precision method and corresponding means for measuring and compensating the refractive index including fluctuations in the refractive index of a gas. The limitations in the prior art arise principally from the following, unresolved technical difficulties: (1) the refractivity technique does not measure for example the refractivity of a gas in a measurement path of a distance measuring interferometer directly and as a consequence, requires detailed high precision knowledge of the environmental conditions at two separated sites; (2) the dispersion technique does not measure the refractivity of a gas in a measurement path of a distance measuring interferometer directly and as a consequence requires knowledge of the constituents of the gas in the measurement path and knowledge of the reciprocal dispersive powers of the gas constituents; (3) the gas composition may not be known with sufficient accuracy for the dispersion technique in either a turbulent or a non-turbulent gas; (4) the composition of a gas may be changing significantly on relative short time scales; (5) the data age of composition determinations may be too long; and (6) the refractivity and reciprocal dispersive powers of the gas constituents may not be known with sufficient accuracy.

Consequently, while prior-art techniques for measuring the refractive index of a gas are useful for some applications, none known to the applicant provide the technical performance in a commercially viable form for applications requiring the determination of the reciprocal dispersive power of a gas with the high accuracy required in dispersion interferometry for compensation of air in distance measuring interferometry.

Accordingly, it is an object of the invention to provide a method and apparatus for measuring and monitoring intrinsic optical properties of a gas, particularly its reciprocal dispersive power.

It is another object of the invention to provide a method and apparatus for measuring and monitoring a reciprocal dispersive power of a gas wherein the method and apparatus does not require measurement and monitoring of environmental conditions such as temperature and pressure.

It is another object of the invention to provide a method and apparatus for measuring and monitoring a reciprocal dispersive power of a gas wherein the method and apparatus does not require knowledge of the gas composition.

It is another object of the invention to provide a method and apparatus for measuring and monitoring a reciprocal dispersive power of a gas wherein the method and apparatus is operative over a wide temporal frequency range with respect to changes in gas composition.

It is another object of the invention to provide a method and apparatus for measuring and monitoring a reciprocal dispersive power of a gas wherein the method and apparatus does not require knowledge of the refractivities and of the dispersions of the refractivities for constituents of the gas.

It is another object of the invention to provide a method and apparatus for measuring and monitoring a reciprocal dispersive power of a gas wherein the method and apparatus may use but does not require the use of two or more optical beams of differing wavelengths which are phase locked.

It is another object of the invention to provide a method and apparatus for measuring and monitoring a reciprocal dispersive power of a gas wherein the lengths of measuring paths in an interferometric measurement and monitoring of a reciprocal dispersive power are substantially not used in a computation of the reciprocal dispersive power of the gas.

It is another object of the invention to provide a method and apparatus for measuring and monitoring a reciprocal dispersive power of a gas wherein the frequencies of the optical beams used in an interferometric measurement and monitoring of a reciprocal dispersive power are substantially not used in a computation of the reciprocal dispersive power of the gas.

Other objects of the invention will, in part, be obvious and will, in part, appear hereinafter. The invention accordingly comprises methods and apparatus possessing the construction, steps, combination of elements, and arrangement of parts exemplified in the detailed description to follow when read in connection with the drawings.

SUMMARY OF THE INVENTION

The present invention generally relates to apparatus and methods by which information about select intrinsic optical properties of gases can be measured and monitored for use in electro-optical metrology and other applications. More specifically, the invention operates to provide measurements of relative refractivities, relative dispersions, and reciprocal dispersive power, the relative refractivity, relative dispersion, and reciprocal dispersive power being substantially independent of environmental conditions such as gas temperature and pressure. In making these measurements, the gas may be turbulent, the gas composition may not be known, the gas composition may be variable in time, and knowledge of refractivities and dispersions of the refractivities for constituents of the gas is not required. The information generated by the inventive apparatus is particularly suitable for use in interferometric distance measuring instruments (DMI) to compensate for errors related to refractive index in the measurement leg and especially to refractive index changes in the measurement leg brought about by environmental effects and turbulence induced by rapid stage slew rates.

Several embodiments of the invention have been made and these fall into three groups which address the need for more or less precision in final measurements and the need for more or less sensitivity of final measured quantities to changes in wavelengths of the light beams used in determination of the final measured quantities. While the various embodiments share common features, they differ in some details to achieve individual goals.

In general, the inventive apparatus comprises interferometer means having reference legs and measurement legs. Each of the constituent legs has a predetermined physical path length with one reference leg configured and arranged to be occupied by a predetermined medium, preferably a vacuum, a second reference leg configured to have substantially zero physical length, and the measurement legs configured and arranged to be occupied by the gas whose intrinsic optical properties are to be measured and monitored. In preferred form, the interferometer means comprises a concentric cell having a closed inner chamber that serves as one of the reference legs and an outer chamber, surrounding the inner chamber, that serves as the measurement legs. The inner chamber is substantially evacuated to provide the vacuum, and the outer chamber is opened to the ambient surroundings which, in a typical interferometric DMI application, is air. The concentric cell is preferably in form a right circular cylinder with end sections capped with wavelength selective mirrors fixed normal to the cell's longitudinal axis.

Means for generating at least two light beams having different wavelengths are included. In preferred embodiments, a source generates a set of light beams, the set of light beams comprising at least two light beams, each beam of the set of light beams having a different wavelength. The approximate relationship between the wavelengths of the beams of the set of light beams, the approximate relationship, is known.

A set of frequency-shifted light beams is generated from the set of light beams by introducing a frequency difference between two orthogonally polarized components of each beam of the set of light beams such that no two beams of the set of frequency-shifted light beams have the same frequency difference. In a number of the embodiments, the ratios of the wavelengths are the same as the known approximate relationship to respective relative precisions, the respective relative precisions of the ratios of the wavelengths, wherein a respective relative precision of the respective relative precisions of the ratios of the wavelengths is of an order of magnitude less than the respective dispersive power of the gas times the relative precision required for the measurement of the respective reciprocal dispersive power of the gas. In certain ones of the embodiments, the approximate relationship is expressed as a sequence of ratios, each ratio comprising a ratio of low order non-zero integers, e.g. ½, to respective relative precisions, the respective relative precisions of the sequence of ratios, wherein a respective relative precision of the respective relative precisions of the sequence of ratios is of an order of magnitude less than the respective dispersive power of the gas times the relative precision required for the measurement of the respective reciprocal dispersive power. In other embodiments, where the respective relative precisions of the ratios of the wavelengths is inappropriate to the desired respective relative precisions of the ratios of the wavelengths, means are provided for monitoring the ratios of the wavelengths and either providing feedback to control the respective relative precisions of the ratios of the wavelengths, information to correct subsequent calculations influenced by undesirable departures of the respective relative precisions of the ratios of the wavelengths from the desired respective relative precisions of the ratios of the wavelengths, or some combination of both.

At least a portion of each of the frequency shifted light beams is introduced into the interferometer means by suitable optical means so that each light beam portion travels through either the reference leg of predetermined medium and/or the reference leg of substantially zero physical length and the gas along predetermined paths, the predetermind paths of the reference leg of predetermined medium and of the gas having substantially the same physical path lengths. Afterwards, the light beam portions emerge from the interferometer means as exit beams containing information about the optical path length through the gas in the measurement leg, about the optical path length through the predetermined medium (preferably a vacuum) in one reference leg, a first reference leg, and/or about the optical path length through a second reference leg of substantially zero physical length, a second reference leg. In preferred form, the optical means for introducing the light beam portions into the interferometer means is configured and arranged to introduce one of the light beam portions corresponding to one wavelength through one of the wavelength selective end mirrors of the concentric cell and another of the light beam portions corresponding to another of the wavelengths through the other wavelength selective mirror of the end sections of the concentric cell. In one of the embodiments three sets of light beam portions are generated, one at one wavelength being introduced into one end of the concentric cell and two at another wavelength into the other end of the concentric cell.

In yet another embodiment, the optical means are configured to cause certain of the light beam portions to undergo multiple passes as they travel through the concentric cell.

Combining means are provided for receiving the exit beams to produce mixed optical signals which contain information corresponding to the phase differences between the exit beams of each light beam portion from a first reference leg and a measurement leg and/or from a second reference leg and the measurement leg. The mixed optical signals are then sensed by photodetectors which operate to generate electrical interference signals that contain a combination of information corresponding to the refractivities of the gas at the different beam wavelengths, of information corresponding to the index of refraction of the gas at the different beam wavelengths, and of information corresponding to the beam wavelengths.

The electrical interference signals are then analyzed by electronic means that operate to determine the select intrinsic optical properties of the gas. The electronic means can be in the form of a microprocessor or a general purpose computer suitably programmed in well-known ways to perform the needed calculations. The electronic means is configured to determine the intrinsic optical property, the reciprocal dispersive power, $\Gamma$, of the gas, as $$\Gamma = \frac{[n_1(\lambda_1) - 1]}{[n_3(\lambda_3) - n_2(\lambda_2)]}$$

where $\lambda_1$, $\lambda_2$, and $\lambda_3$ are wavelengths and $n_1$, $n_2$, and $n_3$ are indices of refraction and wherein the denominator may be replaced by $[n_3(\lambda_3)-n_1(\lambda_1)]$ or $[n_2(\lambda_2)-n_1(\lambda_1)]$. The electronic means can also be configured to determine the intrinsic optical property, the reciprocal dispersive power, $\Gamma$, of the gas, as $$\Gamma = \frac{[n_i(\lambda_i)-1]}{[n_{j+1}(\lambda_{j+1})-1]-[n_j(\lambda_j)-1]}$$

where i and j are integers corresponding to wavelengths. The electronic means can further be configured to determine other intrinsic optical properties, the relative refractivities and the relative dispersions of the gas at different beam wavelengths, where the relative refractivities of the gas are of the form $$\frac{n_{\lambda_i}-1}{n_{\lambda_j}-1}$$

and where the relative dispersions of the gas are of the form $$\frac{n_i - n_j}{n_r - n_s}$$

where i, j, r, and s are integers corresponding to wavelengths, i≠j, r≠s, and at least either i or j different from either r or s.

In a preferred form, the electrical interference signals comprise heterodyne signals containing phase information corresponding to the refractivities of the gas, to the indices of refraction of the gas, and to the beam wavelengths and the apparatus further comprises means for mixing, i.e. multiplying, the heterodyne signals to generate at least one superheterodyne signal containing phase information corresponding to the dispersion of the index of refraction of the gas, the dispersion of the index of refraction of the gas being obtained either from the index of refraction of the gas or from the refractivities of the gas. Means are also included for resolving phase ambiguities of the heterodyne and superheterodyne signals. Depending on the details of the optical paths experienced by the light beam portions as they travel through the interferometer means of the various embodiments, additional or different electronics are provided which, in one embodiment, requires the production of modified heterodyne signals prior to final data processing.

While the inventive method disclosed may be carried out using the preferred apparatus described, it will be evident that it may also be practiced using other well-known apparatus. In addition, it is shown that apparatus may be employed which uses homodyne signals.

BRIEF DESCRIPTION OF THE DRAWINGS

The structure and operation of the invention, together with other objects and advantages thereof, may best be understood by reading the detailed description in conjunction with the drawings wherein the invention's parts have an assigned reference numeral that is used to identify them in all of the drawings in which they appear and wherein:

FIG. 1b illustrates differential plane mirror interferometer 69;

FIG. 1c illustrates differential plane mirror interferometer 70;

FIG. 1d illustrates measurement cell 90 furnishing the external mirrors for differential plane mirror interferometer 69;

FIG. 1e illustrates measurement cell 90 furnishing the external mirrors for differential plane mirror interferometer 70;

FIG. 1f is a drawing showing a block diagram of the processing electronics 109;

FIGS. 1a–1e and 1g taken together illustrate, in diagrammatic form, the presently preferred first variant of the first embodiment of the present invention with FIG. 1g showing a block diagram of the processing electronics 109A;

FIG. 2b illustrates differential plane mirror interferometer group 170;

FIG. 2c illustrates measurement cell 90 furnishing the external mirrors for differential plane mirror interferometer group 170;

FIG. 2d is a drawing showing a block diagram of the processing electronics 209;

FIGS. 2a–2c and 2e taken together illustrate, in diagrammatic form, the presently preferred variant of the second embodiment of the present invention with FIG. 2e showing a block diagram of the processing electronics 209A;

FIG. 3b illustrates differential plane mirror interferometer 169 for the case of light beam 11 entering differential plane mirror interferometer 169;

FIG. 3c illustrates differential plane mirror interferometer 169 for the case of light beam 345 exiting differential plane mirror interferometer 169;

FIG. 3d is a drawing showing a block diagram of the processing electronics 309;

FIGS. 3a–3c and 3e taken together illustrate, in diagrammatic form, the presently preferred variant of the third embodiment of the present invention with FIG. 3e showing a block diagram of the processing electronics 309A;

FIG. 4b illustrates differential plane mirror interferometer group 269;

FIG. 4c illustrates differential plane mirror interferometer 270;

FIG. 4d illustrates measurement cell 90 furnishing the external mirrors for differential plane mirror interferometer group 269;

FIG. 4e illustrates measurement cell 90 furnishing the external mirrors for differential plane mirror interferometer 270;

FIG. 4f is a drawing showing a block diagram of the processing electronics 409;

FIGS. 4a–4e and 4g taken together illustrate, in diagrammatic form, the presently preferred variant of the fourth embodiment of the present invention with FIG. 4g showing a block diagram of the processing electronics 409A;

FIG. 5b illustrates differential plane mirror interferometer group 370;

FIG. 5c illustrates measurement cell 90 furnishing the external mirrors for differential plane mirror interferometer group 370;

FIG. 5d is a drawing showing a block diagram of the processing electronics 509;

FIGS. 5a–5c and 5e taken together illustrate, in diagrammatic form, the presently preferred variant of the fifth embodiment of the present invention with FIG. 5e showing a block diagram of the processing electronics 509A;

FIG. 6b illustrates differential plane mirror interferometer group 369 for the case of light beam 11 entering differential plane mirror interferometer group 369;

FIG. 6c illustrates differential plane mirror interferometer 369 for the case of light beams 345 and 1345 exiting differential plane mirror interferometer group 369;

FIG. 6d illustrates measurement cell 90 furnishing the external mirrors for differential plane mirror interferometer group 369;

FIG. 6e is a drawing showing a block diagram of the processing electronics 609;

FIGS. 6a–6d and 6f taken together illustrate, in diagrammatic form, the presently preferred variant of the sixth embodiment of the present invention with FIG. 6f showing a block diagram of the processing electronics 609A;

FIG. 7b illustrates differential plane mirror interferometer group 470;

FIG. 7c illustrates measurement cell 90 furnishing the external mirrors for differential plane mirror interferometer group 470;

FIG. 8b illustrates differential plane mirror interferometer group 570;

FIG. 8c illustrates measurement cell 90 furnishing the external mirrors for differential plane mirror interferometer group 570;

DETAILED DESCRIPTION OF THE INVENTION

Figure 1A:
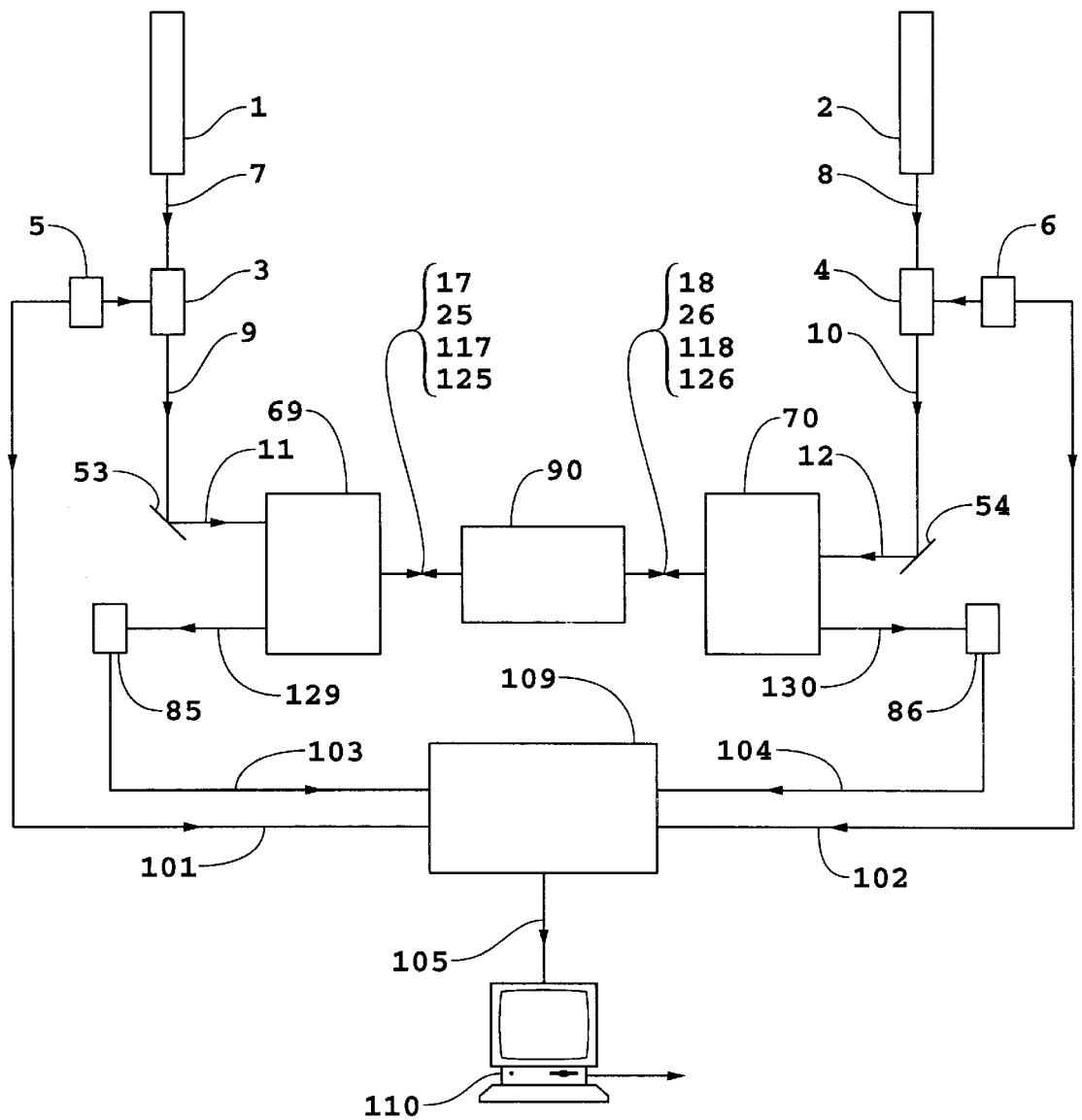
FIGS. 1a–1f taken together illustrate, in diagrammatic form, the presently preferred first embodiment of the present invention with FIG. 1a showing optical paths between indicated elements source 1, modulator 3, source 2, modulator 4, differential plane mirror interferometers 69 and 70, measurement cell 90, detectors 85 and 86 and the paths of electrical signals between indicated elements driver 5, modulator 3, driver 6, modulator 4, detectors 85 and 286, electronic processor 109, and computer 110.

The present invention relates to apparatus and methods by which intrinsic optical properties of a gas, especially its reciprocal dispersive power, may be quickly measured and used in subsequent downstream or contemporaneous applications as, for example, in an interferometric distance measuring instrument to enhance accuracy by compensating for index of refraction of gas in measuring path, especially changes in index of refraction that take place proximate to or during the distance measuring instrument measuring period because of changing environmental conditions or air turbulence induced in the measurement leg by rapid stage slew rates.

A number of different embodiments of the apparatus of the invention are shown and described. While they differ in some details, the disclosed embodiments otherwise share many common elements and naturally fall into three groups depending on the end use application and on the degree of control demanded of their light sources. As will be seen, the disclosed embodiments within each group also differ in the details of how their interferometric optical paths are implemented and/or how certain information signals are handled electronically. Each group of embodiments to be described comprise three embodiments and variants thereof.

The first group is intended for applications where the end use application substantially does not effect the choice of the particular manner in which the intrinsic optical properties of the gas are determined and where the stability of the adopted light sources is sufficient and the ratio of the wavelengths of the light beams generated by the adopted light sources is matched to a known ratio value with a relative precision sufficient to meet the required precision imposed on the output data by the final end use application.

The second group is particularly suitable for use where the end use application essentially does effect the choice of the particular manner in which the intrinsic optical properties of the gas are determined and where the stability of the adopted light sources is sufficient and the ratio of the wavelengths of the light beams generated by the adopted light sources is matched to a known ratio value with a relative precision sufficient to meet the required precision imposed on the output data by the final end use application although not necessarily sufficient to meet the corresponding requirements of the first group.

The third group is particularly suitable for use where it is necessary to monitor the stability of the light sources and measure the ratio of the wavelengths of the light beams generated by the adopted light sources to meet performance requirements on accuracy. The third group is in addition suitable for use in either of the end use application categories of the first and second groups wherein consideration of the end use application either essentially does not or does effect, respectively, the choice of the particular manner in which the intrinsic optical properties of the gas are determined. For each of the groups, apparatus is disclosed for dealing with phase ambiguities and phase offsets that may arise in analyzing homodyne, heterodyne, and/or superheterodyne signals, and methods are disclosed for implementing the steps of the invention.

Reference is now made to FIGS. 1a–1f which depict in diagrammatic form one preferred embodiment of the apparatus of the present invention from the first group for measuring intrinsic optical properties of a gas, particularly its reciprocal dispersive power wherein the end use application substantially does not effect the particular manner in which the intrinsic optical properties of the gas are determined and where the stability of the adopted light sources is sufficient and the ratio of the wavelengths of the light beams generated by the adopted light sources is matched to a known ratio value with a relative precision sufficient to meet the required precision imposed on the output data by the final end use application. While the apparatus has application for a wide range of radiation sources, the following description is taken by way of example with respect to an optical measuring system.

Referring to FIG. 1a and in accordance with the preferred method of the first preferred embodiment of the present invention, a light beam 7 emitted from source 1 passes through a modulator 3 becoming light beam 9. Modulator 3 is excited by a driver 5. Source 1 is preferably a laser or like source of coherent radiation, preferably polarized, and having a wavelength $\lambda_1$. Modulator 3 may for example be an acousto-optical device or a combination of acousto-optical devices with additional optics for selectively modulating polarization components of beam 7. Modulator 3 preferably shifts the oscillation frequency of one linearly polarized component of beam 7 an amount $f_1$ with respect to an orthogonally linearly polarized component, the directions of polarizations of the components denoted herein as x and y. In the following description of the first embodiment, it will be assumed that the x polarization component of beam 9 has an oscillation frequency shifted an amount $f_1$ with respect to the y polarization component of beam 9 without departing from the spirit or scope of the present invention.

In a next step, a light beam 8 emitted from a source 2 passes through a modulator 4 becoming light beam 10. Modulator 4 is excited by a driver 6, similar to modulator 3 and driver 5, respectively. Source 2, similar to source 1, is preferably a laser or like source of polarized, coherent radiation, but preferably at a different wavelength, $\lambda_2$, wherein the ratio of the wavelengths $(\lambda_1/\lambda_2)$ have a known approximate ratio value 11/12, i.e.

$$(\lambda_1/\lambda_2) \cong (l_1/l_2), \tag{1}$$

where $l_1$ and $l_2$ may assume integer and non-integer values. The x polarized component of beam 10 has an oscillation frequency shifted an amount $f_2$ with respect to the y polarized component of beam 10. In addition, the directions of the frequency shifts of the x components of beams 9 and 10 are the same.

It will be appreciated by those skilled in the art that beams 9 and 10 may be provided alternatively by a single laser source emitting more than one wavelength, or by a single laser source combined with optical frequency doubling means, or any equivalent source configuration capable of generating light beams of two or more wavelengths. It will also be appreciated by those skilled in the art that one or both of the frequency shifts $f_1$ and $f_2$ may be the result of Zeeman splitting or like phenomena characteristic of the laser sources themselves.

Referring to FIG. 1a, beam 9 is reflected by mirror 53 becoming beam 11 and beam 10 is reflected by mirror 54 becoming beam 12. Beam 11 is incident on differential plane mirror interferometer 69 and beam 12 is incident on differential plane mirror interferometer 70. Differential plane mirror interferometers 69 and 70 with external mirrors furnished by measurement cell 90 comprise interferometric means for introducing a phase shift $\phi_1$ between the x and y components of beam 11 and a phase shift $\phi_2$ between the x and y components of beam 12.

Measurement cell 90 is conveniently formed as a set of nested, concentric chambers in the form of a right circular cylinder, the inner chamber of which is evacuated to a vacuum and the outer occupied by the gas whose intrinsic optical properties are to be monitored.

Figure 1B:
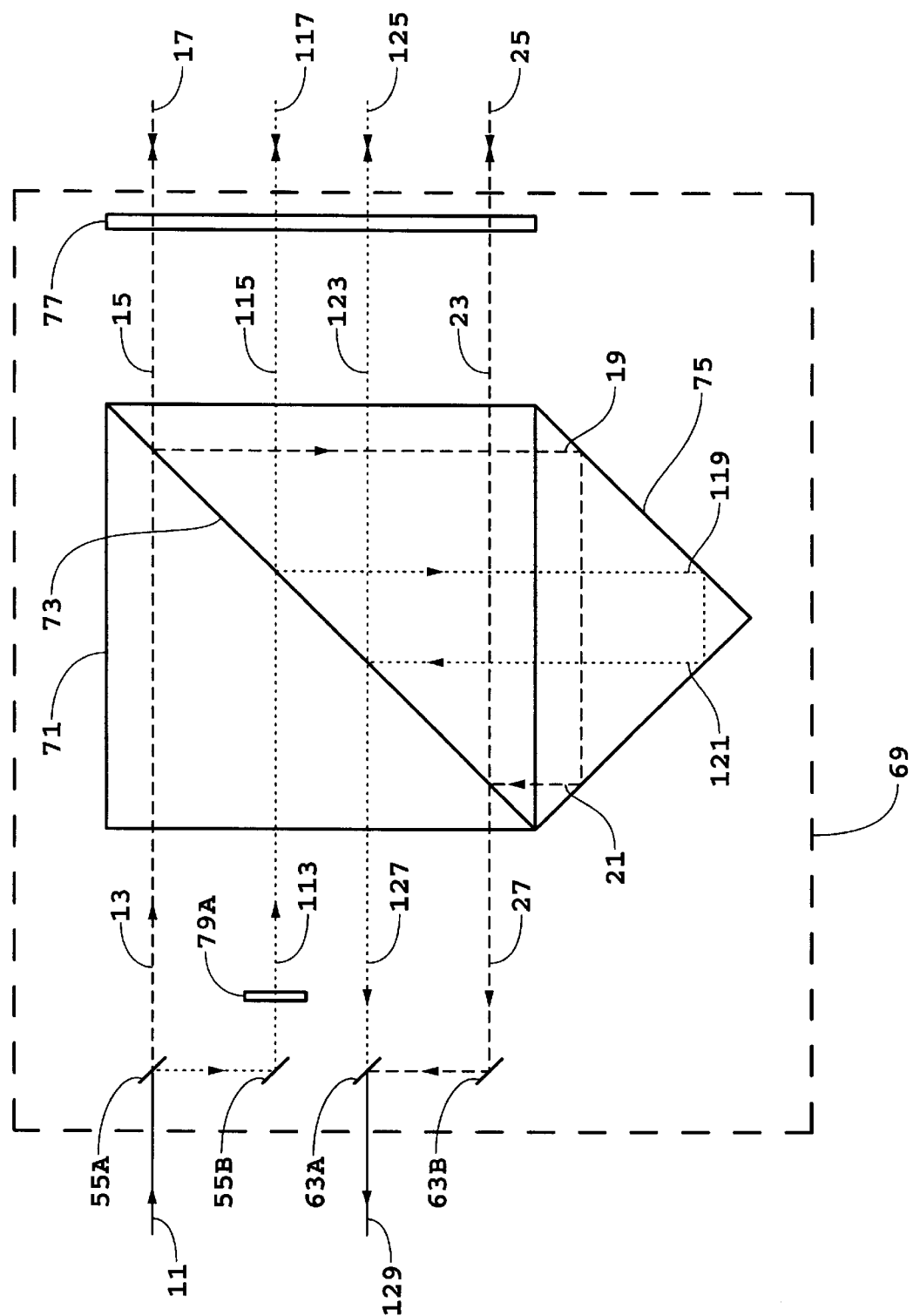

A differential plane mirror interferometer measures the optical path changes between two external plane mirrors. Differential plane mirror interferometer 69 as shown in FIG. 1b has four exit/return beams 17, 25, 117, and 125. Beams 17 and 25 originating from one frequency component of beam 11, the first frequency component, comprise beams for one measurement leg and beams 117 and 125 originating from a second frequency component of beam 11 comprise beams for a second measurement leg. Beams for which the first frequency component of beam 11 is the sole progenitor are indicated in FIG. 1b by dashed lines and beams for which the second frequency component of beam 11 is the sole progenitor are indicated in FIG. 1b by dotted lines.

Figure 1C:
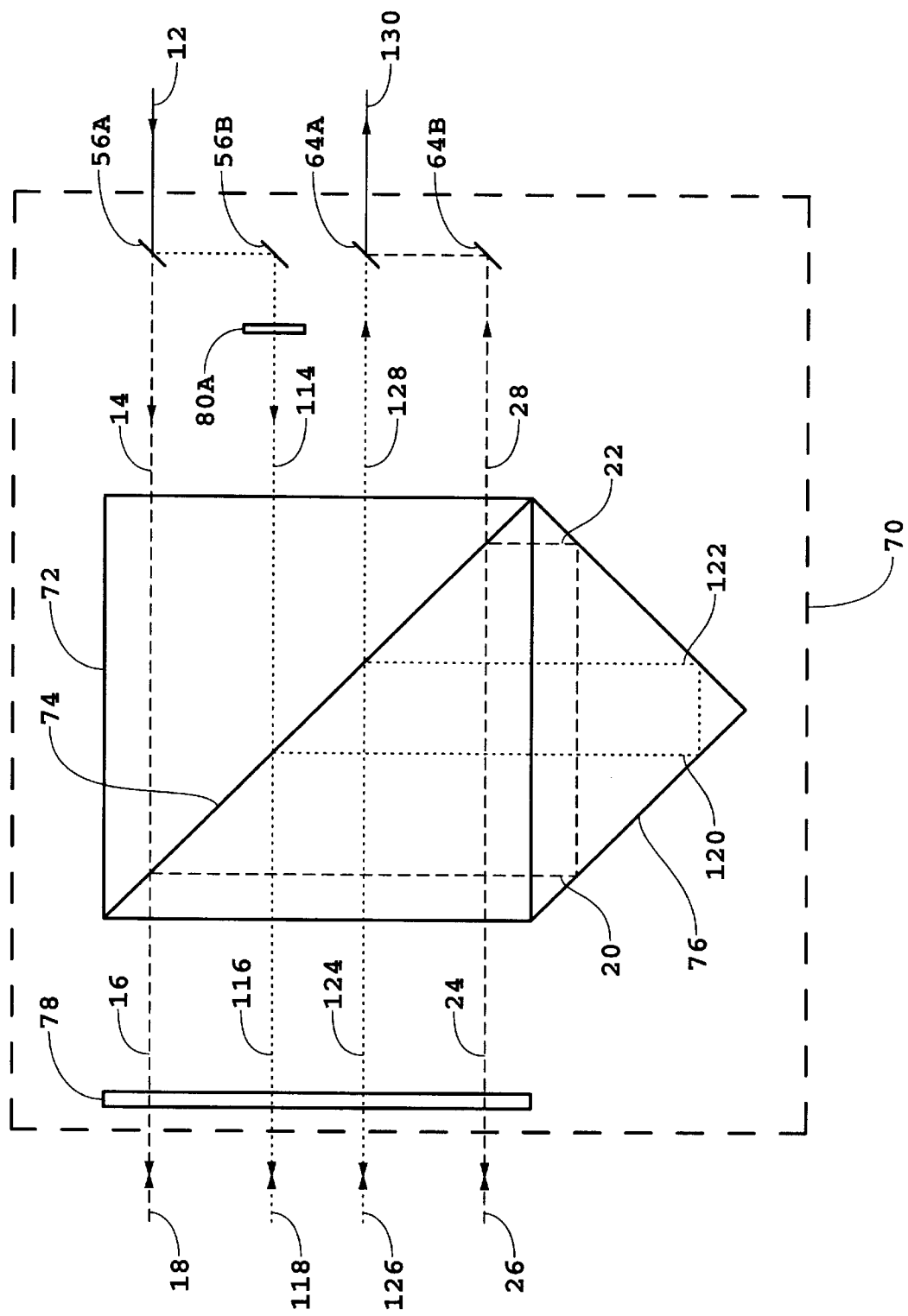

Differential plane mirror interferometer 70 has four exit/return beams 18, 26, 118, and 126 as shown in FIG. 1c. Beams 18 and 26 originating from one frequency component of beam 12 comprise one measurement leg and beams 118 and 126 originating from a second frequency component of beam 12 comprise a second measurement leg. Beams for which the first frequency component of beam 12 is the sole progenitor are indicated in FIG. 1c by dashed lines and beams for which the second frequency component of beam 12 is the sole progenitor are indicated in FIG. 1c by dotted lines.

Figure 1D:
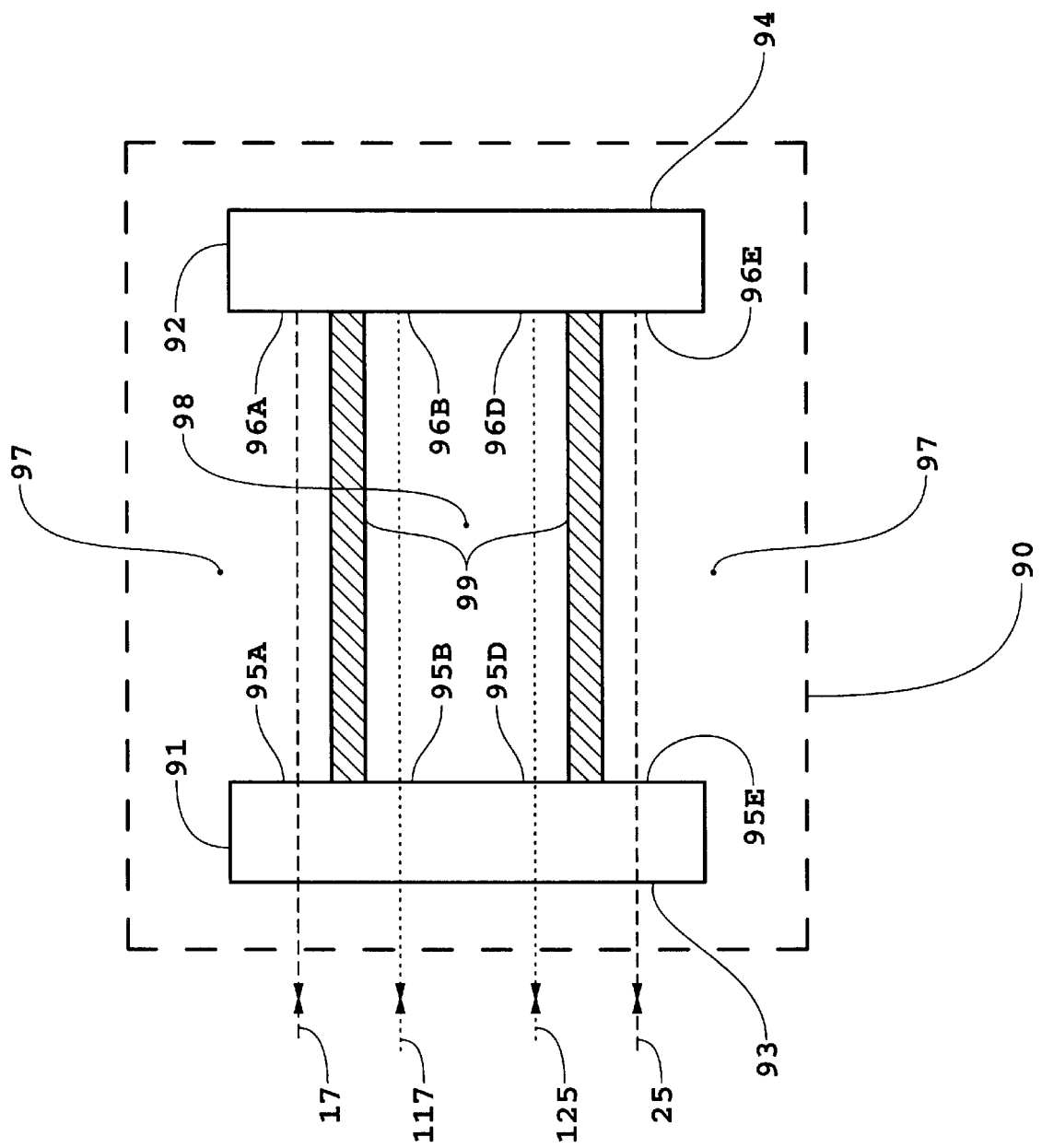

Beams 17, 25, 117, and 125 are incident on measurement cell 90, illustrated in FIG. 1d, which results in beams 27 and 127 (cf. FIG. 1b). Beams for which the first frequency component of beam 11 is the sole progenitor are indicated in FIG. 1d by dashed lines and beams for which the second frequency component of beam 11 is the sole progenitor are indicated in FIG. 1d by dotted lines. Beams 27 and 127 contain information at wavelength $\lambda_1$ about the optical path length through the gas whose reciprocal dispersive power is to be determined and about the optical path length through a vacuum, respectively.

Figure 1E:
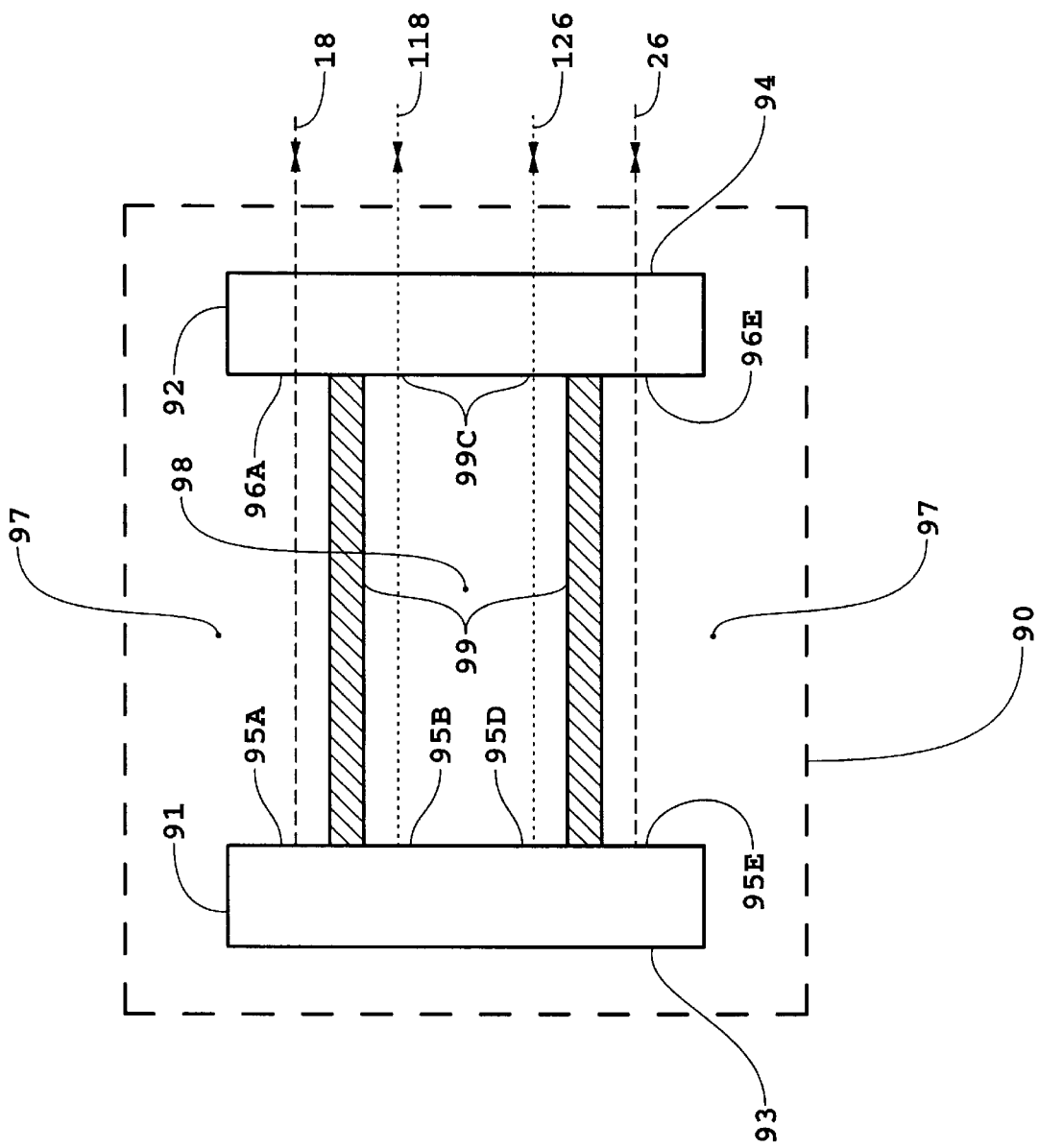

Beams 18, 26, 118, and 126 are incident on measurement cell 90, illustrated in FIG. 1e, which results in beams 28 and 128 (cf. FIG. 1c). Beams for which the first frequency component of beam 12 is the sole progenitor are indicated in FIG. 1e by dashed lines and beams for which the second frequency component of beam 12 is the sole progenitor are indicated in FIG. 1e by dotted lines. Beams 28 and 128 contain information at wavelength $\lambda_2$ about optical path lengths through the gas and about optical path lengths through a vacuum, respectively.

With reference to FIG. 1b, beam 27 is reflected by mirror 63B, a portion of which is reflected by beam splitter 63A, preferably a nonpolarizing type, to become one component of beam 129. A portion of beam 127 is transmitted by beam splitter 63A to become a second component of beam 129. Beam 129 exits differential plane mirror interferometer 69 as a mixed beam, the first and second components of beam 129 having the same linear polarizations with different frequencies.

Beam 28 is reflected by mirror 64B and then a portion reflected by beam splitter 64A, preferably a nonpolarizing beam splitter, to become a first component of phase-shifted beam 130. A portion of beam 128 is transmitted by beam splitter 64A to become a second component of phase-shifted beam 130. Phase-shifted beam 130 exits differential plane mirror interferometer 70 as a mixed beam, the first and second components of beam 130 having the same polarizations with different frequencies.

The magnitude of phase shifts $\phi_1$ and $\phi_2$ are related to the round-trip physical lengths of measurement path 97 and reference path 98 shown in FIGS. 1d and 1e according to the formulae $$\varphi_1 = k_1 \sum_{i=1}^{p} (L_{G,i} n_{1,i} - L_{V,i}) + \zeta_1, \quad (2)$$

$$\varphi_2 = k_2 \sum_{i=1}^{p} (L_{G,i} n_{2,i} - L_{V,i}) + \zeta_2$$

where $n_{j,i}$ is the index of refraction of gas in path i of measurement path 97 corresponding to wavenumber $k_j = (2\pi)/\lambda_j$, the index of refraction in the reference path 98 has been set to 1, and $L_{G,i}$ and $L_{V,i}$ are the round trip physical lengths of path i of measurement path 97 and reference path 98, respectively.

Eqs. (2) are valid for the case where the paths for the two different wavelengths are substantially coextensive, a case chosen to illustrate in the simplest manner the function of the invention in the first embodiment. The illustrations in FIGS. 1b and 1c are for p=2 for the same reason. To those skilled in the art, the generalization to the case where paths for the two different wavelengths are not substantially coextensive and to the case when p≠2 is a straight forward procedure.

Cyclic errors that produce nonlinearities in distance measuring interferometry (cf. the cited articles by Bobroff) have been omitted in Eqs. (2). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer [M. Tanaka, T. Yamagami, and K. Nakayama, "Linear Interpolation of Periodic Error in a Heterodyne Laser Interferometer at Subnanometer Levels," *IEEE Trans. Instrum. and Meas.*, 38(2), 552–554, 1989].

In a next step as shown in FIG. 1a, phase-shifted beams 129 and 130 impinge upon photodetectors 85 and 86, respectively, resulting in two interference signals, heterodyne signals $s_1$ and $s_2$, respectively, preferably by photoelectric detection. The signal $s_1$ corresponds to wavelength $\lambda_1$ and signal $s_2$ corresponds to the wavelength $\lambda_2$. The signals $s_j$ have the form $$s_j = A_j \cos[\alpha_j(t)], j=1 \text{ and } 2 \quad (3)$$

where the time-dependent arguments $\alpha_j(t)$ are given by $$\alpha_j(t) = 2\pi f_j t + \phi_j, j=1 \text{ and } 2. \quad (4)$$

Heterodyne signals $s_1$ and $s_2$ are transmitted to electronic processor 109 for analysis as electronic signals 103 and 104, respectively, in either digital or analog format, preferably in digital format.

The phases of drivers 5 and 6 are transmitted by electrical signals, reference signals 101 and 102, respectively, in either digital or analog format, preferably in digital format to electronic processor 109.

A preferred method for electronically processing the heterodyne signals $s_1$ and $s_2$ is presented herewithin for the case where $l_1$ and $l_2$ are not low order integers. For the case where $l_1$ and $l_2$ are low order integers and the ratio of the wavelengths matched to the known ratio (11/12) with a relative precision sufficient to meet the required precision imposed on the output data by the end use application, the preferred procedure for electronically processing the heterodyne signals $s_1$ and $s_2$ is the same as the one subsequently set down for the variant of the first preferred embodiment of the present invention.

Figure 1F:
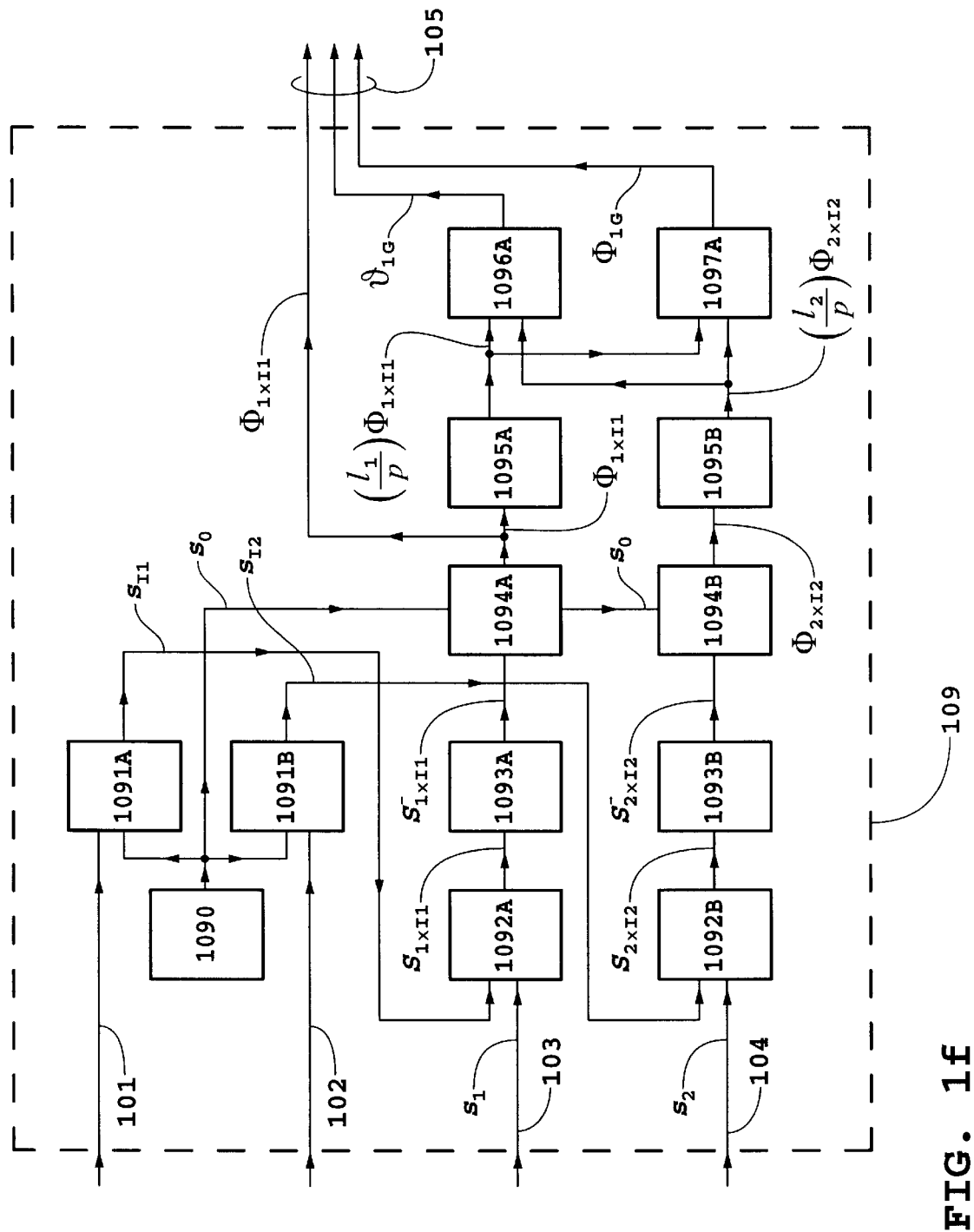

The phases $\phi_p$ and $\phi_2$ of signals $s_1$ and $s_2$, respectively, are obtained preferably by application of superheterodyne receiver techniques wherein the frequencies of signals $s_1$ and $s_2$ are shifted to frequencies substantially lower than $f_1$ and $f_2$ where conditions are generally more favorable for high precision phase measurements. Referring now to FIG. 1f, electronic processor 109 preferably comprises a stable local oscillator 1090 that generates signal $s_0$ at frequency $f_0$, $f_0$ typically being substantially lower than both $f_1$ and $f_2$. Electronic processor 109 further comprises image-reject mixers 1091A and 1091B to create, either as analog or digital processes, preferably a digital process, two mixed signals each with single sidebands at frequencies $f_1-f_0$ and $f_2-f_0$ from the reference signals 101 and 102, respectively, and signal $s_0$. It will be evident to those skilled in the art that the single sideband signals can also be generated by other procedures such as the well known technique of mixing two signals followed by a tuned filter to reject an unwanted image sideband. It will also be evident to those skilled in the art that the image sideband, the higher frequency sideband, could have been selected for retention without departing from the scope or spirit of the present invention. The single sideband signals are of the form $$s_{f1}=A_{f1}\cos[2\pi(f_1-f_0)t+\phi_{f1}]$$

$$s_{f2}=A_{f2}\cos[2\pi(f_2-f_0)t+\phi_{f2}] \quad (5)$$

where $\phi_{f1}$ and $\phi_{f2}$ are phase offset errors.

Electronic processor 109 further comprises electronic processor 1092A for electronically multiplying together, either as an analog or digital process, preferably a digital process, heterodyne signals $s_1$ and $s_{f1}$ to create a superheterodyne signal $S_{1\times f1}$ having the mathematical form $$S_{1\times f1}=s_1 s_{f1} \quad (6)$$

The superheterodyne signal $S_{1\times f1}$ comprises two sidebands with a suppressed carrier and may be rewritten as $$S_{1\times f1}=S_{1\times f1}^{+}+S_{1\times f1}^{-} \quad (7)$$

where $$S_{1\times f1}^{+}=\tfrac{1}{2}A_1 A_{f1}\cos(2\pi v_1 t+\theta_{1\times f1}) \quad (8)$$

$$S_{1\times f1}^{-}=\tfrac{1}{2}A_1 A_{f1}\cos(2\pi F t+\Phi_{1\times f1}) \quad (9)$$

$$v_1=(2f_1-f_0) \quad (10)$$

$$\theta_{1\times f1}=(\phi_1+\phi_{f1}) \quad (11)$$

$$F=f_0 \quad (12)$$

$$\Phi_{1\times f1}=(\phi_1-\phi_{f1}) \quad (13)$$

The superheterodyne signal $S_{1\times f1}$ therefore comprises two sidebands, $S_{1\times f1}^{+}$ and $S_{1\times f1}^{-}$, of equal amplitude, one sideband with frequency $v_1$ and phase $\theta_{1\times f1}$ and a second sideband with frequency $F$ and phase $\Phi_{1\times f1}$.

In a next step, the sidebands $S_{1\times f1}^{+}$ and $S_{1\times f1}^{-}$ are separated by electronic processor 1093A through high pass and low pass filtering or any of the like techniques for separating two signals that are separated in frequency. The frequency $F$ of the lower frequency sideband $S_{1\times f1}^{-}$ can be very much smaller than the frequency $v_1$ of the higher frequency sideband of $S_{1\times f1}^{+}$. Electronic process 109 further comprises electronic processor 1094A to determine the phase $\Phi_{1\times f1}$ using time-based phase detection such as a digital Hilbert transform phase detector [see section 4.1.1 of "Phase-locked loops: theory, design, and applications" 2nd ed. McGraw-Hill (New York) 1993, by R. E. Best; Chapter 10 of "Discrete Hilbert Transforms" in *Discrete-Time Signal Processing*, (Prentice Hall) 1989, by A. V. Opperheim and R. W. Schafer] or the like and the reference signal $s_0$.

Electronic processor 109 further comprises electronic processor 1092B which electronically multiplies together, either as an analog or digital process, preferably a digital process, heterodyne signals $s_2$ and $s_{f2}$ to create a superheterodyne signal $S_{2\times f2}$ having the mathematical form $$S_{2\times f2}=s_2 s_{f2}. \quad (14)$$

The superheterodyne signal $S_{2\times f2}$ also comprises two sidebands with a suppressed carrier and may be rewritten as $$S_{2\times f2}=S_{2\times f2}^{+}+S_{2\times f2}^{-} \quad (15)$$

where $$S_{2\times f2}^{+}=\tfrac{1}{2}A_2 A_{f2}\cos(2\pi v_2 t+\theta_{2\times f2}) \quad (16)$$

$$S_{2\times f2}^{-}=\tfrac{1}{2}A_2 A_{f2}\cos(2\pi F t+\Phi_{2\times f2}) \quad (17)$$

$$v_2=(2f_2-f_0), \quad (18)$$

$$\theta_{2\times f2}=(\phi_2+\phi_{f2}) \quad (19)$$

$$\Phi_{2\times f2}=(\phi_2-\phi_{f2}) \quad (20)$$

The superheterodyne signal $S_{2\times f2}$ therefore comprises two sidebands, $S_{2\times f2}^{+}$ and $S_{2\times f2}^{-}$, of equal amplitude, one sideband with frequency $v_2$ and phase $\theta_{2\times f2}$ and a second sideband with frequency $F$ and phase $\Phi_{2\times f2}$.

In a next step, the sidebands $S_{2\times f2}^{+}$ and $S_{2\times f2}^{-}$ are separated by electronic processor 1093B through high pass and low pass filtering or any of the like techniques for separating two signals that are separated in frequency. As noted in the discussion of electronic processor 1093A, the frequency $F$ of the lower frequency sideband $S_{2\times f2}^{-}$ can be very much smaller than the frequency $v_2$ of the higher frequency sideband $S_{2\times f2}^{+}$, considerably simplifying the separating task of processor 1093B. Electronic processor 109 further comprises processor 1094B to determine the phase $\Phi_{2\times f2}$ using time-based phase detection such as a digital Hilbert transform phase detector (see Best ibid.) or the like and the reference signal $s_0$.

Subsequently, the phase $\Phi_{1\times f1}$ and $\Phi_{2\times f2}$ are multiplied by $l_1$ and $l_2$, respectively, in electronic processors 1095A and 1095B, respectively. Next, phases $(l_1/p)\Phi_{1\times f1}$ and $(l_2/p)\Phi_{2\times f2}$ are added together in electronic processor 1096A and subtracted one from the other in electronic processor 1097A, by analog or digital processes, preferably a digital process, the phases $\theta_{1G}$ and $\Phi_{1G}$, respectively, the subscript 1G of $\theta_{1G}$ and $\Phi_G$ denoting phases obtained with an embodiment belonging to the first group of embodiments. Formally $$\vartheta_{1G}=\left(\frac{l_1}{p}\Phi_{1\times f1}+\frac{l_2}{p}\Phi_{2\times f2}\right) \quad (21)$$

$$\Phi_{1G}=\left(\frac{l_1}{p}\Phi_{1\times f1}-\frac{l_2}{p}\Phi_{2\times f2}\right) \quad (22)$$

Note from Eqs. (21) and (22) that $\theta_{1G}$ and $\Phi_{1G}$ are not sensitive to tilts of either reflecting surfaces 95 or 96 of measurement cell 90 and are insensitive to thermal and mechanical disturbances that may occur in interferometer beam splitting cubes and associated optical components as a consequence of the use of differential plane mirror interferometers.

For a measuring path 97 comprised of a vacuum, phase $\Phi_{1G}$ should be a constant substantially independent of Doppler shifts due to motion of one or both mirrors in measurement cell 90, that motion which changes the mirror separation. This may not be the case in practice due to differences in group delays experienced by the electrical signals $s_1$ and $s_2$. Group delay, often called envelope delay, describes the delay of a packet of frequencies and the group delay at a particular frequency is defined as the negative of the slope of the phase curve at the particular frequency [see H. J. Blinchikoff and A. I. Zverev, *Filtering in the Time and Frequency Domains*, Section 2.6, 1976 (Wiley, New York)]. If phase $\Phi_{1G}$ is not a constant for a measuring path comprised of a vacuum, techniques known to those skilled in the art can be used to compensate for such departures of phase $\Phi_{1G}$ from the constant (cf. Blinchikoff and Zverev, ibid.). Compensation for a particular group delay can generally be introduced before or after, or in part before and in part after, the processing elements producing the particular group delay.

It is important to note that the group delay effects in $\Phi_{1G}$ can not only be detected but can also be determined by measuring $\Phi_{1G}$ as a function of different translational velocities of mirror 92 arranged to be moveable wherein the measuring path comprises a vacuum. It is also important to note that the group delay effects in $\Phi_{1G}$ can be significantly reduced by performing analog-to-digital conversion of signals $s_1$ and $s_2$ as close as practical to the photoelectric detectors in detectors 85 and 86, respectively, followed by digital signal processing as opposed to transmitting the signals $s_1$ and $s_2$ as analog signals for subsequent analog signal processing and/or analog-to-digital conversion downstream.

Reference signals, alternatives to reference signals 101 and 102, may also be generated by an optical pick-off means and detectors (not shown in figures) by splitting off portions of beams 9 and 10 with beam splitters, preferably nonpolarizing beam splitters, mixing the split off portion of beam 9 and the split off portion of beam 10, and detecting the mixed portions to produce heterodyne reference signals.

The reciprocal dispersive power $\Gamma$ of the gas defined as $$\Gamma \equiv \frac{n_1 - 1}{n_2 - n_1} \quad (23)$$

can be expressed in terms of other quantities by the formulae $$(n_1 - 1) = \frac{1}{(\chi + K)L_G}\left(\frac{l_1}{p}\right)[\Phi_{1\times II} - (\zeta_1 - \varphi_{II})] - \frac{(L_G - L_V)}{L_G} \quad (24)$$

$$(n_2 - n_1)_{1G} = \frac{1}{\chi L_G[1 - (K/\chi)^2]}\{[\vartheta_{1G}(K/\chi) - \Phi_{1G}] - [\xi(K/\chi) - Z]\} \quad (25)$$

where $L_G$ and $L_V$ are the average of the physical path lengths in measurement path 97 and reference path 98, respectively, $$\chi = (l_1 k_1 + l_2 k_2)/2 \quad (26)$$

$$K = (l_1 k_1 - l_2 k_2)/2 \quad (27)$$

$$\xi = \left[\frac{l_1}{p}(\zeta_1 - \varphi_{II}) + \frac{l_2}{p}(\zeta_2 - \varphi_{I2})\right] \quad (28)$$

$$Z = \left[\frac{l_1}{p}(\zeta_1 - \varphi_{II}) + \frac{l_2}{p}(\zeta_2 - \varphi_{I2})\right] \quad (29)$$

The ratio $(\lambda_1/\lambda_2)$ can be expressed from Eqs. (26) and (27) in terms of $K/\chi$ with the result $$\frac{\lambda_1}{\lambda_2} = \left(\frac{l_1}{l_2}\right)\left[\frac{1 - (K/\chi)}{1 + (K/\chi)}\right] \quad (30)$$

When operating under the condition $$|K/\chi| \ll \frac{1}{2\Gamma + 1} \quad (31)$$

the ratio of the phases $\Phi_{1G}$ and $\theta_{1G}$ has the approximate value $$(\Phi_{1G}/\vartheta_{1G}) \cong -\frac{1}{2\Gamma + 1}. \quad (32)$$

Therefore, for the case where the ratio $(\lambda_1/\lambda_2)$ is the same as the known ratio $(l_1/l_2)$ to a relative precision of an order of magnitude or more less than the half the dispersive power of the gas, $1/(2\Gamma)$, times the relative precision $\epsilon$ desired for the measurement of the reciprocal dispersive power $\Gamma$, Eq. (24) reduces to the more simple form $$(n_2 - n_1)_{1G} = \frac{1}{\chi L_G}(-\Phi_{1G} + Z). \quad (33)$$

Note that only the difference of the lengths $L_G$ and $L_V$, $(L_G - L_V)$, enter as a factor in a correction term in the computation of $\Gamma$, the factor $(1/L_G)$ being common to both $(n_1 - 1)$ and $(n^2 - n_1)_{1G}$. The quantity $(L_G - L_V)$ can be made less than the magnitude of the wavelengths $\lambda_1$ and $\lambda_2$ as a consequence of the design of and use of differential plane mirror interferometers and the design of the measurement cell 90. Thus the quantities $L_G$ and $L_V$ need not be explicitly measured for the computation of F but only the difference $(L_G - L_V)$ is required to a precision relative to $L_G$ of the order of $\epsilon(n_1 - 1)$. Also note the wavenumber $\chi$ enters into the computation of $\Gamma$ only as a factor in the correction term $\chi(L_G - L_V)$, a correction term wherein $\chi(L_G - L_V) \ll (l_1/p)\Phi_{1\times}n$ as a result of $L_G$ and $L_V$ being substantially equal. Thus the relative precision required for quantity $\chi$ in the computation of $\Gamma$ is of the order of $\epsilon(n_1 - 1)L_G/(L_G - L_V)$, a quantity which generally is substantially larger than the relative precision obtained for $\Gamma$.

Eq. (33) is the equation used in the first embodiment to compute the reciprocal dispersive power $\Gamma$. The condition on the wavelengths $\lambda_1$ and $\lambda_2$ which leads to Eq. (33) from Eq. (25) expressed as an equation is $$\left|\frac{\lambda_2}{\lambda_1} - \frac{l_2}{l_1}\right| \ll \left(\frac{l_2}{l_1}\right)\left(\frac{\varepsilon}{\Gamma}\right) \quad (34)$$

There is a case of special interest that occurs when the ratio $(l_1/l_2)$ is expressible as the ratio of low order non-zero integers, i.e.

$$l_1 = p_1, l_2 = p_2, \left(\frac{l_1}{l_2}\right) = \left(\frac{p_1}{p_2}\right), p_1, p_2 = 1, 2, \ldots, p_1 \neq p_2 \quad (35)$$

which corresponds to the wavelengths $\lambda_1$ and $\lambda_2$ being approximately harmonically related. For this case, there exist the possibility for having the sources 1 and 2 phase locked. Eq. (34) is actually a weak condition when viewed in terms of a phase-locked requirement for sources 1 and 2. Consider for an example a desired precision of $\epsilon \approx 3 \times 10^{-6}$ for the reciprocal dispersive power, corresponding to a relative distance measuring precision of approximately $1 \times 10^{-9}$ in a distance measuring interferometer, $(n_1 - 1) \approx 3 \times 10^{-4}$, and $(n_2 - n_1) \approx 1 \times 10^{-5}$. For the example, the condition expressed by Eq. (34) written in terms of source frequencies $v_1$ and $v_2$ instead of wavelengths $\lambda_1$ and $\lambda_2$, respectively, is $$\left| v_2 - \frac{p_1}{p_2} v_1 \right| \leq 10^{-7} v_2. \quad (36)$$

For source wavelengths in the visible part of the spectrum, Eq. (36) translates into a condition $$\left| v_2 - \frac{p_1}{p_2} v_1 \right| \leq 100 \text{MHz} \quad (37)$$

The result expressed in Eq. (37) is clearly a significantly less restrictive condition on the frequencies of sources 1 and 2 than a phase-locked condition.

In a next step, electronic processing means 109 transmits to the computer 110 $\Phi_{1 \times \Pi}$ and $\Phi_{1G}$ as electronic signal 105 in either digital or analog format for the computation of $\Gamma$ according to Eqs. (23), (24), and (33) substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The computation of $\Gamma$ using Eqs. (24) and (33) may require resolution of the phase redundancy in $\Phi_{1 \times \Pi}$ and $(1/l_1)\Phi_{1G}$ to a given level determined by the required relative precision in a determination of $\Gamma$. In the first embodiment, the equivalent wavelengths comprising $\Phi_{1 \times \Pi}$ and $(1/l_1)\Phi_{1G}$ are significantly larger than either of the wavelengths $\lambda_1$ and $\lambda_2$ and as a consequence, produces a significant simplification in a procedure implemented for resolution of phase redundancy in $\Phi_{x\Pi}$ and $(1/l_1)\Phi_{1G}$. The equivalent wavelengths $\lambda_{\Phi_{1 \times \Pi}}$ and $\lambda_{(1/l_1)\Phi_{1G}}$ for $\Phi_{1 \times \Pi}$ and $(1/l_1)\Phi_{1G}$, respectively, are $$\lambda_{\Phi_{1 \times \Pi}} = \frac{\lambda_1}{p(n_1 - 1)}, \quad (38)$$

$$\lambda_{(1/l_1)\Phi_{1G}} = \frac{\lambda_1}{(n_2 - n_1)}. \quad (39)$$

For the example of $\lambda_1 = 0.633 \, \mu\text{m}$, $(n_1 - 1) \approx 3 \times 10^{-4}$, and $(n_2 - n_1) \approx 1 \times 10^{-5}$, the equivalent wavelengths given by Eqs. (38) and (39) are $$\lambda_{\Phi_{1 \times \Pi}} \cong \left(\frac{2}{p}\right) \text{mm} \quad (40)$$

$$\lambda_{(1/l_1)\Phi_{1G}} \cong 63 \text{ mm}. \quad (41)$$

Any one of several procedures may be easily employed to resolve the phase redundancy in $\Phi_{1 \times \Pi}$ and $(1/l_1)\Phi_{1G}$, given their equivalent wavelengths as expressed by Eqs. (38) and (39). One procedure which may be employed to resolve the phase redundancy in $\Phi_{1 \times \Pi}$ is based on the use of a series of measurement cells where the physical lengths, not the round trip physical lengths, for the measuring and reference paths of the series of measurement cells form a geometric progression. The smallest or first physical length in the series will be approximately $(\lambda_{\Phi_{1 \times \Pi}}/8)$ divided by the relative precision that the initial value of $\Phi_{1 \times \Pi}$ is known. The physical length of the second measurement cell in the series will be approximately the length of the first measurement cell divided by the relative precision that $\Phi_{1 \times \Pi}$ is measured using the first measurement cell. This is a geometric progression procedure, the resulting physical lengths forming a geometric progression, which is continued until the length of the measurement cell used to measure $\Gamma$ would be exceeded if the number of measurement cells in the series were incremented by one. For a value of $10^{-3}$ as the initial value for the known relative precision of $\Phi_{1 \times \Pi}$ and $p=2$, a typical physical length for the first measurement cell in the series is of the order of 10 cm and a typical physical length for the second measurement cell in the series is of the order of 10 m. The phase redundancy in $(1/l_1)\Phi_{1G}$ is resolved using the same series of measuring cells as used to resolve the phase redundancy in $\Phi_{1 \times \Pi}$ since $\lambda_{\Phi_{1 \times \Pi}} < \lambda_{(1/l_1)\Phi_{1G}}$.

A second procedure is based upon the use of a source (not shown in FIGS. 1a–1f) of a series of known wavelengths and measuring $\Phi_{1 \times \Pi}$ and $(1/l_1)\Phi_{1G}$ for these wavelengths. The number of known wavelengths required for the resolution of the phase redundancy is generally comprised of a small set as a direct consequence of the relatively large equivalent wavelengths as expressed by Eqs. (38) and (39).

Another procedure to resolve the phase redundancy in $\Phi_{1 \times \Pi}$ and $(1/l_1)\Phi_{1G}$ would be to observe the changes in $\Phi_{1 \times \Pi}$ and $(1/l_1)\Phi_{1G}$ as the reference path 98 is changed from gas as present in the measuring path 97 to an evacuated state (the vacuum pump and requisite gas handling system are not shown in FIGS. 1a–1e) to resolve the phase redundancy in $\Phi_{1 \times \Pi}$ and $(1/l_1)\Phi_{1G}$. The problems normally encountered in measuring absolute values for refractivity and dispersion of refractivity based in part on changing the gas pressure from a non-zero value to a vacuum are not present in the first preferred embodiment because of the relatively large equivalent wavelengths as expressed by Eqs. (38) and (39).

The offset terms involving $(\zeta_1 - \phi_{l1})$ and Z that are present in Eq. (33) and defined in Eqs. (2), (5), and (29) are terms that may require determination and monitoring to a given level of precision determined by the required relative precision in a determination of $\Gamma$ and $\chi$ if $\chi$ is variable in time, the relative precision required for $\chi$ being also determined in part by the magnitude of $(L_G - L_V)$. One procedure for the determination of $(\zeta_1 - \phi_{l1})$ and Z is based on replacement of measurement cell 90 with a single mirror R91 (not shown in FIGS. 1d and 1e) having a surface R93 corresponding to surface 93 of mirror 91 coated so as be a reflecting surface for wavelength $\lambda_1$ and having a second surface R95 corresponding to surface 95 of mirror 91 coated so as be a reflecting surface for wavelength $\lambda_2$ and measuring the resulting values of $\Phi_{1 \times \Pi}$ and $\Phi_{1G}$. Let the resulting values of $\Phi_{1\times I1}$ and $\Phi_{1G}$ be $(\Phi_{1\times I1})_R$ and $(\Phi_{1G})_S$, respectively. The quantities $(\zeta_1-\phi_{I1})$ and Z are related to $(\Phi_{1\times I1})_R$ and $(\Phi_{1G})_R$, respectively, cf. Eqs. (2), (13), and (25), by the formulae $$(\zeta_1-\phi_{I1})=(\Phi_{1\times I1})_R \quad (42)$$

$$Z=(\Phi_{1G})_R \quad (43)$$

The non-electronic contributions to $(\zeta_1-\phi_{I1})$ and Z should be substantially constant in time because of the significant level of compensation that takes place in the differential plane mirror interferometer 69, the differential plane mirror interferometer group 70, and measurement cell 90. The electronic contributions to $\zeta_1$ and Z may be monitored by purely electronic means (not shown).

A second reciprocal dispersive power, $\Gamma_2$, may also be defined for the gas where $$\Gamma_2 \equiv \frac{(n_2-1)}{(n_2-n_1)} \quad (44)$$

However, $\Gamma_2$ can be obtained directly from $\Gamma$ since $$\Gamma_2 = \Gamma + 1. \quad (45)$$

Therefore, the description of first preferred embodiment with regard to $\Gamma_2$ is substantially the same as the description of first preferred embodiment with regard to $\Gamma$.

The intrinsic property of a gas represented by $\Gamma$ may be obtained and subsequently used downstream in another form such as the ratio $(n_1-1)/(n_2-1)$. The ratio $(n_1-1)/(n_2-1)$ can be written in terms of measured quantities by the formula $$\frac{(n_1-1)}{(n_2-1)} = \quad (46)$$

$$\left\{\frac{l_1[\Phi_{1\times I1}-(\zeta_1-\varphi_{I1})]-p\chi(L_G-L_V)[1+(K/\chi)]}{l_2[\Phi_{2\times I2}-(\zeta_2-\varphi_{I2})]-p\chi(L_G-L_V)[1-(K/\chi)]}\right\} \times \left[\frac{1-(K/\chi)}{1+(K/\chi)}\right].$$

The ratio $(n_1-1)/(n_2-2)$ can also be expressed in terms of $\Gamma$ or $\Gamma$ and $\Gamma_2$ by the equations $$\frac{(n_1-1)}{(n_2-1)} = \frac{\Gamma}{\Gamma_2} = \frac{\Gamma}{\Gamma+1}. \quad (47)$$

As a consequence of Eq. (47), the description of the first embodiment with regard to measuring and monitoring the ratio $(n_1-1)/(n_2-1)$ is substantially the same as the description of first preferred embodiment with regard to $\Gamma$ and $\Gamma_2$.

For those applications requiring measurement of the relative dispersion $(n_i-n_j)/(n_r-n_s)$, it will be apparent to those skilled in the art that the relative dispersion can be determined using Eq. (33) for the determination of both the numerator and denominator of the relative dispersion. In the relative dispersion, $i \neq j$, $r \neq s$, and at least i or j are different from either r or s.

It will be appreciated by those skilled in the art that a reciprocal dispersive power $\Gamma_3$ can also be defined in terms of indices of refraction at three different wavelengths, $\lambda_1, \lambda_2$, and $\lambda_3$, according to the formula $$\Gamma_3 = \frac{(n_3-1)}{(n_2-n_1)} \quad (48)$$

where $n_3$ is the index of refraction at $\lambda_3$ without departing from the spirit and scope of the invention.

It will be further appreciated by those skilled in the art that phases $\phi_1$ and $\phi_2$ may be directly measured with analog or digital techniques to relative precisions sufficient to meet the required precision imposed on the output data by the final end use application output. With direct phase measurement, superheterodyne receiver techniques may be omitted in the first embodiment, and subsequent embodiments as noted, without departing from the scope and spirit of the first embodiment.

The beams 129 and 130 are shown in FIG. 1a as being detected in two different detectors, detectors 85 and 86, respectively. It will be appreciated by those skilled in the art that the beams 129 and 130 can be detected by a single detector with the appropriate modification of the signal processor 109. The use of a single detector generally will produce reduced group delay differences compared to the group delay differences arising when using two separate detectors.

It will be also appreciated by those skilled in the art that data processing steps comprised of multiplications performed by processors 1095A and 1095B for the first embodiment may instead be comprised of divisions wherein a multiplication by $l_1$ is replaced by a division by $l_2$ and vice versa without departing from the spirit and scope of the first embodiment of the present invention.

The description of the first embodiment noted that the configuration of interferometers illustrated in FIGS. 1a–1e are known in the art as differential plane mirror interferometers. Other forms of the differential plane mirror interferometer and forms of other interferometers such as the plane mirror interferometer or the angle-compensating interferometer or similar device such as is described in an article entitled "Differential interferometer arrangements for distance and angle measurements: Principles, advantages and applications" by C. Zanoni, *VDI Berichte Nr.* 749, 93–106 (1989), may be incorporated into the apparatus of the first embodiment of the present invention without departing from the spirit or scope of the present invention.

FIG. 1b depicts in schematic form one embodiment of the differential plane mirror interferometer 69 shown in FIG. 1a. It operates in the following way: beam 11 is incident on beam splitter 55A, preferably a polarizing beam splitter, with a portion of beam 11 being transmitted as beam 13. A second portion of beam 11 is reflected by beam splitter 55A, subsequently reflected by mirror 55B, and then transmitted by half-wave phase retardation plate 79A as beam 113, the half-wave phase retardation plate 79A rotating the plane of polarization of the reflected portion of beam 11 by 90°. Beams 13 and 113 have the same polarizations but still have different frequencies. Beam 13 and beams for which beam 13 is the sole progenitor are indicated in FIGS. 1b and 1d by dashed lines and beam 113 and beams for which beam 113 is the sole progenitor are indicated in FIGS. 1b and 1d by dotted lines. The function of beam splitter 55A and mirror 55B is to spatially separate the two frequency components of beam 11 using conventional polarization techniques.

Beams 13 and 113 enter polarizing beam splitter 71, which has a polarizing coating 73, and are transmitted as beams 15 and 115, respectively. Beams 15 and 115 pass through quarter-wave phase retardation plate 77 and are converted into circularly polarized beams 17 and 117, respectively. Beams 17 and 117 are reflected back on themselves by mirrors within measurement cell 90, pass back through quarter-wave retardation plate 77, and are converted back into linearly polarized beams that are orthogonally polarized to the original incident beams 15 and 115. These beams are reflected by polarizing coating 73 to become beams 19 and 119, respectively. Beams 19 and 119 are reflected by retroreflector 75 to become beams 21 and 121, respectively. Beams 21 and 121 are reflected by polarizing coating 73 to become beams 23 and 123, respectively. Beams 23 and 123 pass through quarter-wave phase retardation plate 77 and are converted into circularly polarized beams 25 and 125, respectively. Beams 25 and 125 are reflected back on themselves by mirrors within measurement cell 90, pass back through quarter-wave retardation plate 77, and are converted back into linearly polarized beams the same as the original incident beams 15 and 115. These beams are transmitted by coating 73 to become beams 27 and 127, respectively. Beams 27 and 127 contain information at wavelength $\lambda_1$ about the optical path lengths through the gas whose reciprocal dispersive power $\Gamma$ is to be determined and about the optical path lengths through a vacuum, respectively.

Beam 27 is reflected by mirror 63B, and then a portion reflected by beam splitter 63A, preferably a nonpolarizing type, as a first component of beam 129. Beam 127 is incident on beam splitter 63A with a portion of beam 127 being transmitted as a second component of beam 129, the first and second components of beam 129 having the same linear polarizations but still having different frequencies.

FIG. 1c depicts in schematic form one embodiment of differential plane mirror interferometer 70 shown in FIG. 1a. It operates in the following way: beam 12 is incident on beam splitter 56A, preferably a polarizing beam splitter, with a portion of beam 12 being transmitted as beam 14. A second portion of beam 12 is reflected by beam splitter 56A, subsequently reflected by mirror 56B, and then transmitted by half-wave phase retardation plate 80A as beam 114, the half-wave phase retardation plate 80 rotating the plane of polarization of the reflected portion of beam 12 by 90°. Beams 14 and 114 have the same polarizations but still have different frequencies. Beam 14 and beams for which beam 14 is the sole progenitor are indicated in FIGS. 1c and 1e by dashed lines and beam 114 and beams for which beam 114 is the sole progenitor are indicated in FIGS. 1c and 1e by dotted lines. The function, in part, of beam splitter 56A and mirror 56B is to spatially separate the frequency components of beam 12 using conventional polarization techniques.

Beams 14 and 114 enter polarizing beam splitter 72, which has a polarizing coating 74, and are transmitted as beams 16 and 116, respectively. Beams 16 and 116 pass through quarter-wave phase retardation plate 78 and are converted into circularly polarized beams 18 and 118, respectively. Beams 18 and 118 are reflected back on themselves by mirrors within measurement cell 90, pass back through quarter-wave retardation plate 78, and are converted back into linearly polarized beams that are orthogonally polarized to the original incident beams 16 and 116. These beams are reflected by polarizing coating 74 to become beams 20 and 120, respectively. Beams 20 and 120 are reflected by retroreflector 76 to become beams 22 and 122, respectively. Beams 22 and 122 are reflected by polarizing coating 74 to become beams 24 and 124, respectively. Beams 24 and 124 pass through quarter-wave phase retardation plate 78 and are converted into circularly polarized beams 26 and 126, respectively. Beams 26 and 126 are reflected back on themselves by mirrors within measurement cell 90, pass back through quarter-wave retardation plate 78, and are converted back into linearly polarized beams the same as the original incident beams 16 and 116. These beams are transmitted by coating 74 to become beams 28 and 128, respectively. Beams 28 and 128 contain information at wavelength 2 about the optical path lengths through the gas whose reciprocal dispersive power r is to be determined and about the optical path lengths through a vacuum, respectively.

Beam 28 is reflected by mirror 64B, and then a portion reflected by beam splitter 64A, preferably a nonpolarizing type, as a first component of beam 130. Beam 128 is incident on beam splitter 64A with a portion of beam 128 being transmitted as a second component of beam 130, the first and second components of beam 130 having the same linear polarizations but still having different frequencies.

Reference is now made to FIGS. 1a–1e and 1g which taken together depict in diagrammatic form a variant of the first preferred embodiment of the present invention for measuring intrinsic optical properties of a gas, particularly its reciprocal dispersive power where the end use application substantially does not effect the choice of the particular manner in which the intrinsic optical properties of the gas are determined and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to a special case of the first embodiment in which the ratio $(l_1/l_2)$ is expressible as the ratio of low order non-zero integers $(p_1/p_2)$, cf. Eq. (35). The description of the sources of light beams 9 and 10 and of light beams 9 and 10 for the variant of the first embodiment is the same as that for description of the sources of light beams 9 and 10 and of light beams 9 and 10 given for the first embodiment with the additional requirement that the wavelengths be harmonically related to a relative precision sufficient to meet the required precision imposed on the output data by the final end use application. The description of the apparatus for the variant of the first embodiment is the same as corresponding portions of the description given for the first embodiment.

Figure 1G:
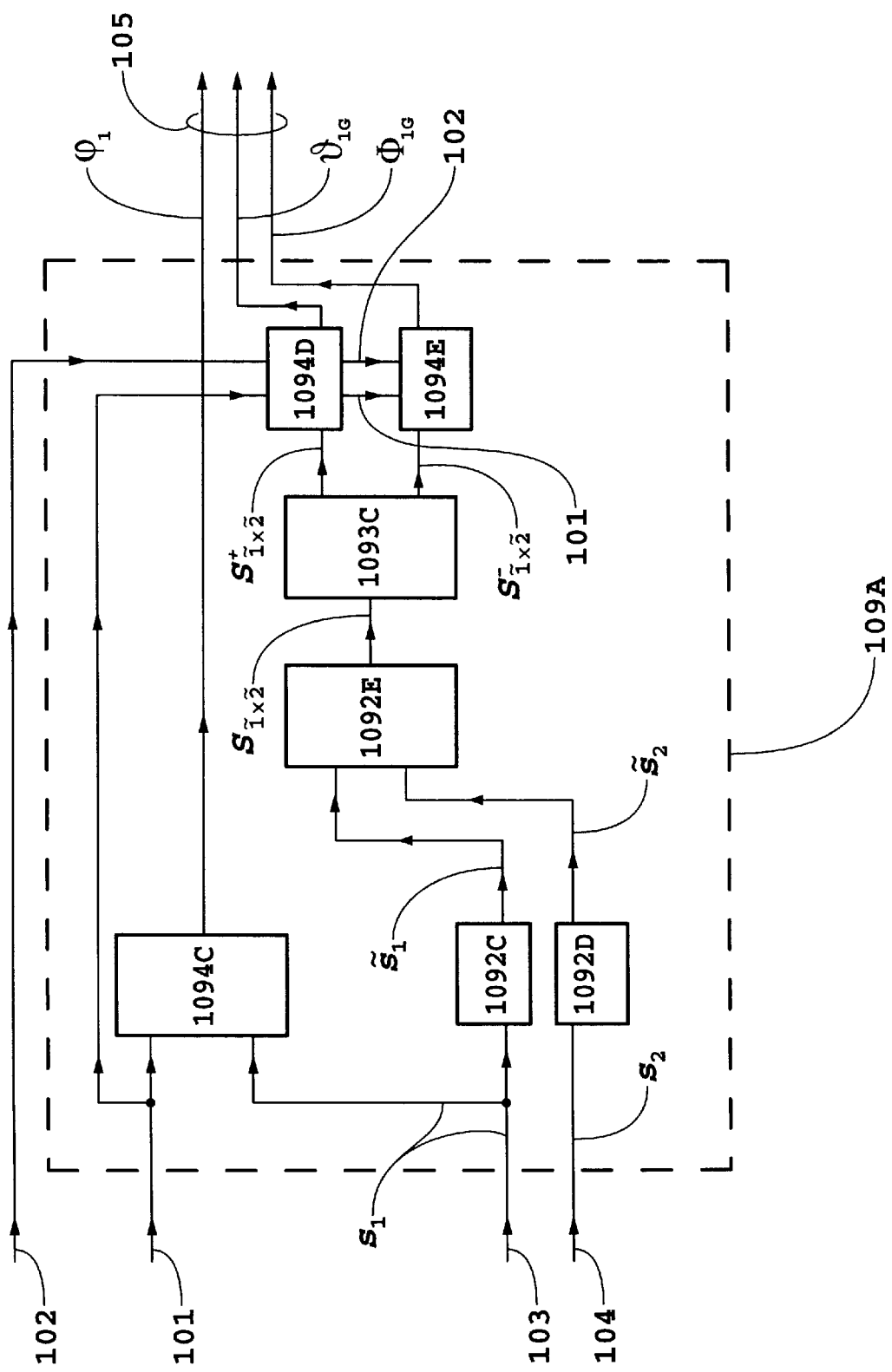

The dispersion information contained in phases $\phi_1$ and $\phi_2$ is obtained in the variant of the first embodiment preferably through the creation of a superheterodyne signal wherein the frequency of the superheterodyne signal is at a frequency much lower than $f_1$ and $f_2$ where it is generally possible to make more accurate phase measurements. Referring to FIG. 1g and in accordance with the preferred method of the variant of the first embodiment, electronic processing means 109A preferably comprises means, mixers 1092C and 1092D, for electronically multiplying time-dependent arguments $\alpha_1(t)$ and $\alpha_2(t)$ of heterodyne signals $s_1$ and $s_2$, respectively, by coefficients $p_1$ and $p_2$, respectively, so as to create two modified heterodyne signals $\underline{s}_1$ and $\underline{s}_2$ having the form $$\underline{s}_j = A_j \cos[p_j \alpha_j(t)], \quad j=1,2. \tag{49}$$

The multiplication may be achieved by any one of the conventional frequency multiplying techniques commonly known in the art, such as signal squaring followed by electronic filtering, preferably by a digital process.

Referring again to FIG. 1g, electronic processing means 109A preferably comprises means mixer 1092E for electronically multiplying together, either as an analog or digital process, preferably a digital process, modified heterodyne signals $\underline{s}_1$ and $\underline{s}_2$ to create a superheterodyne signal $S_1 \times 2$ having the mathematical form $$S_x = \underline{s}_1 \underline{s}_2 \tag{50}$$

The superheterodyne signal $S_1 \times 2$ is comprised of two sidebands with a suppressed carrier and may be rewritten as $$S_x = S_x^+ + S_x^- \tag{51}$$

where $$S_x^+ = \tfrac{1}{2} l_{12} \cos(2\pi t + g\nu_{1G}) \tag{52}$$

$$S_x^- = \tfrac{1}{2} l_{12} \cos(2\pi t + gF_{1G}) \tag{53}$$

$$\nu = (p_1 f_1 + p_2 f_2) \tag{54}$$

$$\theta_{1G} = (p_1 \phi_1 + p_2 \phi_2) \tag{55}$$

$$F = (p_1 f_1 - p_2 f_2) \tag{56}$$

$$\Phi_{1G} = (p_1 \phi_1 - p_2 \phi_2) \tag{57}$$

The superheterodyne signal $S_1 \times 2$ is therefore comprised of two sidebands, $S_1 \times 2^+$ and $S_1 \times 2^-$, of equal amplitude, one sideband with frequency $\nu$ and phase $\theta_{1G}$ and a second sideband with frequency $F$ and phase $\Phi_{1G}$. 25 Electronic processor 109A further comprises processor 1094D to determine phase $\theta_{1G}$ and electronic processor 1094E to determined phase $\Phi_{1G}$ both using time-based phase detection such as a digital Hilbert transform phase detector (see Best ibid.) or the like and the reference signals 101 and 102. Electronic processor 109A further comprises electronic processor 1094C for determination of $\phi_1$ by phase sensitive detection with reference signal 101 or like technique for determination of the phases of a heterodyne signal. In a next step, $\phi_1$, $\theta_{1G}$, and $\Phi_{1G}$ are transmitted, either in analog or digital format, to computer 110 for the calculation of the Γ wherein the phase offsets $\xi$ and $Z$ are defined as $$\xi = (p_1 \zeta_1 + p_2 \zeta_2) \tag{58}$$

$$Z = (p_1 \zeta_1 - p_2 \zeta_2) \tag{59}$$

Note that phases $\phi_1$, $p\theta_{1G}$, and $p\Phi_{1G}$ phase offsets $p\xi$ and $pZ$ are formally equivalent to $\Phi_{1 \times 1R}$, $\theta_{1G}$, $\Phi_{1G}$, $\xi$, and $Z$, respectively, of the first embodiment with $\phi_{f1}$ and $\phi_{f2}$ equal to zero, $l_1 = p_1$, and $l_2 = p_2$. Therefore, the remaining description of the variant of the first embodiment is the same as corresponding portions of the description given for the first embodiment.

The principal advantage of the variant of the first embodiment lies in a simplified electronic processing in relation to that of the first embodiment although at the risk of possibly enhancing frequency sensitive phase offset errors due to differences in group delays experienced by heterodyne and/ or modified heterodyne signals having significantly different frequencies. The discussion of the effects of group delay for the variant of the first embodiment is the same as corresponding portions of the description given for the first embodiment.

It will be appreciated by those skilled in the art that alternative data processing may be considered for the variant of the first preferred embodiment without departing from the spirit and scope of the present invention. For example, it may prove useful to generate the modified heterodyne signals by electronically dividing time-dependent arguments $\alpha_1(t)$ and $\alpha_2(t)$ of heterodyne signals $s_1$ and $s_2$, respectively, by coefficients $p_2$ and $p_1$, respectively, so as to create two modified heterodyne signals $\underline{s}_1'$ and $\underline{s}_2'$ having the forms $$\underline{s}_1' = A_1' \cos[\alpha_1(t)/p_2],$$

$$\underline{s}_2' = A_2' \cos[\alpha_2(t)/p_1] \tag{60}$$

The dividing may be achieved by any one of the conventional frequency dividing techniques commonly known in the art, such as the use of phase-locked loops or generation of a rectangle wave signal which changes sign at every other zero crossing of the signal whose argument is being divided by two. The subsequent description of the variant of the first embodiment based on modified heterodyne signals $\underline{s}_1'$ and $\underline{s}_2'$ is the same as corresponding portions of the description given for the variant of the first embodiment based on modified heterodyne signals $\underline{s}_1$ and $\underline{s}_2$ with the replacements of $p_1$ by $p_2$ and visa versa in the equations.

Another alternative data processing that may be considered for the variant of the first embodiment without departing from the spirit and scope of the present invention is the addition of the modified heterodyne signals $\underline{s}_1$ and $\underline{s}_2$ together, rather than multiplying them as was proposed above, resulting in the expression:

$$S_+ = \underline{s}_1 + \underline{s}_2 \tag{61}$$

A superheterodyne signal would be obtained from $S_1+2$ by conventional techniques commonly known in the art such square law detection or by signal rectification. (cf. Dändliker et al., ibid., and Redman and Wall, ibid..) Further, another alternative signal to $S_1+2$ may be generated by selecting the appropriate term in the binomial expansion of $(s_1+s_2)^{p+q}$ through the use of phase sensitive detection.

Figure 1H:
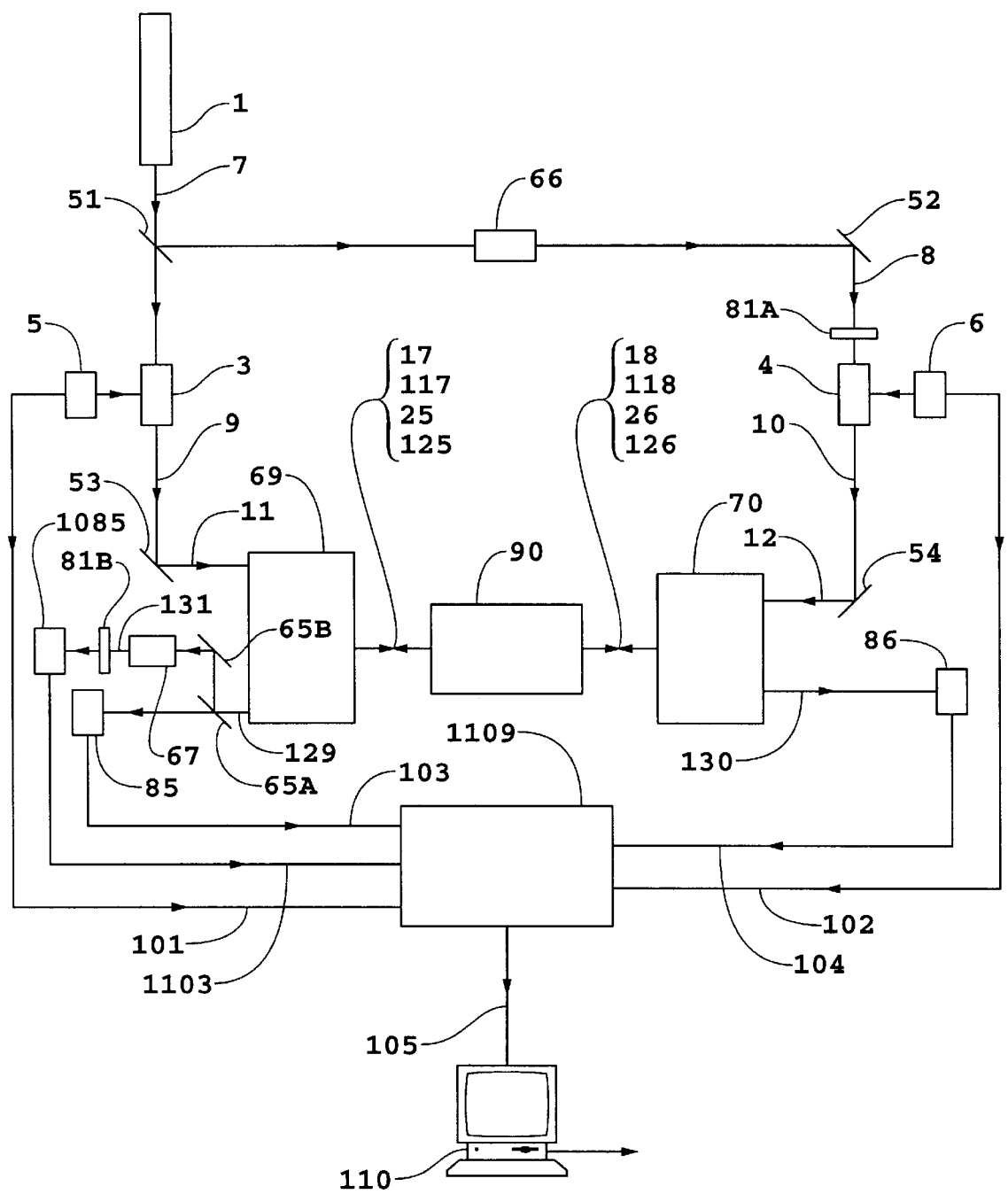
FIG. 1h illustrates, in diagrammatic form, the components, optical paths, and paths of electronic signals of the presently preferred second variant of the first embodiment of the present invention.
Figure 1I:
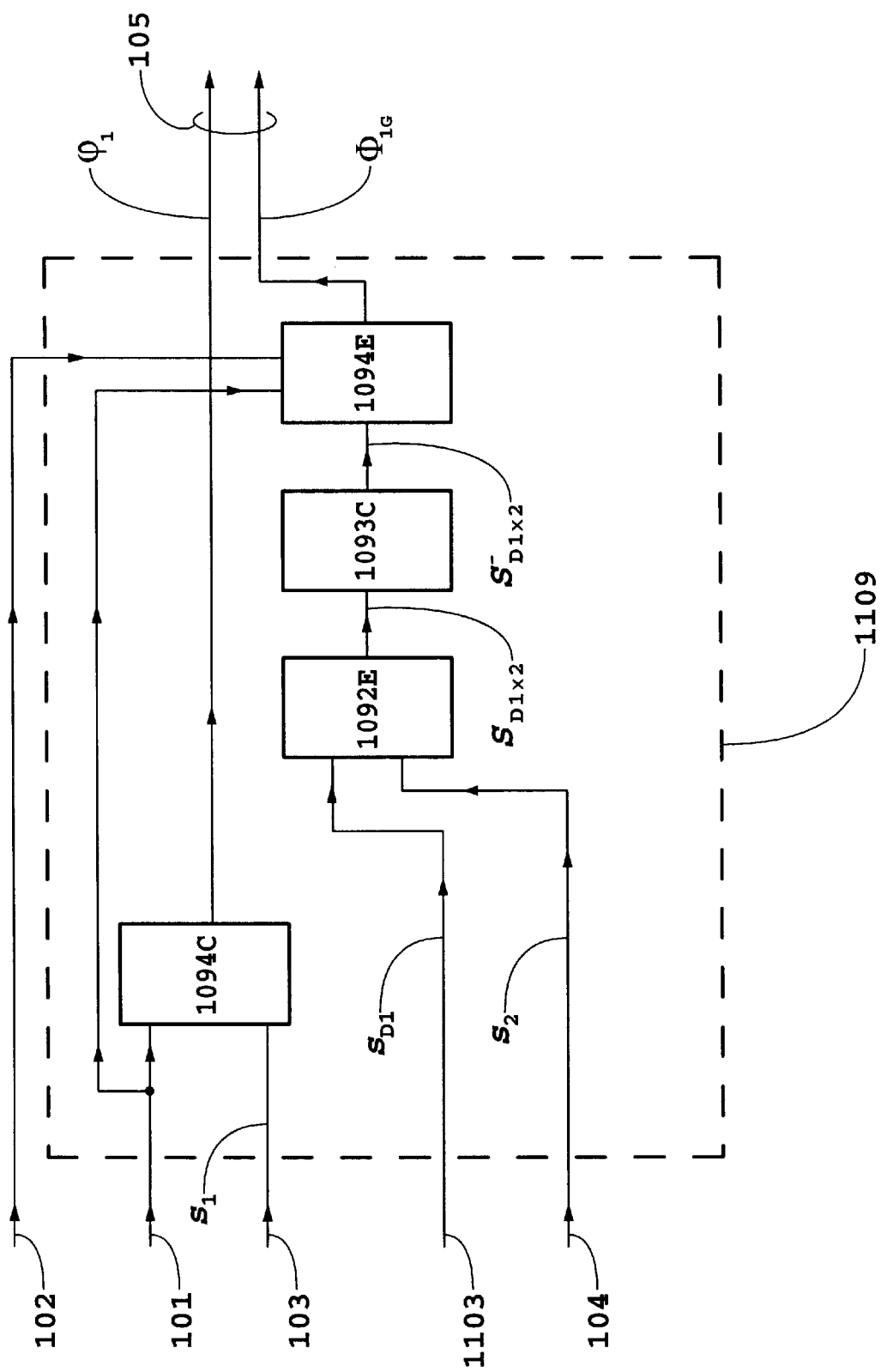
FIG. 1i shows a block diagram of the processing electronics 1109 used in the second variant of the first embodiment of the present invention.

Reference is now made to FIGS. 1h and 1i that depict in diagrammatic form a variant of the first variant of the first preferred embodiment, the second variant of the first preferred embodiment of the present invention, for measuring the reciprocal dispersive power or other intrinsic optical properties of a gas. The primary difference between the second variant of the first embodiment and the first variant of the first embodiment lies principally in the means for generating input light beams and the means for generating heterodyne signals.

The description of the source of light beam 7 and of light beam 7 illustrated in FIG. 1h is the same as the description given for the source of light beam 7 and of light beam 7 of the first variant of the first embodiment. The description of light beam 11 of the second variant of the first embodiment, light beam 11 being derived from a portion of beam 7 transmitted by nonpolarizing beam splitter 51, is the same as the corresponding portion of the description given in the first variant of the first embodiment for light beam 11 derived from beam 7.

As illustrated in FIG. 1h, a second portion of beam 7 is reflected by nonpolarizing beam splitter 51, passes through a nonlinear crystal 66, is reflected by mirror 52, and a portion thereof transmitted by optical filter 81A to form light beam 8. Nonlinear crystal 66, e.g. β-BaB$_2$O$_4$ (BBO), is aligned so as to double the frequency of a portion of the second portion of beam 7 passing through nonlinear crystal 66 by second harmonic generation, SHG. That portion thereof transmitted by optical filter 81A is the frequency doubled portion of the second portion of the beam 7 passing through nonlinear crystal 66. As a consequence, the ratio of the wavelength of beam 7 to the wavelength of beam 8 is 2/1. The description of light beam 12 derived from beam 8 for the second variant of the first embodiment is the same as the corresponding portion of the description given for light beam 12 derived from beam 8 of the first variant of the first embodiment. Alternatively, a nonlinear crystal may be placed in the cavity of a laser used for the source of beam 7 and the second beam corresponding to beam 8 generated by SHG internal to the cavity of the laser.

The description of the propagation of beams 11 and 12 of the second variant of the first embodiment through interferometers 69 and 70, respectively, to form output beams 129 and 130, respectively, is the same as the corresponding portions of the description given for the propagation of beams 11 and 12 of the first variant of the first embodiment through interferometers 69 and 70, respectively, to form output beams 129 and 130, respectively. Differential plane mirror interferometers 69 and 70 with external mirrors furnished by measurement cell 90 comprise interferometric means for introducing a phase shift $\phi_1$ between the x and y components of beam 11 and a phase shift $\phi_2$ between the x and y components of beam 12 where $\phi_1$ and $\phi_2$ are given by equations the same as Eqs. (2) for $\phi_p$ and $\phi_2$ of the first embodiment.

In a next step as shown in FIG. 1*h*, a portion of phase-shifted beam 129 is reflected by nonpolarizing beam splitter 65A, reflected by mirror 65B, and passes through a nonlinear crystal 67 to form light beam 131. Beam 131 is comprised of two pairs of components, one pair of components with frequencies the same as the frequencies of beam 129 and a second pair of components with frequencies twice the frequencies of the components of beam 129. Nonlinear crystal 67, e.g. BBO, is aligned so as to double by SHG the frequencies of a portion of the portion of beam 129 entering nonlinear crystal 67 to form the second pair of components of beam 131. The first pair of components of beam 131 are the remaining portion of the portion of beam 129 entering nonlinear crystal 67 and that is not frequency doubled. Differential plane mirror interferometer 69 with external mirrors furnished by measurement cell 90 and nonlinear crystal 67 comprise interferometric means for introducing a phase shift $\phi_{D1}$ between the x and y components of the second pair of components of beam 131. Phase $\phi_{D1}$ is substantially twice the phase $\phi_1$ of beam 129 and is given by the formula $$\varphi_{DI} = \sum_{i=1}^{i=p} 2k_1(L_{G,i}n_{1i} - L_{V,i}) + \zeta_{DI} \tag{62}$$

where the phase offset $\zeta_{D1}$ comprises all contributions to phase $\phi_{D1}$ not related to the measurement path 97 or reference path 98.

In a subsequent step as depicted in FIG. 1*h*, a second portion of phase-shifted beam 129 is transmitted by nonpolarizing beam splitter 65A and impinges on detector 85, the second pair of components of beam 131 is transmitted by optical filter 81B, the frequencies of the first and second pairs of components of beam 131 being located outside and inside, respectively, the passband of optical filter 81B, to impinge on detector 1085, and phase-shifted beam 130 impinges on detector 86 resulting in three electrical interference signals, heterodyne signals $s_1$, $s_{D1}$, and $s_2$, respectively, preferably by photoelectric detection. Signals $s_1$ and $s_{D1}$ correspond to optical path information at wavelength $\lambda_1$ and signal $s_2$ corresponds to optical path information at wavelength $\lambda_2$.

Signals $s_1$ and $s_2$ have forms the same as the forms $s_1$ and $s_2$, respectively, of the first variant of the first embodiment and $s_{D1}$ has the form $$s_{D1} = A_{D1}(t)\cos[\alpha_{D1}(t)] \tag{63}$$

where $$\alpha_{D1}(t) = 9\pi(2f_1)t + \phi_{D1}. \tag{64}$$

Heterodyne signals $s_1$, $s_{D1}$, and $s_2$ are transmitted to electronic processor 1109 for analysis as electronic signals 103, 1103, and 104, respectively, preferably in digital format.

Referring to FIG. 1*i*, electronic processor 1109 comprises electronic processor 1094C to determine the phase shift $\phi_1$ the same as described for the first embodiment with signal 101 serving as the reference signal in the phase sensitive detection. Electronic processor 1109 further comprises means 1092E for electronically multiplying together, by either an analog or a digital process, heterodyne signals $s_{D1}$ and $s_2$ to create a superheterodyne signal $S_{D1\times 2}$. Superheterodyne signal $S_{D1\times 2}$ has the form $$S_{D1\times 2} = s_{D1}s_2. \tag{65}$$

Superheterodyne signal $S_{D1\times 2}$ is comprised of two sidebands with a suppressed carrier and may be written as $$S_{D1\times 2} = S_{D1\times 2}^+ + S_{D1\times 2}^- \tag{66}$$

where $$S_{D1\times 2}^+ = \frac{1}{2}A_{D1}A_2 \cos(2\pi vt + \theta_{1G}),$$

$$S_{D1\times 2}^- = \frac{1}{2}A_{D1}A_2 \cos(2\pi Ft + \Phi_{1G}), \tag{67}$$

$$v = (2f_1 + f_2), \tag{68}$$

$$\theta_{1G} = (\phi_{D1} + 100\ _2), \tag{69}$$

$$F = (2f_1 - f_2), \tag{70}$$

$$\Phi_{1G} = (\phi_{D1} - \phi_2). \tag{71}$$

In a next step, the phase $\Phi_{1G}$ of Eq. (71) is determined by electronic processor 1094E of electronic processor 1109 using frequency F of Eq. (70) in the phase determination, the description of the process being the same as corresponding portions of the description given for determination of phase $\Phi_{1G}$ of the first variant of the first embodiment.

The equation for the reciprocal dispersive power Γ of the gas defined by Eq. (23) can be expressed in terms of quantities of the second variant of the first embodiment by the formulae $$(n_1 - 1) = \frac{2}{p\chi L_G}(\varphi_1 - \zeta_1) - \frac{(L_G - L_V)}{L_V}, \tag{72}$$

-continued $$(n_2 - n_1)_{1G} = \frac{1}{p\chi L_G}(-\Phi_{1G} + Z), \quad (73)$$

where $$Z = (\zeta_{D1} - \zeta_2), \quad (74)$$

$$\chi = 2k_1, \quad (75)$$

$$K = 0. \quad (76)$$

The remaining description of the second variant of the first embodiment of the present invention is the same as corresponding portions of the description given for the first variant of the first embodiment of the present invention.

Second harmonic generation may be incorporated in other variants of the first variant of the first embodiment, such as in the third variant of the first embodiment subsequently described herein, without departing from the scope and spirit of the present invention. In the third variant of the first embodiment (not shown in a figure), SHG is employed in both the source and heterodyne signal detection scheme. The primary differences between the third and second variants of the first embodiment lie principally in the definition and use of reference and measurement paths in an interferometer and in respective intrinsic properties determined for a gas.

The input beam for the third variant of the first embodiment is comprised of three frequency components, a first low frequency component comprised of a portion of a single frequency laser beam, a second low frequency, frequency-shifted component generated, e.g. by an acousto-optical modulator, from another portion of the single frequency laser beam, and a third high frequency component generated from yet another portion of the single frequency laser beam by SHG. The description of the laser source is the same as the corresponding portion of the description given for the laser source of the second variant of the first embodiment.

The three frequency components are transported as substantially coextensive beam components from the source of the components to the interferometer. At the interferometer, the input beam is divided by a combination of polarizing beam splitters, nonpolarizing beamsplitters, and dichroic beam splitters into three input beams. The first input beam of the three input beams comprises portions of each of the low frequency and the low frequency, frequency-shifted components of the input beam and each of the second and third input beams comprise other portions of each of the low frequency, frequency-shifted component of the input beam and of the high frequency component of the input beam.

A phase shift $\phi_1$ is introduced by the interferometer of the third variant of the first embodiment between the reference and measurement output beams corresponding to the first input beam. The description of introduction and detection of the phase shift $\phi_1$ for the third variant of the first embodiment is the same as corresponding portions of the description given for the description of introduction and detection of the phase shift $\phi_1$ of the second variant of the first embodiment.

A phase $\Phi_{2G}$ is determined for the third variant of the first embodiment, the phase $\Phi_{2G}$ corresponding to the phase $\Phi_{2G}$ subsequently described with respect to the second group of preferred embodiments. The second input beam enters the interferometer and exits the interferometer as an intermediate second output beam wherein the optical path for both frequency components of the second input beam are substantially coextensive in the interferometer and over a measurement path comprising the gas. The third input beam enters the interferometer and exits the interferometer as an intermediate third output beam wherein the optical path for both frequency components of the third input beam are substantially coextensive in the interferometer and over a measurement path comprising a vacuum path. The physical length of the path of the second input beam in the gas is nominally the same as the physical length of the path of the third input beam in the vacuum. The optical paths for the second and third input beams in the interferometer are substantially the same except for the respective portions of paths in the gas and the vacuum.

In a next step, the intermediate second and third output beams are each passed through a nonlinear crystal to form the second and third output beams. Each of the second and third output beams comprise frequency doubled portions, frequency doubled by SHG, of each of the low frequency, frequency-shifted components of the intermediate second and third output beams, respectively, and portions of each of non-frequency doubled higher frequency components of the intermediate second and third output beams, respectively.

Second and third interference electrical signals are generated by photoelectric detection of the frequency doubled, frequency-shifted components and the respective non-frequency doubled higher frequency components of the second and third output beams, respectively. The difference of the phases of the second and third interference electrical signals, $\Phi_{2G}$, contains information about the dispersion of the optical path lengths of the portions of optical paths in the gas.

The difference of the phases $\Phi_{2G}$ is used with a measurement of the refractivity of the gas related to $\phi_1$ to determine the reciprocal dispersive power of the gas as subsequently described with respect to the second group of preferred embodiments.

The remaining description of the third variant of the first embodiment of the present invention is the same as corresponding portions of the description given for the second variant of the first embodiment and corresponding portions of the descriptions given for embodiments from the second group of preferred embodiments.

It will be appreciated by those skilled in the art that the length of the vacuum path for the third input beam of the third variant of the first embodiment may be reduced to a value of zero without substantially altering the properties of $\Phi_{2G}$ and without departing from the scope and spirit of the present invention.

Reference is now made to FIGS. 2a–2d which depict in diagrammatic form the second preferred embodiment of the present invention from the first group of preferred embodiments for measuring intrinsic optical properties of a gas, particularly its reciprocal dispersive power where the end use application substantially does not effect the choice of the particular manner in which the intrinsic optical properties of the gas are determined and where the stability of the adopted light sources is sufficient and the ratio of the wavelengths of the light beams generated by the adopted light sources are matched to a known ratio value to a relative precision sufficient to meet the required precision imposed on the output data by the final end use application. The second embodiment uses a configuration of differential plane mirror interferometers different from the configuration of differential plane mirror interferometers used in the first embodiment and variant thereof. The configuration of differential plane mirror interferometers in the second embodiment has the effect of producing a number of multiple passes through a measurement path at one wavelength different from the number of multiple passes through the measurement path for a second wavelength, the measurement paths for the two wavelengths being substantially coextensive.

The description of the sources of light beams 9 and 10 and of light beams 9 and 10 for the second embodiment is the same as that for description of the sources of light beams 9 and 10 and of light beams 9 and 10 given for the first preferred embodiment.

Figure 2A:
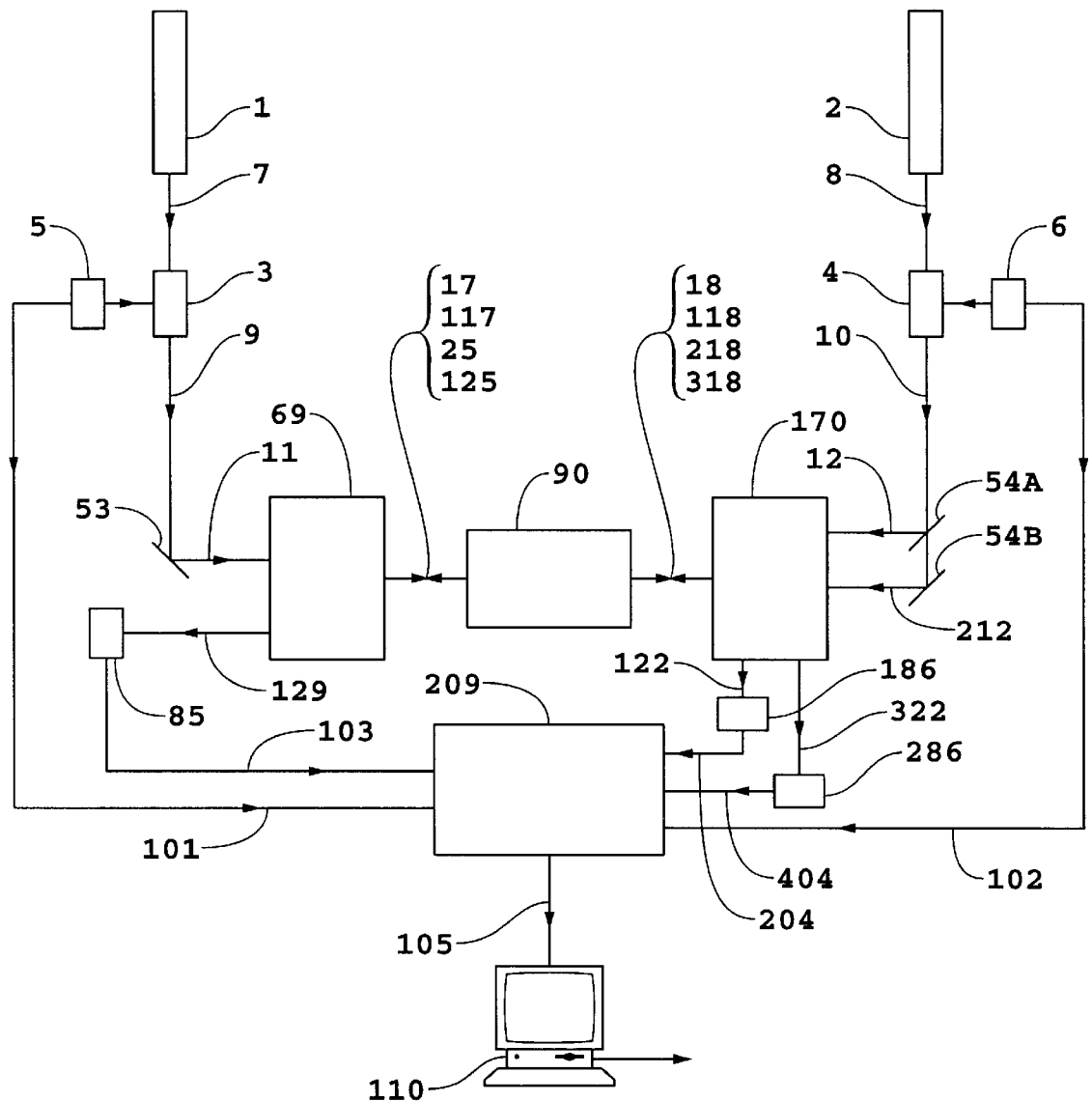
FIGS. 2a–2d taken together illustrate, in diagrammatic form, the presently preferred second embodiment of the present invention with FIG. 2a showing optical paths and the paths of electrical signals between indicated elements source 1, modulator 3, source 2, modulator 4, differential plane mirror interferometer 69, differential plane mirror interferometer group 170, measurement cell 90, detectors 85, 186, and 286, and the paths of electrical signals between indicated elements driver 5, modulator 3, driver 6, modulator 4, detectors 85, 186, and 286, electronic processor 209, and computer 110.

Referring to FIG. 2a, beam 9 is reflected by mirror 53 becoming beam 11. A portion of beam 10 is reflected by a beam splitter 54A, preferably a nonpolarizing type, as beam 12, and a second portion of beam 10 is transmitted by beam splitter 54A and subsequently reflected by mirror 54B becoming beam 212. Beam 11 is incident on differential plane mirror interferometer 69 and beams 12 and 212 are incident on differential plane mirror interferometer group 70 comprised of two differential plane mirror interferometers. Differential plane mirror interferometer 69 and differential plane mirror interferometer group 70 with external mirrors furnished by measurement cell 90 comprise interferometric means for introducing a phase shift $\phi_1$ between the x and y components of beam 11, a phase shift $\phi_3$ between the x and y components of beam 12, and a phase shift $\phi_4$ between the x and y components of beam 212.

The description of differential plane mirror interferometer 69 and propagation of beams in differential plane mirror interferometer 69 is the same as that given for corresponding portions of the descriptions of differential plane mirror interferometer 69 and the propagation of beams in differential plane mirror interferometer 69 of the first embodiment shown in FIG. 1b.

Figure 2B:
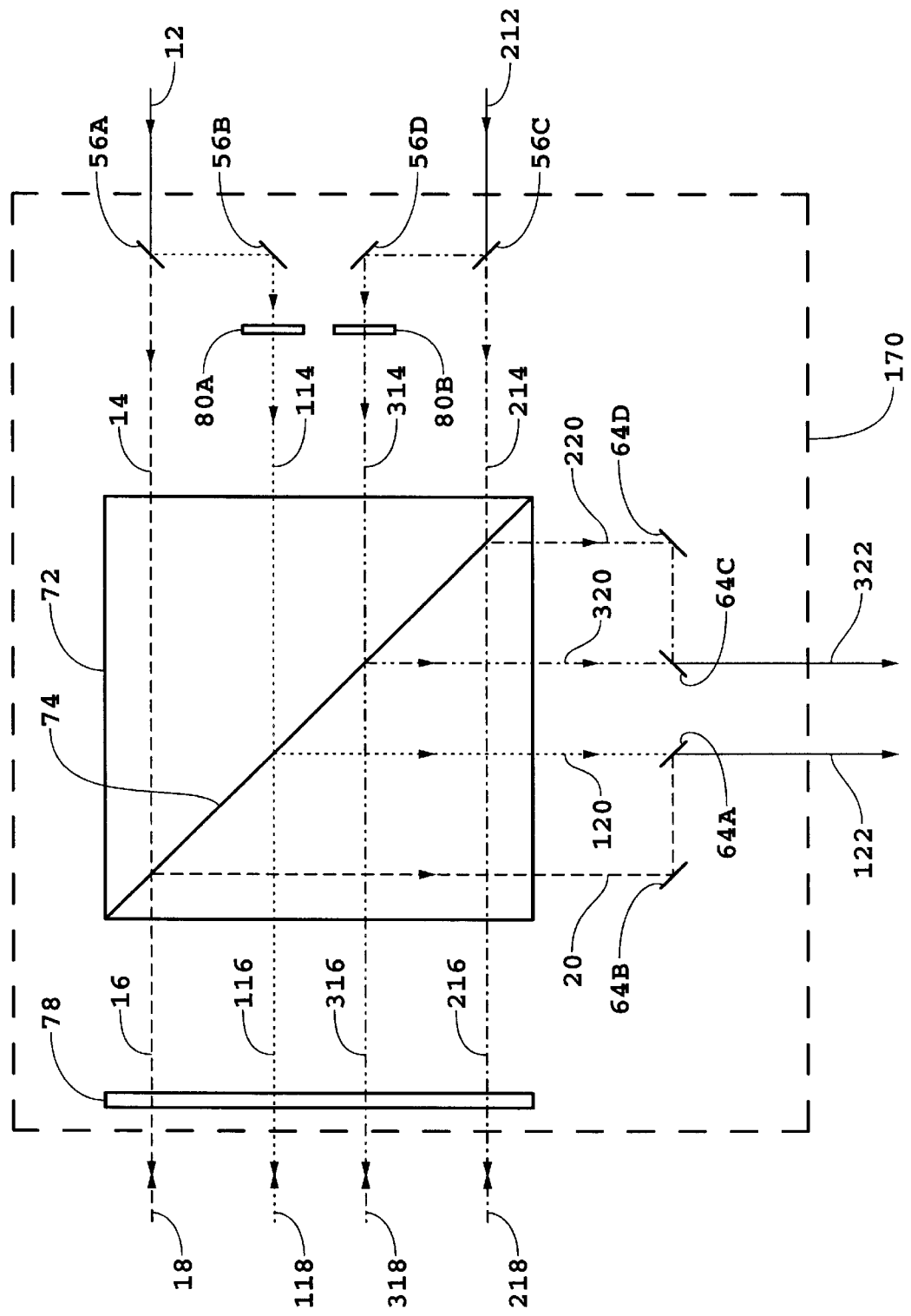

One differential plane mirror interferometer of differential plane mirror interferometer group 170 as shown in FIG. 2b has two exit/return beams 18 and 118. Beam 18 originating from one frequency component, a first frequency component, of beam 12 comprises a beam for one measurement leg and beam 118 originating from a second frequency component of beam 12 comprises a beam for a second measurement leg. Beams for which the first frequency component of beam 12 is the sole progenitor are indicated in FIG. 2b by dashed lines and beams for which the second frequency component of beam 12 is the sole progenitor are indicated in FIG. 2b by dotted lines.

A second differential plane mirror interferometer of differential plane mirror interferometer group 170 as shown in FIG. 2b has two exit/return beams 218 and 318. Beam 218 originating from one frequency component, a first frequency component, of beam 212 comprises a beam for one measurement leg and beam 318 originating from a second frequency component of beam 212 comprises a beam for a second measurement leg. Beams for which the first frequency component of beam 212 is the sole progenitor are indicated in FIG. 2b by lines comprised of alternating dots and dashes and beams for which the second frequency component of beam 212 is the sole progenitor are indicated in FIG. 2b by lines comprised of alternating dot pairs and dashes.

Beams 17, 25, 117, and 125 are incident on measurement cell 90 which results in beams 27 and 127, the same as illustrated for the first embodiment in FIGS. 1b and 1d. Beams 27 and 127 contain information at wavelength $\lambda_1$ about the optical path length through the gas whose reciprocal dispersive power is to be determined and about the optical path length through a vacuum, respectively.

Figure 2C:
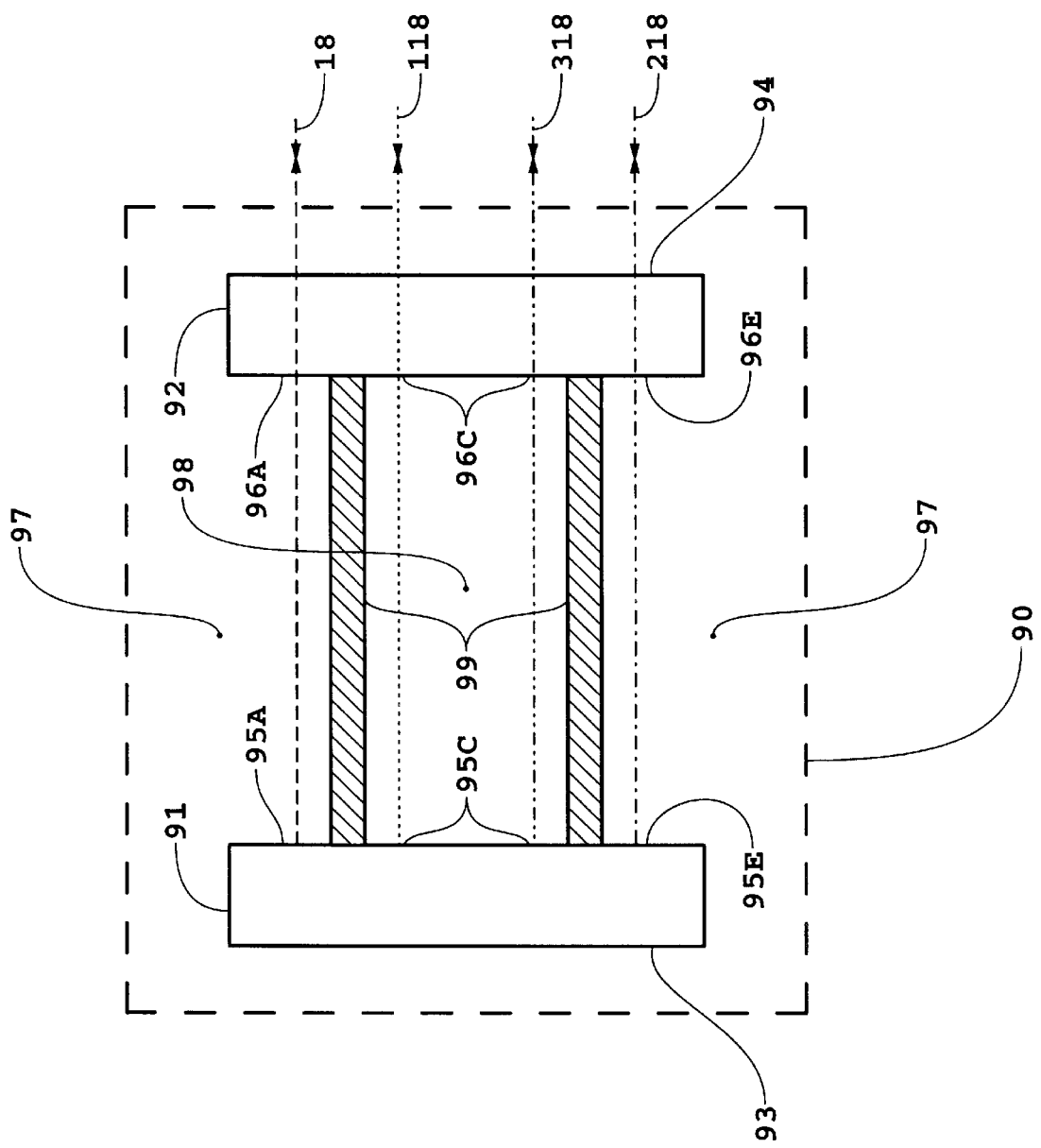

Likewise, beams 18 and 118 are incident on measurement cell 90, illustrated in FIG. 2c, which results in beams 20 and 120 (cf. FIG. 2b). Beams for which the first frequency component of beam 12 is the sole progenitor are indicated in FIG. 2c by dashed lines and beams for which the second frequency component of beam 12 is the sole progenitor are indicated in FIG. 2c by dotted lines. Similarly, beams 218 and 318 are incident on measurement cell 90, as shown in FIG. 2c, which results in beams 220 and 320 (cf. FIG. 2b). Beams for which the first frequency component of beam 212 is the sole progenitor are indicated in FIG. 2c by lines comprised of alternating dots and dashes and beams for which the second frequency component of beam 212 is the sole progenitor are indicated in FIG. 2c by lines comprised of alternating dot pairs and dashes. Beams 20 and 220 contain information at wavelength $\lambda_2$ about optical path lengths through the gas whose reciprocal dispersive power is to be determined and beams 120 and 320 contain information at wavelength $\lambda_2$ about optical path lengths through a vacuum.

Beam 27 and beam 127 are combined to form beam 129, the same as described for the corresponding portion of the first embodiment. Beam 129 exits differential plane mirror interferometer 69 as a mixed beam, the first and second components of beam 129 having the same linear polarizations.

Referring to FIG. 2b, beam 20 is reflected by mirror 64B, a portion of which is reflected by beamsplitter 64A, preferably a nonpolarizing beamsplitter, to become a first component of beam 122. A portion of beam 120 is transmitted by beamsplitter 64A to become a second component of beam 122. Beam 122 is a mixed beam, the first and second components of beam 122 having the same linear polarizations. Beam 220 is reflected by mirror 64D, a portion of which is reflected by beam splitter 64C, preferably a nonpolarizing beamsplitter, to become a first component of beam 322. A portion of beam 320 is transmitted by beamsplitter 64C to become a second component of beam 322. Beam 322 is a mixed beam, the first and second components of beam. 322 having the same linear polarizations. Beams 122 and 322 exit differential plane mirror interferometer group 170.

The magnitude of phase shifts $\phi_1$, $\phi_3$, and $\phi_4$ are related to the round-trip physical lengths of measurement path 97 and reference path 98 (cf. FIGS. 1d and 2c) according to formulae $$\varphi_1 = k_1 \sum_{i=1}^{p_1} (L_{G,i} n_{1,i} - L_{V,i}) + \zeta_1, \qquad (77)$$

$$\varphi_3 = k_2 \sum_{i=1}^{p_2} (L_{G,i} n_{2,i} - L_{V,i}) + \zeta_3,$$

$$\varphi_4 = k_2 \sum_{i=p_2+1}^{p_1} (L_{G,i} n_{2,i} - L_{V,i}) + \zeta_4$$

for the case of $p_1 = 2p_2$. The phase offsets $\zeta_j$ comprise all contributions to the phase shifts $\phi_j$ that are not related to the measurement path 97 or reference path 98. Eqs. (77) are valid for the case where the paths for the two different wavelengths are substantially coextensive, a case chosen to illustrate in the simplest manner the function of the invention in the second embodiment.

Cyclic errors that produce nonlinearities in distance measuring interferometry (cf. the cited articles by Bobroff) have been omitted in Eqs. (77). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

To those skilled in the art, generalization to a case where paths for the two different wavelengths are not substantially coextensive and to a case when $p_1 \neq 2p_2$ is a straight forward procedure. In FIGS. 2a–2c, differential plane mirror interferometer 69, differential plane mirror interferometer group 70, and cell 90 are configured with $p_1=2$ and $p_2=1$ so as to illustrate in the simplest manner the function of the apparatus of the second embodiment.

In a next step as shown in FIG. 2a, beams 129, 122, and 322 impinge upon photodetectors 85, 186, and 386, respectively, resulting in three interference signals, heterodyne signals $s_1$, $s_3$, and $s_4$, respectively, preferably by photoelectric detection. The signal $s_1$ corresponds to wavelength $\lambda_1$ and signals $s_3$ and $s_4$ correspond to the wavelength $\lambda_2$. The signals $s_j$ have the form $$s_j = A_j \cos[\alpha_j(t)], \; j=1, 3, \text{ and } 4 \tag{78}$$

where the time-dependent arguments $\alpha_j(t)$ are given by $$\alpha_1(t) = 2\pi f_1 t + \phi_1,$$
$$\alpha_3(t) = 2\pi f_2 t + \phi_3$$
$$\alpha_4(t) = 2\pi f_2 t + \phi_4. \tag{79}$$

Heterodyne signals $s_1$, $s_3$, and $s_4$ are transmitted as electronic signals 103, 204, and 404, respectively, to processor 209, preferably in digital format, for analysis.

A preferred method for electronically processing the heterodyne signals $s_1$, $s_3$, and $s_4$ is presented herewithin for the case when $l_1$ and $l_2$ are not low order integers. For the case when $l_1$ and $l_2$ are low order integers and the ratio of the wavelengths matched to the ratio $(l_1/l_2)$ with a relative precision sufficient to meet the required precision imposed on the output data by the end use application, the preferred procedure for electronically processing the heterodyne signals $s_1$, $s_3$, and $s_4$ is the same as the one subsequently set down for the variant of the second preferred embodiment of the present invention.

The phases $\phi_1$, $\phi_3$, and $\phi_4$ of signals $s_1$, $s_3$, and $s_4$, respectively, are obtained preferably by application of superheterodyne receiver techniques wherein frequencies of $s_1$, $s_3$, and $s_4$ are shifted to frequencies substantially lower than $f_1$ and $f_2$ where conditions are generally more favorable for high precision phase measurements.

Figure 2D:
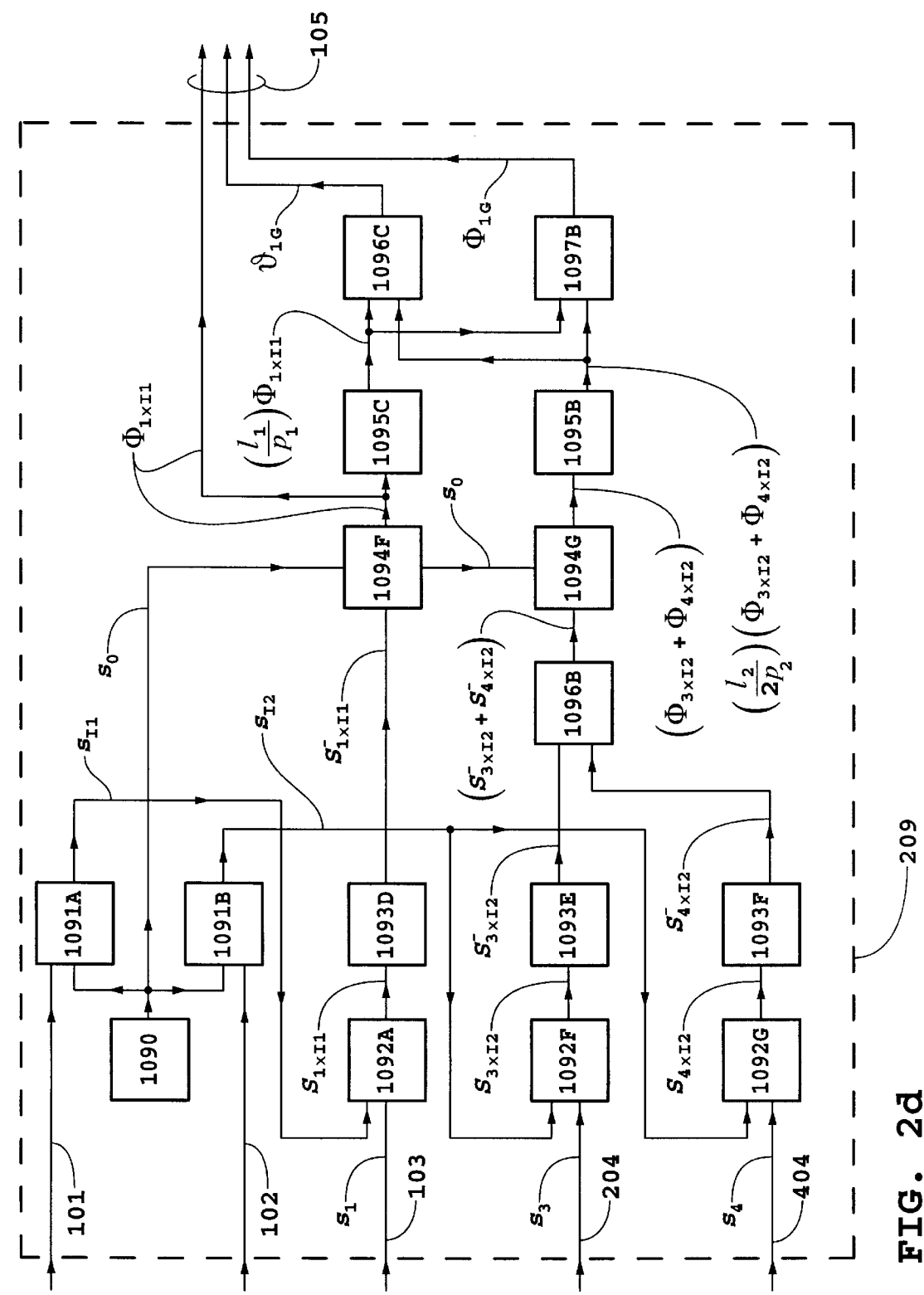

Referring now to FIG. 2d, electronic processor 209 preferably is comprised of alphameric numbered elements wherein the numeric component of the alphameric numbers indicate the function of an element, the same numeric component/function association as described for the electronic processing elements of the first embodiment depicted in FIG. 1f. The description of the steps in processing of the heterodyne signals $s_1$, $s_3$, and $s_4$ by electronic processor 209 is the same as corresponding portions, according to the numeric component of the alphameric numbers of elements, of the descriptions of steps in the processing of the heterodyne signals $s_1$ and $s_2$ of the first embodiment by electronic processor 109. The processing of the heterodyne signals $s_1$, $s_3$, and $s_4$ by processor 209 creates three sideband phases $\Phi_{1 \times I1}$, $\Phi_{3 \times I2}$, and $\Phi_{4 \times I2}$ where $$\Phi_{1 \times I1} = (\phi_1 - \phi_{f1}),$$

$$\Phi_{3 \times I2} = (\phi_3 - \phi_{f2}),$$

$$\Phi_{4 \times I2} = (\phi_4 - \phi_{f2}), \tag{80}$$

and $\phi_{f1}$ and $\phi_{f2}$ are phase offset errors [cf. Eqs. (5)].

Referring again to FIG. 2d, electronic processor 209 comprises electronic processors 1096B to add together $\Phi_{3 \times I2}$, and $\Phi_{4 \times I2}$. Next, the phase $\Phi_{1 \times I1}$ and the resulting phase sum $(\Phi_{3 \times I2} + \Phi_{4 \times I2})$ are multiplied by $l_1/p_1$ and $(l_2/p_2)$ (½), respectively, in electronic processors 1095C and 1095D, respectively, resulting in phases $(l_1/p_1)\Phi_{1 \times I1}$ and $(l_2/p_2)(\Phi_{3 \times I2} + \Phi_{4 \times I2})/2$. The phases $(l_1/p_1)\Phi_{1 \times I1}$ and $(l_2/p_2)(\Phi_{\times I2} + \Phi_{4 \times I2})/2$ are next added together in electronic processor 1096C and subtracted one from the other in electronic processor 1097B, by analog or digital processes, preferably a digital process, to create the phases $\theta_{1G}$ and $\Phi_{1G}$, respectively. Formally, $$\vartheta_{1G} = \left[ \frac{l_1}{p_1} \Phi_{1 \times II} + \frac{l_2}{p_2} \frac{(\Phi_{3 \times I2} + \Phi_{4 \times I2})}{2} \right] \tag{81}$$

$$\Phi_{1G} = \left[ \frac{l_1}{p_1} \Phi_{1 \times II} - \frac{l_2}{p_2} \frac{(\Phi_{3 \times I2} + \Phi_{4 \times I2})}{2} \right]. \tag{82}$$

Note from Eqs. (81) and (82) that $\theta_{1G}$ and $\Phi_{1G}$ are not sensitive to tilts of either reflecting surfaces 95 or 96 of measurement cell 90 and insensitive to thermal and mechanical disturbances that may occur in interferometer beam splitting cubes and associated optical components as a consequence of the use of differential plane mirror interferometers. The phases $\Phi_{1 \times 1I}$, $\theta_{1G}$, and $\Phi_{1G}$ are transmitted to computer 110 as signal 105, preferably in digital format.

The reciprocal dispersive power $\Gamma$ of the gas defined by Eq. (23) can be expressed in terms of other quantities obtained in the second embodiment by a formula $$(n_1 - 1) = \frac{1}{(\chi + K)L_G}\left(\frac{l_1}{p_1}\right)[\Phi_{1 \times II} - (\zeta_1 - \varphi_{II})] - \frac{(L_G - L_V)}{L_G} \tag{83}$$

$$(n_2 - n_1)_{1G} = \frac{1}{\chi L_G [1 - (K/\chi)^2]}\{[\vartheta_{1G}(K/\chi) - \Phi_{1G}] - [\xi(K/\chi) - Z]\} \tag{84}$$

where $\chi$ and $K$ are given by Eqs. (26) and (27), $$\xi = \left[\frac{l_1}{p_1}(\zeta_1 - \varphi_{II}) + \frac{l_2}{p_2}\left(\frac{\zeta_3 + \zeta_4}{2} - \varphi_{I2}\right)\right] \tag{85}$$

$$Z = \left[\frac{l_1}{p_1}(\zeta_1 - \varphi_{II}) + \frac{l_2}{p_2}\left(\frac{\zeta_3 + \zeta_4}{2} - \varphi_{I2}\right)\right] \tag{86}$$

and second order correction terms have been omitted. The correction terms are due to variations in the index of refraction along the measurement path and due to differences in the physical length of path i in the measurement path and the reference path from the respective average physical lengths. In addition, Eq. (84) is valid for the case where the paths for the two different wavelengths are substantially coextensive, a case chosen to illustrate in the simplest manner the function of the invention in the second embodiment. To those skilled in the art, generalization to the case where paths for the different wavelengths are not substantially coextensive is a straight forward procedure.

The remaining description of the second embodiment is the same as corresponding portions of the description given for the first embodiment.

Reference is now made to FIGS. 2a–2c and 2e which taken together depict in diagrammatic form a variant of the second preferred embodiment of the present invention for measuring intrinsic optical properties of a gas, particularly its reciprocal dispersive power where the end use application substantially does not effect the choice of the particular manner in which the intrinsic optical properties of the gas are determined and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the first embodiment in which the ratio $(l_1/l_2)$ is expressible as the ratio of low order non-zero integers $(p_1/p_2)$, cf. Eq. (35).

The description of the sources of light beams 9 and 10 and of light beams 9 and 10 for the variant of the second embodiment is the same as that for description of the sources of light beams 9 and 10 and of light beams 9 and 10 given for the first embodiment with the additional requirement that the wavelengths be harmonically related to a relative precision sufficient to meet the required precision imposed on the output data by the final end use application. The description of the apparatus for the variant of the second embodiment depicted in FIGS. 2a–2c is the same as corresponding portions of the description given for the second embodiment for the case where $p_1=2$ and $p_2=1$.

Figure 2E:
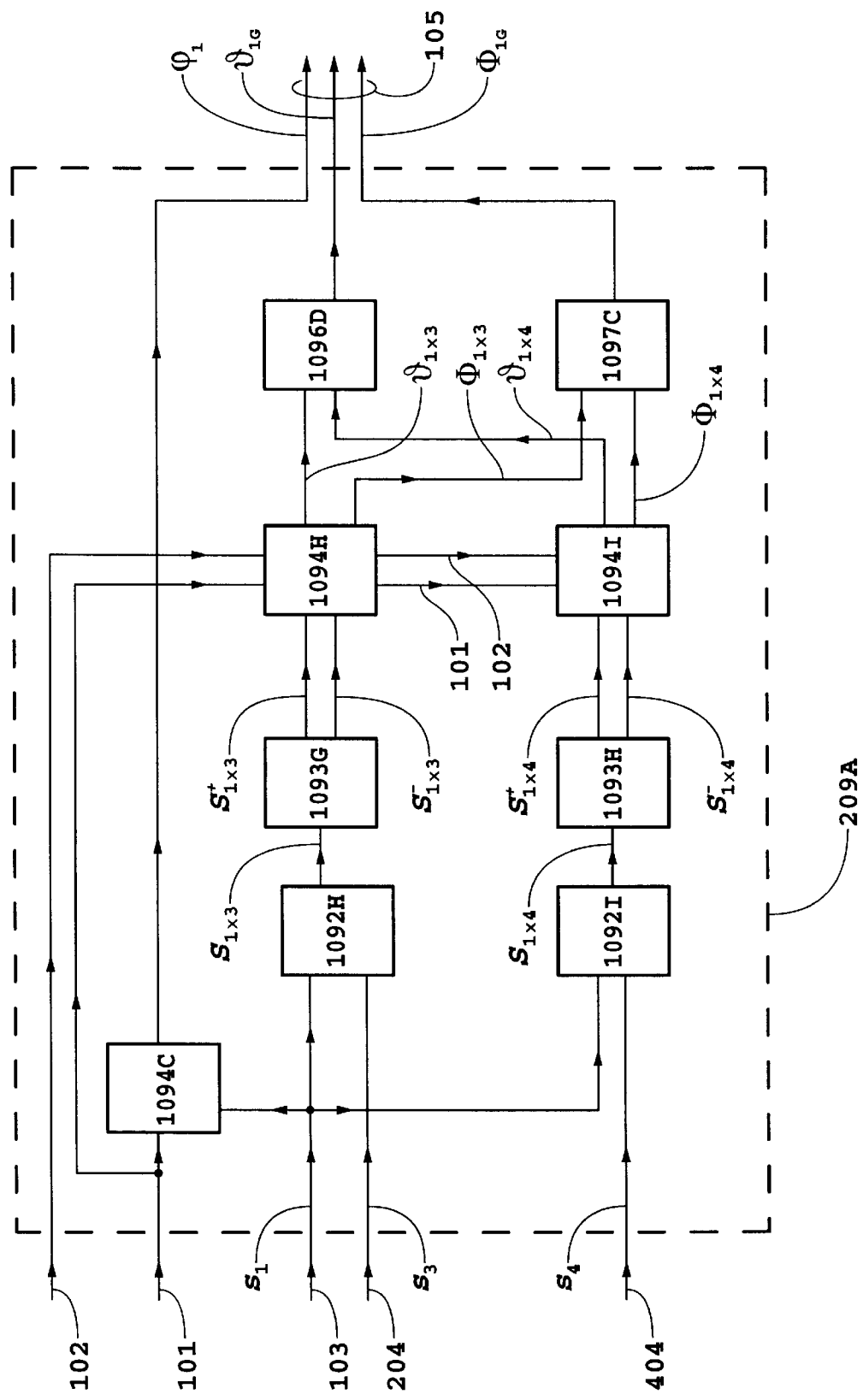

Referring now to FIG. 2e, electronic processor 209A preferably comprises electronic processor 1092H for electronically multiplying together, either as an analog or digital process, preferably a digital process, heterodyne signals $s_1$ and $s_3$ to create a superheterodyne signal $S_{1\times3}$ having the mathematical form $$S_{1\times3}=s_1 s_3. \tag{87}$$

The superheterodyne signal $S_{1\times3}$ may be rewritten as $$S_{1\times3}=S_{1\times3}^{+}+S_{1\times3}^{-} \tag{88}$$

where $$S_{1\times3}^{+}=\tfrac{1}{2}A_1 A_3 \cos(2\pi v t+\theta_{1\times3}) \tag{89}$$

$$S_{1\times3}^{-}=\tfrac{1}{2}A_1 A_3 \cos(2\pi F t+\Phi_{1\times3}) \tag{90}$$

$$v=(f_1+f_2) \tag{91}$$

$$\theta_{1\times3}=(\phi_1+\phi_3) \tag{92}$$

$$F=(f_1-f_2) \tag{93}$$

$$\Phi_{1\times3}=(\phi_1-\phi_3) \tag{94}$$

The superheterodyne signal $S_{1\times3}$ is therefore comprised of two sidebands, $S_{1\times3}^{+}$ and $S_{1\times3}^{-}$, of equal amplitude, one sideband with frequency v and phase $\theta_{1\times3}$ and a second sideband with frequency F and phase $\Phi_{1\times3}$.

In a next step, the sidebands $S_{1\times3}^{+}$ and $S_{1\times3}^{-}$, are separated by electronic processor 1093G through high pass and low pass filtering or any of the like techniques for separating two signals that are separated in frequency. The frequency F of the lower frequency sideband of the superheterodyne signal can be very much smaller than the frequency v of the higher frequency sideband of the superheterodyne signal as described in the corresponding portion of the discussion of the first embodiment, considerably simplifying the separating task of processor 1093G. Electronic processor 209A further comprises electronic processor 1094H to determine the phases $\theta_{1\times3}$ and $\Phi_{1\times3}$ using time-based phase detection such as a digital Hilbert transform phase detector (see R. E. Best, ibid.; Oppenheim and Schafer, ibid.) or the like and the phases of the drivers 5 and 6.

Electronic processor 209A further comprises electronic processor 1092I which electronically multiplies together, either as an analog or digital process, preferably a digital process, heterodyne signals $s_1$ and $s_4$ to create a superheterodyne signal $S_{1\times4}$ having the mathematical form $$S_{1\times4}=s_1 s_4. \tag{95}$$

The superheterodyne signal $S_{1\times4}$ also comprises two sidebands with a suppressed carrier and may be rewritten as $$S_{1\times4}=S_{1\times4}^{+}+S_{1\times4}^{-} \tag{96}$$

where $$S_{1\times4}^{+}=\tfrac{1}{2}A_1 A_4 \cos(2\pi v t+\theta_{1\times4}) \tag{97}$$

$$S_{1\times4}^{-}=\tfrac{1}{2}A_1 A_4 \cos(2\pi F t+\Phi_{1\times4}) \tag{98}$$

$$\theta_{1\times4}=(\phi_1+\phi_4) \tag{99}$$

$$\Phi_{1\times4}=(\phi_1-\phi_4) \tag{100}$$

The superheterodyne signal $S_{1\times4}$ therefore comprises two sidebands, $S_{1\times4}^{+}$ and $S_{1\times4}^{-}$, of equal amplitude, one sideband with frequency v and phase $\theta_{1\times4}$ and a second sideband with frequency F and phase $\Phi_{1\times4}$.

In a next step, the sidebands $S_{1\times4}^{+}$ and $S_{1\times4}^{-}$ are separated by electronic processor 1093H through high pass and low pass filtering or any of the like techniques for separating two signals that are separated in frequency. As noted in the discussion of electronic processor 1093G, the frequency F of the lower frequency sideband of superheterodyne signal $S_{1\times4}$ can be very much smaller than the frequency v of the higher frequency sideband of superheterodyne signal $S_{1\times4}$, considerably simplifying the separating task of processor 1093H. Electronic process 209A further comprises processor 1094I to determine the phases $\theta_{1\times4}$ and $\Phi_{1\times4}$ using time-based phase detection such as a digital Hilbert transform phase detector (see Best ibid.; Oppenheim and Schafer, ibid.) or the like and the phases of the drivers 5 and 6.

Subsequently, the phases $\theta_{1\times3}$ and $\theta_{1\times4}$ are added together in electronic processor 1096D, by an analog or digital process, and phases $\Phi_{1\times3}$ and $\Phi_{1\times4}$ are subtracted one from the other in electronic processor 1097C, by an analog or digital process, preferably a digital process, to create the phases $2\theta_{1G}$ and $2\Phi_{1G}$, respectively. Formally, $$\vartheta_{1G}=\frac{(\Phi_{1\times3}+\Phi_{1\times4})}{2}=\left[\varphi_1+\frac{(\varphi_3+\varphi_4)}{2}\right] \tag{101}$$

$$\Phi_{1G}=\frac{(\Phi_{1\times3}-\Phi_{1\times4})}{2}=\left[\varphi_1-\frac{(\varphi_3+\varphi_4)}{2}\right] \tag{102}$$

Note from Eqs. (101) and (102) that $\theta_{1G}$ and $\Phi_{1G}$ are not sensitive to tilts of either reflecting surfaces 95 or 96 and insensitive to thermal and mechanical disturbances that may occur in the interferometer beam splitting cubes and associated optical components as a consequence of the use of differential plane mirror interferometers.

Electronic processor 209A, and shown in FIG. 2e, comprises electronic processor 1094C to determine phase $\phi_1$ from heterodyne signal $s_1$ using time-based phase sensitive detection with reference signal 101 or the like. Phases $\phi_1$, $\theta_{1G}$, and $\Phi_{1G}$ are transmitted, preferably in digital format, to computer 110 as signal 105 for the calculation of $\Gamma$.

The reciprocal dispersive power $\Gamma$ of the gas defined by Eq. (23) can be expressed in terms of other quantities obtained in the variant of the second embodiment by Eqs. (26), (27), (83), (84), (85), and (86) with $$\phi_1 = \Phi_{1 \times l_1},$$

$$\phi_{l1} = 0, \phi_{l2} = 0,$$

$$l_1 = p_1, l_2 = p_2. \tag{103}$$

The remaining discussion of the variant of the second embodiment is the same as corresponding portions of the descriptions given for the second embodiment.

The principal advantage of the variant of the second embodiment is an option for the execution of critical electronic processing steps, such as the determination of phases $\Phi_{1 \times 3}$ and $\Phi_{1 \times 4}$ at substantially identical frequencies, frequencies low compared to the frequencies of heterodyne signals $s_1$, $s_3$, and $s_4$ which are also substantially identical, with a simplified electronic processing in relation to that of the first embodiment and variant thereof and of the second embodiment without the risk of possibly enhancing frequency sensitive phase offset errors due to differences in group delays experienced by heterodyne and/or modified heterodyne signals having significantly different frequencies. The discussion of the effects of group delay for the variant of the second embodiment is the same as corresponding portions of the description given for the second embodiment.

Reference is now made to FIGS. 3a–3d which depict in diagrammatic form the third preferred embodiment of the present invention from the first group of preferred embodiments for measuring the reciprocal dispersive power or other intrinsic optical properties of a gas, particularly its reciprocal dispersive power where the end use application substantially does not effect the choice of the particular manner in which the intrinsic optical properties of the gas are determined and where the stability of the adopted light sources is sufficient and the ratio of the wavelengths of the light beams generated by the adopted light sources are matched to a known ratio value to a relative precision sufficient to meet the required precision imposed on the output data by the final end use application. The third embodiment uses a configuration of differential plane mirror interferometers different from the configuration of differential plane mirror interferometers used in the first and second embodiments and variants thereof. The configuration of differential plane mirror interferometers in the third embodiment has the effect, as for the second embodiment and variant thereof, of producing a different number of multiple passes through a measurement path at one wavelength relative to the number of multiple passes through the measurement path for a second wavelength. The primary difference between the third embodiment and the first and second embodiments lies in a relatively more complicated system of differential plane mirror interferometers and generally a reduced number of elements in the signal processor.

The description of the sources of light beams 9 and 10 and of light beams 9 and 10 for the third embodiment is the same as that for description of the sources of light beams 9 and 10 and of light beams 9 and 10 given for the first preferred embodiment of the present invention.

Figure 3A:
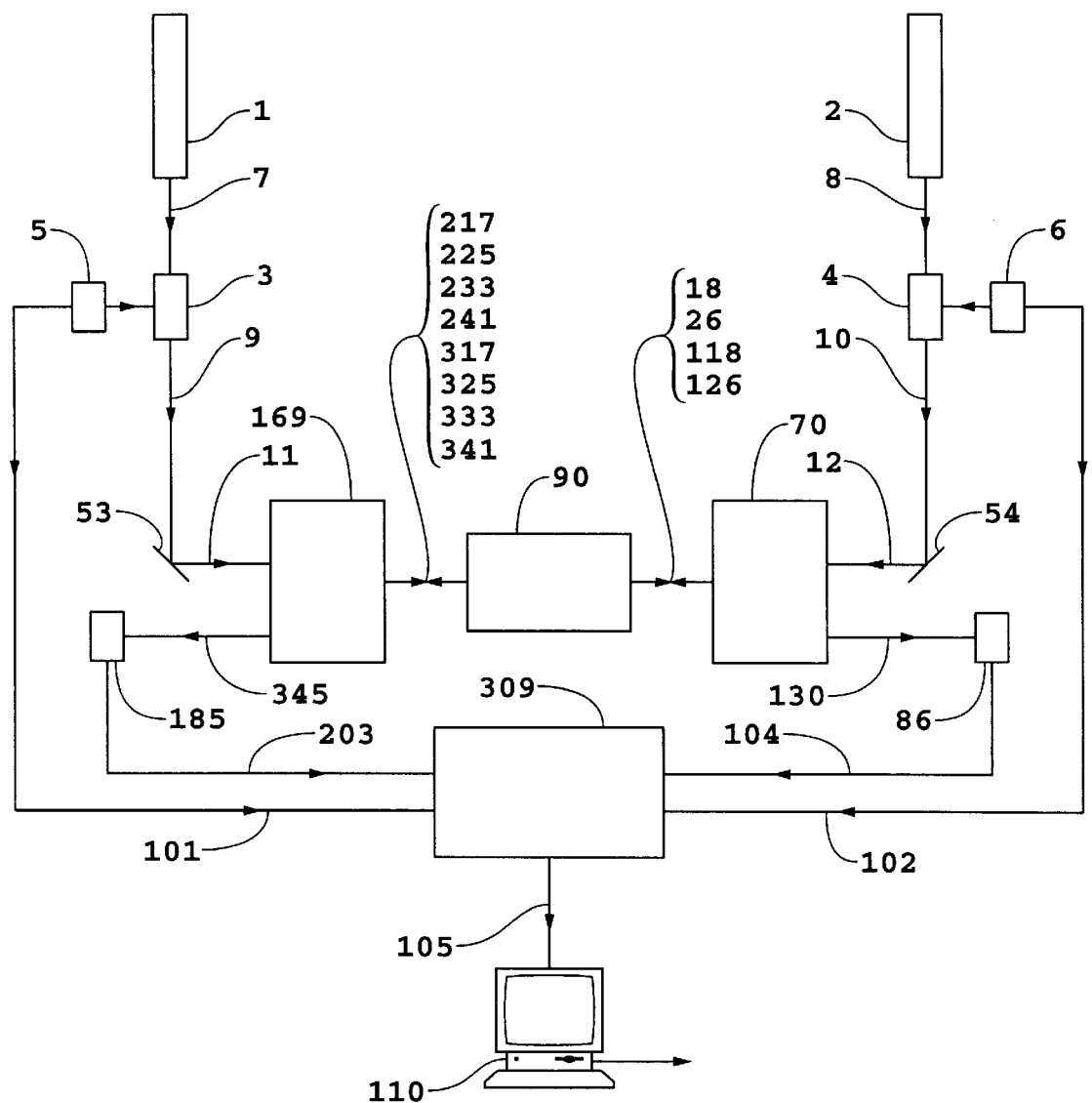
FIGS. 3a–3d taken together illustrate, in diagrammatic form, the presently preferred third embodiment of the present invention with FIG. 3a showing optical paths and the paths of electrical signals between indicated elements source 1, modulator 3, source 2, modulator 4, differential plane mirror interferometers 169 and 70, measurement cell 90, detectors 185 and 86, and the paths of electrical signals between indicated elements driver 5, modulator 3, driver 6, modulator 4, detectors 185 and 86, electronic processor 309, and computer 110.
Figure 3B:
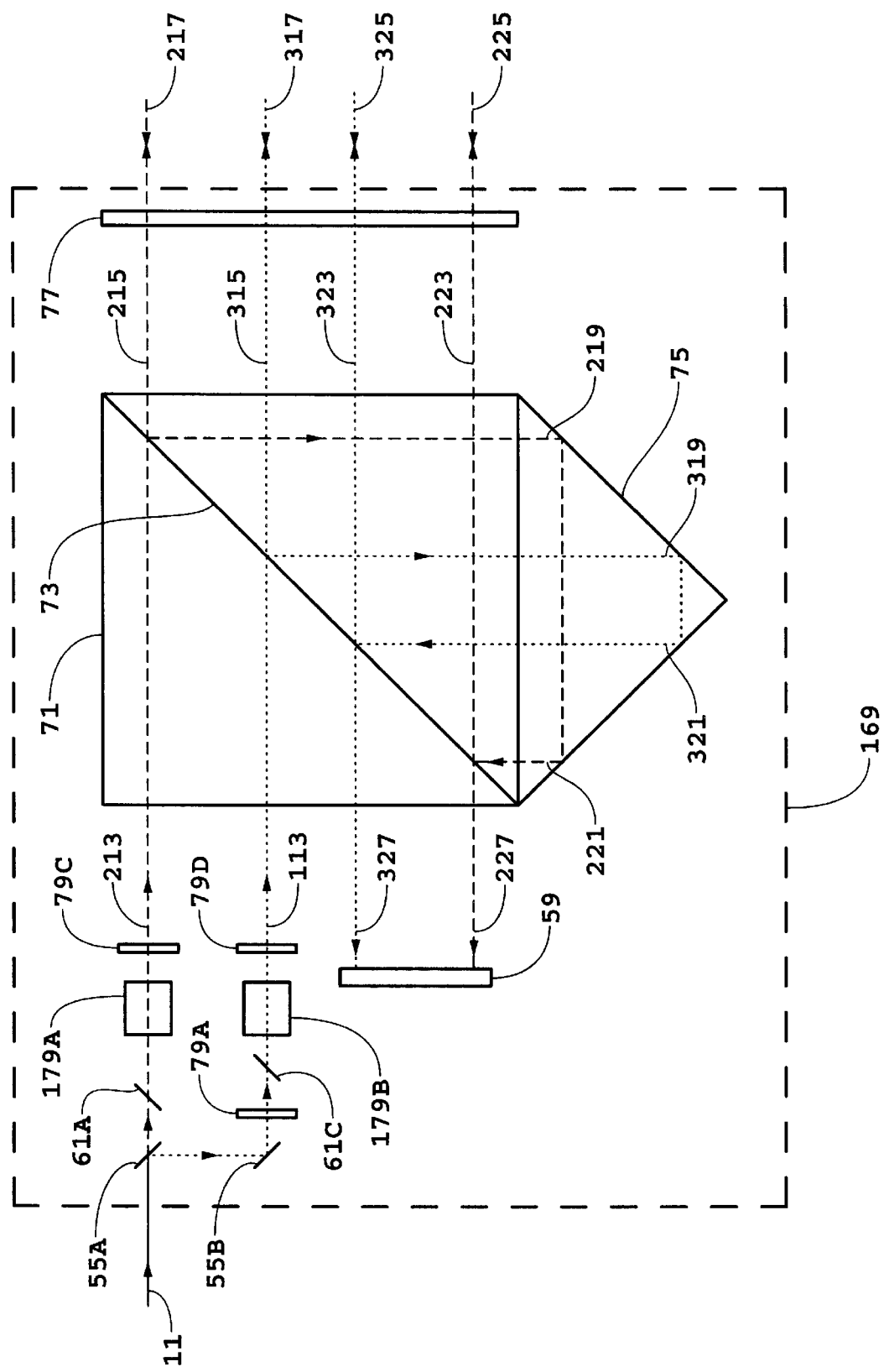
Figure 3C:
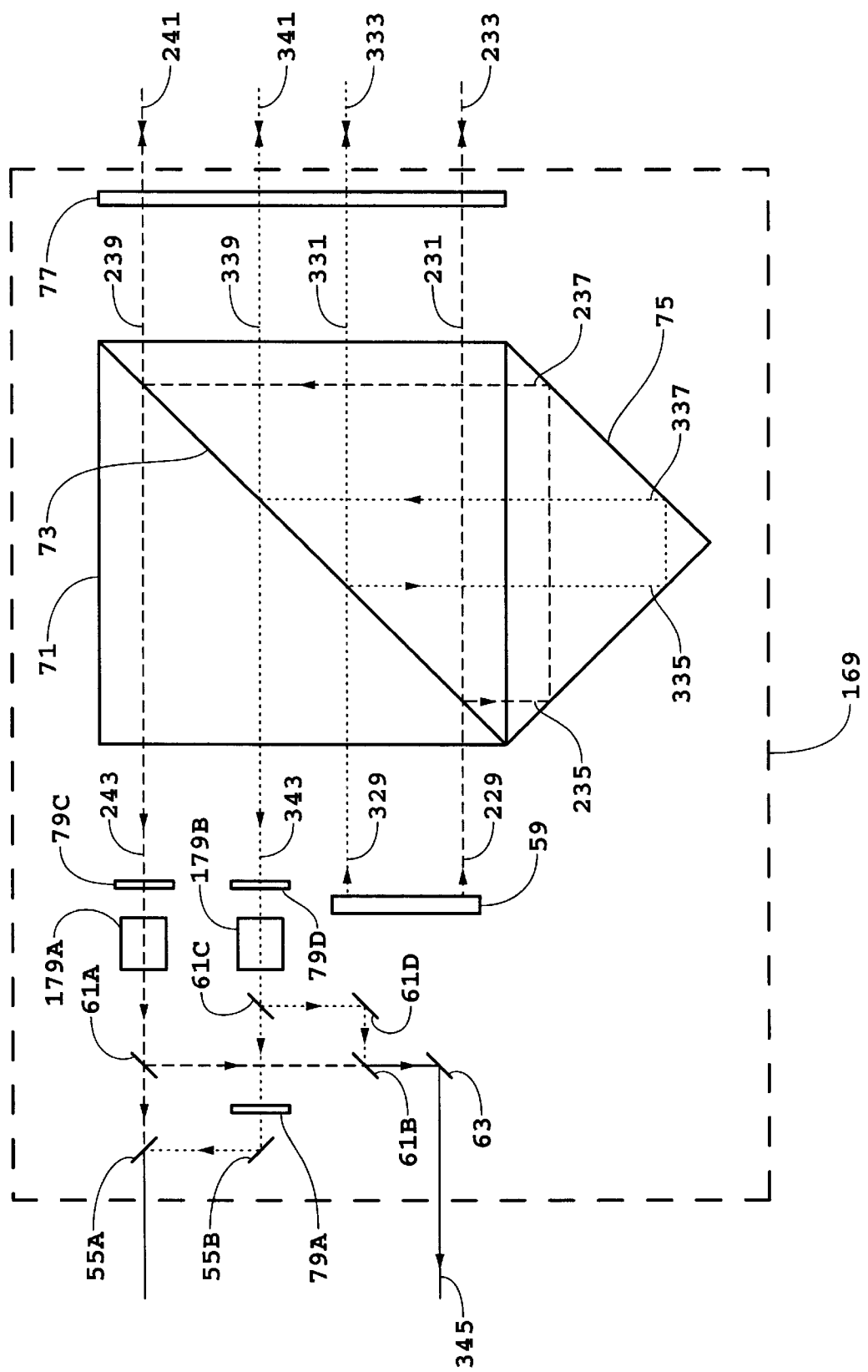

As illustrated in FIG. 3a, beam 9 is reflected by mirror 53 becoming beam 11 and beam 10 is reflected by mirror 54 becoming beam 12. Beam 11 is incident on differential plane mirror interferometer 169 and beam 12 is incident on differential plane mirror interferometer 70, differential plane mirror interferometer 70 of the third embodiment being the same as differential plane mirror interferometer 70 depicted in FIGS. 1a and 1c for the first preferred embodiment. Beams for which the first frequency component of beam 11 is the sole progenitor are indicated in FIGS. 3b and 3c by dashed lines and beams for which the second frequency component of beam 11 is the sole progenitor are indicated in FIGS. 3b and 3c by dotted lines. Differential plane mirror interferometers 169 and 70 with external mirrors furnished by measurement cell 90 comprise interferometric means for introducing a phase shift $\phi_5$ between the x and y components of beam 11 and a phase shift $\phi_2$ between the x and y components of beam 12.

Differential plane mirror interferometer 169 has eight exit/return beams, four exit/return beams 217, 225, 317, and 325 as shown in FIG. 3b and four exit/return beams 233, 241, 333, and 341 as shown in FIG. 3c. Beams 217, 225, 233, and 241 originating from one frequency component of beam 11 comprise one measurement leg and beams 317, 325, 333, and 341 originating from a second frequency component of beam 11 comprise a second measurement leg. Beams 217, 225, 233, 241, 317, 325, 333, and 341 are incident on measurement cell 90, as illustrated in FIGS. 3b and 3c, which results in beams 243 and 343. The description of the propagation of beams 217, 225, 233, and 241 in measurement cell 90 is the same as corresponding portions of descriptions given for the propagation of beams 17, 25, 33, and 41, respectively, in measurement cell 90 for the first preferred embodiment. Similarly, the description of the propagation of beams 317, 325, 333, and 341 in measurement cell 90 is the same as corresponding portions of descriptions given for the propagation of beams 17, 25, 33, and 41, respectively, in measurement cell 90 for the first preferred embodiment. Beam 243 and 343 contain information at wavelength $\lambda_1$ about optical path lengths through the gas whose reciprocal dispersive power $\Gamma$ is to be determined and about optical path lengths through a vacuum, respectively.

The description of differential plane mirror interferometer 70 and the propagation of beams in differential plane mirror interferometer 70 is the same as that given for corresponding portions of the descriptions of differential plane mirror interferometer 70 and the propagation of beams in differential plane mirror interferometer 70 of the first embodiment shown in FIG. 1b.

Beams 18, 26, 118, and 126 are incident on measurement cell 90, which results in beams 28 and 128, the same as illustrated for the first embodiment in FIGS. 1c and 1e. Beams 28 and 128 contain information at wavelength $\lambda_2$ about the optical path length through the gas whose reciprocal dispersive power is to be determined and about the optical path length through a vacuum, respectively.

The magnitude of phase shifts $\phi_5$ and $\phi_2$ are related to $L_i$ the round-trip physical length of path i of measurement path 97 or reference path 98 the same as shown in FIGS. 1d and 1e for the first embodiment according to the formulae $$\varphi_5 = \sum_{i=1}^{i=p_1} k_1(L_{G,i}n_{1i} - L_{V,i}) + \zeta_5 \qquad (104)$$

$$\varphi_2 = \sum_{i=1}^{i=p_2} k_2(L_{G,i}n_{2i} - L_{V,i}) + \zeta_2,$$

where the illustrations in FIGS. 3b, 3c, and 1c, as used in reference to the third embodiment, is for $p_1$=4 and $p_2$=2 so as to illustrate in the simplest manner the function of the invention in the third preferred embodiment.

Cyclic errors that produce nonlinearities in distance measuring interferometry (cf. the cited articles by Bobroff) have been omitted in Eqs. (104). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

The operation of differential plane mirror interferometer 169 depicted in FIGS. 3b and 3c is the same as the operation described for differential plane mirror interferometer 69 except for the means used to separate the two frequency components of input beam 11 and the means used to create the mixed output beam 345. Referring to FIG. 3b, a first portion of beam 11 is reflected by beam splitter 55A, preferably a polarizing beam splitter, reflected by mirror 55B, transmitted by half-wave phase-retardation plate 79A, transmitted by beam splitter 61C, preferably a polarizing beam splitter, transmitted by Faraday rotator 179B, and transmitted by half-wave phase-retardation plate 79D to become beam 313. The Faraday rotator 179B and the half-wave phase-retardation plate 79D rotate the plane of polarization of transmitted beams by ±45° and ∓45°, respectively, producing no net rotation of the plane of polarization of transmitted beams.

A second portion of beam 11 is transmitted by beam splitter 55A, transmitted by beam splitter 61A, preferably a polarizing beamsplitter, transmitted by Faraday rotator 179A, and transmitted by half-wave phase-retardation plate 79C to become beam 213. The Faraday rotator 179A and the half-wave phase-retardation plate 79C rotate the plane of polarization of transmitted beams by ±45° and ∓45°, respectively, producing no net rotation of the plane of polarization of transmitted beams. Half-wave phase-retardation plate 79 rotates the plane of polarization of transmitted beam by 90° so that beams 213 and 313 have the same polarizations but have different frequencies. The purpose of the Faraday rotators 179A and 179B and the half-wave phase-retardation plates 79C and 79D is to have substantially no effect on the properties of beams 213 and 313 but to rotate the polarizations of beams 243 and 343 by 90° so as to achieve an efficient spatial separation of beams 243 and 343 from the path of beam 11.

Referring to FIG. 3c, beam 243 is transmitted by half-wave phase retardation plate 79C and Faraday rotator 179A, reflected by beam splitter 61A, transmitted by beam splitter 61B, and then reflected by mirror 63 to become a first component of phase shifted beam 345. Half-wave phase retardation plate 79C and Faraday rotator 179A each rotate the polarization of beam 243 by 45° so that the first component of phase shifted beam 345 is orthogonally polarized to the polarization of beam 243. Beam splitter 61A is preferably a polarizing beam splitter and beam splitter 61B is preferably a nonpolarizing beam splitter. Beam 343 is transmitted by half-wave phase-retardation plate 79D and Faraday rotator 179B, reflected by beam splitter 61C, reflected by mirror 61D, reflected by beam splitter 61B, and then reflected by mirror 63 to become a second component of phase shifted beam 345. Half-wave phase-retardation plate 79D and Faraday rotator 179B each rotate the polarization of beam 343 by 45° so that the second component of phase shifted beam 345 is orthogonally polarized to the polarization of beam 343. Beam splitter 61C is preferably a polarizing beam splitter. Phase shifted beam 345 is a mixed beam, the first and second components of phase shifted beam 345 having the same polarizations but different frequencies.

Beam 28 and beam 128 are combined to form beam 130, the same as described for the corresponding portion of the first embodiment. Beam 130 exits differential plane mirror interferometer 70 as a mixed beam, the first and second components of beam 130 having the same linear polarizations.

In a next step as shown in FIG. 3a, phase-shifted beams 345 and 130 impinge upon photodetectors 185 and 86, respectively, resulting in two interference signals, heterodyne signals $s_5$ and $s_2$, respectively, preferably by photoelectric detection. The signal $s_5$ corresponds to wavelength $\lambda_1$ and signal $s_2$ corresponds to the wavelength $\lambda_2$. The signals $s_j$ have the form expressed by Eq. (3) with time-dependent arguments $\alpha_j(t)$ of the form expressed by Eq. (4) except j=5 and 2 instead of 1 and 2, respectively. Heterodyne signals $s_5$ and $s_2$ are transmitted to electronic processor 309 for analysis as electronic signals 203 and 104, respectively, in either digital or analog format.

A preferred method for electronically processing the heterodyne signals $s_5$ and $s_2$ is presented herewithin for the case when $l_1$ and $l_2$ are not low order integers. For the case when $l_1$ and $l_2$ are low order integers and the ratio of the wavelengths matched to the ratio $(l_1/l_2)$ with a relative precision sufficient to meet the required precision imposed on the output data by the end use application, the preferred procedure for electronically processing the heterodyne signals $s_5$ and $s_2$ is the same as the one subsequently set down for the variant of the third preferred embodiment of the present invention.

The phases $\phi_5$ and $\phi_2$ of signals $s_5$ and $s_2$, respectively, are obtained preferably by application of superheterodyne receiver techniques wherein the frequencies of signals $s_5$ and $s_2$ are shifted to frequencies substantially lower than $f_1$ and $f_2$ where conditions are generally more favorable for high precision phase measurements.

Figure 3D:
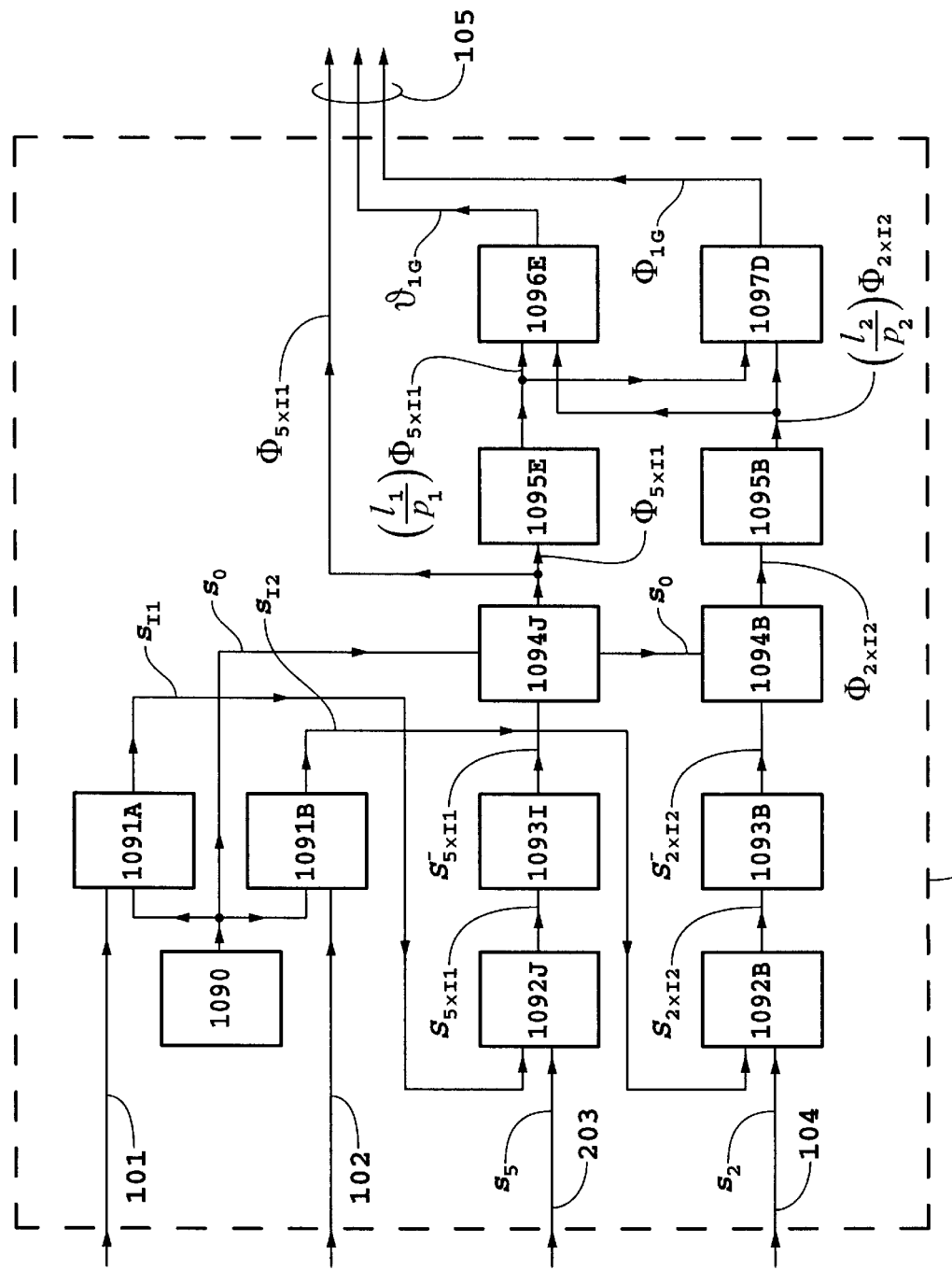

Referring now to FIG. 3d, electronic processor 309 preferably is comprised of alphameric numbered elements wherein the numeric component of the alphameric numbers indicate the function of an element, the same numeric component/function association as described for the electronic processing elements of the first embodiment depicted in FIG. 1f. The description of the steps in processing of the heterodyne signals $s_5$ and $s_2$ by electronic processor 309 is the same as corresponding portions, according to the numeric component of the alphameric numbers of elements, of the descriptions of steps in the processing of the heterodyne signals $s_1$ and $s_2$ of the first embodiment by electronic processor 109. The processing of the heterodyne signals $s_5$ and $s_2$ by electronic processor 309 creates two sideband phases $\Phi_{5 \times I1}$ and $\Phi_{2 \times I2}$ where $$\Phi_{5 \times I1} = (\phi_5 - \phi_{f1})$$

$$\Phi_{2 \times I2} = (\phi_2 - \phi_{f2}) \qquad (105)$$

and $\phi_{f1}$ and $\phi_{f2}$ are phase offset errors [cf. Eqs. (5)].

Referring again to FIG. 3d, phases $\Phi_{5\times I1}$ and $\Phi_{2\times I2}$ are multiplied by $(l_1/p_1)$ and $(l_2/p_2)$, respectively, in electronic processors 1095E and 1095B, respectively, resulting in phases $(l_1/p_1)\Phi_{5\times I1}$ and $(l_2/p_2)\Phi_{2\times I2}$. The phases $(l_1/p_1)\Phi_{5\times I1}$ and $(l_2/p_2)\Phi_{2\times I2}$ are next added together in electronic processor 1096E and subtracted one from the other in electronic processor 1097D, by analog or digital processes, to create the phases $\theta_{1G}$ and $\Phi_{1G}$, respectively. Formally, $$\vartheta_{1G} = \left(\frac{l_1}{p_1}\Phi_{5\times I1} + \frac{l_2}{p_2}\Phi_{2\times I2}\right) \tag{106}$$

$$\Phi_{1G} = \left(\frac{l_1}{p_1}\Phi_{5\times I1} - \frac{l_2}{p_2}\Phi_{2\times I2}\right). \tag{107}$$

Note from Eqs. (106) and (107) that $\theta_{1G}$ and $\Phi_{1G}$ are not sensitive to tilts of either reflecting surfaces 95 or 96 of measurement cell 90 and insensitive to thermal and mechanical disturbances that may occur in the interferometer beam splitting cubes and associated optical components as a consequence of the use of differential plane mirror interferometers.

The reciprocal dispersive power $\Gamma$ of the gas defined by Eq. (23) can be expressed in terms of other quantities obtained in the third embodiment by a formulae $$(n_1 - 1) = \frac{1}{(\chi + K)L_G}\left(\frac{l_1}{p_1}\right)[\Phi_{5\times II} - (\zeta_5 - \varphi_{II})] - \frac{(L_G - L_V)}{L_G} \tag{108}$$

$$(n_2 - n_1)_{1G} = \tag{109}$$
$$\frac{1}{\chi L_G[1 - (K/\chi)^2]}\{[\vartheta_{1G}(K/\chi) - \Phi_{1G}] - [\xi(K/\chi) - Z]\}$$

where $\chi$ and $K$ are given by Eqs. (26) and (27), respectively, and $\xi$ and $Z$ are given by $$\xi = \left[\frac{l_1}{p_1}(\zeta_5 - \varphi_{II}) + \frac{l_2}{p_2}(\zeta_2 - \varphi_{I2})\right] \tag{110}$$

$$Z = \left[\frac{l_1}{p_1}(\zeta_5 - \varphi_{II}) - \frac{l_2}{p_2}(\zeta_2 - \varphi_{I2})\right] \tag{111}$$

Eq. (109) is valid for the case where the paths for the two different wavelengths are substantially coextensive, a case chosen to illustrate in the simplest manner the function of the invention in the second embodiment. To those skilled in the art, the generalization to the case where paths for the two different wavelengths are not substantially coextensive is a straight forward procedure.

The remaining description of the third embodiment is the same as corresponding portions of the description given for the first and second embodiments.

Reference is now made to FIGS. 3a–3c and 3e which taken together depict in diagrammatic form a variant of the third preferred embodiment of the present invention for measuring intrinsic optical properties of a gas, particularly its reciprocal dispersive power where the end use application substantially does not effect the choice of the particular manner in which the intrinsic optical properties of the gas are determined and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the first embodiment in which the ratio $(l_1/l_2)$ is expressible as the ratio of low order non-zero integers $(p_1/p_2)$, cf. Eq. (35).

The description of the sources of light beams 9 and 10 and of light beams 9 and 10 for the variant of the third embodiment is the same as that for description of the sources of light beams 9 and 10 and of light beams 9 and 10 given for the first embodiment with the additional requirement that the wavelengths be harmonically related to a relative precision sufficient to meet the required precision imposed on the output data by the final end use application. The description of the apparatus for the variant of the third embodiment depicted in FIGS. 3a–3c is the same as corresponding portions of the description given for the third embodiment for the case where $p_1=4$ and $p_2=2$.

Figure 3E:
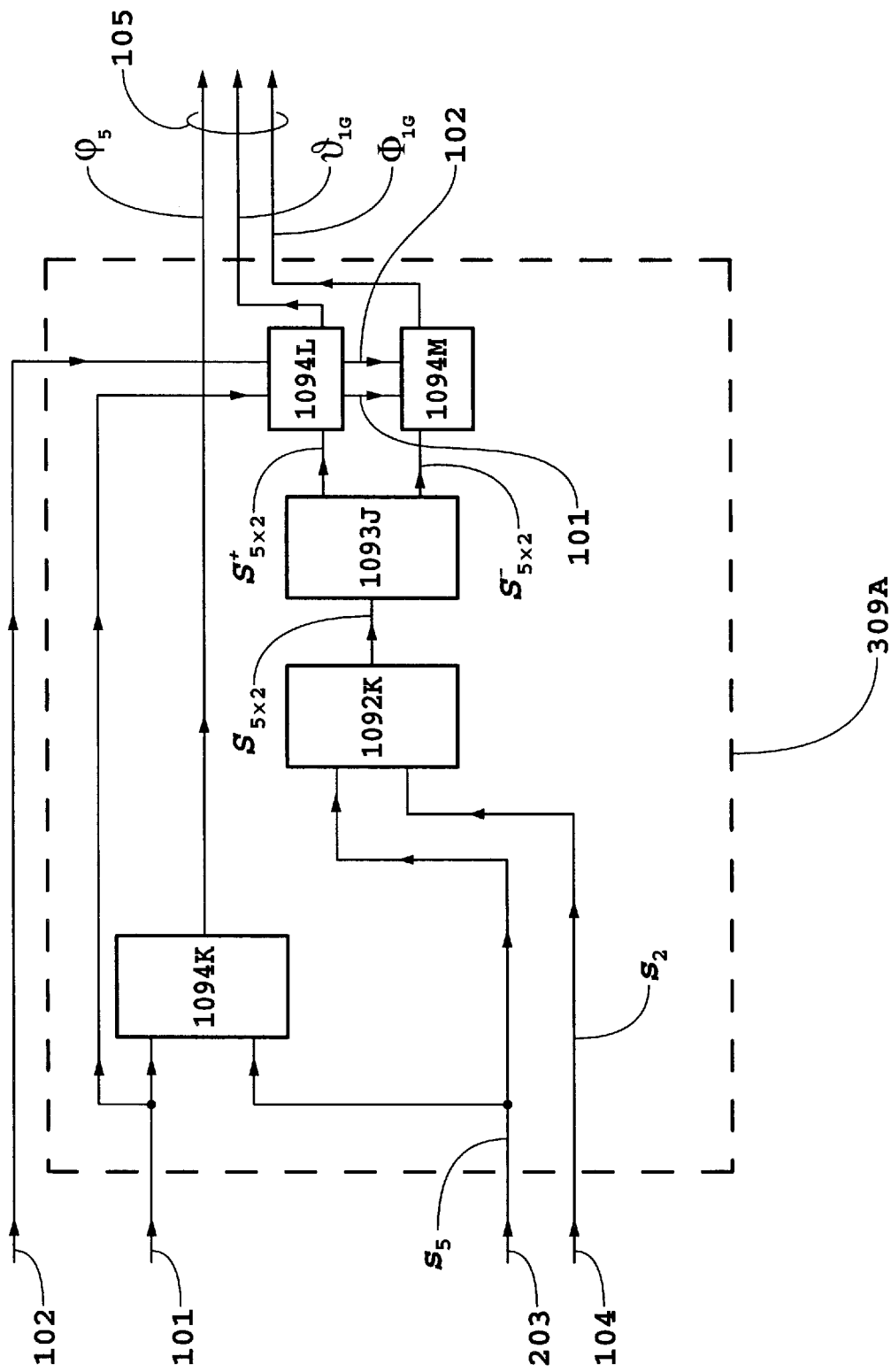

Referring to FIG. 3e, electronic processing means 309A preferably comprises means 1092K for electronically mixing the two heterodyne signals $s_5$ and $s_2$ to create a superheterodyne signal $S_{5\times 2}$ having the mathematical form $$S_{5\times 2}=S_5 S_2 \tag{112}$$

The superheterodyne signal $S_{5\times 2}$ is comprised of two sidebands with a suppressed carrier and may be rewritten as $$S_{5\times 2}=S_{5\times 2}{}^+ + S_{5\times 2}{}^- \tag{113}$$

where $$S_{5\times 2}{}^+ \frac{1}{2} A_5 A_2 \cos(2\pi vt+\theta_{1G}) \tag{114}$$

$$S_{5\times 2}{}^- \frac{1}{2} A_5 A_2 \cos(2\pi Ft+\Phi_{1G}) \tag{115}$$

and $$v=(f_1+f_2) \tag{116}$$

$$\theta_{1G}=(\phi_5+\phi_2) \tag{117}$$

$$F=(f_1-f_2) \tag{118}$$

$$\Phi_{1G}=(\phi_5-\phi_2) \tag{119}$$

The superheterodyne signal $S_{5\times 2}$ is therefore comprised of two sidebands, $S_{5\times 2}{}^+$ and $S_{5\times 2}{}^-$, of equal amplitude, one sideband with frequency $v$ and phase $\theta_{1G}$ and a second sideband with frequency F and phase $\Phi_{1G}$.

In a next step, the sidebands $S_{5\times 2}{}^+$ and $S_{5\times 2}{}^-$ are separated by electronic processor 1093J through high pass and low pass filtering or any of the like techniques for separating two signals that are separated in frequency. The frequency F of the lower frequency sideband of the superheterodyne signal can be very much smaller than the frequency $v$ of the higher frequency sideband of the superheterodyne signal as described in the corresponding portion of the discussion of the first embodiment, considerably simplifying the separating task of processor 1093I. Electronic processor 209A further comprises electronic processors 1094L and 1094M to determine the phases $\theta_{1G}$ and $\Phi_{1G}$, respectively, using time-based phase detection such as a digital Hilbert transform phase detector (see R. E. Best, ibid.; Oppenheim and Schafer, ibid.) or the like and the phases of the drivers 5 and 6.

Electronic processor 309A, and shown in FIG. 3e, is comprised of electronic processor 1094K to determine phase $\phi_5$ from heterodyne signal $s_5$ using time-based phase sensitive detection with reference signal 101 or the like. Phases $\phi_5$, $\theta_{1G}$, and $\Phi_{1G}$ are transmitted, in digital or analog format, preferably a digital format, to computer 110 as signal 105 for the calculation of $\Gamma$.

The reciprocal dispersive power $\Gamma$ of the gas defined by Eq. (23) can be expressed in terms of other quantities obtained in the variant of the third embodiment by formulae which correspond to Eqs. (108), (109), (110), and (111) with $$\phi_5 = \phi_{5 \times l1},$$

$$\phi_{f1} = 0, \ \phi_{f2} = 0,$$

$$l_1 = p_1, \ l_2 = p_2. \tag{120}$$

The remaining description of the variant of the third embodiment is the same as corresponding portions of the description given for the third embodiment of the present invention.

The principal advantage of the variant of the third embodiment is an option for the execution of critical electronic processing steps, such as the mixing of signals $s_5$ and $s_2$, which are also substantially identical, with a simplified electronic processing in relation to that of the first embodiment and variant thereof and of the second embodiment without the risk of possibly enhancing frequency sensitive phase offset errors due to differences in group delays experienced by heterodyne and/or modified heterodyne signals having significantly different frequencies. The discussion of the effects of group delay for the variant of the third embodiment is the same as corresponding portions of the description given for the third embodiment.

The second group of preferred embodiments of the present invention represent preferred modes for the determination of intrinsic optical properties such as r for a subsequent downstream use wherein the properties of the subsequent downstream use effects the choice of the particular manner in which the intrinsic optical properties are determined. An example of a downstream use with such properties is found in distance measuring interferometry wherein dispersion interferometry is used to obtain a measurement of $(n_2-n_1)$ as a proxy for the column density of a gas in a measuring path and using the measured value of $(n_2-n_1)$ for making a correction for the gas present in the measuring path.

The distinction between the first group of preferred embodiments and the second group of preferred embodiments with respect to $\Gamma$, for example, is in the particular manner in which the denominator $(n_2-n_1)$ is obtained for use in the calculation of $\Gamma$ according to Eq. (23). For the first group of preferred embodiments, a measurement of the respective denominator, $(n_2-n_1)_{1G}$, is obtained as a difference of two refractivities, $(n_2-1)$ and $(n_1-1)$ [cf. Eqs. (2)]. For the second group of preferred embodiments, the respective denominator, $(n^2-n_1)_{2G}$, is obtained as the difference of two measured indices of refraction $n_2$ and $n_1$. In distance measuring interferometry wherein dispersion interferometry is used to obtain as a proxy $(n_2-n_1)$ for the gas column density in a measuring path, the proxy, $(n^2-n_1)_{DMI}$, is also obtained as the difference of two measured indices of refraction $n_2$ and $n_1$. As a consequence, the measured ratio of $(n_2-n_1)_{DMI}$ and $(n_2-n_1)_{2G}$ is substantially independent of errors in measured values of wavelengths $\lambda_2$ and $\lambda_1$ for the lower spatial frequency components of $(n_2-n_1)$ whereas the measured ratio of $(n_2-n_1)_{DMI}$ and $(n_2-n_1)_{1G}$ in general is not independent of errors in measured values of wavelengths $\lambda_2$ and $\lambda_1$ for any part of the spectrum of spatial frequency components of $(n_2-n_1)$. The substantially null sensitivity of the measured ratio of $(n_2-n_1)_{DMI}$ and $(n^2-n_1)_{2G}$ to errors in measured values of $\lambda_2$ and $\lambda_1$ for the lower spatial frequency components of $(n_2-n_1)$ is discussed further in the description of the fourth preferred embodiment and can lead to a significant advantage in precision distance measuring interferometry such as required in micro-lithography.

Reference is now made to FIGS. 4a–4f which depict in diagrammatic form the fourth preferred embodiment of the present invention, from the second group of preferred embodiments, for measuring intrinsic optical properties of a gas, particularly its reciprocal dispersive power $\Gamma$, where the end use application effects the choice of the particular manner in which the intrinsic optical properties of the gas are determined and where the stability of the adopted light sources is sufficient and the ratio of the wavelengths of the light beams generated by the adopted light sources is matched to a known ratio value with a relative precision sufficient to meet the required precision imposed on the output data by the final end use application. The configuration of differential plane mirror interferometers in the fourth embodiment permits measurement of a refractivity $(n_1-1)$ for use as the numerator and a measurement of $(n_2-n_1)_{2G}$ equivalent to a measurement of $(n_2-n_1)$ as a difference of two measured indices of refraction $n_2$ and $n_1$ for use as the denominator of Eq. (23) in the calculation of $\Gamma$.

The description of the sources of light beams 9 and 10 and of light beams 9 and 10 for the fourth embodiment is the same as that for description of the sources of light beams 9 and 10 and of light beams 9 and 10 given for the first preferred embodiment.

Figure 4A:
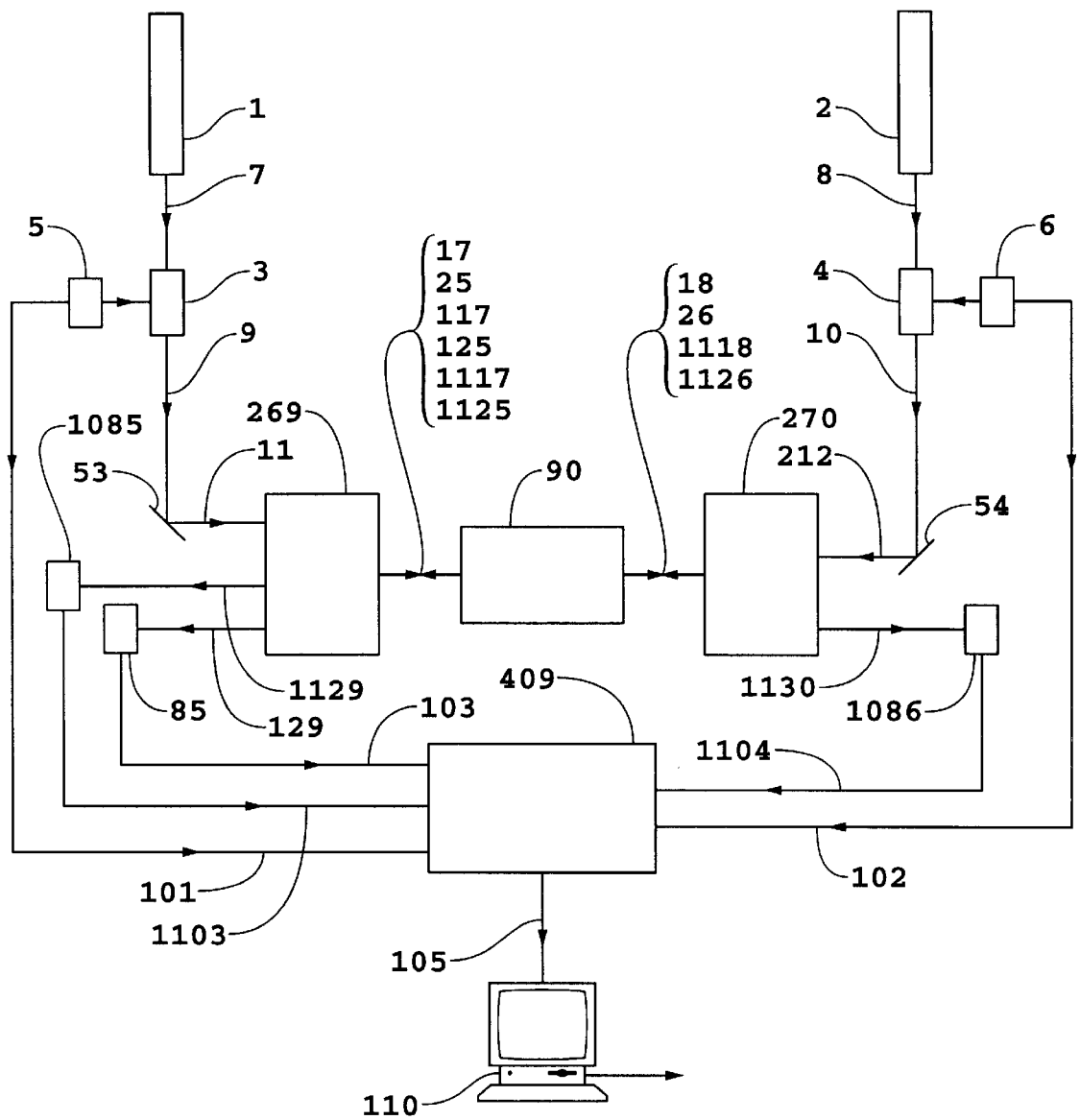
FIGS. 4a–4f taken together illustrate, in diagrammatic form, the presently preferred fourth embodiment of the present invention with FIG. 4a showing optical paths and the paths of electrical signals between indicated elements source 1, modulator 3, source 2, modulator 4, differential plane mirror interferometer group 269, differential plane mirror interferometer 270, measurement cell 90, detectors 85, 1085, and 1086, and the paths of electrical signals between indicated elements driver 5, modulator 3, driver 6, modulator 4, detectors 85, 1085, and 1086, electronic processor 409, and computer 110.

Referring to FIG. 4a, beam 9 is reflected by mirror 53 becoming beam 11. Beam 10 is reflected by a mirror 54 as beam 212. Beam 11 is incident on differential plane mirror interferometer group 269 and beam 212 is incident on differential plane mirror interferometer 270. Differential plane mirror interferometer group 269 and differential plane mirror interferometer 270 with external mirrors furnished by measurement cell 90 comprise interferometric means for introducing a phase shift $\phi_1$ between a first portion of the x and y components of beam 11, a phase shift $\phi_6$ between a second portion of the x and y components of beam 11, and a phase shift $\phi_7$ between the x and y components of beam 212.

Figure 4B:
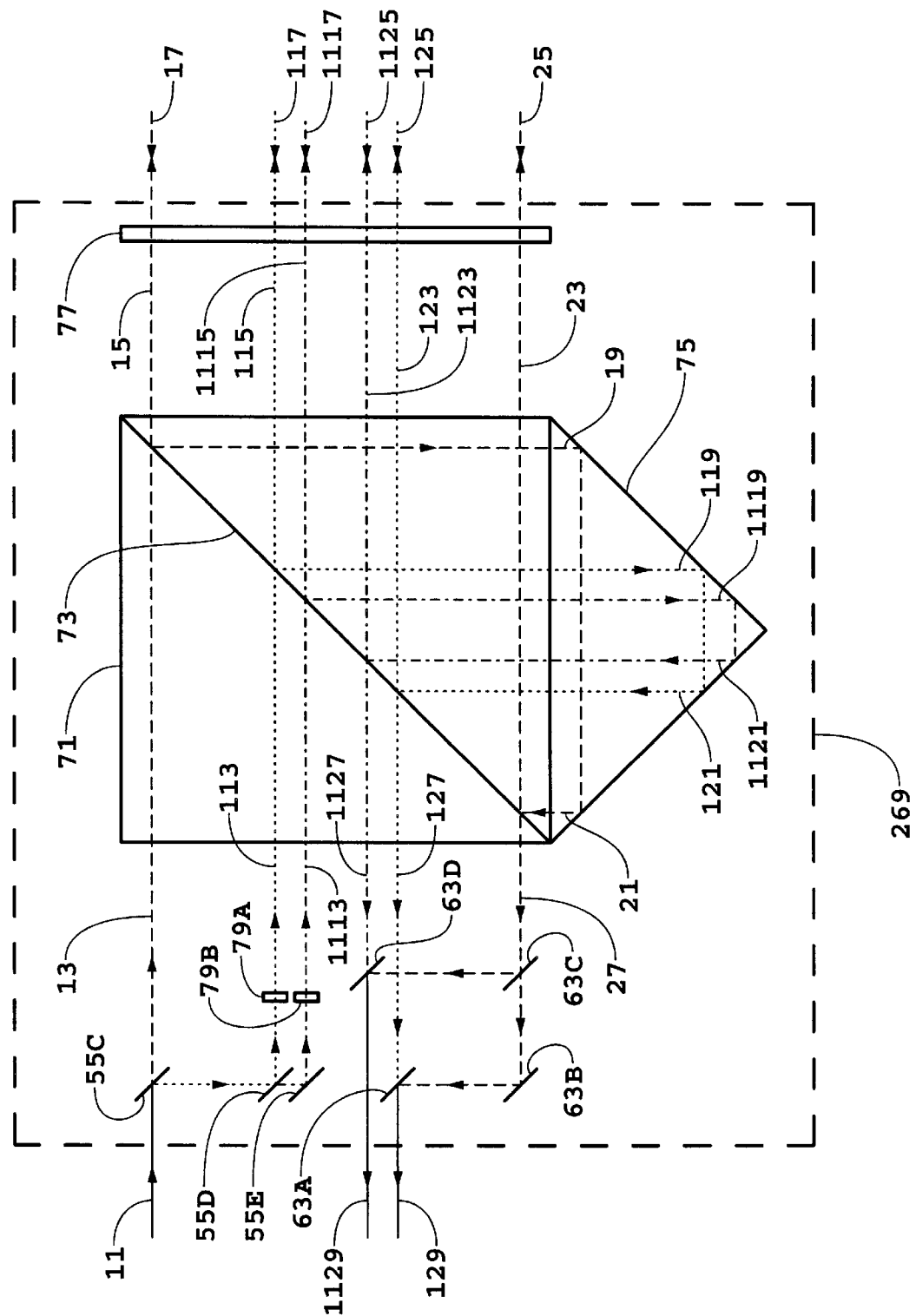

Referring to FIG. 4b, a portion of beam 11 is transmitted by beam splitter 55A, preferably a polarizing type, as beam 13 and a second portion of beam 11 is reflected by beam splitter 55A which impinges on beam splitter 55C, preferably a nonpolarizing type. A first portion of the second portion of beam 11 is reflected by beam splitter 55C and than transmitted by half-wave phase retardation plate 79 as beam 113. A second portion of the second portion of beam 11 is transmitted by beam splitter 55C, reflected by mirror 55D, and than transmitted by half-wave phase retardation plate 79 as beam 1113. The half-wave phase retardation plate 79 is orientated so as to rotate the planes of polarizations of the first and second portions of the second portion of beam 11 by 90 degrees so that beams 13, 113, and 1113 have the same polarizations. However, beam 13 has a frequency different from the frequencies of beams 113 and 1113, the frequencies of beams 113 and 1113 being the same. Beams for which the first frequency component of beam 11 is the sole progenitor are indicated in FIG. 4b by dashed lines and beams for which the second frequency component of beam 11 is the sole progenitor are indicated in FIG. 4b either by dotted lines or by lines of alternating dots and dashes.

Differential plane mirror interferometer group 269 comprises many of the same elements as differential plane mirror interferometer 69 of the first embodiment, like numbered elements in the two differential plane mirror interferometers performing like functions. Many of the beams shown in FIG. 4b for differential plane mirror interferometer group 269 have the same properties as beams shown in FIG. 1b for differential plane mirror interferometer 69, like numbered beams in the two differential plane mirror interferometers having like properties. Further, the beams shown in FIG. 4b for differential plane mirror interferometer group 269 with numbers of (1000+N) have the same properties as beams with numbers N shown in FIG. 1b for differential plane mirror interferometer 69 except for the lengths of the corresponding reference paths in the vacuum path 98 have nominal values of zero (cf. FIG. 4d). Beams 27, 127, and 1127 created by differential plane mirror interferometer 269 and measurement cell 90 (cf. FIG. 4b) contain information at wavelength $\lambda_1$ about the optical path length through the gas whose reciprocal dispersive power is to be determined, about the optical path length through a vacuum, and about an optical path length of zero length, respectively.

With reference to FIG. 4b, a first portion of beam 27 is transmitted by beam splitter 63C, preferably a nonpolarizing type, and reflected by mirror 63B and a portion of the first portion of beam 27 is reflected by beamsplitter 63A, preferably a nonpolarizing type, to become one component of beam 129. A portion of beam 127 is transmitted by beam splitter 63A to become a second component of beam 129. Beam 129 exits differential plane mirror interferometer group 269 as a mixed beam, the first and second components of beam 129 having the same linear polarizations with different frequencies. A second portion of beam 27 is reflected by beam splitter 63C and a portion of the second portion of beam 27 is reflected by beamsplitter 63D, preferably a nonpolarizing type, to become one component of beam 1129. A portion of beam 1127 is transmitted by beam splitter 63D to become a second component of beam 1129. Beam 1129 exits differential plane mirror interferometer group 269 as a mixed beam, the first and second components of beam 1129 having the same linear polarizations with different frequencies.

Figure 4C:
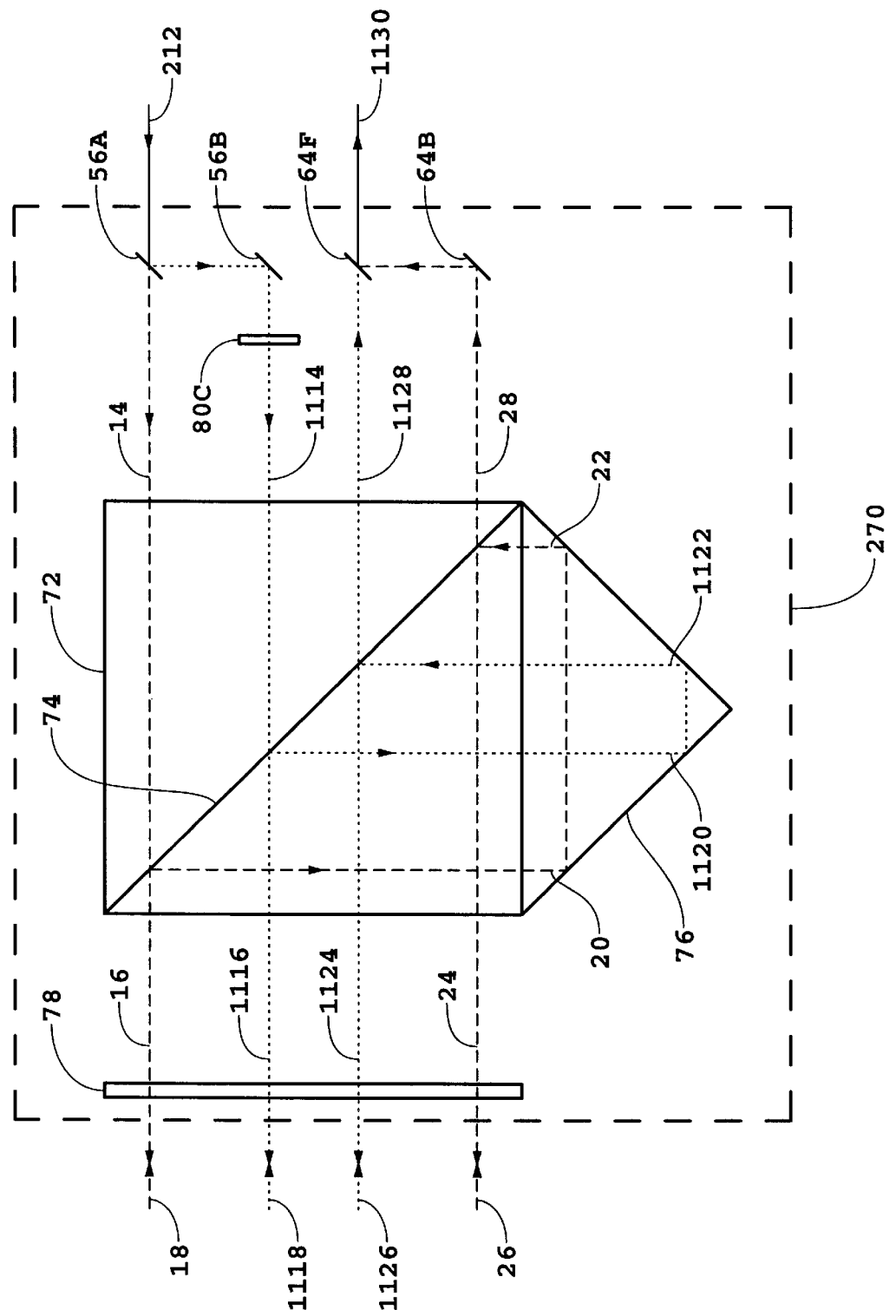

Differential plane mirror interferometer 270 shown in FIG. 4c comprises many of the same elements as differential plane mirror interferometer 70 of the first embodiment, like numbered elements of the two differential plane mirror interferometers performing like functions. Many of the beams shown in FIG. 4c for differential plane mirror interferometer 270 have the same properties as beams shown in FIG. 1c for differential plane mirror interferometer 70, like numbered beams of the two differential plane mirror interferometers having like properties. Further, the beams shown in FIG. 4c for differential plane mirror interferometer 270 with numbers of (1000+N) have the same properties as beams with numbers N shown in FIG. 1c for differential plane mirror interferometer 70 except for the lengths of the corresponding reference paths in vacuum path 98 have nominal values of zero. Beams 28 and 1128 created by differential plane mirror interferometer 270 and measurement cell 90 contain information at wavelength $\lambda_2$ about the optical path length through the gas whose reciprocal dispersive power is to be determined and about a reference path with an optical path length of zero length, respectively.

With reference to FIG. 4c, beam 28 is reflected by mirror 64B and a portion of beam 28 reflected by beam splitter 64A, preferably a nonpolarizing type, to become one component of beam 1130. A portion of beam 1128 is transmitted by beam splitter 64A to become a second component of beam 1130. Beam 1130 exits differential plane mirror interferometer 270 as a mixed beam, the first and second components of beam 1130 having the same linear polarizations with different frequencies.

Figure 4D:
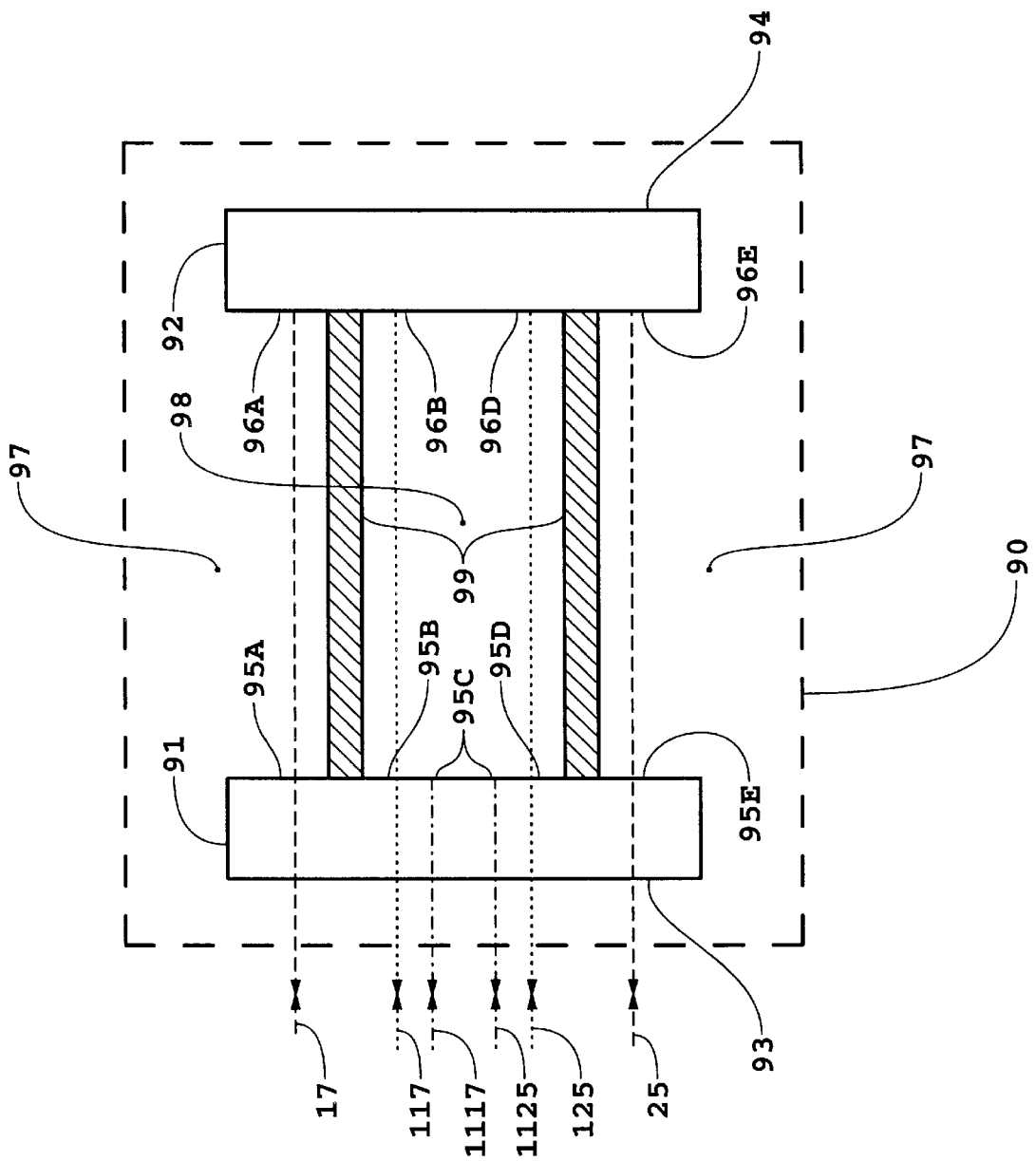
Figure 4E:
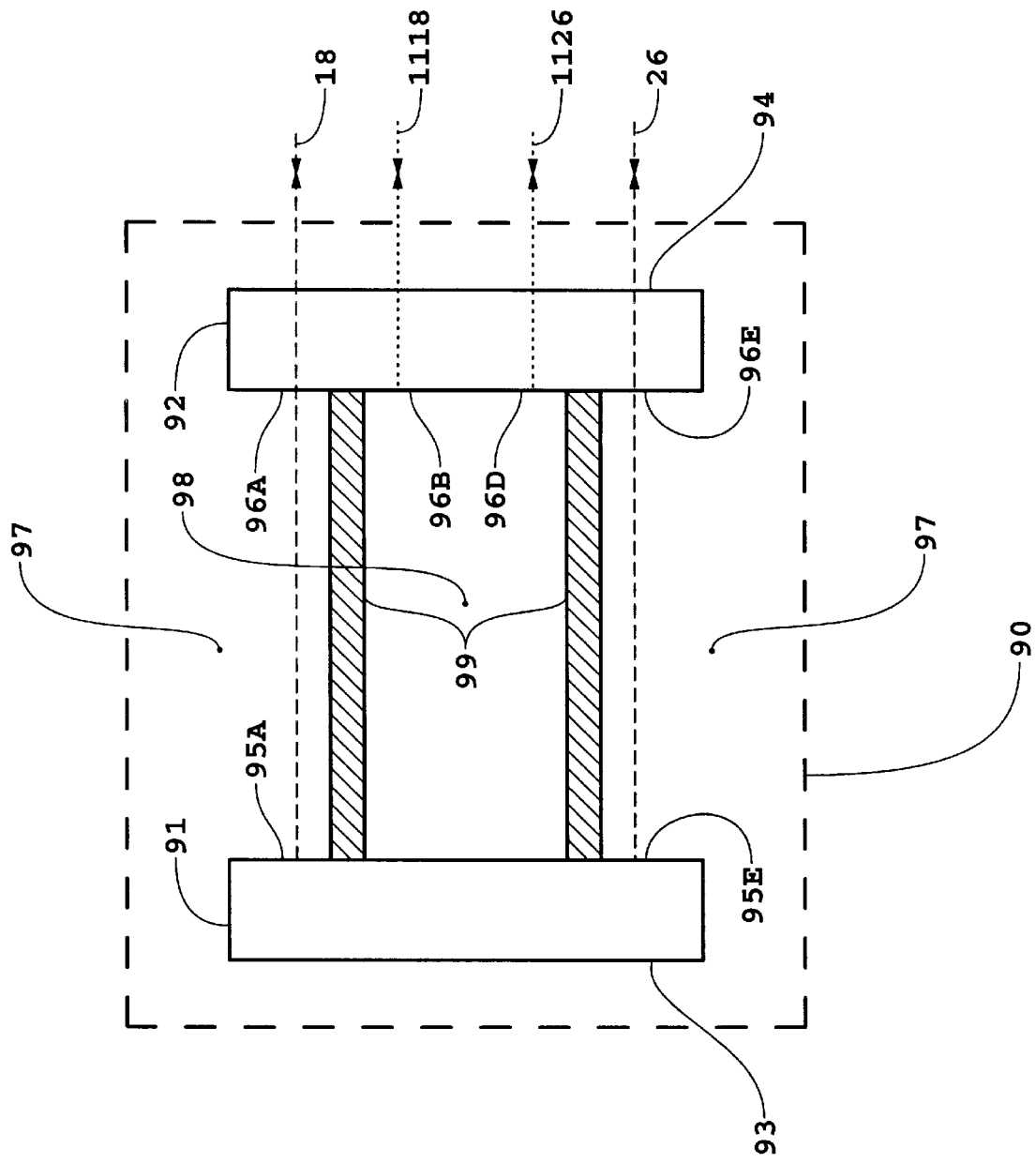

The magnitude of phase shifts $\phi_1$, $\phi_6$, and $\phi_7$ are related to the $L_i$ the round-trip physical length of path i of measurement path 97, reference path 98, or a reference path of zero physical length as shown in FIG. 4d according to the formulae $$\varphi_1 = \sum_{i=1}^{i=p} k_1(L_{G,i}n_{1i} - L_{V,i}) + \zeta_1 \tag{121}$$

$$\varphi_6 = \sum_{i=1}^{i=p} k_1 L_{G,i} n_{1i} + \zeta_6,$$

$$\varphi_7 = \sum_{i=1}^{i=p} k_2 L_{G,i} n_{2i} + \zeta_7,$$

where the index of refraction in the reference path 98 has been set to 1. The illustrations in FIGS. 4b and 4c are for p=2 so as to illustrate in the simplest manner the function of the invention in the fourth embodiment. To those skilled in the art, the generalization to the case when p≠2 is a straight forward procedure.

Cyclic errors that produce nonlinearities in distance measuring interferometry (cf. the cited articles by Bobroff) have been omitted in Eqs. (121). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

In a next step as shown in FIG. 4a, phase-shifted beams 129, 1129, and 1130 impinge upon photodetectors 85, 1085, and 1186, respectively, resulting in three interference signals, heterodyne signals $s_1$, $s_6$, and $s_7$, respectively, preferably by photoelectric detection. The signals $s_1$ and $s_6$ correspond to wavelength $\lambda_1$ and signal 57 corresponds to wavelength $\lambda_2$. The signals $s_j$ have the form $$s_j = A_j \cos[\alpha_j(t)], \ j=1, \ 6, \ \text{and} \ 7 \tag{122}$$

where the time-dependent arguments $\alpha_j(t)$ are given by $$\alpha_1(t) = 2\pi f_1 t + \phi_1,$$

$$\alpha_6(t) = 2\pi f_1 t + \phi_6,$$

$$\alpha_7(t) = 2\pi f_2 t + \phi_7 \tag{123}$$

Heterodyne signals $s_1$, $s_6$, and $s_7$ are transmitted to electronic processor 409 for analysis as electronic signals 103, 1103, and 1104, respectively, in either digital or analog format, preferably in digital format.

The phases of drivers 5 and 6 are transmitted by electrical signals, reference signals 101 and 102, respectively, preferably in either digital format, to electronic processor 409.

A preferred method for electronically processing the heterodyne signals $s_1$, $s_6$, and $s_7$ is presented herewithin for the case when $l_1$ and $l_2$ are not low order integers. For the case when $l_1$ and $l_2$ are low order integers and the ratio of the wavelengths matched to the known ratio $(l_1/l_2)$ with a relative precision sufficient to meet the required precision imposed on the output data by the end use application, the preferred procedure for electronically processing the heterodyne signals $s_1$, $s_6$, and $s_7$ is the same as the one subsequently set down for the variant of the fourth preferred embodiment of the present invention.

The phases $\phi_1$, $\phi_6$, and $\phi_7$ of signals $s_1$, $s_6$, and $s_7$, respectively, are obtained preferably by application of superheterodyne receiver techniques wherein the frequencies of signals $s_1$, $s_6$, and $s_7$ are shifted to frequencies substantially lower than respective frequencies $f_1$ and $f_2$ [cf. Eqs. (123)] where conditions are generally more favorable for high precision phase measurements.

Figure 4F:
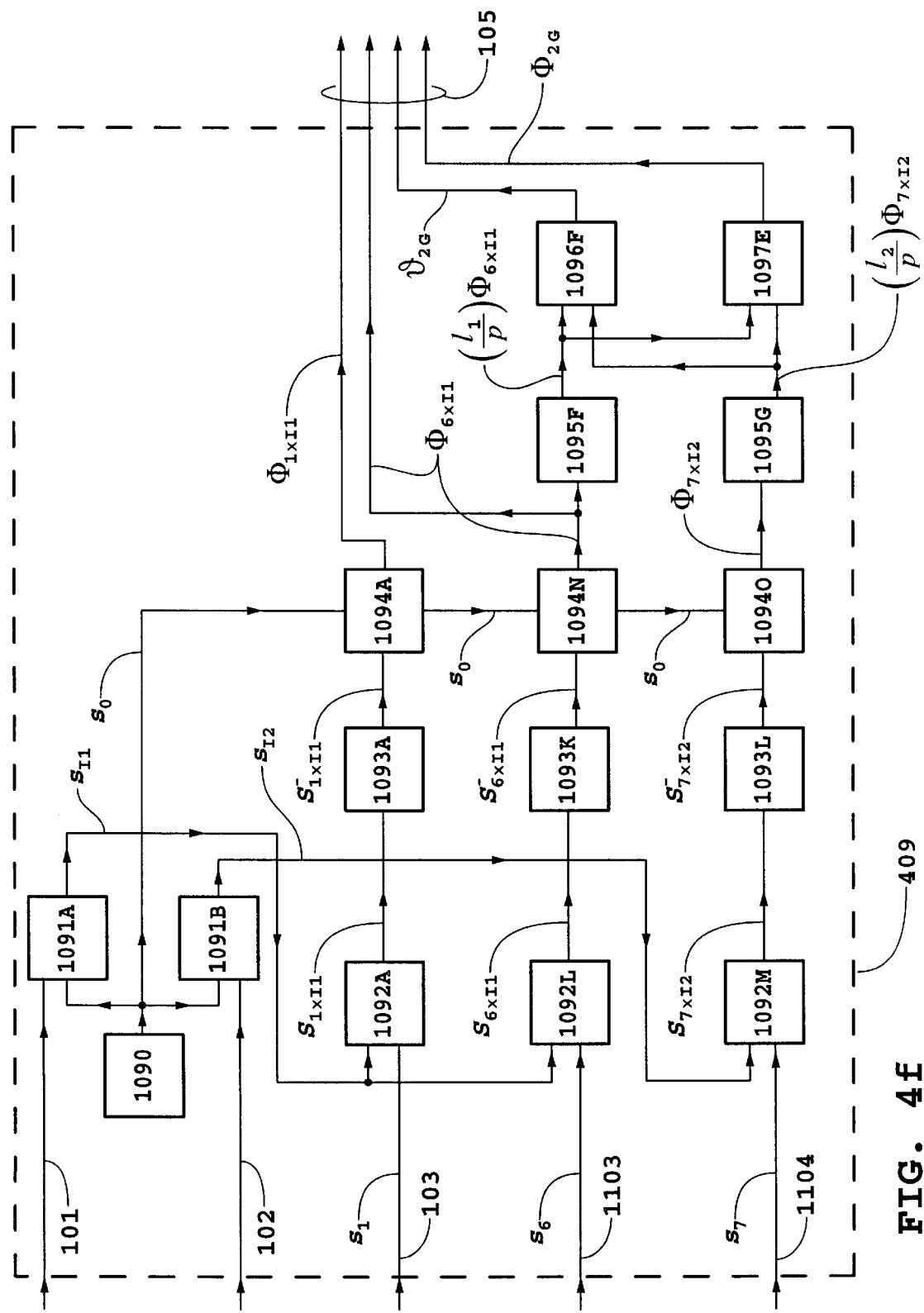

Referring now to FIG. 4f, electronic processor 409 preferably comprises alphameric numbered elements wherein the numeric component of the alphameric numbers indicate the function of an element, the same numeric component/function association as described for the electronic processing elements of the first embodiment depicted in FIG. 1f. The heterodyne signals $s_1$ and $s_6$ of the fourth embodiment are each processed by the same sequence of electronic processing steps as signal $s_1$ of the first embodiment and $s_7$ of the fourth embodiment is processed by the same sequence of electronic processing steps as signal $s_2$ of the first embodiment. The results of that analysis as indicated in FIG. 4f are phases $$\Phi_{1 \times I1} = \phi_1 - \phi_{f1}$$

$$\Phi_{6 \times I1} = \phi_6 - \phi_{f1}$$

$$\Phi_{7 \times I2} = \phi_7 - \phi_{f2} \tag{124}$$

where $\phi_{f1}$ and $\phi_{f2}$ are defined in Eqs. (5).

Subsequently, the phases $\Phi_{6 \times I1}$ and $\Phi_{7 \times I2}$ are multiplied by $(l_1/p)$ and $(l_2/p)$, respectively, in electronic processors 1095F and 1095G, respectively. Next, the phases $(l_1/p)\Phi_{6 \times I1}$ and $(l_2/p)\Phi_{7 \times I2}$ are added together in electronic processor 1096F and subtracted one from the other in electronic processor 1097E, by analog or digital processes, preferably digital processes, to create the phases $\theta_{2G}$ and $\Theta_{2G}$, respectively. Formally, $$\vartheta_{2G} = \left(\frac{l_1}{p}\Phi_{6 \times I1} + \frac{l_2}{p}\Phi_{7 \times I2}\right) \tag{125}$$

$$\Phi_{2G} = \left(\frac{l_1}{p}\Phi_{6 \times I1} - \frac{l_2}{p}\Phi_{7 \times I2}\right) \tag{126}$$

Note from Eqs. (125) and (126) that $\theta_{2G}$ and $\Phi_{2G}$ are not sensitive to tilts of either reflecting surfaces 95 or 96 of measurement cell 90 and insensitive to thermal and mechanical disturbances that may occur in the interferometer beam splitting cubes and associated optical components as a consequence of the use of differential plane mirror interferometers.

The refractivity $(n_1-1)$, the dispersion $(n_2-n_1)_{2G}$, and the wavenumber $k_1$ can be expressed in terms of other quantities obtained with the fourth embodiment by the formulae $$(n_1 - 1) = \frac{1}{(\chi + K)L_G}\left(\frac{l_1}{p_1}\right)[\Phi_{5 \times I1} - (\zeta_5 - \varphi_{I1})] - \frac{(L_G - L_V)}{L_G} \tag{127}$$

-continued $$(n_2 - n_1)_{1G} = \tag{128}$$

$$\frac{1}{\chi L_G[1 - (K/\chi)^2]}\{[\vartheta_{2G}(K/\chi) - \Phi_{2G}] - [\xi(K/\chi) - Z]\}$$

$$k_1 = \frac{1}{pL_V}[(\Phi_{6 \times I1} - \Phi_{1 \times I1}) - (\zeta_6 - \zeta_1)] \tag{129}$$

where $\chi$ and $K$ are given by Eqs. (26) and (27), respectively, and $\xi$ and $Z$ are given by $$\xi = \frac{l_1}{p}(\zeta_6 - \varphi_{I1}) + \frac{l_2}{p}(\zeta_7 - \varphi_{I2}) \tag{130}$$

$$Z = \frac{l_1}{p}(\zeta_6 - \varphi_{I1}) - \frac{l_2}{p}(\zeta_7 - \varphi_{I2}). \tag{131}$$

Eq. (128) is valid for the case where the paths for the two different wavelengths are substantially coextensive, a case chosen to illustrate in the simplest manner the function of the invention in the second embodiment. To those skilled in the art, the generalization to the case where paths for the two different wavelengths are not substantially coextensive is a straight forward procedure.

The ratio $(\lambda_1/\lambda_2)$ can be expressed from Eqs. (26) and (27) in terms of $(K/\chi)$ with the same result as given in Eq. (30). When operating under the condition $$|K/\chi| \ll \frac{(n_2 - n_1)}{(n_2 + n_1)} \tag{132}$$

the ratio of the phases $\Phi_{2G}$ and $\theta_{2G}$ has the approximate value $$(\Phi_{2G}/\vartheta_{2G}) \cong -\frac{(n_2 - n_1)}{(n_2 + n_1)} \tag{133}$$

Therefore, for the case where the ratio $(\lambda_1/\lambda_2)$ is the same as the known ratio $(l_1/l_2)$ to a relative precision of an order of magnitude or more less than the dispersion of the index of refraction of the gas, $(n_2-n_1)$, times the relative precision s desired for the measurement of the reciprocal dispersive power $\Gamma$, Eq. (128) reduces to the more simple form $$(n_2 - n_1)_{2G} = \frac{1}{\chi L_G}(-\Phi_{2G} + Z) \tag{134}$$

The condition on the wavelengths $\lambda_1$ and $\lambda_2$ which leads to Eq. (134) expressed as an equation is $$\left|\frac{\lambda_2}{\lambda_1} - \frac{l_2}{l_1}\right| \ll \left(\frac{l_2}{l_1}\right)(n_2 - n_1)\varepsilon. \tag{135}$$

Eq. (135) represents a tighter restriction on acceptable departures of the ratio of the wavelengths from the known ratio $(l_2/l_1)$ as compared to the corresponding restriction for the first group of preferred embodiments expressed by Eq. (34). The basis for the tighter restriction is evident from examination of Eqs. (32) and (133) wherein a $\Gamma$ obtained by the first group of preferred embodiments is less sensitive to an error in $(K/\chi)$ relative to a $\Gamma$ obtained by the fourth embodiment, a representative of the second group of preferred embodiments, by a factor equal to the ratio $(\Phi_{2B}/\theta_{2G})/(\Phi_{1G}/\theta_{1G})$ where $$\frac{(\Phi_{2G}/\vartheta_{2G})}{(\Phi_{1G}/\vartheta_{1G})} = (2\Gamma+1)\frac{(n_2-n_1)}{(n_2+n_1)} \quad (136)$$

$$\cong (n_1-1).$$

Thus the first group of preferred embodiments are the preferred group of embodiments in relation to the fourth embodiment for a determination of the reciprocal dispersive power $\Gamma$ with respect to sensitivity of the end use result to errors in $(K/\chi)$.

It was noted in the introductory paragraphs to the second group of preferred embodiments that when the end use application is in distance measuring interferometry wherein dispersion interferometry is used to obtain a measurement of $(n_2-n_1)$ as a proxy for the column density of a gas in a measuring path and using the measured value of $(n_2-n_1)$ for making a correction for the gas present in the measuring path, the fourth embodiment is preferred over the embodiments of the first group of preferred embodiments for the determination of $\Gamma$. The basis for the preceding statement follows from the properties expressed by Eqs. (32) and (133). The sensitivity of the ratio of $(n^2-n_1)_{DMI}$ and $(n_2-n_1)_{1G}$, to errors in $(K/\chi)$ is the same as expressed by Eq. (136). In contrast, the sensitivities of $(n_2-n_1)_{DMI}$ and $(n_2-n_1)_{2G}$, as obtained by the fourth embodiment, to errors in $(K/\chi)$ are substantially the same. As a consequence, the net sensitivity of the ratio of $(n_2-n_1)_{DMI}$ and $(n_2-n_1)_{2G}$, as obtained by the fourth embodiment, to errors in $(K/\chi)$ can be substantially reduced compared to the corresponding sensitivity of the ratio of $(n^2-n_1)_{DMI}$ and $(n_2-n_1)_{1G}$ to errors in $(K/\chi)$. To the extent that the net sensitivity of the ratio of $(n^2-n_1)_{DMI}$ and $(n_2-n_1)_{2G}$, as obtained by the fourth embodiment, to errors in $(K/\chi)$ is reduced to a value less than the corresponding sensitivity of the ratio of $(n^2-n)_{DMI}$ and $(n_2-n_1)_{1G}$ to errors in $(K/\chi)$, the second group of preferred embodiments is the preferred embodiment for the determination of $\Gamma$.

The degree of reduced net sensitivity of the ratio of $(n_2-n_1)_{DMI}$ and $(n_2-n_1)_{2G}$, as obtained by the fourth embodiment, to errors in $(K/\chi)$ will depend on the degree to which $(n^2-n_1)_{DMI}$ and $(n_2-n_1)_{2G}$ are spatially correlated, i.e. the greater the correlation, the greater the reduction of net sensitivity. For the lower spatial frequency components of $(n_2-n_1)$, the cross correlation coefficient between $(n^2-n^1)_{DMI}$ and $(n_2-n_1)_{2G}$ will be substantially one. The spatial frequency beyond which the cross correlation coefficient between $(n^2-n_1)_{DMI}$ and $(n_2-n_1)_{2G}$ will significantly deviate from the maximum value of one will be a function of the spatial separation of the apparatus of the distance measuring/dispersion interferometry and the apparatus of the fourth embodiment.

It will be evident to those skilled in the art that the condition on the wavelengths $\lambda_1$ and $\lambda_2$ as expressed Eq. (135) for the fourth embodiment will be relaxed by a factor related to one minus the cross correlation coefficient between $(n^2-n_1)_{DMI}$ and $(n_2-n^1)_{2G}$ for the end use application of distance measuring interferometry wherein dispersion interferometry is used to obtain a measurement of $(n_2-n_1)$ as a proxy for the column density of a gas in a measuring path and the measured value of $(n_2-n_1)$ is used for making a correction for the gas present in the measuring path.

In a next step, electronic processing means 409 transmits to the computer 110 $\Phi_{1\times I1}$, $\Phi_{6\times I1}$, $\theta_{2G}$, and $\Phi_{2G}$ as electronic signal 105, preferably in digital format, for the computation of $\Gamma$ according to Eq. (23) and Eqs. (127), (128), and (129) and the calculation of $k_1$ if required, substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The remaining description of the fourth embodiment is the same as corresponding portions of the description given for the first embodiment of the present invention.

Reference is now made to FIGS. 4a–4e and 4g which taken together depict in diagrammatic form a variant of the fourth preferred embodiment of the present invention for measuring intrinsic optical properties of a gas, particularly its reciprocal dispersive power where the end use application effects the choice of the particular manner in which the intrinsic optical properties of the gas are determined and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the fourth embodiment in which ratio $(l_1/l_2)$ is expressible as the ratio of low order non-zero integers $(p_1/p_2)$, cf. Eq. (35).

The description of the sources of light beams 9 and 10 and of light beams 9 and 10 for the variant of the fourth embodiment is the same as that for description of the sources of light beams 9 and 10 and of light beams 9 and 10 given for the first embodiment with the additional requirement that the wavelengths be harmonically related to a relative precision sufficient to meet required precision imposed on the output data by the final end use application. The description of the apparatus for the variant of the fourth embodiment depicted in FIGS. 4a–4e is the same as corresponding portions of the description given for the fourth embodiment.

The phase information contained in phases $\phi_1$, $\phi_6$, and $\phi_7$ is obtained in the variant of the fourth embodiment preferably through the creation of a superheterodyne signal wherein the frequency of the superheterodyne signal is at a frequency much lower than $f_1$ and $f_2$ where it is general possible to make more accurate phase measurements.

Figure 4G:
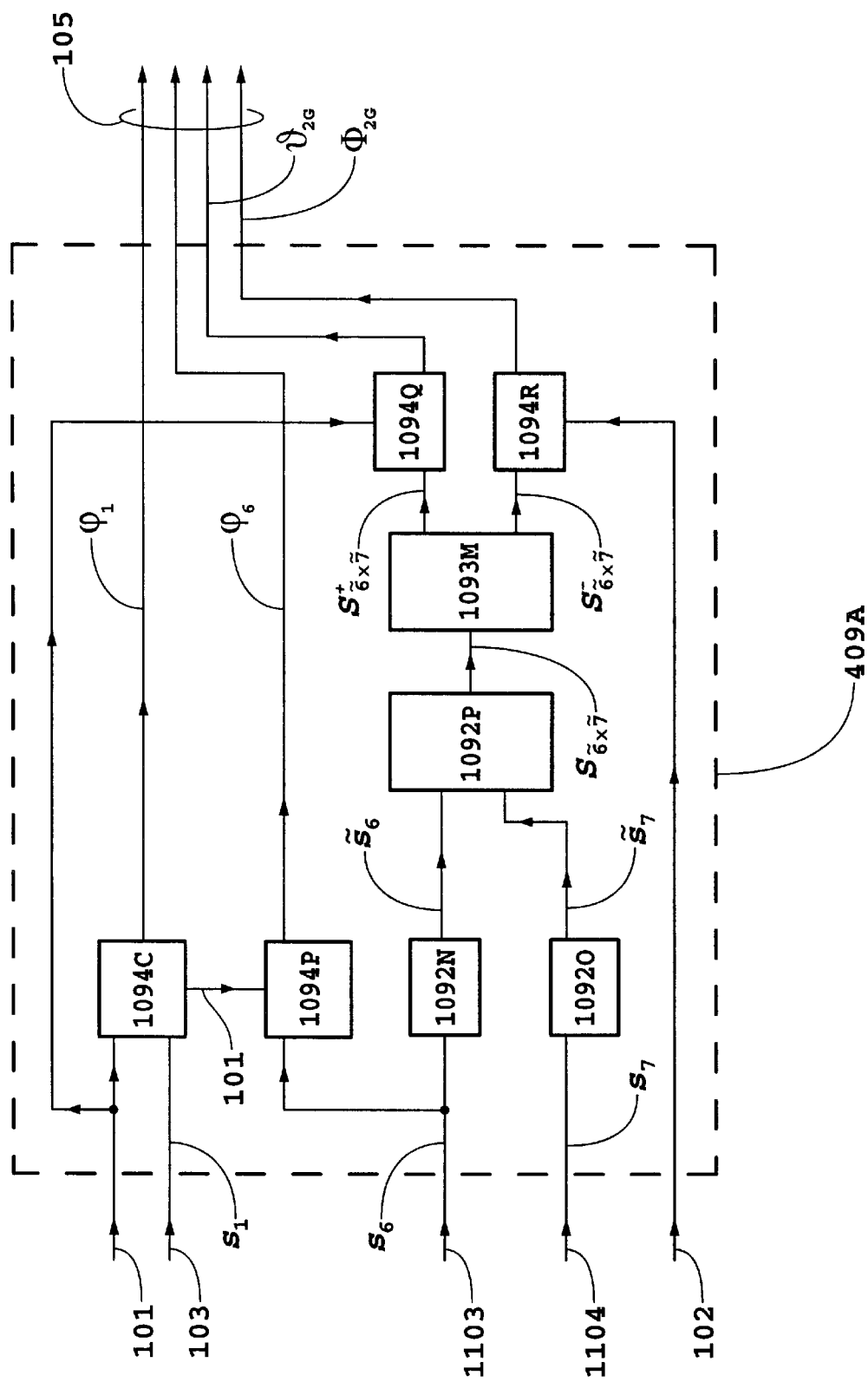

Referring now to FIG. 4g, and in accordance with the preferred method of the variant of the fourth embodiment, electronic processor 409A preferably comprises alphameric numbered elements wherein the numeric component of the alphameric numbers indicate the function of an element, the same numeric component/function association as described for the electronic processing elements of the first embodiment depicted in FIG. 1f. As depicted in FIG. 4g, the heterodyne signals $s_1$ and $s_6$ of the variant of the fourth embodiment are each processed by the same sequence of electronic processing steps as signal $s_1$ of the variant of the first embodiment and $s_6$ and $s_7$ of the variant of the fourth embodiment are processed by the same sequence of electronic processing steps as signal $s_2$ of the variant of the first embodiment, there being two separate sequences of electronic processing steps for $s_6$. The results of that analysis are $\phi_1$, $\phi_6$, $\theta_{2G}$, and $\Phi_{2G}$ where $$\theta_{2G}=(p_1\phi_6+p_2\phi_7) \quad (137)$$

$$\Phi_{2G}=(p_1\phi_6-p_2\phi_7) \quad (138)$$

$\underline{v}$ and $\underline{F}$ are given by Eqs. (53) and (55), respectively.

In a next step, $\phi_1$, $\phi_6$, $\theta_{2G}$, and $\Phi_{2G}$ are transmitted, preferably in digital format, to computer 110 for computation of the refractivity $(n_1-1)$, dispersion $(n_2-n_1)_{2G}$, $\Gamma$, and/or $k_1$. The quantities $\phi_1$, $\phi_6$, $p\theta_{2G}$, $p\Phi_{2G}$, $p\underline{\xi}$, and $p\underline{Z}$ of the variant of the fourth embodiment are formally equivalent to $\Phi_{1\times I1}$, $\Phi_{6\times I1}$, $\theta_{2G}$, $\Phi_{2G}$, $\underline{\xi}$, and $\underline{Z}$, respectively, of the fourth embodiment with $\Phi_{f1}$ and $\Phi_{f2}$ set equal to zero, $l_1=p_1$, and $l_2=p_2$. Thus, the refractivity $(n_1-1)$, dispersion $(n_2-n_1)_{2G}$, and $k_1$ can be expressed in terms of the quantities measured by the variant of the fourth embodiment with Eqs. (127), (128), and (129), respectively, using the relationships cited in this paragraph, $\chi$ and K given by Eqs. (26) and (27), respectively, $\phi_{f1}$ and $\phi_{f2}$ set equal to zero, $l_1=p_1$, and $l_2=p_2$. The remaining description of the variant of the fourth embodiment is the same as corresponding portions of the descriptions given for the fourth embodiment.

Reference is now made to FIGS. 5a–5d which depict in diagrammatic form the fifth preferred embodiment of the present invention from the second group of preferred embodiments for measuring intrinsic optical properties of a gas, particularly its reciprocal dispersive power $\Gamma$, where the end use application effects the choice of the particular manner in which the intrinsic optical properties of the gas are determined and where the stability of the adopted light sources is sufficient and the ratio of the wavelengths of the light beams generated by the adopted light sources is matched to a known ratio value with a relative precision sufficient to meet the required precision imposed on the output data by the final end use application. The configuration of differential plane mirror interferometers in the fifth embodiment permits measurement of a refractivity $(n_1-1)$ for use as the numerator and a measurement of $(n_2-n_1)_{2G}$ equivalent to a measurement of $(n_2-n_1)$ as a difference of two measured indices of refraction $n_2$ and $n_1$ for use as the denominator of Eq. (23) in the calculation of $\Gamma$.

The description of the sources of light beams 9 and 10 and of light beams 9 and 10 for the fifth embodiment is the same as that for description of the sources of light beams 9 and 10 and of light beams 9 and 10 given for the second preferred embodiment.

Figure 5A:
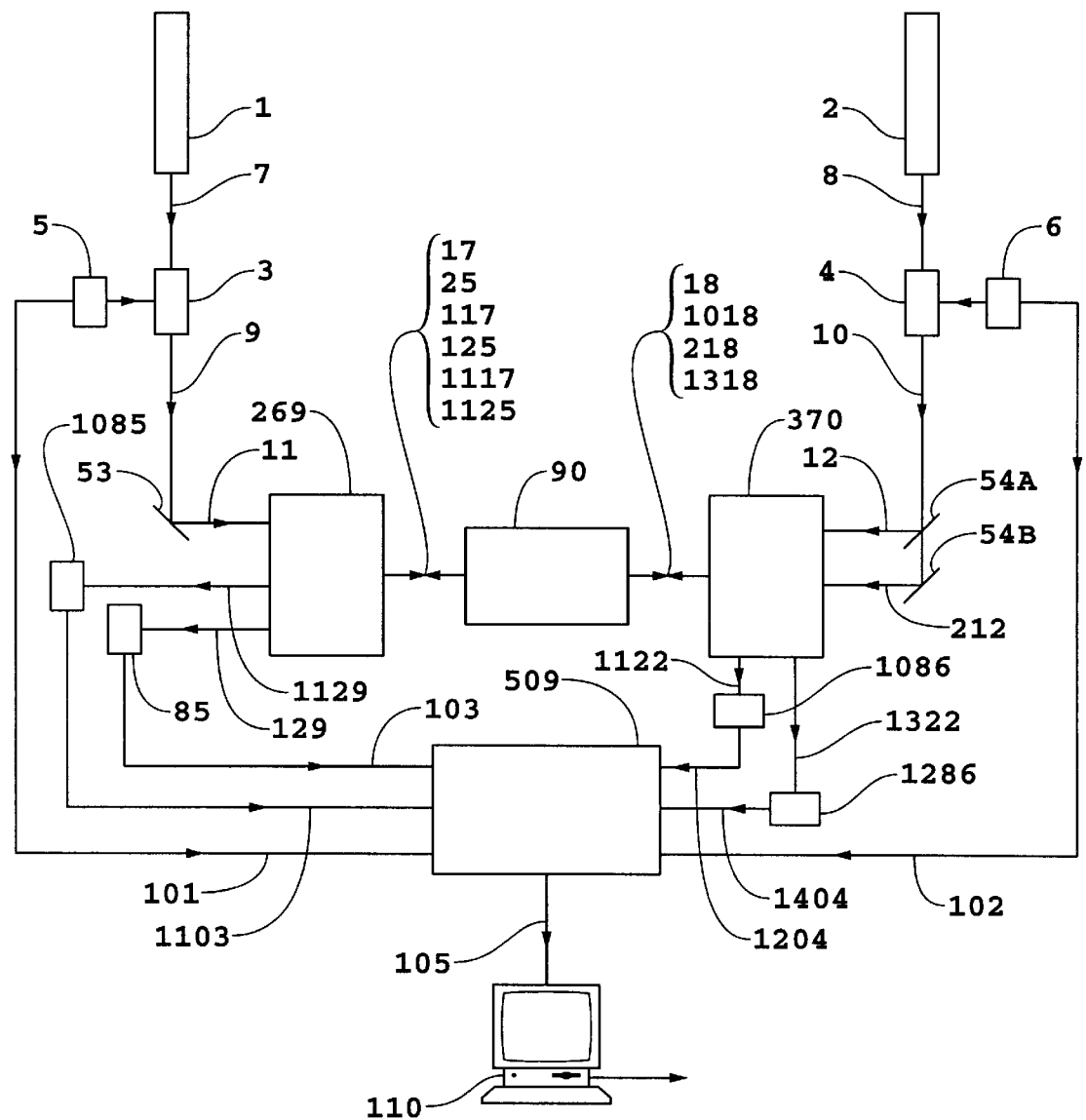
FIGS. 5a–5d taken together illustrate, in diagrammatic form, the presently preferred fifth embodiment of the present invention with FIG. 5a showing optical paths and the paths of electrical signals between indicated elements source 1, modulator 3, source 2, modulator 4, differential plane mirror interferometer groups 269 and 370, measurement cell 90, detectors 85, 1085, 1086, and 1286, and the paths of electrical signals between indicated elements driver 5, modulator 3, driver modulator 4, detectors 85, 1085, 1086, and 1286, electronic processor 509, and computer 110.

Referring to FIG. 5a, beam 9 is reflected by mirror 53 becoming beam 11. A portion of beam 10 is reflected by beam splitter 54A, preferably a non-polarizing type, as beam 12. A second portion of beam 10 is transmitted by beam splitter 54A and subsequently reflected by mirror 54B as beam 212. Beam 11 is incident on differential plane mirror interferometer group 269 and beams 12 and 212 are incident on differential plane mirror interferometer group 370 comprising two differential plane mirror interferometers. Differential plane mirror interferometer group 269 and differential plane mirror interferometer group 370 with external mirrors furnished by measurement cell 90 comprise interferometric means for introducing a phase shift $\phi_1$ between a first portion of the x and y components of beam 11, a phase shift $\phi_6$ between a second portion of the x and y components of beam 11, a phase shift $\phi_8$ between the x and y components of beam 12, and a phase shift $\phi_9$ between the x and y components of beam 212.

The description of differential plane mirror interferometer group 269 and the propagation of beams in differential plane mirror interferometer group 269 is the same as that given for corresponding portions of the descriptions of differential plane mirror interferometer group 269 and the propagation of beams in differential plane mirror interferometer group 269 of the fourth embodiment shown in FIG. 4b.

Differential plane mirror interferometer group 370 is comprised of many of the same elements as differential plane mirror interferometer group 170 of the second embodiment, like numbered elements in the two differential plane mirror interferometer groups performing like functions. Many of the beams shown in FIG. 5b for differential plane mirror interferometer group 370 have the same properties as beams shown in FIG. 2b for differential plane mirror interferometer group 170, like numbered beams in the two differential plane mirror interferometer groups having like properties. Further, the beams shown in FIG. 5b for differential plane mirror interferometer group 370 with numbers of (1000+N) have the same properties as beams with numbers N shown in FIG. 2b for differential plane mirror interferometer group 170 except for the lengths of the corresponding reference paths in the vacuum path 98 have nominal values of zero (cf. FIG. 5c). Beams 20, 220, 1120, and 1320 created by differential plane mirror interferometer group 370 and measurement cell 90 (cf. FIG. 5b) contain information at wavelength $\lambda_2$ about the optical path length through the gas whose reciprocal dispersive power is to be determined and about an optical path length of zero length, respectively.

Figure 5B:
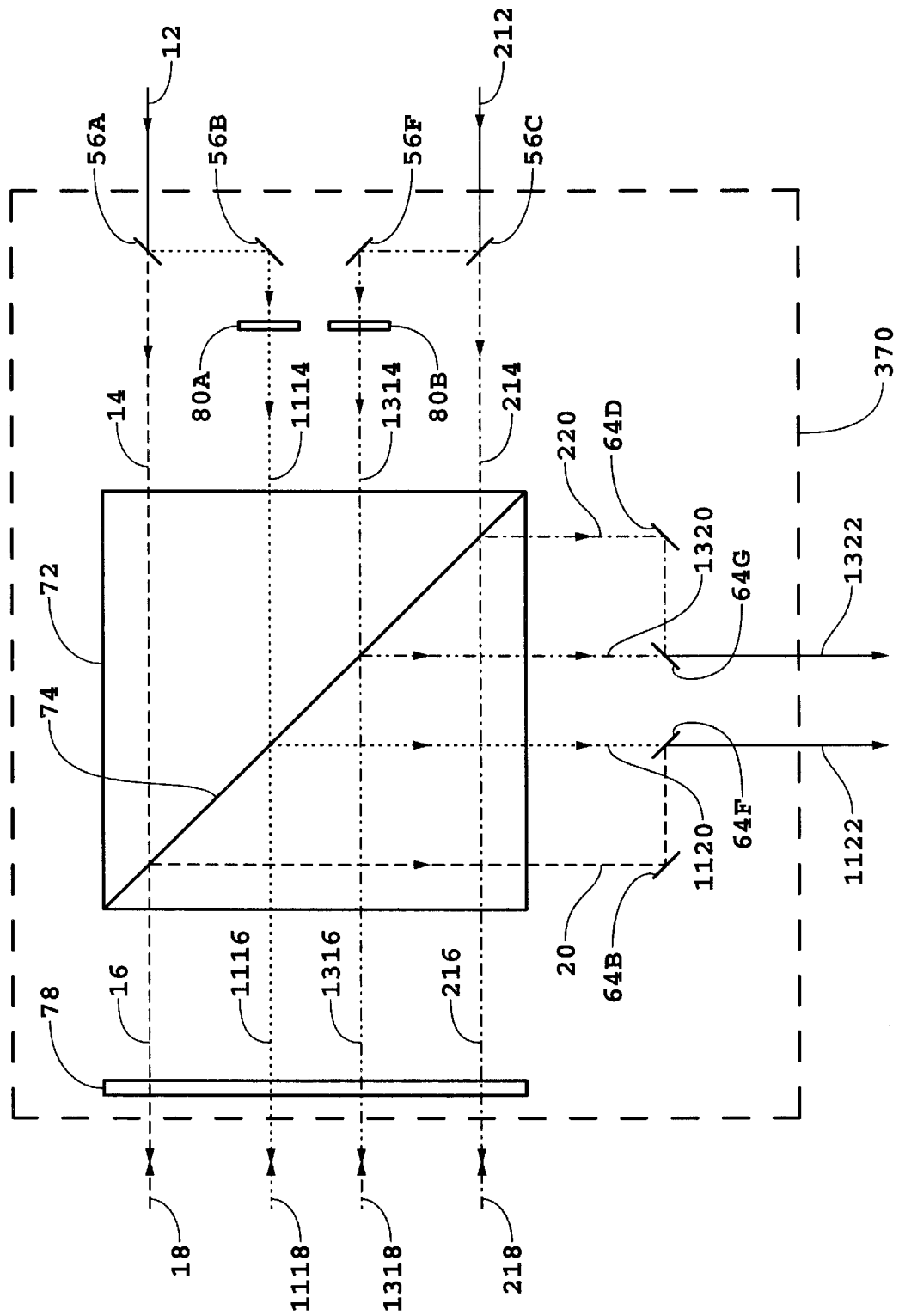

One differential plane mirror interferometer of differential plane mirror interferometer group 370 as shown in FIG. 5b has two exit/return beams 18 and 1118. Beam 18 originating from one frequency component, a first frequency component, of beam 12 comprises a beam for one measurement leg and beam 1118 originating from a second frequency component of beam 12 comprises a beam for a second measurement leg. Beams for which the first frequency component of beam 12 is the sole progenitor are indicated in FIG. 5b by dashed lines and beams for which the second frequency component of beam 12 is the sole progenitor are indicated in FIG. 5b by dotted lines.

A second differential plane mirror interferometer of differential plane mirror interferometer group 370 as shown in FIG. 5b has two exit/return beams 218 and 1318. Beam 218 originating from one frequency component, a first frequency component, of beam 212 comprises a beam for one measurement leg and beam 1318 originating from a second frequency component of beam 212 comprises a beam for a second measurement leg. Beams for which the first frequency component of beam 212 is the sole progenitor are indicated in FIG. 5b by lines comprised of alternating dots and dashes and beams for which the second frequency component of beam 212 is the sole progenitor are indicated in FIG. 5b by lines comprised of alternating dot pairs and dashes.

Referring to FIG. 5b, beam 20 is reflected by mirror 64B, a portion of which is reflected by beamsplitter 64F, preferably a non-polarizing beam splitter, to become a first component of beam 1122. A portion of beam 1120 is transmitted by beamsplitter 64F to become a second component of beam 1122. Beam 1122 is a mixed beam, the first and second components of beam 1122 having the same linear polarizations. Beam 220 is reflected by mirror 64D, a portion of which is reflected by beam splitter 64G, preferably a non-polarizing beam splitter, to become a first component of beam 1322. A portion of beam 1320 is transmitted by beamsplitter 64G to become a second component of beam 1322. Beam 1322 is a mixed beam, the first and second components of beam 1322 having the same linear polarizations. Beams 1122 and 1322 exit differential plane mirror interferometer group 370.

The magnitude of phase shifts $\phi_1$, $\phi_6$, $\phi_8$, and $\phi_9$ are related to the round-trip physical lengths of measurement path 97, reference path 98, or a reference path of zero physical length as shown in FIG. 4d according to the formulae $$\varphi_1 = \sum_{i=1}^{i=p_1} k_1(L_{G,i}n_{1i} - L_{V,i}) + \zeta_1 \qquad (139)$$

$$\varphi_6 = \sum_{i=1}^{i=p_1} k_1 L_{G,i}n_{1i} + \zeta_6,$$

$$\varphi_8 = \sum_{i=1}^{i=p_2} k_2 L_{G,i}n_{2i} + \zeta_8,$$

$$\varphi_9 = \sum_{i=p_2+1}^{i=p_1} k_2 L_{G,i}n_{2i} + \zeta_9,$$

for the case of $p_1=2p_2$. The phase offsets $\zeta_j$ comprise all contributions to the phase shifts $\phi_j$ that are not related to the measurement path 97 or reference path 98. To those skilled in the art, the generalization to the case when $p_1 \neq 2p_2$ is a straight forward procedure. Differential plane mirror interferometer group 269 (c.f. FIG. 4b) and differential plane mirror interferometer group 370 shown in FIG. 5b, along with measurement cell 90, are configured with $p_1=2$ and $p_2=1$ so as to illustrate in the simplest manner the function of the apparatus of the fifth embodiment.

Cyclic errors that produce nonlinearities in distance measuring interferometry (cf. the cited articles by Bobroff) have been omitted in Eqs. (139). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.)

In a next step as shown in FIG. 5a, phase-shifted beams 129, 1129, 1122, and 1322 impinge upon photodetectors 85, 1085, 1186, and 1286, respectively, resulting in four interference signals, heterodyne signals $s_1$, $s_6$, $s_8$, and $s_9$, respectively, preferably by photoelectric detection. The signals $s_1$ and $s_6$ correspond to wavelength $\lambda_1$ and signals $s_8$ and $s_9$ correspond to wavelength $\lambda_2$. The signals $s_j$ have the form $$s_j = A_j \cos[\alpha_j(t)], j=1, 6, 8, \text{ and } 9 \qquad (140)$$

where the time-dependent arguments $\alpha_j(t)$ are given by $$\alpha_1(t)=2\pi f_1 t + \phi_1,$$
$$\alpha_6(t)=2\pi f_1 t + \phi_6,$$
$$\alpha_8(t)=2\pi f_2 t + \phi_8,$$
$$\alpha_9(t)=2\pi f_2 t + \phi_9. \qquad (141)$$

Heterodyne signals $s_1$, $s_6$, $s_8$, and $s_9$ are transmitted to electronic processor 509 for analysis as electronic signals 103, 1103, 1204, and 1404, respectively, in either digital or analog format.

The phases of drivers 5 and 6 are transmitted by electrical signals, reference signals 101 and 102, respectively, in either digital or analog format, preferably a digital format, to electronic processor 509.

A preferred method for electronically processing the heterodyne signals $s_1$, $s_6$, $s_8$, and $s_9$ is presented herewithin for the case when $l_1$ and $l_2$ are not low order integers. For the case when $l_1$ and $l_2$ are low order integers and the ratio of the wavelengths matched to the ratio $(l_1/l_2)$ with a relative precision sufficient to meet the required precision imposed on the output data by the end use application, the preferred procedure for electronically processing the heterodyne signals $s_1$, $s_6$, $s_8$, and $s_9$ is the same as the one subsequently set down for the variant of the fifth preferred embodiment of the present invention.

The phases $\phi_1$, $\phi_6$, $\phi_8$, and $\phi_9$ of signals $s_1$, $s_6$, $s_8$, and $s_9$, respectively, are obtained preferably by application of superheterodyne receiver techniques wherein the frequencies of signals $s_1$, $s_6$, $s_8$, and $s_9$ are shifted to frequencies substantially lower than $f_1$ and $f_2$ [cf. Eqs. (141)] where conditions are generally more favorable for high precision phase measurements.

Figure 5C:
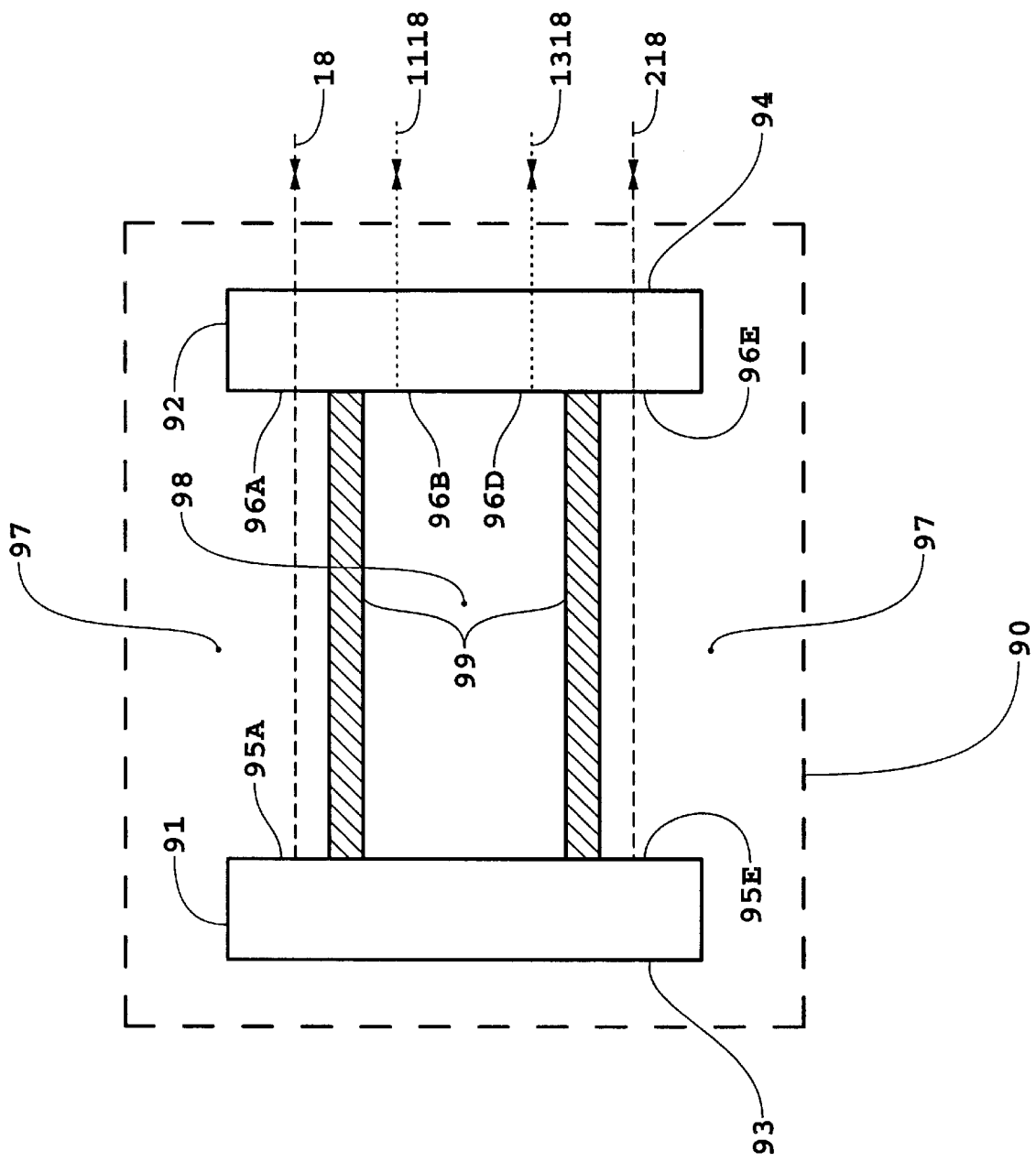
Figure 5D:
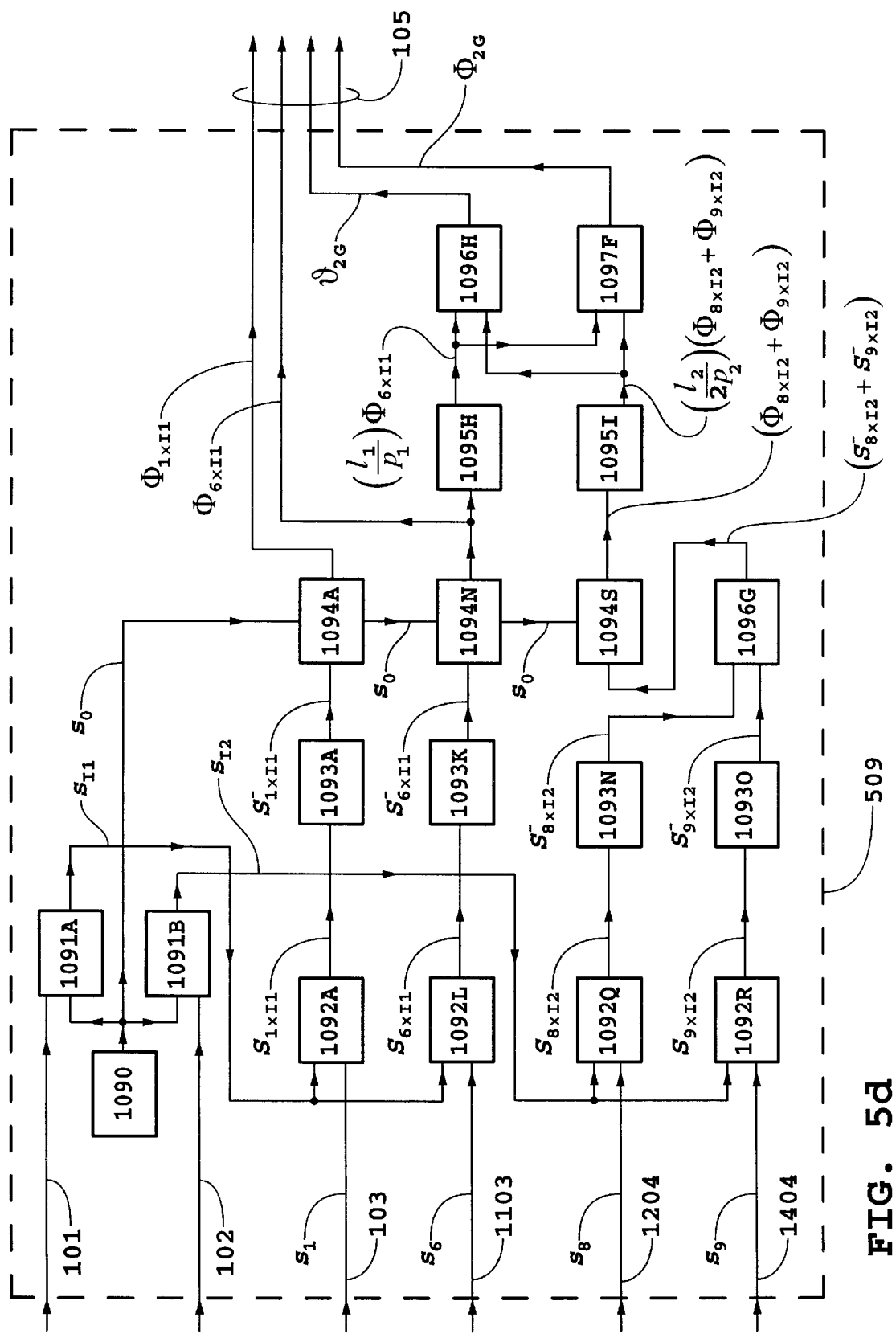

Referring now to FIG. 5d, electronic processor 509 preferably comprises alphameric numbered elements wherein the numeric component of the alphameric numbers indicate the function of an element, the same numeric component/function association as described for the electronic processing elements of the first embodiment depicted in FIG. 1f. The description of the steps in processing of the heterodyne signals $s_1$, $s_6$, $s_8$, and $s_9$ by electronic processor 509 is the same as corresponding portions, according to the numeric component of the alphameric numbers of elements, of the descriptions of steps in the processing of the heterodyne signals $s_1$ and $s_2$ of the first embodiment by electronic processor 109. The processing of the heterodyne signals $s_1$, $s_6$, $s_8$, and $s_9$ by electronic processor 509 creates four sideband phases $\Phi_{1 \times I1}$, $\Phi_{6 \times I1}$, $\Phi_{8 \times I2}$, and $\Phi_{9 \times I2}$ where $$\Phi_{1 \times I1} = \phi_1 - \phi_{I1}$$
$$\Phi_{6 \times I1} = \phi_6 - \phi_{I1}$$
$$\Phi_{8 \times I2} = \phi_8 - \phi_{I2}$$
$$\Phi_{9 \times I2} = \phi_9 - \phi_{I2} \qquad (142)$$

where $\phi_{I1}$ and $\phi_{I2}$ are defined in Eqs. (5).

Referring again to FIG. 5d, electronic processor 509 comprises electronic processors 1096G to add together $\Phi_{8 \times I2}$ and $\Phi_{9 \times I2}$. Next, the phase $\Phi_{6 \times I1}$ and the resulting phase sum $(\Phi_{8 \times I2} + \Phi_{9 \times I2})$ are multiplied by $l_1/p_1$ and $(l_2/p_2)$ (½), respectively, in electronic processors 1095H and 1095I, respectively, resulting in phases $(l_1/p_1)\Phi_{4 \times I1}$ and $(l_2/p_2)(\Phi_{8 \times I2} + \Phi_{9 \times I2})/2$. The phases $(l_1/p_1)\Phi_{1 \times I1}$ and $(l_2/p_2)(\Phi_{8 \times I2} + \Phi_{9 \times I2})/2$ are next added together in electronic processor 1096H and subtracted one from the other in electronic processor 1096F, by analog or digital processes, preferably digital processes, to create the phases $\theta_{2G}$ and $\Phi_{2G}$, respectively. Formally, $$\vartheta_{2G} = \left[\frac{l_1}{p_1}\Phi_{6 \times I1} + \frac{l_2}{p_2}\frac{(\Phi_{8 \times I2} + \Phi_{9 \times I2})}{2}\right] \qquad (143)$$

$$\Phi_{2G} = \left[\frac{l_1}{p_1}\Phi_{6 \times I1} - \frac{l_2}{p_2}\frac{(\Phi_{8 \times I2} + \Phi_{9 \times I2})}{2}\right] \qquad (144)$$

Note from Eqs. (143) and (144) that $\theta_{2G}$ and $\Phi_{2G}$ are not sensitive to tilts of either reflecting surfaces 95 or 96 of measurement cell 90 and insensitive to thermal and mechanical disturbances that may occur in the interferometer beam splitting cubes and associated optical components as a consequence of the use of differential plane mirror interferometers.

The refractivity $(n_1-1)$, the dispersion $(n_2-n_1)_{2G}$, and the wavenumber $k_1$ can be expressed in terms of other quantities obtained by the fifth embodiment by the formulae $$(n_1 - 1) = \frac{1}{(\chi + K)L_G}\left(\frac{l_1}{p_1}\right)[\Phi_{1\times II} - (\zeta_1 - \varphi_{II})] - \frac{(L_G - L_V)}{L_G} \quad (145)$$

$$(n_2 - n_1)_{2G} = \quad (146)$$
$$\frac{1}{\chi L_G[1 - (K/\chi)^2]}\{[\vartheta_{2G}(K/\chi) - \Phi_{2G}] - [\xi(K/\chi) - Z]\}$$

$$k_1 = \frac{1}{p_1 L_V}[(\Phi_{6\times II} - \Phi_{1\times II}) - (\zeta_6 - \zeta_1)] \quad (147)$$

$$\xi = \left(\frac{l_1}{p_1}\right)(\zeta_6 - \varphi_{II}) + \left(\frac{l_2}{p_2}\right)\left(\frac{\zeta_8 + \zeta_9}{2} - \varphi_{I2}\right) \quad (148)$$

$$Z = \left(\frac{l_1}{p_1}\right)(\zeta_6 - \varphi_{II}) - \left(\frac{l_2}{p_2}\right)\left(\frac{\zeta_8 + \zeta_9}{2} - \varphi_{I2}\right) \quad (149)$$

where $\chi$ and K are given by Eqs. (26) and (27), respectively, and second order correction terms have been omitted. The correction terms are due to variations in the index of refraction along the measurement path and due to differences in the physical length of path i in the measurement path and the reference path from the respective average physical lengths. In addition, Eq. (146) is valid for the case where the paths for the two different wavelengths are substantially coextensive, a case chosen to illustrate in the simplest manner the function of the invention in the fifth embodiment. To those skilled in the art, the generalization to the case where paths for the two different wavelengths are not substantially coextensive is a straight forward procedure.

In a next step, electronic processing means 509 transmits to the computer 110 $\Phi_{1\times I1}$, $\Phi_{6\times I1}$, $\theta_{2G}$, and $\Phi_{2G}$ as electronic signal 105 in either digital or analog format for the computation of Γ and the calculation of $k_1$ if required according to Eqs. (23), (145), (146), and (147) substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The remaining description of the fifth embodiment is the same as corresponding portions of the description for the second embodiment of the present invention.

Reference is now made to FIGS. 5a–5c and 5e which taken together depict in diagrammatic form a variant of the fifth preferred embodiment of the present invention for measuring intrinsic optical properties of a gas, particularly its reciprocal dispersive power where the end use application effects the choice of the particular manner in which the intrinsic optical properties of the gas are determined and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the fifth embodiment in which the ratio $(l_1/l_2)$ is expressible as the ratio of low order non-zero integers $(p_1/p_2)$, cf. Eq. (35).

The description of the sources of light beams 9 and 10 and of light beams 9 and 10 for the variant of the fifth embodiment is the same as that for description of the sources of light beams 9 and 10 and of light beams 9 and 10 given for the first embodiment with the additional requirement that the wavelengths be harmonically related to a relative precision sufficient to meet the required precision imposed on the output data by the final end use application. The description of the apparatus for the variant of the fifth embodiment depicted in FIGS. 5a–5c is the same as corresponding portions of the description given for the fifth embodiment.

The information contained in phases $\phi_1$, $\phi_6$, $\phi_8$, and $\phi_9$ of signals $s_1$, $s_6$, $s_8$, and $s_9$, respectively, is obtained in the variant of the fifth embodiment preferably through the creation of a superheterodyne signal wherein the frequency of the superheterodyne signal is at a frequency much lower than $f_1$ and $f_2$ where it is general possible to make more accurate phase measurements.

Figure 5E:
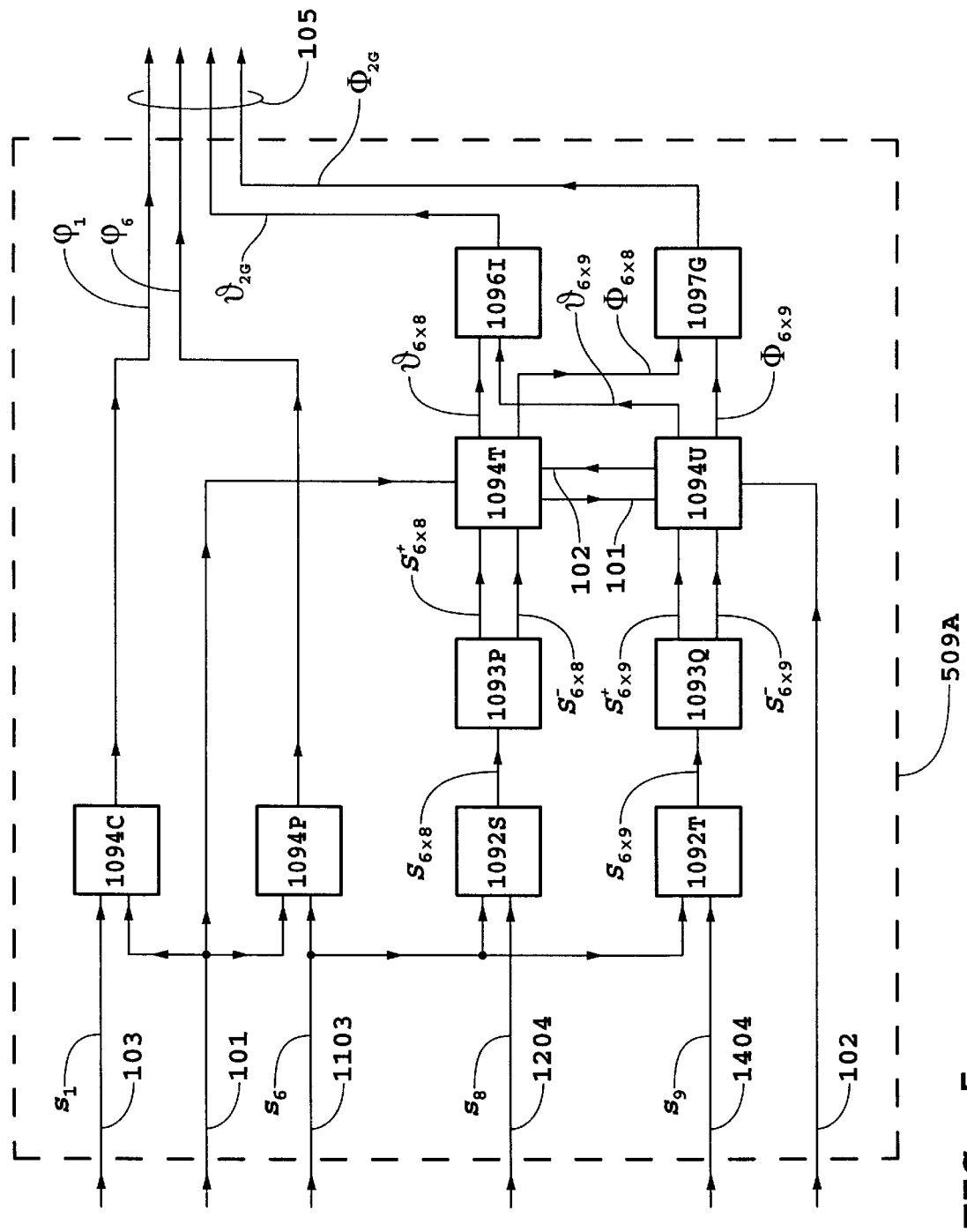

Referring now to FIG. 5e, and in accordance with the preferred method of the variant of the fifth embodiment, electronic processor 509A preferably comprises alphameric numbered elements wherein the numeric component of the alphameric numbers indicate the function of an element, the same numeric component/function association as described for the electronic processing elements of the first embodiment depicted in FIG. 1f. As depicted in FIG. 5e, the heterodyne signals $s_1$ and $s_6$ of the variant of the fifth embodiment are each processed by the same sequence of electronic processing steps as signal $s_1$ of the variant of the second embodiment and heterodyne signals $s_8$ and $s_9$ of the variant of the fifth embodiment are processed by the same sequence of electronic processing steps as signals S3 and 54 of the variant of the second embodiment. The results of that analysis are $\phi_1$, $\phi_6$, $\theta_{2G}$, and $\Phi_{2G}$ where $$\vartheta_{2G} = \frac{(\vartheta_{6\times 8} + \vartheta_{6\times 9})}{2} = \left[\varphi_6 + \frac{(\varphi_8 + \varphi_9)}{2}\right] \quad (150)$$

$$\Phi_{2G} = \frac{(\Phi_{6\times 8} - \Phi_{6\times 9})}{2} = \left[\varphi_6 - \frac{(\varphi_8 + \varphi_9)}{2}\right] \quad (151)$$

Note from Eqs. (150) and (151) that $\theta_{2G}$ and $\Phi_{2G}$ are not sensitive to tilts of either reflecting surfaces 95 or 96 and insensitive to thermal and mechanical disturbances that may occur in the interferometer beam splitting cubes and associated optical components as a consequence of the use of differential plane mirror interferometers.

In a next step, $\phi_1$, $\phi_6$, $\theta_{2G}$, and $\Phi_{2G}$ are transmitted, preferably in digital format, to computer 110 for computation refractivity, dispersion, Γ and/or $k_1$. Quantities $\phi_1$, $\phi_6$, $\theta_{2G}$, $\Phi_{2G}$, $\xi$, and Z of the variant of the fifth embodiment are formally equivalent to $\Phi_{1\times I1}$, $\Phi_{6\times I1}$, $\theta_{2G}$, $\Phi_{2G}$, $\xi$, and Z, respectively, of the fifth embodiment with $\phi_{f1}$ and $\phi_{f2}$ set equal to zero, $l_1=p_1$, and $l_2=p_2$. Thus, Γ, the refractivity $(n_1-1)$, dispersion $(n_2-n_1)_{2G}$, and $k_1$ can be expressed in terms of the quantities measured by the variant of the fifth embodiment by Eqs. (23), (145), (146), and (147), respectively, wherein the phase offsets $\xi$ and Z are defined by equations corresponding to Eqs. (148) and (149), respectively, and $\chi$ and K are given by Eqs. (26) and (27), respectively, with $\phi_{f1}$ and $\phi_{f2}$ set equal to zero, $l_1=p_1$, and $l_2=p_2$. The remaining description of the variant of the fifth embodiment is the same as corresponding portions of the descriptions given for the fifth embodiment.

Reference is now made to FIGS. 6a–6e which depict in diagrammatic form the sixth preferred embodiment of the present invention from the second group of preferred embodiments for measuring intrinsic optical properties of a gas, particularly its reciprocal dispersive power ΓF, where the end use application effects the choice of the particular manner in which the intrinsic optical properties of the gas are determined and where the stability of the adopted light sources is sufficient and the ratio of the wavelengths of the light beams generated by the adopted light sources is matched to a known ratio value with a relative precision sufficient to meet the required precision imposed on the output data by the final end use application. The configuration of differential plane mirror interferometers in the sixth embodiment permits measurement of a refractivity $(n_1-1)$ for use as the numerator and a measurement of $(n_2-n_1)_{2G}$ equivalent to a measurement of $(n_2-n_1)$ as a difference of two measured indices of refraction $n_2$ and $n_1$ for use as the denominator of Eq. (23) in the calculation of Γ.

The description of the sources of light beams 9 and 10 and of light beams 9 and 10 for the sixth embodiment is the same as that for description of the sources of light beams 9 and 10 and of light beams 9 and 10 given for the first preferred embodiment.

Figure 6A:
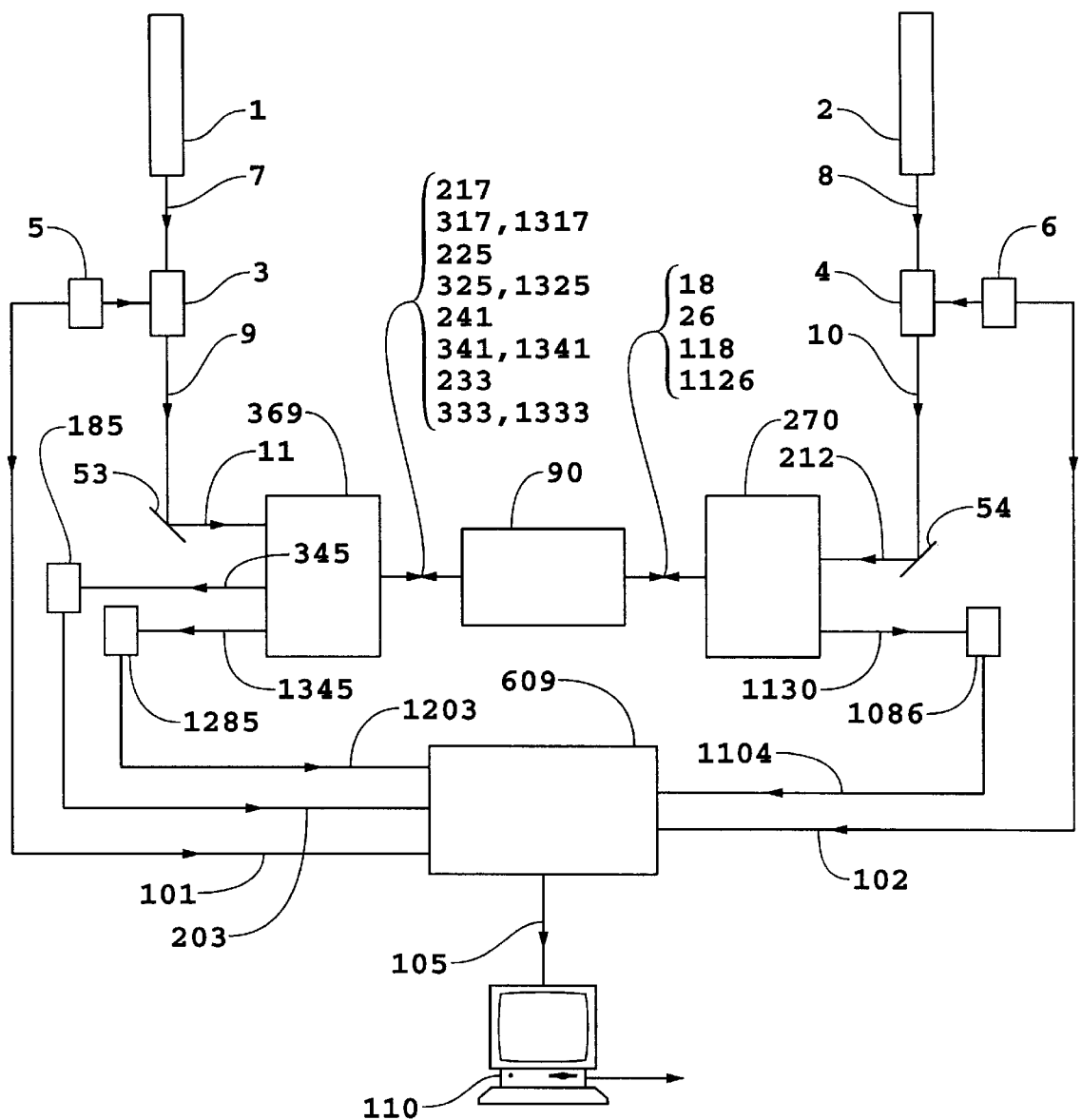
FIGS. 6a–6e taken together illustrate, in diagrammatic form, the presently preferred sixth embodiment of the present invention with FIG. 6a showing optical paths and the paths of electrical signals between indicated elements source 1, modulator 3, source 2, modulator 4, differential plane mirror interferometer group 369, differential plane mirror interferometer 270, measurement cell 90, detectors 185, 1285, and 1086, and the paths of electrical signals between indicated elements driver 5, modulator 3, driver 6, modulator 4, detectors 185, 1285, and 1086, electronic processor 609, and computer 110.

Referring to FIG. 6a, beam 9 is reflected by mirror 53 becoming beam 11 and beam 10 is reflected by mirror 54 as beam 212. Beam 11 is incident on differential plane mirror interferometer group 369 and beam 212 is incident on differential plane mirror interferometer 270. Differential plane mirror interferometer group 369 and differential plane mirror interferometer 270 with external mirrors furnished by measurement cell 90 comprise interferometric means for introducing a phase shift $\phi_5$ between a first portion of the x and y components of beam 11, a phase shift $\phi_{10}$ between a second portion of the x and y components of beam 11, and a phase shift $\phi_7$ between the x and y components of beam 212.

Differential plane mirror interferometer group 369 comprises many of the same elements as differential plane mirror interferometer 169 of the third embodiment, like numbered elements in the two differential plane mirror interferometers performing like functions. Many of the beams shown in FIGS. 6b and 6c for differential plane mirror interferometer group 369 have the same properties as beams shown in FIGS. 3b and 3c for differential plane mirror interferometer 169, like numbered beams in the two differential plane mirror interferometers having like properties. Further, the beams shown in FIGS. 6b and 6c for differential plane mirror interferometer group 369 with numbers of (1000+N) have the same properties as beams with numbers N shown in FIGS. 3b and 3c for differential plane mirror interferometer 169 except for the lengths of the corresponding reference paths in the vacuum path 98 have nominal values of zero (cf. FIG. 6d). Beams 243, 343, and 1343 created by differential plane mirror interferometer group 369 and measurement cell 90 (cf. FIG. 6c) contain information at wavelength $\lambda_1$ about the optical path length through the gas whose reciprocal dispersive power is to be determined, about the optical path length through a vacuum, and an optical path length of zero length, respectively.

The description of differential plane mirror interferometer 270 and the propagation of beams in differential plane mirror interferometer 270 is the same as that given for corresponding portions of the descriptions of differential plane mirror interferometer 270 and the propagation of beams in differential plane mirror interferometer 270 of the fourth embodiment shown in FIG. 4c.

A first portion of beam 11 is transmitted by beam splitter 55C, preferably a polarizing beamsplitter. A portion of the first portion of beam 11 is next transmitted by beam splitter 61A, preferably a polarizing beamsplitter, transmitted by Faraday rotator 179A, and then transmitted by half-wave phase-retardation plate 79C to become beam 213. The Faraday rotator 179A and the half-wave phase-retardation plate 79C rotate the plane of polarization of transmitted beams by ±45° and ∓45°, respectively, producing no net rotation of the plane of polarization of transmitted beams. A second portion of beam 11 is reflected by beam splitter 55C. A first portion of the second portion of beam 11 is reflected by beam splitter 55D, preferably a polarizing beam splitter, transmitted by half-wave phase-retardation plate 79A, transmitted by beam splitter 61C, preferably a polarizing beam splitter, transmitted by Faraday rotator 179B, and transmitted by half-wave phase-retardation plate 79D to become beam 313. A second portion of second portion of beam 11 is transmitted by beam splitter 55D, reflected by mirror 55E, transmitted by half-wave phase-retardation plate 79B, next transmitted by beam splitter 61H, preferably a polarizing beamsplitter, transmitted by Faraday rotator 179C, and then transmitted by half-wave phase-retardation plate 79E to become beam 1313. Half-wave phase-retardation plates 79A and 79B rotate the planes of polarization of transmitted beams by 90° so that beams 213, 313 and 1313 have the same polarizations but beam 213 has a frequency different from the frequencies of beams 313 and 1313, beams 313 and 1313 having the same frequency. The purpose of the Faraday rotators 179A, 179B, and 179C and the half-wave phase-retardation plates 79C, 79D, and 79E is to have substantially no effect on the properties of beams 213, 313, and 1313 but to rotate the polarizations of beams 243, 343, and 1343 by 90° so as to achieve an efficient spatial separation of beams 243, 343, and 1343 from the path of beam 11 (cf. FIG. 6c).

Figure 6B:
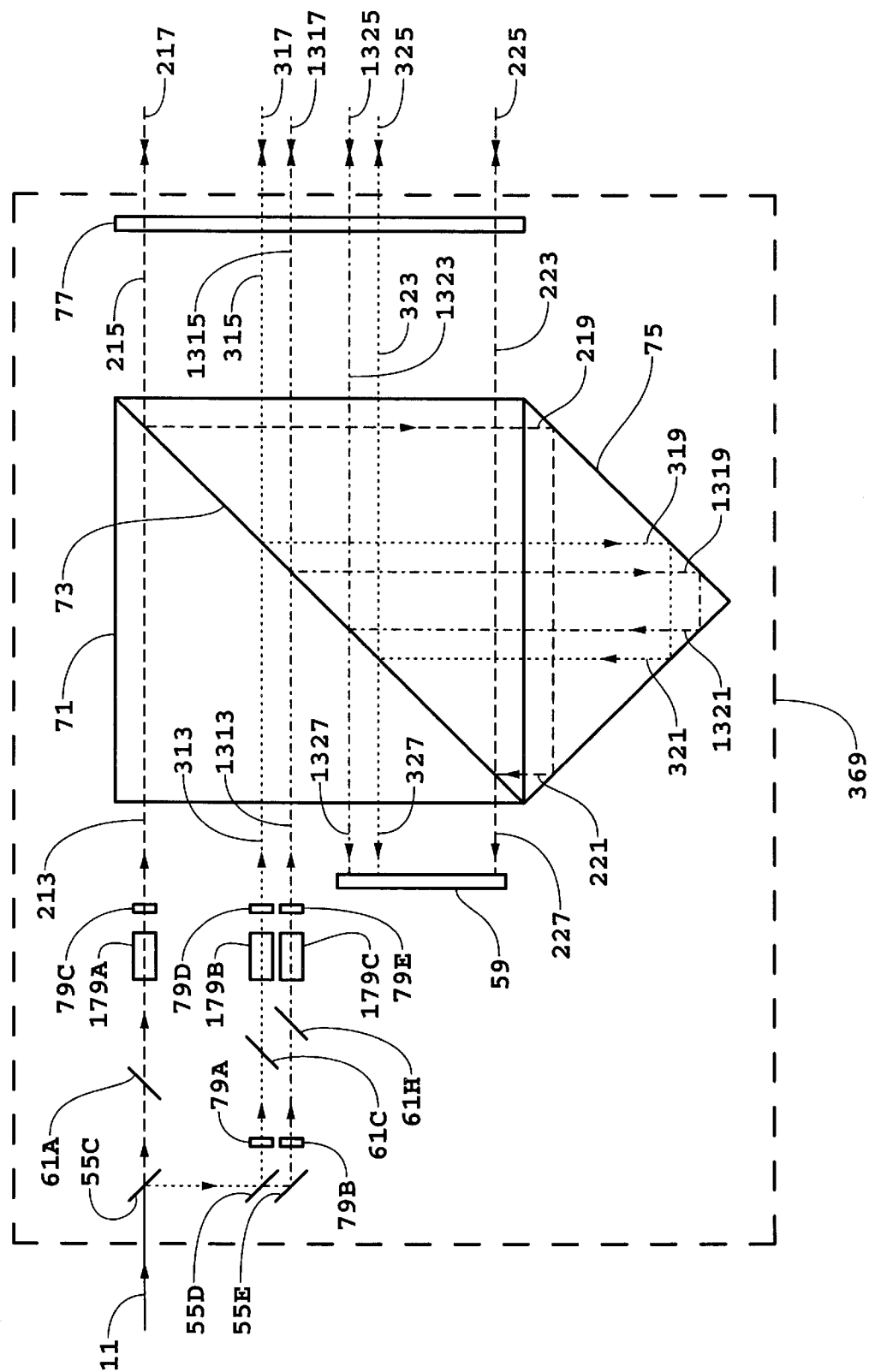
Figure 6C:
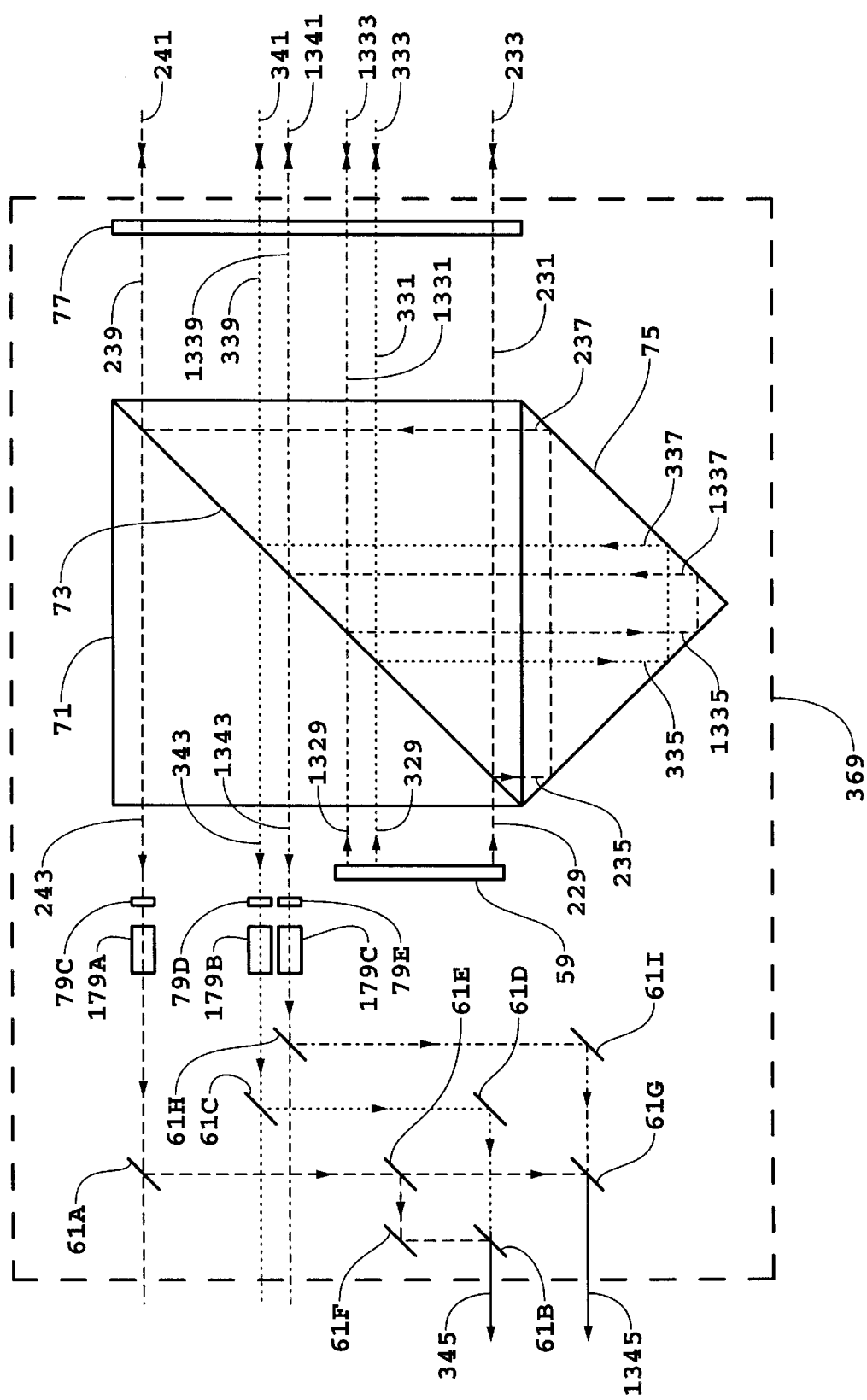

Referring to FIG. 6c, a portion of beam 243 transmitted by half-wave phase retardation plate 79C and Faraday rotator 179A is reflected by beam splitter 61A. A first portion of the portion of beam 243 is reflected by beam splitter 61E, preferably a nonpolarizing type, and reflected by mirror 61F. A portion of the first portion of the portion of beam 243 is reflected by beam splitter 61B, preferably a nonpolarizing type to become a first component of phase shifted beam 345. Half-wave phase retardation plate 79C and Faraday rotator 179A each rotate the polarization of beam 243 by 45° so that the first component of phase shifted beam 345 is orthogonally polarized to the polarization of beam 243. Beam splitter 61A is preferably a polarizing beam splitter. A portion of beam 343 transmitted by half-wave phase retardation plate 79D and Faraday rotator 179B is reflected by beam splitter 61C. A portion of the portion of beam 343 reflected by mirror 61D is transmitted by beam splitter 61B to become a second component of phase shifted beam 345. Half-wave phase retardation plate 79D and Faraday rotator 179B each rotate the polarization of beam 343 by 45° so that the second component of phase shifted beam 345 is orthogonally polarized to the polarization of beam 343. Beam splitter 61C is preferably a polarizing beam splitter. Phase shifted beam 345 is a mixed beam, the first and second components of phase shifted beam 345 having the same polarizations but different frequencies.

A second portion of the portion of beam 243 is transmitted by beam splitter 61E. A portion of the second portion of the portion of beam 243 is reflected by beam splitter 61G, preferably a nonpolarizing type to become a first component of phase shifted beam 1345. A portion of beam 1343 transmitted by half-wave phase retardation plate 79E and Faraday rotator 179C is reflected by beam splitter 61H. A portion of the portion of beam 1343 reflected by mirror 61H is transmitted by beam splitter 61G to become a second component of phase shifted beam 1345. Half-wave phase retardation plate 79E and Faraday rotator 179C each rotate the polarization of beam 1343 by 45° so that the second component of phase shifted beam 1345 is orthogonally polarized to the polarization of beam 1343. Beam splitter 61H is preferably a polarizing beam splitter. Phase shifted beam 1345 is a mixed beam, the first and second components of phase shifted beam 1345 having the same polarizations but different frequencies.

Figure 6D:
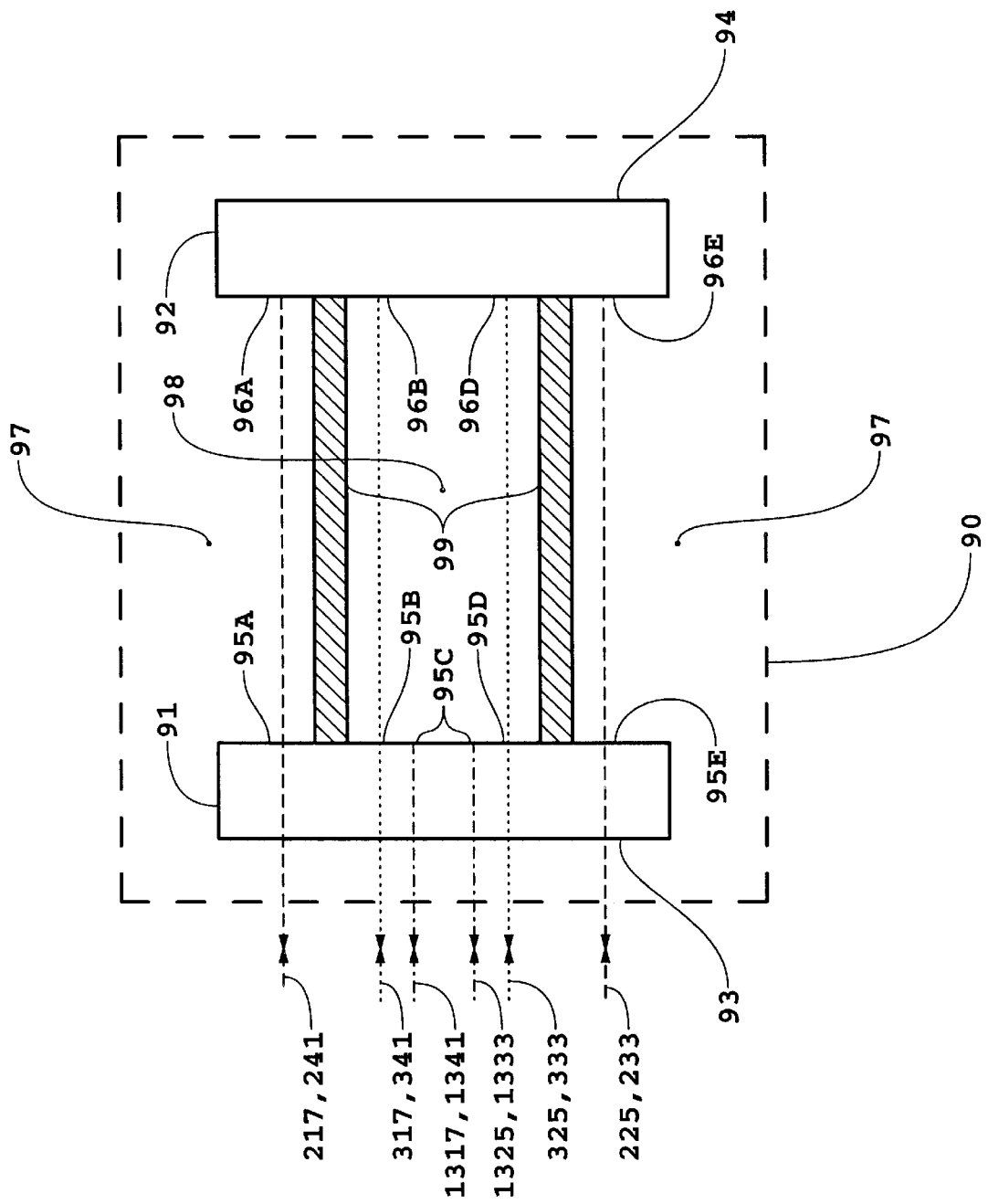

The magnitude of phase shifts $\phi_5$, $\phi_{10}$ and $\phi_7$ are related to the round-trip physical lengths of measurement path 97, reference path 98, or a reference path of zero physical length as shown in FIGS. 4d and 6d according to the formulae $$\varphi_5 = \sum_{i=1}^{i=p_1} k_1(L_{G,i}n_{1i} - L_{V,i}) + \zeta_5 \qquad (152)$$

$$\varphi_{10} = \sum_{i=1}^{i=p_1} k_1 L_{G,i}n_{1i} + \zeta_{10},$$

$$\varphi_7 = \sum_{i=1}^{i=p_2} k_2 L_{G,i}n_{2i} + \zeta_7,$$

for the case of $p_1=2p_2$ and where the index of refraction in the reference path 98 has been set to 1. The phase offsets e comprise all contributions to the phase shifts $\phi_j$ that are not related to the measurement path 97 or reference path 98. To those skilled in the art, the generalization to the case when $p_1 \neq 2p_2$ is a straight forward procedure. Differential plane mirror interferometer group 369 (cf. FIGS. 6b and 6c) and differential plane mirror interferometer 270 shown in FIG. 4c, along with measurement cell 90, are configured with $p_1=2$ and $p_2=1$ so as to illustrate in the simplest manner the function of the apparatus of the sixth embodiment.

Cyclic errors that produce non-linearities in distance measuring interferometry (cf. the cited articles by Bobroff) have been omitted in Eqs. (137). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

In a next step as shown in FIG. 6a, phase-shifted beams 345, 1345, and 1130 impinge upon photodetectors 185, 1285, and 1086, respectively, resulting in three interference signals, heterodyne signals $s_5$, $s_{10}$, and $s_7$, respectively, preferably by photoelectric detection. The signals $s_5$ and $s_{10}$ correspond to wavelength $\lambda_1$ and signal $s_7$ corresponds to wavelength $\lambda_2$. The signals $s_j$ have the form $$s_j = A_j \cos[\alpha_j(t)], j=5, 10, \text{ and } 7 \qquad (153)$$

where the time-dependent arguments $\alpha_j(t)$ are given by $$\alpha_5(t) = 2\pi f_1 t + \phi_5,$$

$$\alpha_{10}(t) = 2\pi f_1 t + \phi_{10},$$

$$\alpha_7(t) = 2\pi f_2 t + \phi_7. \qquad (154)$$

Heterodyne signals $s_5$, $s_{10}$ and $s_7$ are transmitted to electronic processor 609 for analysis as electronic signals 203, 1203, and 1104, respectively, in either digital or analog format, preferably a digital format.

The phases of drivers 5 and 6 are transmitted by electrical signals, reference signals 101 and 102, respectively, in either digital or analog format to electronic processor 609.

A preferred method for electronically processing the heterodyne signals $s_5$, $s_{10}$, and $s_7$ is presented herewithin for the case when $l_1$ and $l_2$ are not low order integers. For the case when $l_1$ and $l_2$ are low order integers and the ratio of the wavelengths matched to the ratio $(l_1/l_2)$ with a relative precision sufficient to meet the required precision imposed on the output data by the end use application, the preferred procedure for electronically processing the heterodyne signals $s_5$, $s_{10}$, and $s_7$ is the same as the one subsequently set down for the variant of the sixth preferred embodiment of the present invention.

The phases $\phi_5$, $\phi_{10}$ and $\phi_7$ of signals $s_5$, $s_{10}$, and $s_7$, respectively, are obtained preferably by application of superheterodyne receiver techniques wherein the frequencies of signals $s_5$, $s_{10}$, and $s_7$ are shifted to frequencies substantially lower than $f_1$ and $f_2$ [cf. Eqs. (154)] where conditions are generally more favorable for high precision phase measurements.

Figure 6E:
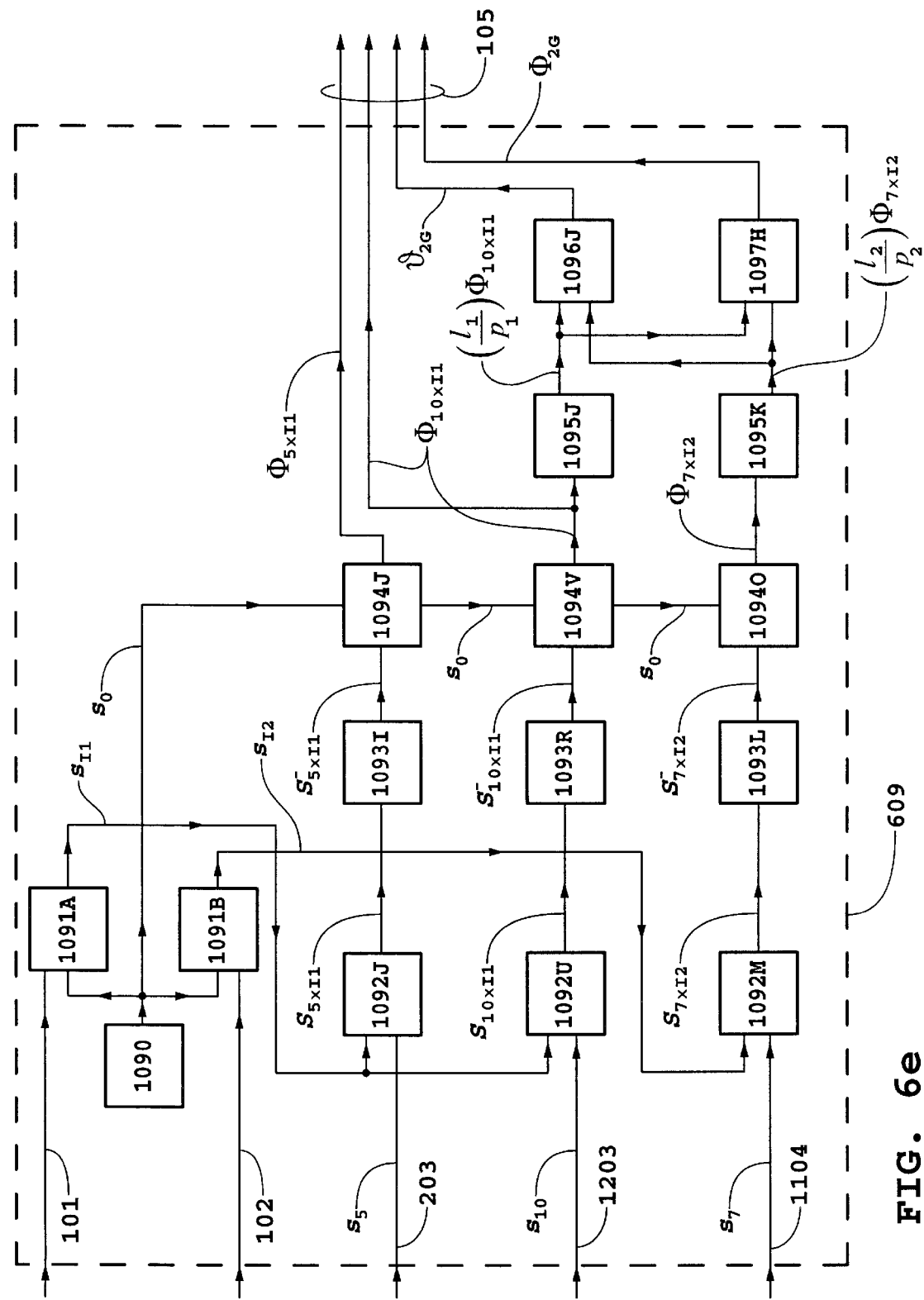

Referring now to FIG. 6e, electronic processor 609 preferably comprises alphameric numbered elements wherein the numeric component of the alphameric numbers indicate the function of an element, the same numeric component/function association as described for the electronic processing elements of the first embodiment depicted in FIG. 1f. The description of the steps in processing of the heterodyne signals $s_5$, $s_{10}$, and $s_7$ by electronic processor 609 is the same as corresponding portions, according to the numeric component of the alphameric numbers of elements, of the descriptions of steps in the processing of the heterodyne signals $s_1$ and $s_2$ of the first embodiment by electronic processor 109. The processing of the heterodyne signals $s_5$, $s_{10}$ and $s_7$ by electronic processor 609 creates three sideband phases $\Phi_{5 \times I1}$, $\Phi_{10 \times I1}$, and $\Phi_{7 \times I2}$ where $$\Phi_{5 \times I1} = \phi_5 - \phi_{I1},$$

$$\Phi_{10 \times I1} = \phi_{10} - \phi_{I1},$$

$$\Phi_{7 \times I2} = \phi_7 - \phi_{I2}. \qquad (155)$$

where $\phi_{I1}$ and $\phi_{I2}$ are defined in Eqs. (5).

Subsequently, the phases $\Phi_{10 \times I1}$ and $\Phi_{7 \times I2}$ are multiplied by $l_1/p_1$ and $(l_2/p_2)$, respectively, in electronic processors 1095J and 1095K, respectively. Next, the phases $(l_1/p_1)\Phi_{5 \times I1}$ and $(l_2/p_2)\Phi_{10 \times I2}$ are added together in electronic processor 1096J and subtrated one from the other in electronic processor 1097H, by analog or digital processes, preferably digital processes, to create the phases $\theta_{2G}$ and $\Phi_{2G}$, respectively. Formally, $$\vartheta_{2G} = \left[\left(\frac{l_1}{p_1}\right)\Phi_{10 \times I1} + \left(\frac{l_2}{p_2}\right)\Phi_{7 \times I2}\right] \qquad (156)$$

$$\Phi_{2G} = \left[\left(\frac{l_1}{p_1}\right)\Phi_{10 \times I1} - \left(\frac{l_2}{p_2}\right)\Phi_{7 \times I2}\right]. \qquad (157)$$

Note from Eqs. (156) and (157) that $\theta_{2G}$ and $\Phi_{2G}$ are not sensitive to tilts of either reflecting surfaces 95 or 96 of measurement cell 90 and insensitive to thermal and mechanical disturbances that may occur in the interferometer beam splitting cubes and associated optical components as a consequence of the use of differential plane mirror interferometers.

The refractivity $(n_1-1)$, the dispersion $(n_2-n_1)_{2G}$, and the wavenumber $k_1$ can be expressed in terms of other quantities obtained by the sixth embodiment by the formulae $$(n_1 - 1) = \frac{1}{(\chi + K)L_G}\left(\frac{l_1}{p_1}\right)[\Phi_{5\times II} - (\zeta_5 - \varphi_{II})] - \frac{(L_G - L_V)}{L_G} \quad (158)$$

$$(n_2 - n_1)_{2G} = \quad (159)$$
$$\frac{1}{\chi L_G[1-(K/\chi)^2]}\{[\vartheta_{2G}(K/\chi) - \Phi_{2G}] - [\xi(K/\chi) - Z]\}$$

$$k_1 = \frac{1}{p_1 L_V}[(\Phi_{10\times II} - \Phi_{5\times II}) - (\zeta_{10} - \zeta_5)] \quad (160)$$

$$\xi = \left(\frac{l_1}{p}\right)(\zeta_{10} - \varphi_{II}) - \left(\frac{l_2}{p}\right)(\zeta_7 + \varphi_{I2}) \quad (161)$$

$$Z = \left(\frac{l_1}{p_1}\right)(\zeta_{10} - \varphi_{II}) - \left(\frac{l_2}{p_2}\right)(\zeta_7 - \varphi_{I2}) \quad (162)$$

where $\chi$ and K are given by Eqs. (26) and (27), respectively.

In a next step, electronic processing means 609 transmits to the computer 110 $\Phi_{5\times I1}$, $\Phi_{10\times I1}$, $\theta_{2G}$, and $\Phi_{2G}$ as electronic signal 105 in either digital or analog format, preferably a digital format, for the computation of $\Gamma$ and the calculation of $k_1$ if required according to Eqs. (23), (158), (159), and (160) substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The remaining description of the sixth embodiment is the same as corresponding portions of the description for the third embodiment of the present invention.

Reference is now made to FIGS. 6a–6d and 6f which taken together depict in diagrammatic form a variant of the sixth preferred embodiment of the present invention for measuring intrinsic optical properties of a gas, particularly its reciprocal dispersive power where the end use application effects the choice of the particular manner in which the intrinsic optical properties of the gas are determined and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the sixth embodiment in which the ratio $(l_1/i_2)$ is expressible as the ratio of low order non-zero integers $(p_1/p_2)$, cf. Eq. (35).

The description of the sources of light beams 9 and 10 and of light beams 9 and 10 for the variant of the sixth embodiment is the same as that for description of the sources of light beams 9 and 10 and of light beams 9 and 10 given for the first embodiment with the additional requirement that the wavelengths be harmonically related to a relative precision sufficient to meet the required precision imposed on the output data by the final end use application. The description of the apparatus for the variant of the sixth embodiment depicted in FIGS. 6a–6d is the same as corresponding portions of the description given for the sixth embodiment.

The information contained in phases $\phi_5$, $\phi_{10}$, and $\phi_7$ of signals $s_5$, $s_{10}$, and $s_7$, respectively, is obtained in the variant of the sixth embodiment preferably through the creation of a superheterodyne signal wherein the frequency of the superheterodyne signal is at a frequency much lower than $f_1$ and $f_2$ where it is general possible to make more accurate phase measurements.

Figure 6F:
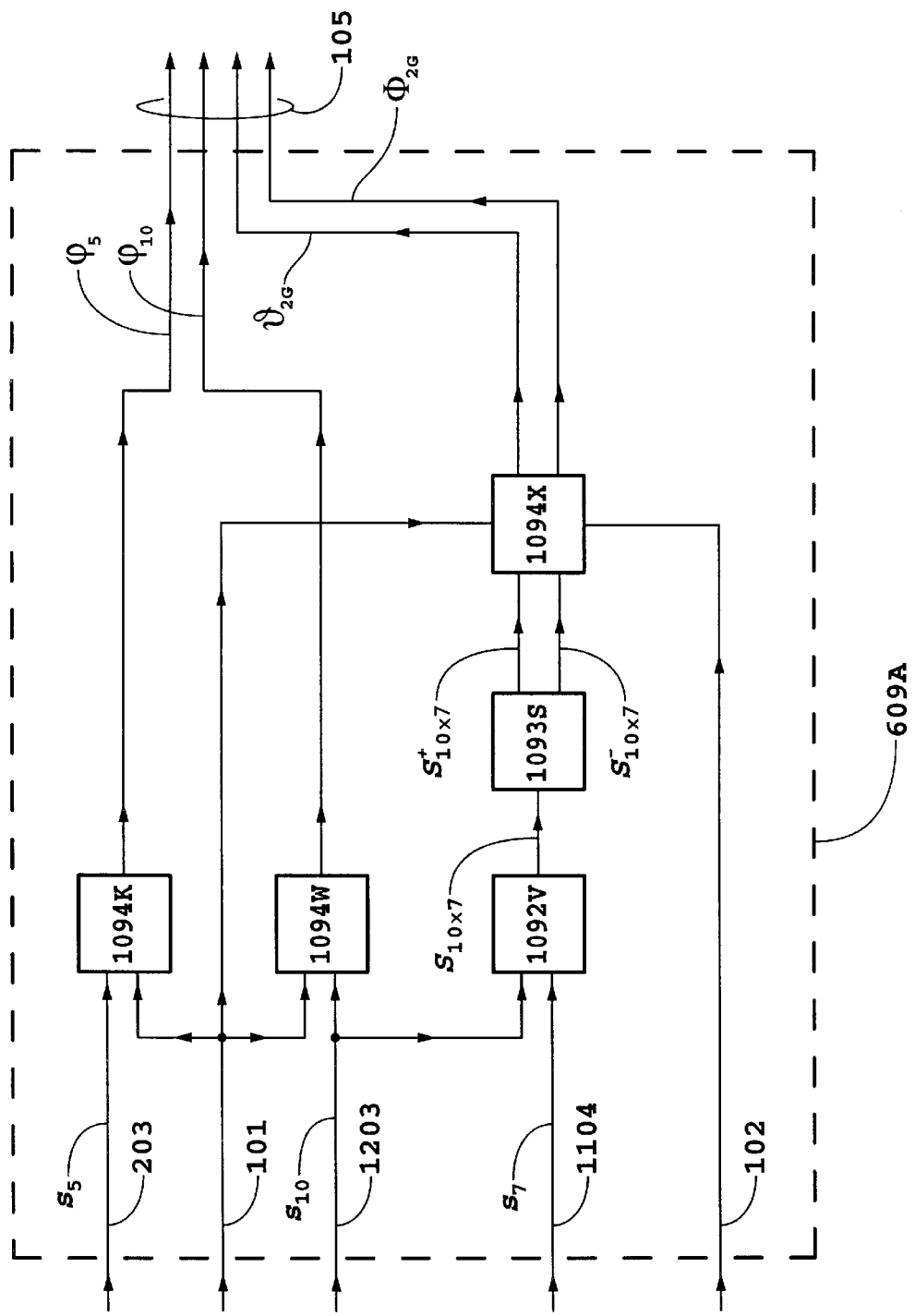

Referring now to FIG. 6f, and in accordance with the preferred method of the variant of the sixth embodiment, electronic processor 609A preferably comprises alphameric numbered elements wherein the numeric component of the alphameric numbers indicate the function of an element, the same numeric component/function association as described for the electronic processing elements of the first embodiment depicted in FIG. 1f. As depicted in FIG. 6f, the heterodyne signals $s_5$ and $s_{10}$ of the variant of the sixth embodiment are each processed by the same sequence of electronic processing steps as signal $s_5$ of the variant of the third embodiment and heterodyne signal $s_7$ of the variant of the sixth embodiment are processed by the same sequence of electronic processing steps as signal $s_2$ of the variant of the third embodiment. The results of that analysis are $\phi_5$, $\phi_{10}$, $\theta_{2G}$, and $\Phi_{2G}$ where $$\theta_{2G} = (\phi_{10} + \phi_7) \quad (163)$$

$$\Phi_{2G} = (\phi_{10} - \phi_7) \quad (164)$$

Note from Eqs. (163) and (164) that $\theta_{2G}$ and $\Phi_{2G}$ are not sensitive to tilts of either reflecting surfaces 95 or 96 and insensitive to thermal and mechanical disturbances that may occur in the interferometer beam splitting cubes and associated optical components as a consequence of the use of differential plane mirror interferometers.

In a next step $\phi_5$, $\phi_{10}$, $\theta_{2G}$, and $\Phi_{2G}$ are transmitted, preferably in digital format, to computer 110 for computation of refractivity, dispersion, $\Gamma$, and/or $k_1$. Quantities $\phi_5$, $\phi_{10}$, $\theta_{2G}$, $\xi$, and Z of the variant of the sixth embodiment are formally equivalent to $\Phi_{5\times I1}$, $\Phi_{10\times I1}$, $\theta_{2G}$, $\Phi_{2G}$, $\xi$, and Z, respectively, of the sixth embodiment with $\phi_{f1}$ and $\phi_{f2}$ set equal to zero, $l_1 = p_1$, and $l_2 = p_2$. Thus, $\Gamma$, refractivity $(n_1 - 1)$, dispersion $(n^2 - n_1)_{2G}$, and $k_1$ can be expressed in terms of the quantities measured by the variant of the sixth embodiment by Eqs. (23), (158), (159), and (160), respectively, wherein the phase offsets $\xi$ and Z are defined by equations corresponding to Eqs. (161) and (162), respectively, and $\chi$ and K are given by Eqs. (26) and (27), respectively, with $\phi_{f1}$ and $\phi_{f2}$ set equal to zero, $l_1 = p_1$, and $l_2 = p_2$. The remaining description of the variant of the sixth embodiment is substantially the same as corresponding portions of the descriptions given for the sixth embodiment.

The third group of preferred embodiments of the present invention represent preferred modes for the determination of intrinsic optical properties such as $\Gamma$ for a subsequent downstream use wherein the properties of the subsequent downstream use can either effect or not effect the choice of the particular manner in which the intrinsic optical properties are determined and the stability of the adopted light sources is not sufficient and the ratio of the wavelengths of the light beams generated by the adopted light sources is not matched to a known ratio value with a relative precision sufficient to meet the required precision imposed on the output data by the final end use application. The third group comprises the seventh, eighth, and ninth preferred embodiments and variants thereof.

Figure 7A:
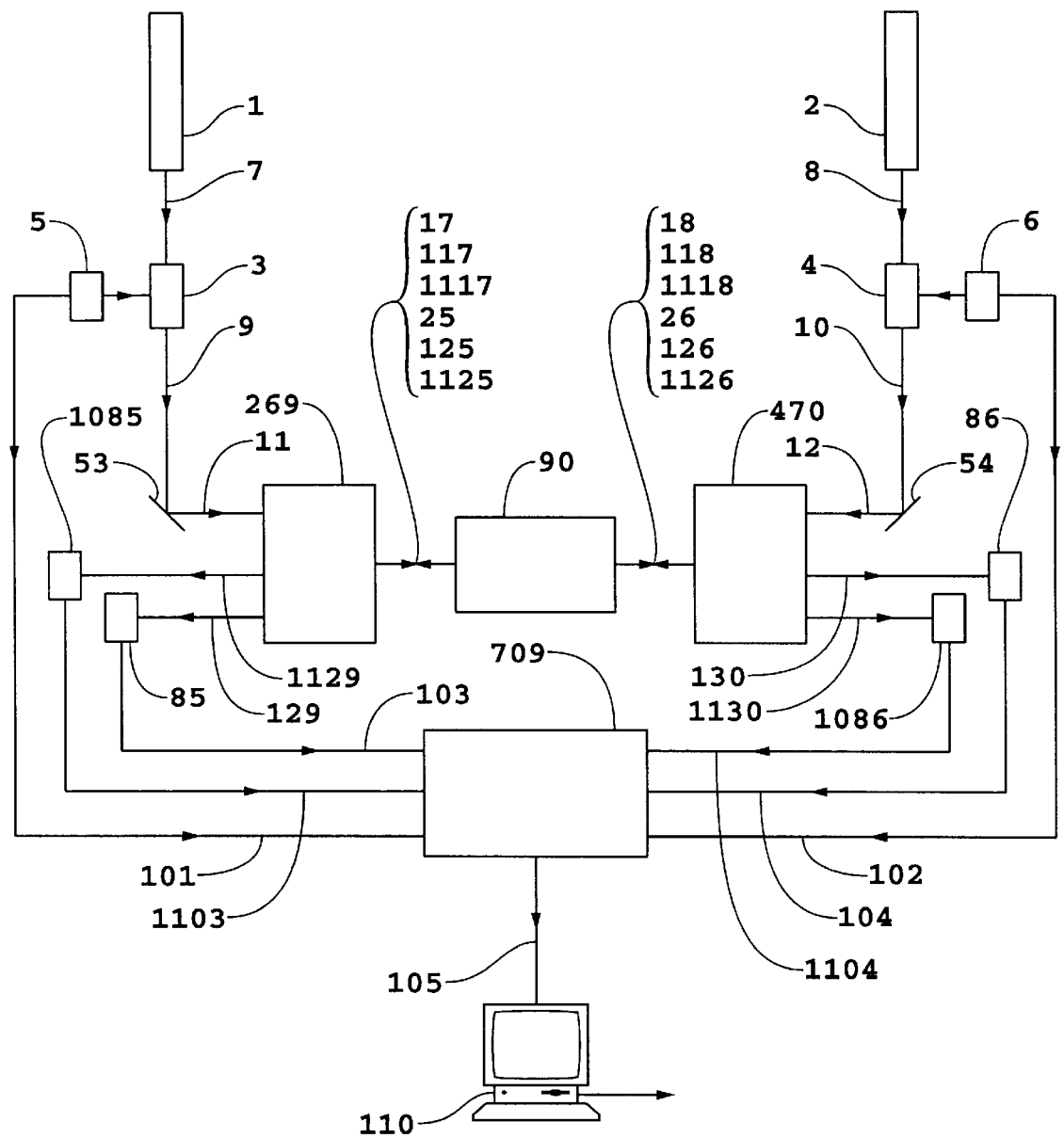
FIGS. 7a–7c taken together illustrate, in diagrammatic form, the presently preferred seventh embodiment of the present invention with FIG. 7a showing optical paths and the paths of electrical signals between indicated elements source 1, modulator 3, source 2, modulator 4, differential plane mirror interferometer groups 269 and 470, measurement cell 90, detectors 85, 1085, 86, and 1086, and the paths of electrical signals between indicated elements driver 5, modulator 3, driver 6, modulator 4, detectors 85, 1085, 86, and 1086, electronic processor 709, and computer 110.
Figure 7B:
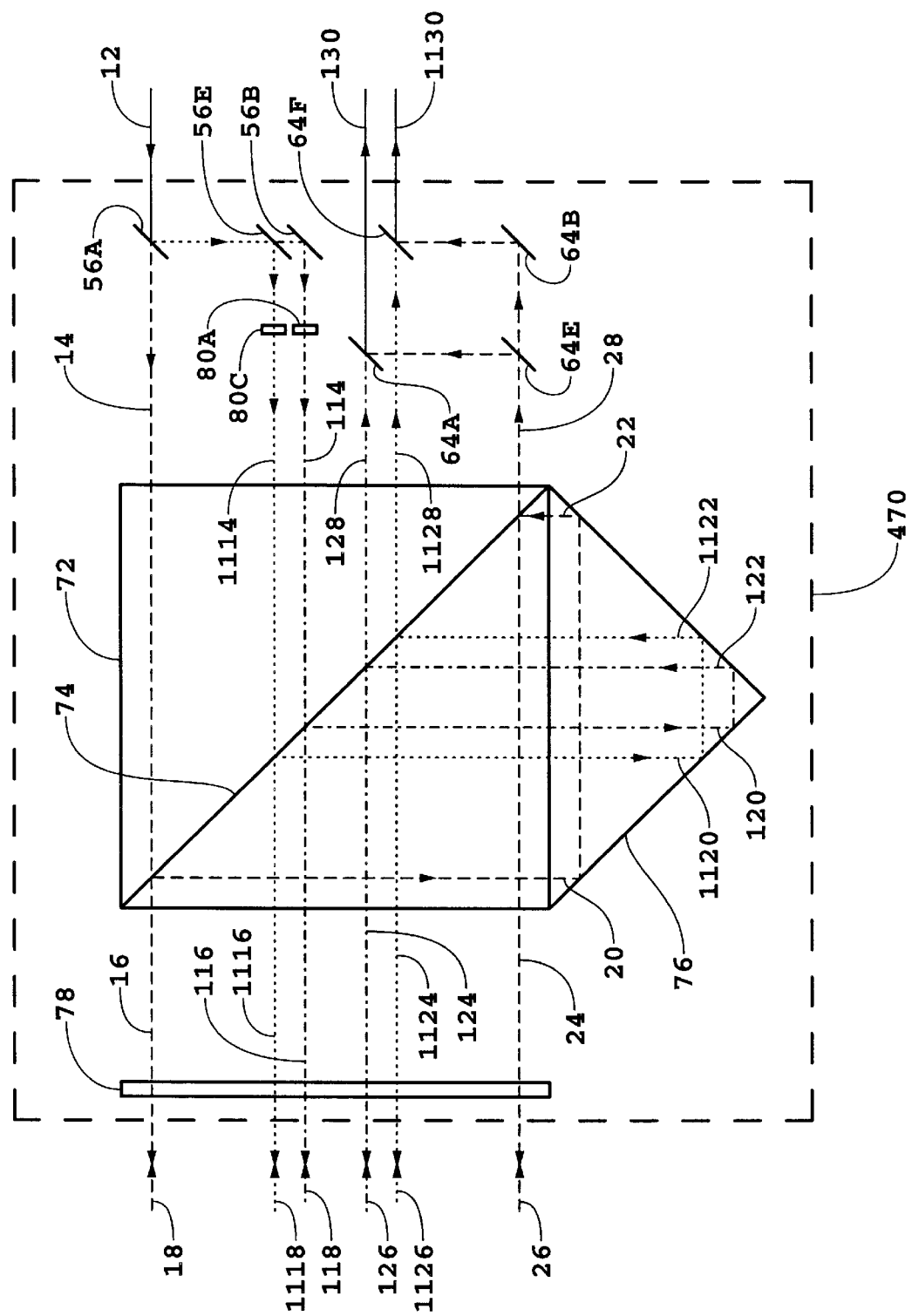
Figure 7C:
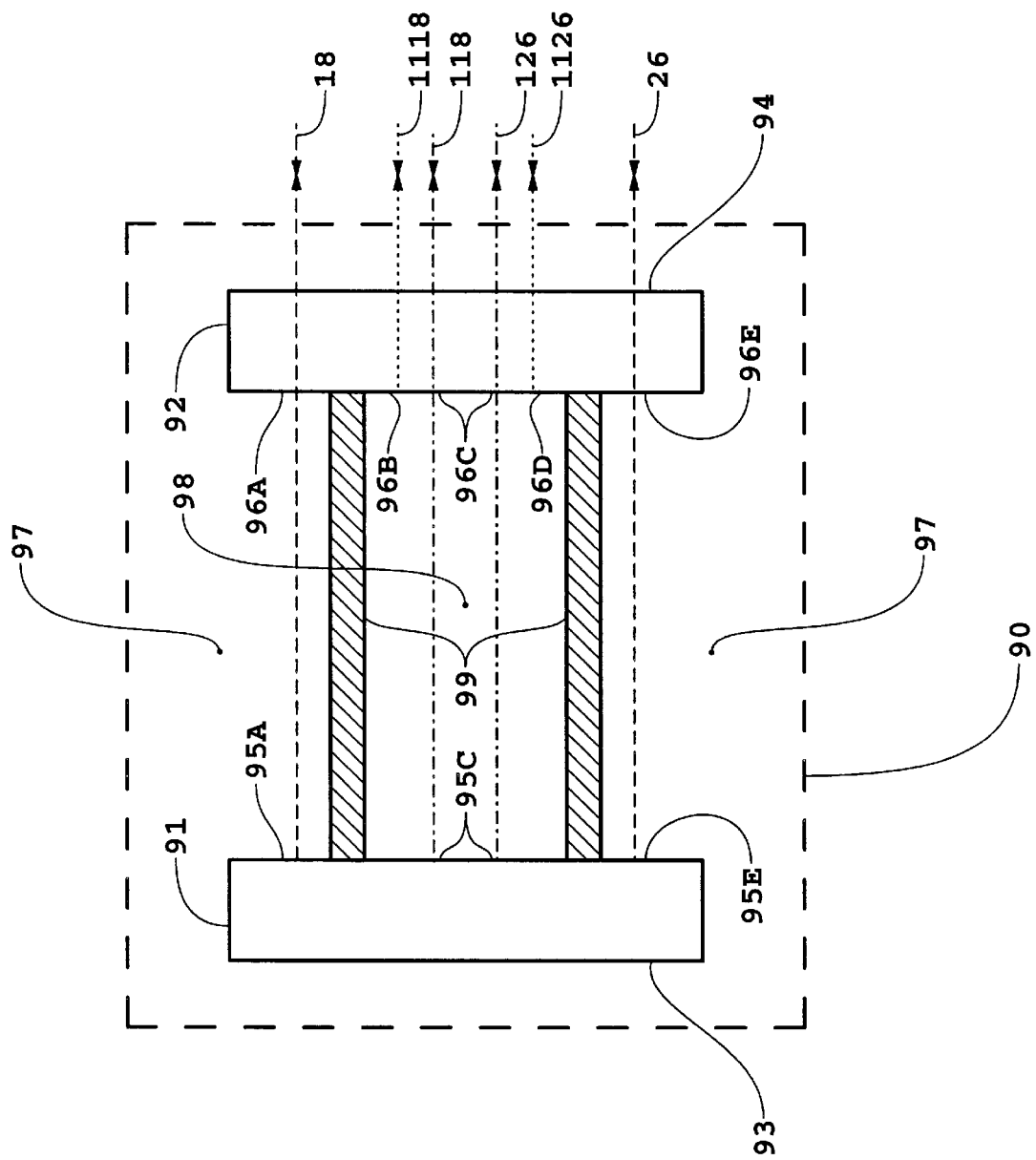

Reference is now made to FIGS. 7a–7c which depict in diagrammatic form the seventh embodiment of the present invention from the third group. The description of the sources of light beams 9 and 10 and of light beams 9 and 10 for the seventh embodiment is the same as that for description of the sources of light beams 9 and 10 and of light beams 9 and 10 given for the first preferred embodiment.

Referring to FIG. 7a, beam 9 is reflected by mirror 53 becoming beam 11 and beam 10 is reflected by mirror 54 as beam 12. Beam 11 is incident on differential plane mirror interferometer group 269 and beam 12 is incident on differential plane mirror interferometer group 470. Differential plane mirror interferometer groups 269 and 470 with external mirrors furnished by measurement cell 90 comprise interferometric means for introducing a phase shift $\phi_2$ between a first portion of the x and y components of beam 11, a phase shift $\phi_6$ between a second portion of the x and y components of beam 11, a phase shift $\phi_2$ between a first portion of the x and y components of beam 12 and a phase shift $\phi_7$ between a second portion of the x and y components of beam 12.

Differential plane mirror interferometer group 269 is the same as differential plane mirror interferometer group 269 of the fourth embodiment. Differential plane mirror interferometer group 470 comprises the differential plane mirror interferometer 70 of the first embodiment and the differential plane mirror interferometer 270 of the fourth embodiment as depicted in FIG. 7b. With reference to FIG. 7b, a portion of beam 12 is transmitted by beam splitter 56A, preferably a polarizing type, as beam 14. A second portion of beam 12 is reflected by beam splitter 56A. A first portion of the second portion of beam 12 is transmitted by beam splitter 56E, preferably a non polarizing type, reflected by mirror 56B, and transmitted by half-wave phase retardation plate 80A as beam 114. A second portion of the second portion of beam 12 is reflected by beam splitter 56E and transmitted by half-wave phase retardation plate 80C as beam 1114. The function of half-wave phase retardation plates 80A and 80C is to rotate the planes of polarization of beams 114 and 1114, respectively, by 90° such that beams 14, 114, and 1114 have the same polarizations. The paths of the external beams 18, 118, 1118, 26, 126, and 1126 of the differential plane mirror interferometer group 470 in relation to measurement cell 90 is shown diagramatically in FIG. 7c.

The magnitude of phase shifts $\phi_1$, $\phi_6$, $\phi_2$, and $\phi_7$ are related to the round-trip physical length of measurement path 97, reference path 98, or a reference path of zero physical length as shown in FIGS. 4d and 7c according to the formulae $$\varphi_1 = \sum_{i=1}^{i=p} k_1(L_{G,i}n_{1i} - L_{V,i}) + \zeta_1 \quad \varphi_6 = \sum_{i=1}^{i=p} k_1 L_{G,i}n_{1i} + \zeta_6, \quad (165)$$

$$\varphi_2 = \sum_{i=1}^{i=p} k_2(L_{G,i}n_{2i} - L_{V,i}) + \zeta_2, \quad \varphi_7 = \sum_{i=1}^{i=p} k_2 L_{G,i}n_{2i} + \zeta_7$$

where the index of refraction in the reference path 98 has been set to 1. The illustrations in FIGS. 4b and 7b are for p=2 so as to illustrate in the simplest manner the function of the invention in the seventh embodiment. To those skilled in the art, the generalization to the case when p≠2 is a straight forward procedure.

Cyclic errors that produce non linearities in distance measuring interferometry (cf. the cited articles by Bobroff) have been omitted in Eqs. (165). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

In a next step as shown in FIG. 7a, phase-shifted beams 129, 1129, 130, and 1130 impinge upon photodetectors 85, 1085, 86, and 1086, respectively, resulting in four interference signals, heterodyne signals $s_1$, $s_6$, $s_2$, and $s_7$, respectively, preferably by photoelectric detection. The signals $s_1$ and $s_6$ correspond to wavelength $\lambda_1$ and signals $s_2$ and $s_7$ correspond to wavelength $\lambda_2$. The signals $s_j$ have the form $$s_j = A_j \cos[\alpha_j(t)], \ j=1, 6, 2, \text{ and } 7 \quad (166)$$

where the time-dependent arguments $\alpha_j(t)$ are given by $$\alpha_1(t) = 2\pi f_1 t + \phi_1,$$

$$\alpha_6(t) = 2\pi f_1 t + \phi_6,$$

$$\alpha_2(t) = 2\pi f_2 t + \phi_2,$$

$$\alpha_7(t) = 2\pi f_2 t + \phi_7. \quad (167)$$

Heterodyne signals $s_1$, $s_6$, $s_2$, and $s_7$ are transmitted to electronic processor 709 for analysis as electronic signals 103, 1103, 104, and 1104, respectively, preferably in digital format.

The phases of drivers 5 and 6 are transmitted by electrical signals, reference signals 101 and 102, respectively, in either digital or analog format to electronic processor 709.

A preferred method for electronically processing the heterodyne signals $s_1$, $s_6$, $s_2$, and $s_7$ is presented herewithin for the case when $l_1$ and $l_2$ are not low order integers. For the case when $l_1$ and $l_2$ are low order integers, the preferred procedure for electronically processing the heterodyne signals $s_1$, $s_6$, $s_2$, and $s_7$ is the same as the one subsequently set down for the variant of the seventh preferred embodiment of the present invention.

Referring now to FIG. 7a, electronic processor 709 comprises electronic processors 109 and 409, as depicted in FIGS. 1f and 4f, respectively, with omission of obvious duplications. More formally, electronic processor 709 is the union, as used in set theory, of the elements of electronic processors 109 and 409. Thus, the heterodyne signals $s_1$, $s_6$, and $s_7$ of the seventh embodiment are each processed by the same sequence of electronic processing steps as signals $s_1$, $s_6$, and $s_7$ of the fourth embodiment and signals $s_1$ and $s_2$ of the seventh embodiment are processed by the same sequence of electronic processing steps as signals $s_1$ and $s_2$ of the first embodiment. The results of that analysis are phases $$\Phi_{1 \times II} = \varphi_1 - \varphi_{II}, \qquad \Phi_{6 \times II} = \varphi_6 - \varphi_{II}, \quad (168)$$

$$\vartheta_{1G} = \left(\frac{l_1}{p}\Phi_{1 \times II} + \frac{l_2}{p}\Phi_{2 \times I2}\right), \quad \Phi_{1G} = \left(\frac{l_1}{p}\Phi_{1 \times II} - \frac{l_2}{p}\Phi_{2 \times I2}\right),$$

$$\vartheta_{2G} = \left(\frac{l_1}{p}\Phi_{6 \times II} + \frac{l_2}{p}\Phi_{7 \times I2}\right), \quad \Phi_{2G} = \left(\frac{l_1}{p}\Phi_{6 \times II} - \frac{l_2}{p}\Phi_{7 \times I2}\right).$$

The refractivity $(n_1-1)$, the dispersions $(n^2-n_1)_{1G}$ and $(n_2-n_1)_{2G}$, and the wavenumbers $k_1$ and $k_2$ can be expressed in terms of other quantities by the formulae $$(n_1 - 1) = \frac{1}{(\chi + K)L_G}\left(\frac{l_1}{p}\right)[\Phi_{1 \times II} - (\zeta_1 - \varphi_{II})] - \frac{(L_G - L_V)}{L_G} \quad (169)$$

$$(n_2 - n_1)_{1G} = \quad (170)$$

$$\frac{1}{\chi L_G[1-(K/\chi)^2]}\{[\vartheta_{1G}(K/\chi) - \Phi_{1G}] - [\xi_1(K/\chi) - Z_1]\}$$

-continued $$(n_2 - n_1)_{2G} = \frac{1}{\chi L_G[1-(K/\chi)^2]}\{[\vartheta_{2G}(K/\chi) - \Phi_{2G}] - [\xi_2(K/\chi) - Z_2]\} \quad (171)$$

$$k_1 = \frac{1}{pL_V}[(\Phi_{6\times II} - \Phi_{1\times II}) - (\zeta_6 - \zeta_1)] \quad (172)$$

$$k_2 = \frac{1}{L_V}\left\{\frac{1}{2l_2}[(\vartheta_{2G} - \Phi_{2G}) - (\vartheta_{1G} - \Phi_{1G})] - \frac{1}{p}(\zeta_7 - \zeta_2)\right\} \quad (173)$$

where $$\xi_1 = \frac{l_1}{p}(\zeta_1 - \varphi_{II}) + \frac{l_2}{p}(\zeta_2 - \varphi_{I2}) \quad (174)$$

$$Z_1 = \frac{l_1}{p}(\zeta_1 - \varphi_{II}) - \frac{l_2}{p}(\zeta_2 - \varphi_{I2}), \quad (175)$$

$$\xi_2 = \frac{l_1}{p}(\zeta_6 - \varphi_{II}) + \frac{l_2}{p}(\zeta_7 - \varphi_{I2}) \quad (176)$$

$$Z_2 = \frac{l_1}{p}(\zeta_6 - \varphi_{II}) - \frac{l_2}{p}(\zeta_7 - \varphi_{I2}) \quad (177)$$

and $\chi$ and $K$ are given by Eqs. (26) and (27), respectively.

In a next step, electronic processing means 709 transmits to the computer 110 the phases $\Phi_{1\times I1}$, $\Phi_{6\times I1}$, $\theta_{1G}$, $\theta_{2G}$, $\Phi_{1G}$, and $\Phi_{2G}$ as electronic signal 105 in either digital or analog format, preferably a digital format, for the computation of a $\Gamma$, $K/\chi$, and the calculation of $k_1$ if required according to Eqs. (23), (169), (170) or (171), (172), and (173) substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The remaining description of the seventh embodiment is the same as corresponding portions of the description given for the first and fourth embodiments of the present invention.

Reference is again made to FIGS. 7a–7c which taken together, with electronic processor 709 in FIG. 7a being replaced by electronic processor 709A, depict in diagrammatic form a variant of the seventh preferred embodiment of the present invention wherein the wavelengths of the light beams are approximately harmonically related, the approximate harmonic ratio of the wavelengths of the light beams generated by the adopted light sources is not matched to a known harmonic ratio with a relative precision sufficient to meet the required precision and/or the stability of the adopted light sources is not sufficient to meet the required precision imposed on the output data by the final end use application. The condition wherein the wavelengths are approximately harmonically related corresponds to the special case of the seventh embodiment in which the ratio $(l_1/l_2)$ is expressible as the ratio of low order non-zero integers $(p_1/p_2)$, cf. Eq. (35).

The description of the sources of light beams 9 and 10 and of light beams 9 and 10 for the variant of the seventh embodiment is the same as that for description of the sources of light beams 9 and 10 and of light beams 9 and 10 given for the first embodiment with the additional requirement that the wavelengths be approximately harmonically related although not matched to a known harmonic ratio to a relative precision sufficient to meet the required precision imposed on the output data by the final end use application. The description of the apparatus for the variant of the seventh embodiment depicted in FIGS. 7a–7c is the same as corresponding portions of the description given for the seventh embodiment.

Referring now to FIG. 7a with electronic processor 709 replaced with electronic processor 709A, electronic processor 709A comprises electronic processors 109A and 409A, as depicted in FIGS. 1g and 4g, respectively, with omission of obvious duplications. More formally, electronic processor 709A is the union, as used in set theory, of the elements of electronic processors 109A and 409A. Thus, the heterodyne signals $s_1$, $s_6$, and $s_7$ of the variant of the seventh embodiment are each processed by the same sequence of electronic processing steps as signals $s_1$, $s_6$, and $s_7$ of the variant of the fourth embodiment and signals $s_1$ and $s_2$ of the variant of the seventh embodiment are processed by the same sequence of electronic processing steps as signals $s_1$ and $s_2$ of the variant of the first embodiment. The results of that analysis are phases $\phi_1$, $\phi_6$, $$\theta_{1G}=(p_1\phi_1+p_2\phi_2), \Phi_{1G}=(p_1\phi_1-p_2\phi_2),$$
$$\theta_{2G}=(p_1\phi_6+p_2\phi_7), \Phi_{2G}=(p_1\phi_6-p_2\phi_7) \quad (178)$$

In a next step, $\phi_1$, $\phi_6$, $\theta_{1G}$, $\Phi_{1G}$, $\theta_{2G}$, and $\Phi_{2G}$ are transmitted, either in digital or analog format, preferably in digital format, to computer 110 for computation of $\Gamma$, $(K/\chi)$ and $k_1$ if required. Quantities $\phi_1$, $\phi_6$, $p\theta_{1G}$, $p\Phi_{1G}$, $p\theta_{2G}$, $p\Phi_{2G}$, $p\xi_1$, $pZ_1$, $p\xi_2$, and $pZ_2$ are formally equivalent to $\Phi_{1\times I1}$, $\Phi_{6\times I1}$, $\theta_{1G}$, $\Phi_{1G}$, $\theta_{2G}$, $\Phi_{2G}$, $\xi_1$, $Z_1$, $\xi_2$, and $Z_2$, respectively, of the seventh embodiment with $\phi_{I1}$ and $\phi_{I2}$ set equal to zero, $l_1=p_1$, and $l_2=p_2$. As a consequence, the refractivity $(n_1-1)$, dispersion $(n_2-n^1)_{1G}$, dispersion $(n_2-n_1)_{2G}$, $k_1$, and $k_2$ can be expressed in terms of the quantities measured by the variant of the seventh embodiment according to Eqs. (169), (170), (171), (172), and (173) with $\phi_{I1}$ and $\phi_{I2}$ set equal to zero, $l_1=p_1$, and $l_2=p_2$. Thus, the computation of a $\Gamma$, $K/\chi$, and the calculation of $k_1$ if required is performed according to Eqs. (23), (169), (170) or (171), (172), and (173) with $\phi_{I1}$ and $\phi_{I2}$ set equal to zero, $l_1=p_1$, and $l_2=p_2$ substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents. The remaining discussion of the variant of the seventh embodiment is the same as corresponding portions of the descriptions given for the seventh embodiment.

The principal advantage of the variant of the seventh embodiment lies a simplified electronic processing in relation to that of the seventh embodiment although at the risk of possibly enhancing frequency sensitive phase offset errors due to differences in group delays experienced by heterodyne and/or modified heterodyne signals having significantly different frequencies. The discussion of the effects of group delay for the variant of the seventh embodiment is the same as corresponding portions of the description given for the seventh embodiment.

Figure 8A:
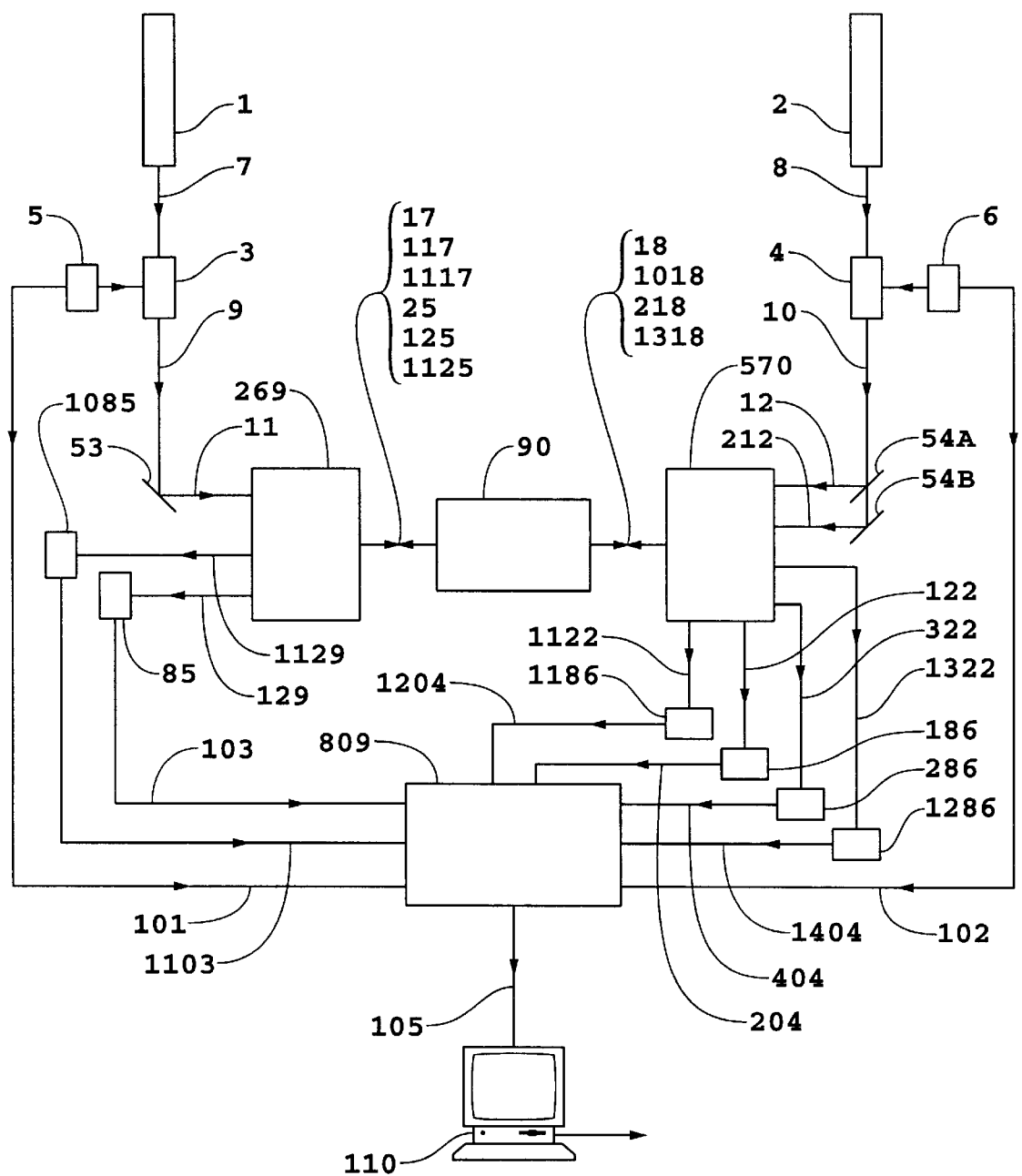
FIGS. 8a–8c taken together illustrate, in diagrammatic form, the presently preferred eighth embodiment of the present invention with FIG. 8a showing optical paths and the paths of electrical signals between indicated elements source 1, modulator 3, source 2, modulator 4, differential plane mirror interferometer groups 269 and 570, measurement cell 90, detectors 85, 1085, 186, 286, 1186, and 1286, and the paths of electrical signals between indicated elements driver 5, modulator 3, driver 6, modulator 4, detectors 85, 1085, 186, 286, 1186, and 1286, electronic processor 809, and computer 110.
Figure 8B:
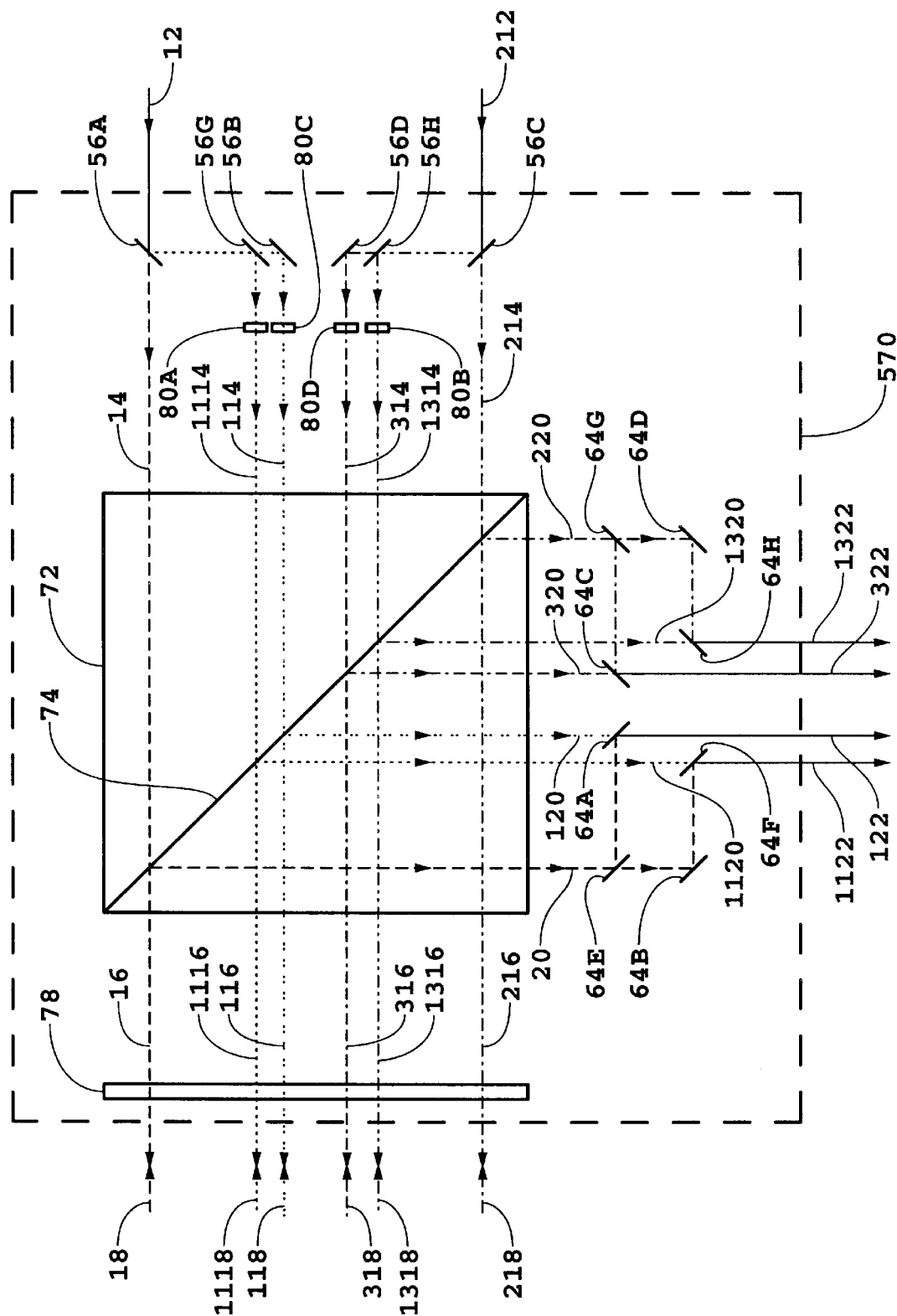
Figure 8C:
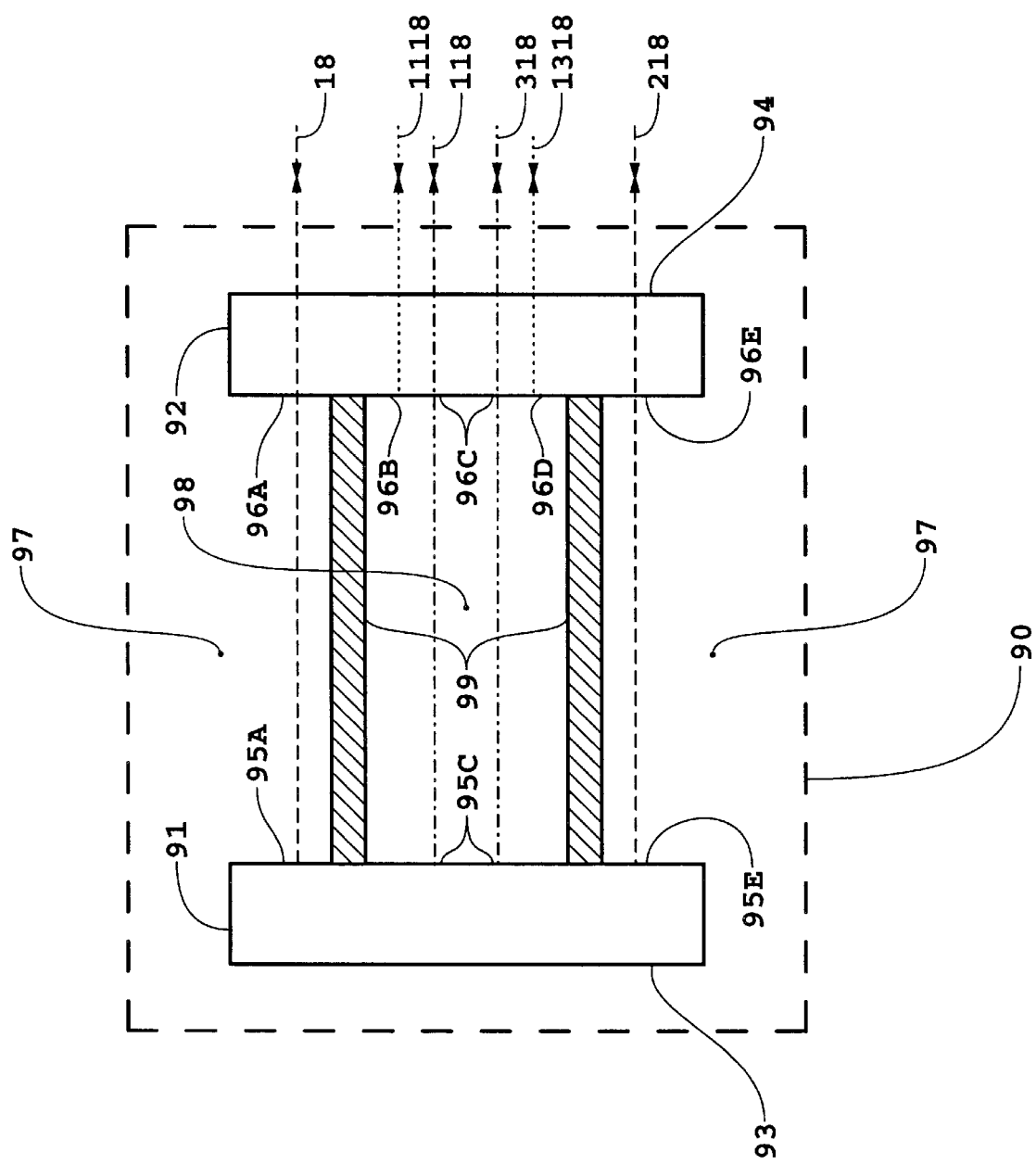

Reference is now made to FIGS. 8a–8c that depict in diagrammatic form the eighth embodiment of the present invention from the third group. The description of the sources of light beams 9 and 10 and of light beams 9 and 10 for the eighth embodiment is the same as that for description of the sources of light beams 9 and 10 and of light beams 9 and 10 given for the first preferred embodiment.

Referring to FIG. 8a, beam 9 is reflected by mirror 53 becoming beam 11. A first portion of beam 10 is reflected by beam splitter 54A, preferably a non polarizing type, as beam 12 and a second portion of beam 10 transmitted by beam splitter 54A is reflected by mirror 54B as beam 212. Beam 11 is incident on differential plane mirror interferometer group 269 and beams 12 and 212 are incident on differential plane mirror interferometer group 570. Differential plane mirror interferometer groups 269 and 570 with external mirrors furnished by measurement cell 90 comprise interferometric means for introducing a phase shift $\phi_1$ between a first portion of the x and y components of beam 11, a phase shift $\phi_6$ between a second portion of the x and y components of beam 11, a phase shift $\phi_8$ between the x and y components of beam 12 and a phase shift $\phi_9$ between the x and y components of beam 212.

Differential plane mirror interferometer group 269 is the same as differential plane mirror interferometer group 269 of the fifth embodiment. Differential plane mirror interferometer group 570 comprises the differential plane mirror interferometer 170 of the second embodiment, the differential plane mirror interferometer 370 of the fifth embodiment, and beam splitters 56G and 56H, preferably of the non polarizing type, as depicted in FIG. 8b. The paths of the external beams 18, 118, 1118, 218, 318, and 1328 of the differential plane mirror interferometer group 570 in relation to measurement cell 90 is shown diagramatically in FIG. 8c.

The magnitude of phase shifts $\phi_1$, $\phi_6$, $\phi_3$, $\phi_4$, $\phi_8$, and $\phi_9$ are related to the round-trip physical length of measurement path 97, reference path 98, or a reference path of zero physical length as shown in FIGS. 5c and 8c according to the formulae $$\varphi_1 = \sum_{i=1}^{i=p_1} k_1(L_{G,i}n_{1i} - L_{V,i}) + \zeta_1, \tag{179}$$

$$\varphi_6 = \sum_{i=1}^{i=p_1} k_1 L_{G,i} n_{1i} + \zeta_6,$$

$$\varphi_3 = \sum_{i=1}^{i=p_2} k_2(L_{G,i}n_{2i} - L_{V,i}) + \zeta_3,$$

$$\varphi_4 = \sum_{i=p_2+1}^{i=p_1} k_2(L_{G,i}n_{2i} - L_{V,i}) + \zeta_4,$$

$$\varphi_8 = \sum_{i=1}^{i=p_2} k_2 L_{G,i} n_{2i} + \zeta_8,$$

$$\varphi_9 = \sum_{i=p_2+1}^{i=p_2} k_2 L_{G,i} n_{2i} + \zeta_9,$$

for the case of $p_1=2p_2$ with the index of refraction in the reference path 98 set to 1. The phase offsets $\zeta_j$ comprise all contributions to the phase shifts $\phi_j$ that are not related to the measurement path 97 or reference path 98. To those skilled in the art, the generalization to the case when $p_1 \neq 2p_2$ is a straight forward procedure. Differential plane mirror interferometer group 269 (c.f. FIG. 4b) and differential plane mirror interferometer group 570 shown in FIG. 8b, along with measurement cell 90, are configured with $p_1=2$ and $p_2=1$ so as to illustrate in the simplest manner the function of the apparatus of the eighth embodiment.

Cyclic errors that produce nonlinearities in distance measuring interferometry (cf. the cited articles by Bobroff) have been omitted in Eqs. (179). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

In a next step as shown in FIG. 8a, phase-shifted beams 129, 1129, 122, 1122, 322, and 1322 impinge upon photodetectors 85, 1085, 186, 1186, 286, and 1286, respectively, resulting in six interference signals, heterodyne signals $s_1$, $s_6$, $s_3$, $s_4$, $s_8$, and $s_9$, respectively, preferably by photoelectric detection. The signals $s_1$ and $s_6$ correspond to wavelength $\lambda_1$ and signals $s_3$, $s_4$, $s_8$, and $s_9$ correspond to wavelength $\lambda_2$. The signals $s_j$ have the form $$s_j = A_j \cos[\alpha_j(t)], j=1, 6, 3, 4, 8, \text{ and } 9 \tag{180}$$

where the time-dependent arguments $\alpha_j(t)$ are given by $$\alpha_1(t)=2\pi f_1 t + \phi_1, \; \alpha_6(t)=9\pi f_1 t + \phi_6,$$

$$\alpha_3(t)=2\pi f_2 t + \phi_3, \; \alpha_4(t)=9\pi f_2 t + \phi_4,$$

$$\alpha_8(t)=2\pi f_2 t + \phi_8, \; \alpha_9(t)=9\pi f_2 t + \phi_9 \tag{181}$$

Heterodyne signals $s_1$, $s_6$, $s_3$, $s_4$, $s_8$, and $s_9$ are transmitted to electronic processor 809 for analysis as electronic signals 103, 1103, 204, 404, 1204, and 1404, respectively, preferably in digital format.

The phases of drivers 5 and 6 are transmitted by electrical signals, reference signals 101 and 102, respectively, in either digital or analog format to electronic processor 809.

A preferred method for electronically processing the heterodyne signals $s_1$, $s_6$, $s_3$, $s_4$, $s_8$, and $s_9$ is presented herewithin for the case when $l_1$ and $l_2$ are not low order integers. For the case when $l_1$ and $l_2$ are low order integers, the preferred procedure for electronically processing the heterodyne signals $s_1$, $s_6$, $s_3$, $s_4$, $s_8$, and $s_9$ is the same as the one subsequently set down for the variant of the eighth preferred embodiment of the present invention.

Referring now to FIG. 8a, electronic processor 809 comprises electronic processors 209 and 509, as depicted in FIGS. 2d and 5d, respectively, with omission of obvious duplications. More formally, electronic processor 809 is the union, as used in set theory, of the elements of electronic processors 209 and 509. Thus, the heterodyne signals $s_1$, $s_6$, $s_8$, and $s_9$ of the eighth embodiment are each processed by the same sequence of electronic processing steps as signal $s_1$, $s_6$, $s_8$, and $s_9$ of the fifth embodiment and $s_1$, $s_3$, and $s_4$ of the eighth embodiment are processed by the same sequence of electronic processing steps as signal $s_1$, $s_3$, and $s_4$ of the second embodiment, respectively. The results of that analysis are phases $$\Phi_{1 \times II} = \varphi_1 - \varphi_{II}, \tag{182}$$

$$\Phi_{6 \times II} = \varphi_6 - \varphi_{II}$$

$$\vartheta_{1G} = \left[\frac{l_1}{p_1}\Phi_{1 \times II} + \frac{l_2}{p_2}\frac{(\Phi_{3 \times I2} + \Phi_{4 \times I2})}{2}\right],$$

$$\Phi_{1G} = \left[\frac{l_1}{p_1}\Phi_{1 \times II} - \frac{l_2}{p_2}\frac{(\Phi_{3 \times I2} + \Phi_{4 \times I2})}{2}\right],$$

$$\vartheta_{2G} = \left[\frac{l_1}{p_1}\Phi_{6 \times II} + \frac{l_2}{p_2}\frac{(\Phi_{8 \times I2} + \Phi_{9 \times I2})}{2}\right],$$

-continued $$\Phi_{2G} = \left[\frac{l_1}{p_1}\Phi_{6\times II} - \frac{l_2}{p_2}\frac{(\Phi_{8\times I2} + \Phi_{9\times I2})}{2}\right].$$

The refractivity $(n_1-1)$, the dispersions $(n_2-n_1)_{1G}$ and $(n_2-n_1)_{2G}$, and the wavenumbers $k_1$ and $k_2$ can be expressed in terms of other quantities by the formulae $$(n_1 - 1) = \frac{1}{(\chi + K)L_G}\left(\frac{l_1}{p_1}\right)[\Phi_{1\times II} - (\zeta_1 - \varphi_{II})] - \frac{(L_G - L_V)}{L_G} \quad (183)$$

$$(n_2 - n_1)_{1G} = \quad (184)$$
$$\frac{1}{\chi L_G[1-(K/\chi)^2]}\{[\vartheta_{1G}(K/\chi) - \Phi_{1G}] - [\xi_1(K/\chi) - Z_1]\}$$

$$(n_2 - n_1)_{2G} = \quad (185)$$
$$\frac{1}{\chi L_G[1-(K/\chi)^2]}\{[\vartheta_{2G}(K/\chi) - \Phi_{2G}] - [\xi_2(K/\chi) - Z_2]\},$$

$$k_1 = \frac{1}{p_1 L_V}[(\Phi_{6\times II} - \Phi_{1\times II}) - (\zeta_6 - \zeta_1)] \quad (186)$$

$$k_2 = \quad (187)$$
$$\frac{1}{L_V}\left\{\frac{1}{2l_2}[(\vartheta_{2G} - \Phi_{2G}) - (\vartheta_{1G} - \Phi_{1G})] - \frac{1}{2p_2}[(\zeta_8 + \zeta_9) - (\zeta_3 + \zeta_4)]\right\},$$

where $$\xi_1 = \frac{l_1}{p_1}(\zeta_1 - \varphi_{II}) + \frac{l_2}{p_2}\left(\frac{\zeta_3 + \zeta_4}{2} - \varphi_{I2}\right) \quad (188)$$

$$Z_1 = \frac{l_1}{p_1}(\zeta_1 - \varphi_{II}) - \frac{l_2}{p_2}\left(\frac{\zeta_3 + \zeta_4}{2} - \varphi_{I2}\right), \quad (189)$$

$$\xi_2 = \frac{l_1}{p_1}(\zeta_6 - \varphi_{II}) + \frac{l_2}{p_2}\left(\frac{\zeta_8 + \zeta_9}{2} - \varphi_{I2}\right) \quad (190)$$

$$Z_2 = \frac{l_1}{p_1}(\zeta_6 - \varphi_{II}) - \frac{l_2}{p_2}\left(\frac{\zeta_8 + \zeta_9}{2} - \varphi_{I2}\right) \quad (191)$$

and $\chi$ and $K$ are given by Eqs. (26) and (27), respectively.

In a next step, electronic processing means 809 transmits to the computer 110 the phases $\Phi_{1\times I1}$, $\Phi_{6\times I1}$, $\theta_{1G}$, $\Phi_{1G}$, $\theta_{2G}$, and $\Phi_{2G}$ as electronic signal 105 in either digital or analog format, preferably a digital format, for the computation of a $\Gamma$, $K/\chi$, and the calculation of $k_1$ if required according to Eqs. (23), (183), (184) or (185), (186), and (187) substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The remaining description of the eighth embodiment is the same as corresponding portions of the description given for the second and fifth embodiments of the present invention.

Reference is again made to FIGS. 8a–8c which taken together, with electronic processor 809 in FIG. 8a being replaced by electronic processor 809A, depict in diagrammatic form a variant of the eighth preferred embodiment of the present invention wherein the wavelengths of the light beams are approximately harmonically related, the approximate harmonic ratio of the wavelengths of the light beams generated by the adopted light sources is not matched to a known harmonic ratio with a relative precision sufficient to meet the required precision and/or the stability of the adopted light sources is not sufficient to meet the required precision imposed on the output data by the final end use application. The condition wherein the wavelengths are approximately harmonically related corresponds to the special case of the eighth embodiment in which the ratio $(l_1/l_2)$ is expressible as the ratio of low order non zero integers $(p_1/p_2)$, cf. Eq. (35). The description of the sources of light beams 9 and 10 and of light beams 9 and 10 for the variant of the eighth embodiment is the same as that for description of the sources of light beams 9 and 10 and of light beams 9 and 10 given for the first embodiment with the additional requirement that the wavelengths be approximately harmonically related although not matched to a known harmonic ratio to a relative precision sufficient to meet the required precision imposed on the output data by the final end use application. The description of the apparatus for the variant of the eighth embodiment depicted in FIGS. 8a–8c is the same as corresponding portions of the description given for the eighth embodiment.

Referring now to FIG. 8a with electronic processor 809 replaced with electronic processor 809A, electronic processor 809A comprises electronic processors 209A and 509A, as depicted in FIGS. 2e and 5e, respectively, with omission of obvious duplications. More formally, electronic processor 809A is the union, as used in set theory, of the elements of electronic processors 209A and 509A. Thus, the heterodyne signals $s_1$, $s_6$, $s_8$, and $s_9$ of the variant of the eighth embodiment are each processed by the same sequence of electronic processing steps as signal $s_1$, $s_6$, $s_8$, and $s_9$ of the variant of the fifth embodiment and $s_1$, $s_3$, and $s_4$ of the variant of the eighth embodiment are each processed by the same sequence of electronic processing steps as signal $s_1$, $s_3$, and $s_4$ of the variant of the second embodiment, respectively. The results of that analysis are phases $\phi_1$, $\phi_6$, $$\vartheta_{1G} = \left[\varphi_1 + \frac{(\varphi_3 + \varphi_4)}{2}\right], \quad (192)$$

$$\Phi_{1G} = \left[\varphi_1 - \frac{(\varphi_3 + \varphi_4)}{2}\right],$$

$$\vartheta_{2G} = \left[\varphi_6 + \frac{(\varphi_8 + \varphi_9)}{2}\right],$$

$$\Phi_{2G} = \left[\varphi_6 - \frac{(\varphi_8 + \varphi_9)}{2}\right]$$

In a next step, $\phi_1$, $\phi_6$, $\theta_{1G}$, $\Phi_{1G}$, $\theta_{2G}$, and $\phi_{2G}$ are transmitted, preferably in digital format, to computer 110 for computation of $\Gamma$, $(K/\chi)$, and $k_1$ if required. Quantities $\phi_1$, $\phi_6$, $\theta_{1G}$, $\Phi_{1G}$, $\theta_{2G}$, $\Phi_{2G}$ $\xi_1$, $Z_1$, $v_2$ and $Z_2$ are formally equivalent to $\Phi_{1\times I1}$, $\Phi_{6\times I1}$, $\theta_{1G}$, $\Phi_{1G}$, $\theta_{2G}$, $\Phi_{2G}$, $\xi_1$, $Z_1$, $\xi_2$, and $Z_2$, respectively, of the eighth embodiment with $\phi_{I1}$ and $\phi_{I2}$ set equal to zero, $l_1=p_1$, $l_2=p_2$. As a consequence, the refractivity $(n_1-1)$, dispersions $(n_2-n_1)_{1G}$ and $(n^2-n_1)_{2G}$, $k_1$, and $k_2$ can be expressed in terms of the quantities measured by the variant of the eighth embodiment according to Eqs. (183), (184), (185), (186), and (187) with $\phi_{I1}$ and $\phi_{I2}$ set equal to zero, $l_1=p_1$, and $l_2=p_2$. Thus, the computation of a $\Gamma$, $K/\chi$, and the calculation of $k_1$ if required is performed according to Eqs. (23), (183), (184) or (185), (186), and (187) with $\phi_{I1}$ and $\phi_{I2}$ set equal to zero, $l_1=p_1$, and $l_2=p_2$ substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents. The remaining description of the variant of the eighth embodiment is the same as corresponding portions of the descriptions given for the eighth embodiment.

The principal advantage of the variant of the eighth embodiment in relation to the eighth embodiment is the same as that described with regard to the advantage of the variant of the second embodiment in relation to the second embodiment.

Figure 9:
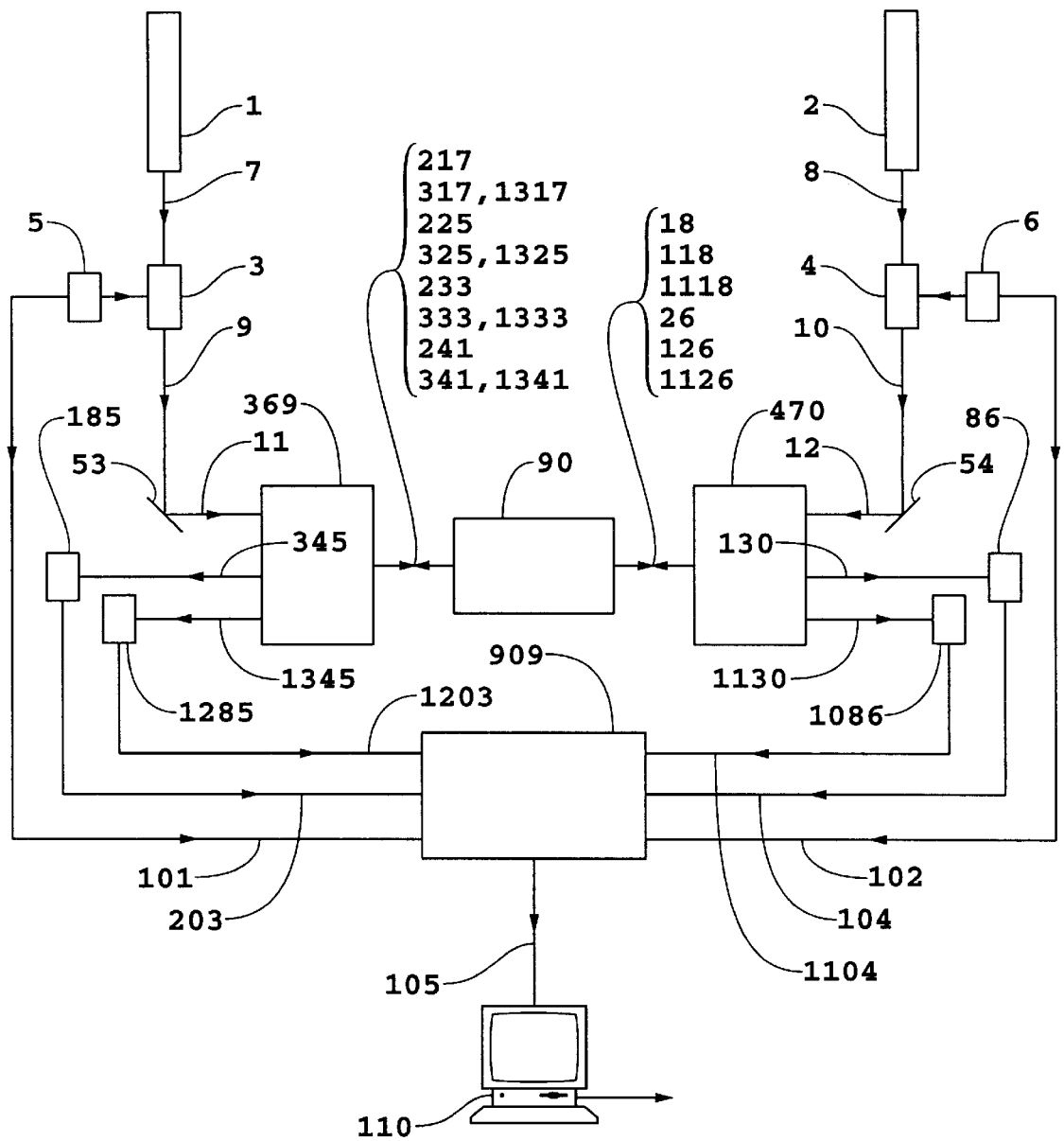
FIG. 9 illustrates, in diagrammatic form, the presently preferred ninth embodiment of the present invention with FIG. 9 showing optical paths and the paths of electrical signals between indicated elements source 1, modulator 3, source 2, modulator 4, differential plane mirror interferometer groups 369 and 470, measurement cell 90, detectors 185, 1285, 86, and 1086, and the paths of electrical signals between indicated elements driver 5, modulator 3, driver 6, modulator 4, detectors 185, 1285, 86, and 1086, electronic processor 909, and computer 110.

Reference is now made to FIG. 9 that depicts in diagrammatic form the ninth embodiment of the present invention from the third group. The description of the sources of light beams 9 and 10 and of light beams 9 and 10 for the ninth embodiment is the same as that for description of the sources of light beams 9 and 10 and of light beams 9 and 10 given for the first preferred embodiment.

Referring to FIG. 9, beam 9 is reflected by mirror 53 becoming beam 11 and beam 10 is reflected by mirror 54 as beam 12. Beam 11 is incident on differential plane mirror interferometer group 369 and beam 12 is incident on differential plane mirror interferometer group 470. Differential plane mirror interferometer groups 369 and 470 with external mirrors furnished by measurement cell 90 comprise interferometric means for introducing a phase shift $\phi_5$ between a first portion of the x and y components of beam 11, a phase shift $\phi_{10}$ between a second portion of the x and y components of beam 11, a phase shift $\phi_2$ between a first portion of the x and y components of beam 12 and a phase shift $\phi_7$ between a second portion of the x and y components of beam 12.

Differential plane mirror interferometer group 369 is the same as differential plane mirror interferometer group 369 of the sixth embodiment and differential plane mirror interferometer group 470 is the same as differential plane mirror interferometer group 470 of the seventh embodiment.

The magnitude of phase shifts $\phi_5$, $\phi_{10}$, $\phi_2$, and $\phi_7$ are related to the round-trip physical length of measurement path 97, reference path 98, or a reference path of zero physical length as shown in FIGS. 6d and 7c according to the formulae $$\varphi_5 = \sum_{i=1}^{i=p_1} k_1(L_{G,i}n_{1i} - L_{V,i}) + \zeta_5,$$

$$\varphi_{10} = \sum_{i=1}^{i=p_1} k_1 L_{G,i}n_{1i} + \zeta_{10},$$

$$\varphi_2 = \sum_{i=1}^{i=p_2} k_2(L_{G,i}n_{2i} - L_{V,i}) + \zeta_2,$$

$$\varphi_7 = \sum_{i=1}^{i=p_2} k_2 L_{G,i}n_{2i} + \zeta_7, \qquad (193)$$

for the case of $p_1 = 2p_2$ with the index of refraction in the reference path 98 set to 1. The phase offsets $\zeta_j$ comprise all contributions to the phase shifts $\phi_j$ that are not related to the measurement path 97 or reference path 98. To those skilled in the art, the generalization to the case when $p_1 \neq 2p_2$ is a straight forward procedure. Differential plane mirror interferometer group 369 (c.f. FIGS. 6b and 6c) and differential plane mirror interferometer group 470 (c.f. FIG. 7b), along with measurement cell 90, are configured with $p_1 = 2$ and $p_2 = 1$ so as to illustrate in the simplest manner the function of the apparatus of the eighth embodiment.

Cyclic errors that produce nonlinearities in distance measuring interferometry (cf. the cited articles by Bobroff) have been omitted in Eqs. (193). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer (Tanaka, Yamagami, and Nakayama, ibid.).

In a next step as shown in FIG. 9, phase-shifted beams 345, 1345, 130, and 1130 impinge upon photodetectors 185, 1285, 86, and 1086, respectively, resulting in four interference signals, heterodyne signals $s_5$, $s_{10}$, $s_2$, and $s_7$, respectively, preferably by photoelectric detection. The signals $s_5$ and $s_{10}$ correspond to wavelength $\lambda_1$ and signals $s_2$ and $s_7$ correspond to wavelength $\lambda_2$. The signals $s_j$ have the form $$s_j = A_j \cos[\alpha_j(t)], \ j=5, 10, 2, \text{ and } 7 \qquad (194)$$

where the time-dependent arguments $\alpha_j(t)$ are given by $$\alpha_5(t) = 2\pi f_1 t + \phi_5, \ \alpha_{10}(t) = 2\pi f_1 t + \phi_{10}$$

$$\alpha_2(t) = 2\pi f_2 t + \phi_2, \ \alpha_7(t) = 2\pi f_2 t + \phi_7. \qquad (195)$$

Heterodyne signals $s_5$, $s_{10}$, $s_2$, and $s_7$ are transmitted to electronic processor 909 for analysis as electronic signals 203, 1203, 104, and 1104, respectively, in either digital or analog format, preferably a digital format.

The phases of drivers 5 and 6 are transmitted by electrical signals, reference signals 101 and 102, respectively, in either digital or analog format, preferably a digital format, to electronic processor 909.

A preferred method for electronically processing the heterodyne signals $s_5$, $s_{10}$, $s_2$, and $s_7$ is presented herewithin for the case when $l_1$ and $l_2$ are not low order integers. For the case when $l_1$ and $l_2$ are low order integers, the preferred procedure for electronically processing the heterodyne signals $s_5$, $s_{10}$, $s_2$, and $s_7$ is the same as the one subsequently set down for the variant of the ninth preferred embodiment of the present invention.

Referring now to FIG. 9, electronic processor 909 comprises electronic processors of electronic processors 309 and 609 that process heterodyne signals $s_5$, $s_{10}$, $s_2$, and $s_7$. Thus, the heterodyne signals $s_5$, $s_{10}$, and $s_7$ of the ninth embodiment are each processed by the same sequence of electronic processing steps as signals $s_5$, $s_{10}$, and $s_7$ of the sixth embodiment and $s_5$ and $s_2$ of the ninth embodiment are processed by the same sequence of electronic processing steps as signal $s_5$ and $s_2$ of the third embodiment, respectively. The results of that analysis are phases $$\Phi_{5 \times ll} = \varphi_5 - \varphi_{ll}, \qquad (196)$$

$$\Phi_{10 \times ll} = \varphi_{10} - \varphi_{ll},$$

$$\vartheta_{1G} = \left(\frac{l_1}{p_1}\Phi_{5 \times ll} + \frac{l_2}{p_2}\Phi_{2 \times l2}\right),$$

$$\Phi_{1G} = \left(\frac{l_1}{p_1}\Phi_{5 \times ll} - \frac{l_2}{p_2}\Phi_{2 \times l2}\right),$$

$$\vartheta_{2G} = \left(\frac{l_1}{p_1}\Phi_{10 \times ll} + \frac{l_2}{p_2}\Phi_{7 \times l2}\right),$$

$$\Phi_{2G} = \left(\frac{l_1}{p_1}\Phi_{10 \times ll} - \frac{l_2}{p_2}\Phi_{7 \times l2}\right)$$

The refractivity $(n_1-1)$, the dispersions $(n^2-n_1)_{1G}$ and $(n^2-n_1)_{2G}$, and the wavenumbers $k_1$ and $k_2$ can be expressed in terms of other quantities by the formulae $$(n_1 - 1) = \frac{1}{(\chi + K)L_G}\left(\frac{l_1}{p_1}\right)[\Phi_{5\times II} - (\zeta_5 - \varphi_{II})] - \frac{(L_G - L_V)}{L_G} \quad (197)$$

$$(n_2 - n_1)_{1G} = \quad (198)$$
$$\frac{1}{\chi L_G[1 - (K/\chi)^2]}\{[\vartheta_{1G}(K/\chi) - \Phi_{1G}] - [\xi_1(K/\chi) - Z_1]\}$$

$$(n_2 - n_1)_{2G} = \quad (199)$$
$$\frac{1}{\chi L_G[1 - (K/\chi)^2]}\{[\vartheta_{2G}(K/\chi) - \Phi_{2G}] - [\xi_2(K/\chi) - Z_2]\},$$

$$k_1 = \frac{1}{p_1 L_V}[(\Phi_{10\times II} - \Phi_{5\times II}) - (\zeta_{10} - \zeta_5)] \quad (200)$$

$$k_2 = \frac{1}{L_V}\left\{\frac{1}{2l_2}[(\vartheta_{2G} - \Phi_{2G}) - (\vartheta_{1G} - \Phi_{1G})] - \frac{1}{p_2}(\zeta_7 - \zeta_2)\right\}, \quad (201)$$

where $$\xi_1 = \frac{l_1}{p_1}(\zeta_5 - \varphi_{II}) + \frac{l_2}{p_2}(\zeta_2 - \varphi_{I2}) \quad (202)$$

$$Z_1 = \frac{l_1}{p_1}(\zeta_5 - \varphi_{II}) - \frac{l_2}{p_2}(\zeta_2 - \varphi_{I2}), \quad (203)$$

$$\xi_2 = \frac{l_1}{p_1}(\zeta_{10} - \varphi_{II}) + \frac{l_2}{p_2}(\zeta_7 - \varphi_{I2}) \quad (204)$$

$$Z_2 = \frac{l_1}{p_1}(\zeta_{10} - \varphi_{II}) - \frac{l_2}{p_2}(\zeta_7 - \varphi_{I2}) \quad (191)$$

and $\chi$ and K are given by Eqs. (26) and (27), respectively.

In a next step, electronic processing means 909 transmits to the computer 110 the phases $\Phi_{5\times I1}$, $\Phi_{10\times I1}$, $\theta_{1G}$, $\theta_{2G}$, $\Phi_{1G}$, and $\Phi_{2G}$ as electronic signal 105 in either digital or analog format, preferably a digital format, for the computation of a $\Gamma$, K/$\chi$, and the calculation of $k_1$ if required according to Eqs. (23), (197), (198) or (199), (200), and (201) substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents.

The remaining description of the ninth embodiment is the same as corresponding portions of the description given for the third and sixth embodiments of the present invention.

Reference is again made to FIG. 9 which, with electronic processor 909 in FIG. 9 being replaced by electronic processor 909A, depict in diagrammatic form a variant of the ninth preferred embodiment of the present invention wherein the wavelengths of the light beams are approximately harmonically related, the approximate harmonic ratio of the wavelengths of the light beams generated by the adopted light sources is not matched to a known harmonic ratio with a relative precision sufficient to meet the required precision and/or the stability of the adopted light sources is not sufficient to meet the required precision imposed on the output data by the final end use application. The condition wherein the wavelengths are approximately harmonically related corresponds to the special case of the ninth embodiment in which the ratio $(l_1/l_2)$ is expressible as the ratio of low order non-zero integers $(p_1/p_2)$, cf. Eq. (35).

The description of the sources of light beams 9 and 10 and of light beams 9 and 10 for the variant of the ninth embodiment is the same as that for description of the sources of light beams 9 and 10 and of light beams 9 and 10 given for the first embodiment with the additional requirement that the wavelengths be approximately harmonically related although not matched to a known harmonic ratio to a relative precision sufficient to meet the required precision imposed on the output data by the final end use application. The description of the apparatus for the variant of the ninth embodiment depicted in FIG. 9 is the same as corresponding portions of the description given for the ninth embodiment.

Referring now to FIG. 9 with electronic processor 909 replaced by electronic processor 909A, electronic processor 909A comprises electronic processors of electronic processors 309A and 609A that process heterodyne signals $s_5$, $s_{10}$, $s_2$, and $s_7$. Thus, the heterodyne signals $s_5$, $s_{10}$, and $s_7$ of the variant of the ninth embodiment are each processed by the same sequence of electronic processing steps as signals $s_5$, $s_{10}$, and $s_7$ of the variant of the sixth embodiment and $s_5$ and $s_2$ of the variant of the ninth embodiment are processed by the same sequence of electronic processing steps as signal $s_5$ and $s_2$ of the variant of the third embodiment, respectively. The results of that analysis are phases $\phi_5$, $\phi_{10}$, $\theta_{1G}$, $\Phi_{1G}$, $\theta_{2G}$, and $\Phi_{2G}$ where $$\theta_{1G}=(\phi_5+\phi_2), \Phi_{1G}=(\phi_5-\phi_2),$$
$$\theta_{2G}=(\phi_{10}+\phi_7), \Phi_{2G}=(\phi_{10}-\phi_7). \quad (206)$$

In a next step, $\phi_5$, $\phi_{10}$, $\theta_{1G}$, $\Phi_{1G}$, $\theta_{2G}$, and $\Phi_{2G}$ are transmitted, preferably in digital format, to computer 110 for computation of $\Gamma$, (K/$\chi$), and $k_1$ if required. Quantities $\phi_5$, $\phi_{10}$, $\theta_{1G}$, $\Phi_{1G}$, $\theta_{2G}$, $\Phi_{2G}$, $\xi_1$, $Z_1$, $\xi_2$, and $Z_2$ of the variant of the ninth embodiment are formally equivalent to $\Phi_{5\times I1}$, $\Phi_{10\times I1}$, $\theta_{1G}$, $\Phi_{1G}$, $\theta_{2G}$, $\Phi_{2G}$, $\xi_1$, $Z_1$, $\xi_2$, and $Z_2$, respectively, of the ninth embodiment with $\phi_{I1}$ and $\phi_{I2}$ set equal to zero, $l_1=p_1$, and $l_2=p_2$. As a consequence, the refractivity $(n_1-1)$, dispersions $(n_2-n_1)_{1G}$ and $(n_2-n_1)_{2G}$, $k_1$, and $k_2$ can be expressed in terms of the quantities measured by the variant of the ninth embodiment according to Eqs. (197), (198), (199), (200), and (201) with $\phi_{I1}$ and $\phi_{I2}$ set equal to zero, $l_1=p_1$, and $l_2=p_2$. Thus, the computation of a $\Gamma$, K/$\chi$, and the calculation of $k_1$ if required is performed according to Eqs. (23), (197), (198) or (199), (200), and (201) with $\phi_{I1}$ and $\phi_{I2}$ set equal to zero, $l_1=p_1$, and $l_2=p_2$ substantially independent of fluctuations in the column density of the gas or turbulence of the gas in the measuring path 97 to the extent that measuring paths experienced by beams of differing wavelengths are coextensive, without knowledge of the gas constituents, without knowledge of the environmental conditions, and without knowledge of the properties of the refractivities of the gas constituents. The remaining discussion of the variant of the ninth embodiment is the same as corresponding portions of the descriptions given for the ninth embodiment.

The principal advantage of the variant of the ninth embodiment in relation to the ninth embodiment is the same as that described with regard to the advantage of the variant of the third embodiment in relation to the third embodiment.

In certain of the embodiments, there will be differences in optical delays experienced by optical beams when the number of passes through an interferometer is different for the different optical beams. It will be apparent to those skill in the art that such differences in delays will generally produce negligible effects as both of the mirrors of the measuring cell 90 are stationary and gas turbulence typically produces small-amplitude, low-frequency effects.

It will be apparent to those skilled in the art that the second, third, fifth, sixth, eighth, and ninth embodiments and variants thereof of the present invention disclosed herein will typically generate a phases $\Phi_{1G}$ and $\Phi_{2G}$ with a reduced sensitivities to relative differences in group delays experienced by the heterodyne signals, the heterodyne signals for a given embodiment or variant thereof each having substantially the same frequency spectrum, in relation to the first, fourth, and seventh embodiments and variants thereof.

It will be further appreciated by those skilled in the art that both the x and y polarization components of beam 9 and/or of beam 10 of the preferred embodiments and variants thereof may be frequency shifted without departing from the scope and spirit of the invention, $f_1$ remaining the difference in frequencies of the x and y polarization components of beam 9 and $f_2$ remaining the difference in frequencies of the x and y polarization components of beam 10. Improved isolation of an interferometer and a laser source is generally possible by frequency shifting both x and y polarization components of a beam, the degree of improved isolation depending on the means used for generating the frequency shifts.

It will also be appreciated by those skilled in the art that the two frequency components of either or both beams 9 and 10 may be spatially separated at any point following the means for introducing the frequency shifts and prior to entering the respective interferometers of the described preferred embodiments and variants thereof without departing from the scope and spirit of the present invention. If the two frequency components of either of the two beams are spatially separated for any significant distance from the respective interferometer, it may be necessary to employ alternative reference beams such as described in the first embodiment.

The illustrations in FIGS. 1a–1e, 1h, 2a–2c, 3a–3c, 4a–4e, 5a–5c, 6a–6d, 7a–7c, 8a–8c, and 9 depict nine preferred embodiments and variants thereof of the present invention wherein all of the optical beams for an embodiment or variant of an embodiment are in a single plane. Clearly, modifications using multiple planes can be made to one or more of the nine embodiments and variants thereof without departing from the scope or spirit of the invention.

The nine preferred embodiments and variants thereof of the present invention have measurement cells 90 wherein the measurement paths for $\lambda_1$ and $\lambda_2$ have the same physical lengths and the reference paths for $\lambda_1$ and $\lambda_2$ have the same physical lengths. It will be appreciated by those skilled in the art that the measurement paths for $\lambda_1$ and $\lambda_2$ can have different physical lengths and the reference paths for $\lambda_1$ and $\lambda_2$ can have different physical lengths without departing from the scope and spirit of the present invention as defined in the claims. It will be further appreciated by those skilled in the art that the measurement paths for $\lambda_1$ and $\lambda_2$ can be physically displaced one from the other and the reference paths for $\lambda_1$ and $\lambda_2$ can be physically displaced one from the other without departing from the scope and spirit of the present invention as defined in the claims.

The nine preferred embodiments and variants thereof of the present invention are all configured for use of heterodyne detection. It will be appreciated by those skilled in the art that homodyne detection can be employed in each of the nine embodiments and variants thereof without departing from the scope and spirit of the present invention as defined in the claims. Homodyne receivers would be employed such as disclosed in commonly owned U.S. Pat. No. 5,663,793 entitled "Homodyne Interferometric Receiver and Method" issued Sep. 2, 1997 in the name of P. de Groot. The computation of the reciprocal dispersive power $\Gamma$ would be obtained for example in the homodyne version of the first preferred embodiment directly from homodyne phases $\phi_{1H}$ and $\phi_{2H}$, the homodyne phases $\phi_{1H}$ and $\phi_{2H}$ corresponding to phases $\phi_1$ and $\phi_2$ of the first preferred embodiment.

The third set of preferred embodiments of the present invention and variants thereof measure the ratio $(K/\chi)$ and use the measured value of $(K/\chi)$ in the computation of the reciprocal dispersive power $\Gamma$. It will be appreciated by those skilled in the art that the measured value of $(K/\chi)$ can be used as an error signal in a feedback system such that the condition expressed either by Eq. (34) or Eq. (135) is satisfied without departing from the scope and spirit of the present invention as defined in the claims. The measured value of $(K/\chi)$ in the feedback system is sent to either source 1 or source 2 and used to control the respective wavelength of either source 1 or source 2, for example by controlling the injection current and/or temperature of a diode laser or the cavity frequency of an external cavity diode laser.

It will also be appreciated by those skilled in the art that the differential plane mirror interferometers and the measurement cell may be configured such that the light beams corresponding to two or more differing wavelengths may enter and exit from the same end of the measurement cell in contrast to opposite ends as disclosed in the preferred embodiments and variants thereof without departing from the scope or spirit of the invention as defined in the claims.

Figure 10:
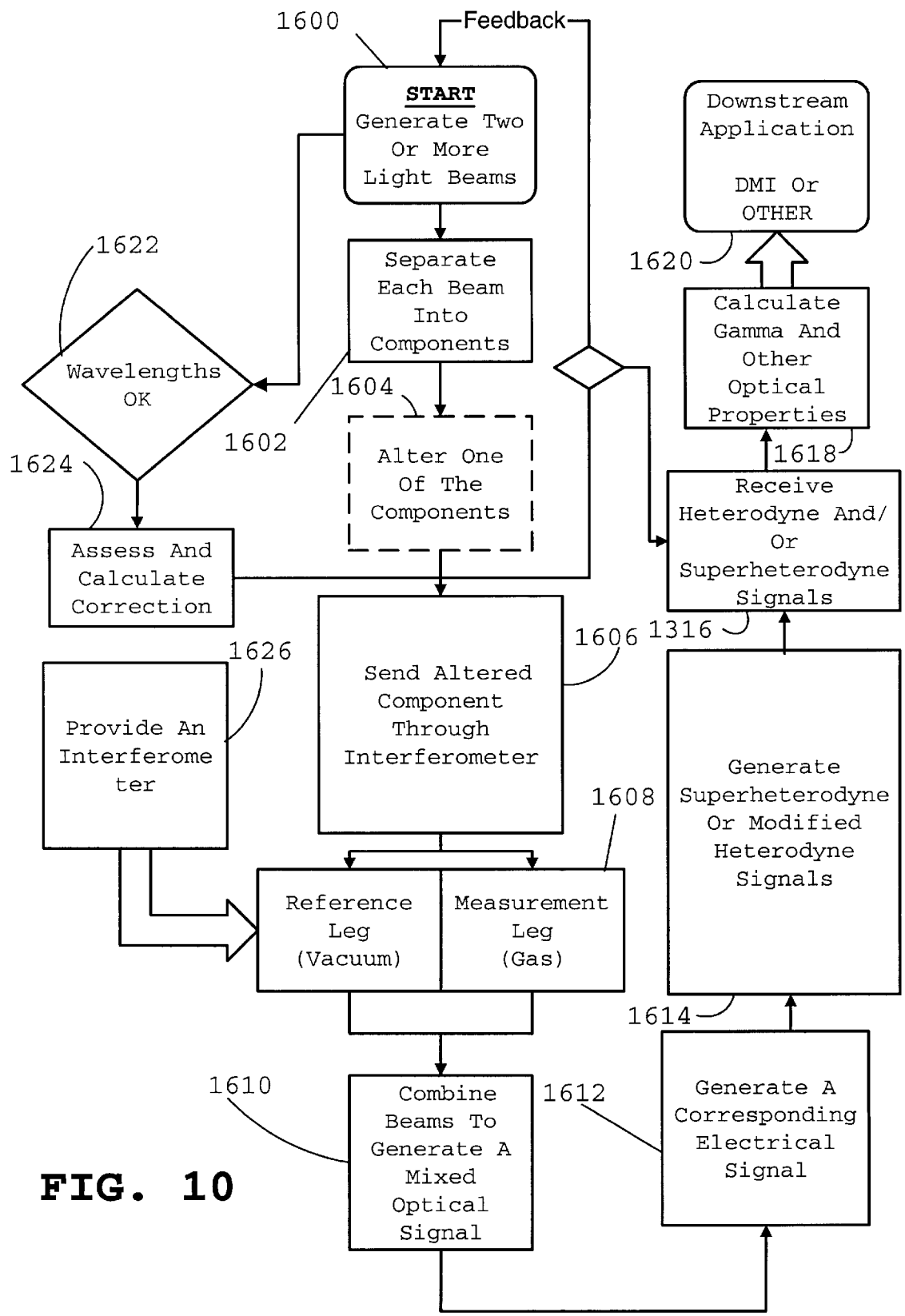
FIG. 10 is a high-level flowchart depicting various steps carried out in practicing a method in accordance with the invention.

Reference is now made to FIG. 10 which is a generalized flowchart depicting via blocks 1600–1626 various steps for practicing an inventive method for measuring intrinsic optical properties of a gas, particularly its reciprocal dispersive power. While it will be evident that the inventive method depicted in FIG. 10 may be carried out using the inventive apparatus disclosed hereinabove, it will also be apparent to those skilled in the art that it may also be implemented with apparatus other than that disclosed. For example, it will be apparent that one need not use a concentric measurement cell arrangement such as that used in the preferred embodiments, but rather may use more conventional interferometric arrangements so long as the required reference and measurement legs are present. In addition, it will be evident that one may use either a homodyne approach or one in which heterodyning techniques are advantageously employed. As will be further appreciated, many of the steps in FIG. 10 may be carried out via appropriate software run on a general purpose computer or a suitably programmed microprocessor either of which may be used to control other elements of the system as needed.

As seen in FIG. 10, one starts in block 1600 by providing two or more light beams having different wavelengths which preferably have a known approximate ratio as previously described. In block 1602, the light beams are separated into components which in block 1604 are preferably altered by either polarization or spatial encoding, or frequency shifting or both. Otherwise, the light beams may simply be left unaltered and passed through to block 1606.

As shown in blocks 1622 and 1624, the relationship of the wavelengths of the light beams may be monitored and if their wavelengths are not within the limits previously discussed, one can adopt corrective measures to compensate from departures of the relationship of the wavelengths from the desired relationship of the wavelengths. Either the departures can be used to provide feedback to control the wavelengths of the light beam sources or corrections can be established and used in subsequent calculations which are influenced by departures or some combination of both approaches can be implemented.

In parallel or contemporaneously with generating the light beams in block 1600, one also provides as indicated in block 1626 an interferometer having two legs, one occupied preferably by a vacuum (reference leg) and the other by the gas whose intrinsic optical properties are to be measured.

As shown by blocks 1606 and 1608, the previously generated light beam components are introduced into the interferometer legs so that each component has its phase shifted based on the optical path length it experiences in traveling through the physical length of its assigned leg. Preferably, the physical length for a commonly related pair of components is the same.

After the beams emerge from block 1608, they are combined in block 1610 to generate mixed optical signals. These mixed optical signals are then sent to block 1612 where by means of photodetection corresponding electrical signals, preferably heterodyne, are generated, and these electrical signals contain information about the relative phases between the light beam components. Preferably the electrical signals are heterodyne signals brought about by previously frequency shifting treatment.

In block 1614, the electrical signals may be directly analyzed to extract relative phase information which can then be passed on to blocks 1616–1620 or, preferably, by superheterodyne signal processing techniques. Alternatively, depending on the wavelength relationships between the original beams and the optical paths over which they subsequently traveled, modified heterodyne signals are generated prior to superheterodyne signal processing.

In block 1616, any phase ambiguities in homodyne, heterodyne, and/or superheterodyne signals are resolved, preferably by means and calculations previously elaborated in connection with describing the preferred apparatus.

In block 1618, the intrinsic optical properties including the relative dispersive power are calculated, corrections are applied as previously decided, and output signals are generated for subsequent downstream applications or data format requirements.

Those skilled in the art may make other changes to the inventive apparatus and methods without departing from the scope of the inventive teachings. Therefore, it is intended that the embodiments shown and described be considered as illustrative and not in a limiting sense.

What is claimed is:

1. Interferometric apparatus or monitoring select intrinsic optical properties of a gas, said interferometric apparatus comprising:

interferometer means comprising a reference leg and a measurement leg, said reference leg being configured and arranged to be occupied by a predetermined medium and said measurement leg being configured and arranged to be occupied by the gas;

means for generating at least two light beams having different wavelengths;

means for introducing at least a portion of each of said light beams into said interferometer means so that each beam portion travels through said gas along predetermined paths and another portion of at least one of said beams so that said another portion travels through said predetermined medium along predetermined paths, said portions and said another portion of said beams emerging from said interferometer means as exit beams containing information about the respective optical path lengths through said predetermined medium in said reference leg and about the respective optical path lengths through said gas in said measurement leg;

means for combining said exit beams to produce mixed optical signals containing information corresponding to the phase differences between each of said exit beams from corresponding ones of said predetermined paths of said reference and measurement legs; and means for detecting said mixed optical signals and generating electrical interference signals containing information corresponding to the select intrinsic optical properties of the gas.

2. The interferometric apparatus of claim 1 wherein two of said exit beams corresponding to one of said wavelengths have traveled through said gas and said predetermined medium, respectively, such that, when combined by said means for combining, provide a mixed optical signal containing information about the refractivity of said gas at said one wavelength.

3. The interferometric apparatus of claim 1 wherein said means for introducing is further configured such that portions of each of said light beams travel through said predetermined medium along predetermined paths.

4. The interferometric apparatus of claim 3 further including means for doubling the frequency of at least one of said exit beams prior to combining said exit beams to produce said mixed optical signals.

5. The interferometric apparatus of claim 3 wherein a first one of said exit beams corresponding to one of said wavelengths has traveled through said gas in said measurement leg, a second one of said exit beams corresponding to the other one of said wavelengths has traveled through said gas in said measurement leg, a third one of said exit beams corresponding to said one wavelength has traveled through said predetermined medium of said reference leg, and a fourth one of said exit beams corresponding to said other wavelength has traveled through said predetermined medium of said reference leg.

6. The interferometric apparatus of claim 5 further including nonlinear optical means for receiving said first, second, third and fourth exit beams and doubling the frequencies of at least two thereof to generate signals containing information about the dispersion of said gas.

7. The interferometric apparatus of claim 1 wherein said means for introducing at least a portion of each of said light beams into said interferometer means further includes means for introducing other portions of each of said light beams into said interferometer means such that said other portions are returned as another set of exit beams without traveling along said reference leg and said measurement leg, said another set of said exit beams containing information about the optical path lengths of said interferometric apparatus other than those of said reference and said measurement legs.

8. The interferometric apparatus of claim 7 further including means for doubling the frequency of at least one of said exit beams and said another set of exit beams prior to combining said exit beams to produce said mixed optical signals.

9. The interferometric apparatus of claim 7 wherein a first one of said exit beams corresponding to one of said wavelengths has traveled through said gas in said measurement leg and a second one of said exit beams corresponding to the other one of said wavelengths has traveled through said gas in said measurement leg.

10. The interferometric apparatus of claim 9 further including nonlinear optical means for receiving said first, second, and said another set of exit beams and doubling the frequency thereof to generate signals containing information about the dispersion of said gas.

11. The interferometric apparatus of claim 1 wherein said means for generating at least two light beams having different wavelengths comprises at least one light source for providing a light beam having one of said wavelengths s and means associated with said one light source for doubling the frequency of said light beam having one of said wavelengths to provide the other of said two beams at the other of said wavelengths.

12. The interferometric apparatus of claim 11 wherein said at least one light source comprises a laser and said means for doubling the frequency of said light beam having one of said wavelengths comprises a nonlinear optical material for second harmonic generation.

13. The apparatus of claim 1 wherein said apparatus further includes electronic means for analyzing said electrical interference signals and determining said select intrinsic optical properties of the gas.

14. The apparatus of claim 13 wherein said electronic means is configured to determine the intrinsic optical property, the reciprocal dispersive power, $\Gamma$, of the gas, as:

$$\Gamma = \frac{[n_1(\lambda_1) - 1]}{[n_3(\lambda_3) - n_2(\lambda_2)]},$$

and $\lambda_1$, $\lambda_2$, and $\lambda_3$ are wavelengths and $n_1$, $n_2$, and $n_3$ are indices of refraction and wherein the denominator may be replaced by $[n_3(\lambda_3) - n_1(\lambda_1)]$ or $[n_2(\lambda_2) - n_1(\lambda_1)]$.

15. The apparatus of claim 13 wherein said electronic means is configured to determine the refractivities of the gas corresponding to each light beam wavelength.

16. The apparatus of claim 13 wherein said electronic means is configured and arranged to calculate the intrinsic optical property, the reciprocal dispersive power, $\Gamma$, as:

$$\Gamma = \frac{[n_i(\lambda_i) - 1]}{[n_{j+1}(\lambda_{j+1}) - 1] - [n_j(\lambda_j) - 1]},$$

where i and j are integers corresponding to wavelengths.

17. The apparatus of claim 13 wherein said electronic means is configured to determine the intrinsic optical property, the relative refractivities at different beam wavelengths, where said relative refractivities are of the form:

$$\frac{n_{\lambda_i} - 1}{n_{\lambda_j} - 1}$$

where i and j are integers corresponding to wavelengths and are different from one another.

18. The apparatus of claim 13 wherein said electronic means is configured to provide output signals representative of said select intrinsic optical properties of the gas for subsequent downstream applications.

19. The apparatus of claim 1 wherein said predetermined medium comprises a vacuum.

20. The apparatus of claim 1 wherein said interferometer means comprises a concentric cell, said concentric cell comprising a closed inner chamber that serves as said reference leg and an outer chamber surrounding said inner chamber that serves as said measurement leg.

21. The apparatus of claim 20 wherein said inner chamber is substantially evacuated so that said predetermined medium is a vacuum and said outer chamber is opened to the ambient surroundings.

22. The apparatus of claim 21 wherein said ambient surroundings comprise air.

23. The apparatus of claim 20 wherein said concentric cell is in form a right circular cylinder with end sections each of which includes wavelength selective mirrors as part of said interferometer means.

24. The apparatus of claim 23 wherein said means for introducing at least a portion of each of said light beams into said interferometer means is configured and arranged to introduce one of said portions of said light beams corresponding to one wavelength into one of said end sections of said concentric cell and another of said portions of said light beams corresponding to another of said wavelengths into the other one of said end sections of said concentric cell.

25. The apparatus of claim 1 wherein said means for generating said light beams further includes means for generating orthogonally polarized components of each of said light beams.

26. The apparatus of claim 25 further including means for separating said light beams with orthogonally polarized components into pairs of orthogonally polarized components having a common wavelength.

27. The apparatus of claim 26 further including means for spatially separating the components of said orthogonally polarized pairs of components for subsequent downstream use in said interferometer means.

28. The apparatus of claim 26 wherein said wavelengths of said light beams have an approximate harmonic relationship to each other, said approximate harmonic relationship being expressed as a sequence of ratios, each ratio being comprised of a ratio of low order non-zero integers.

29. The interferometric apparatus of claim 28 wherein said means for generating at least two light beams having different wavelengths comprises at least one light source for providing a light beam having one of said wavelengths and means associated with said one light source for doubling the frequency of said light beam having one of said wavelengths to provide the other of said two beams at the other of said wavelengths.

30. The apparatus of claim 28 wherein the relative precision of said approximate harmonic relationship expressed as said sequence of ratios is of an order of magnitude less than the dispersive power of the gas times the relative precision required for the measurement of the reciprocal dispersive power of the gas.

31. The apparatus of claim 28 further including means for monitoring the relative precision of said approximate harmonic relationship expressed as said sequence of ratios.

32. The apparatus of claim 31 further including means responsive to said means for monitoring said relative precision of said approximate harmonic relationship for providing a feedback signal to control said means for generating said light beams so that said relative precision of said approximate harmonic relationship is of an order of magnitude less than the dispersive power of the gas times the relative precision required for the measurement of the reciprocal dispersive power of the gas.

33. The apparatus of claim 31 further including means responsive to said means for monitoring said relative precision of said approximate harmonic relationship for correcting said select intrinsic optical properties as determined by said electronic means for analyzing and determining said select intrinsic optical properties.

34. The apparatus of claim 28 further including means for introducing a frequency difference between said orthogonally polarized components of each of said light beams to generate a set of frequency-shifted light beams such that no two beams of said set of frequency-shifted light beams have the same frequency difference.

35. The apparatus of claim 34 further including optical means for dividing each beam of said set of frequency-shifted light beams into one or more beams to provide an expanded set of at least three frequency-shifted light beams from said set of frequency-shifted light beams such that the number of frequency-shifted light beams for each wavelength in said expanded set of frequency-shifted light beams is inversely related in accordance with said approximate harmonic relationship.

36. The apparatus of claim 35 wherein said interferometer means introduces phase shifts between said orthogonally polarized components of each beam of said expanded set of at least three frequency-shifted light beams to produce said exit beams as a set of phase-shifted, frequency-shifted light beams and aligns and directs said beams of said expanded set of at least three frequency-shifted light beams so that the combined measurement and reference paths traversed by each subset of phase-shifted, frequency-shifted light beams are substantially the same where a subset of said phase-shifted, frequency-shifted light beams comprises beams of the phase-shifted, frequency-shifted light beams having the same wavelength, the measurement and reference paths traversed by any two beams of a subset of phase-shifted, frequency-shifted light beams being substantially non-overlapping.

37. The apparatus of claim 36 wherein said physical path lengths for said measurement leg and said reference leg of any beam of said phase-shifted, frequency-shifted light beams are substantially the same.

38. The apparatus of claim 37 wherein the magnitude of said phase shifts introduced into each beam of said expanded set of frequency-shifted light beams is proportional to the product of the number of passes of said each beam over said measurement and reference legs, of the physical lengths of said measurement and reference legs, and the differences in refractivity of the gas in the measurement leg and said predetermined medium in said reference leg, the refractivity of the gas in said measurement leg for each subset of phase-shifted, frequency-shifted light beams being different, one with respect to another, the refractivity of the gas being a function of wavelength.

39. The apparatus of claim 38 wherein said combining means mixes said two different frequency components of each beam of said set of phase-shifted, frequency-shifted light beams to produce said mixed optical signals as a set of mixed output beams comprised of at least three mixed output beams, each beam of the set of mixed output beams being derived from one beam of the set of phase-shifted, frequency-shifted light beams.

40. The interferometric apparatus of claim 39 further including a nonlinear optical material for doubling the frequency of one of said beams of said phase-shifted, frequency shifted light beams prior to entering said combining means.

41. The apparatus of claim 39 wherein said means for detecting comprises a photodetector for generating said electrical interference signals as a set of at least three heterodyne signals from the intensities of said set of mixed output beams, said set of at least three heterodyne signals being characterized by oscillations at heterodyne frequencies related to said frequency differences between said orthogonally polarized components of the beams of said expanded set of frequency-shifted light beams, said set of at least three heterodyne signals being further characterized by a set of heterodyne phases, said set of at least three heterodyne signals being comprised of a set of subsets of heterodyne signals, a subset of heterodyne signals being the heterodyne signals generated from a subset of phase-shifted, frequency-shifted light beams.

42. The apparatus of claim 41 further including means for adding said heterodyne signals of each subset of heterodyne signals to produce a set of superheterodyne signals, each superheterodyne signal of said set of superheterodyne signals being comprised of a signal having a superheterodyne frequency equal to the heterodyne frequency of said subset of heterodyne signals added to produce said superheterodyne signal and a superheterodyne phase equal to the average of the heterodyne phases of said subset of heterodyne signals added to produce said superheterodyne signal, said superheterodyne phases being substantially null except for differences due to the refractivity of the gas in the measurement leg and the predetermined medium in said reference leg of the set of phase-shifted, frequency-shifted light beams.

43. The apparatus of claim 42 wherein said electronic means further includes means for extracting the signals of two of said set of superheterodyne signals and mixing the signals to produce a second level superheterodyne signal, said second level superheterodyne signal being comprised of two sidebands, the sum and difference sidebands, having frequencies, the sum and difference frequencies, equal to the sum and difference of the superheterodyne frequencies, respectively, of the superheterodyne signals mixed to produce the second level superheterodyne signal and having phases, the sum and difference phases, equal to the sum and difference of the superheterodyne phases, respectively, of the superheterodyne signals mixed to produce the second level superheterodyne signal, the difference phase is substantially null except for differences due to the dispersion of the refractivity of gas in said measurement leg and the refractivity of the predetermined medium in said reference leg of the set of phase-shifted, frequency-shifted light beams.

44. The apparatus of claim 43 wherein the relative precision of said approximate harmonic relationship expressed as said sequence of ratios is of an order of magnitude less than the dispersive power of the gas times the relative precision required for the measurement of the reciprocal dispersive power of the gas.

45. The apparatus of claim 44 wherein said electronic means operates on said sum phase and said difference phase and one of said superheterodyne phases to determine the reciprocal dispersive power of the gas.

46. The apparatus of claim 43 further including means for monitoring the relative precision of said approximate harmonic relationship expressed as said sequence of ratios.

47. The apparatus of claim 46 further including means responsive to said means for monitoring said relative precision of said approximate harmonic relationship for providing a feedback signal to control said means for generating said light beams so that said relative precision of said approximate harmonic relationship is of an order of magnitude less than the dispersive power of the gas times the relative precision required for the measurement of the reciprocal dispersive power of the gas.

48. The apparatus of claim 47 wherein said electronic means operates on said sum phase and said difference phase and one of said superheterdyne phases to determine the reciprocal dispersive power of the gas.

49. The apparatus of claim 46 further including means responsive to said means for monitoring said relative precision of said approximate harmonic relationship for correcting reciprocal dispersive power of the gas as determined by said electronic means for analyzing and determining the reciprocal dispersive power of the gas.

50. The apparatus of claim 49 wherein said electronic means operates one of said sum phase and said difference phase and one of said superheterodyne phases to determine the reciprocal dispersive power of the gas.

51. The apparatus of claim 39 wherein said means for combining is configured and arranged to produce said mixed optical signals as a set of mixed output beams comprised of at least two mixed output beams, each mixed output beam being generated from one subset of phase-shifted, frequency-shifted light beams.

52. The apparatus of claim 28 further including electronic processing means to measure the approximate harmonic ratio of the wavelengths of the source and provide a signal for correcting the calculations made in determining said select intrinsic optical properties.

53. The apparatus of claim 34 wherein said interferometer means introduces phase shifts between the orthogonally polarized components of each beam of said set of frequency-shifted light beams to produce a set of phase-shifted, frequency-shifted light beams and aligns and directs said beams of said set of frequency-shifted light beams so that said measurement and reference legs traversed by each beam of said set of phase-shifted, frequency-shifted light beams are substantially the same.

54. The apparatus of claim 53 wherein said physical path lengths for said measurement leg and said reference leg of any beam of said phase-shifted, frequency-shifted light beams are substantially the same.

55. The apparatus of claim 54 wherein the magnitude of the phase shifts introduced into each beam of said set of frequency-shifted light beams is proportional to the product of a number of passes over said measurement and reference legs, of the physical lengths of the measurement and reference legs, and the differences in refractivity of the gas in said measurement leg and the predetermined medium in said reference leg, the refractivity of the gas in said measurement leg for each beam of phase-shifted, frequency-shifted light beams being different, one with respect to another, the refractivity of the gas being a function of wavelength.

56. The apparatus of claim 55 wherein said combining means mixes said two different frequency components of each beam of said set of phase-shifted, frequency-shifted light beams to produce said mixed optical signals as a set of mixed output beams comprised of at least two mixed output beams, each beam of the set of mixed output beams being derived from one, and only one, beam of the set of phase-shifted, frequency-shifted light beams.

57. The apparatus of claim 56 wherein said means for detecting comprises photodetector means for generating said electrical interference signals as a set of heterodyne signals from the intensities of said set of mixed output beams, said set of heterodyne signals being comprised of at least two heterodyne signals and being characterized by oscillations at heterodyne frequencies related to said frequency differences between said orthogonally polarized components of said beams of said set of frequency-shifted light beams, said set of heterodyne signals being further characterized by a set of heterodyne phases, said heterodyne phases being substantially inversely related to said approximate harmonic relationship between said light beam wavelengths except for differences related to the refractivity of the gas in said measurement leg.

58. The apparatus of claim 57 further including means for processing said set of heterodyne signals to generate a set of modified heterodyne signals, said set of modified heterodyne signals being characterized by modified heterodyne frequencies, said modified heterodyne frequencies being harmonically related to said heterodyne frequencies in accordance with said approximate harmonic relationship between said light beam wavelengths and by modified heterodyne phases, said modified heterodyne phases being harmonically related to said heterodyne phases in accordance with said approximate harmonic relationship between the wavelengths, said set of modified heterodyne phases of the set of modified heterodyne signals being substantially equal except for differences due to the refractivity of the gas in said measurement leg and of the predetermined medium in the reference leg of the set of the phase-shifted, frequency-shifted light beams.

59. The apparatus of claim 58 further including electronic means for mixing two of said modified heterodyne signals, said pair of modified heterodyne signals, to produce a superheterodyne signal comprised of two sidebands, the sum and difference sidebands, having frequencies, the sum and difference frequencies, equal to the sum and difference of said modified heterodyne frequencies, respectively, of said pair of modified heterodyne signals and having phases, the sum and difference phases, equal to the sum and difference of said modified heterodyne phases, respectively, of said pair of modified heterodyne signals, said difference phase being substantially null accept for differences due to the dispersion of the refractivity of gas in the measurement leg and of the predetermined medium in the reference leg of said set of phase-shifted, frequency-shifted light beams.

60. The apparatus of claim 59 wherein the relative precision of said approximate harmonic relationship expressed as said sequence of ratios is of an order of magnitude less than the dispersive power of the gas times the relative precision required for the measurement of the reciprocal dispersive power of the gas.

61. The apparatus of claim 60 wherein said electronic means includes means for analyzing said difference phase and the modified heterodyne phase of one of said pair of modified heterodyne signals to determine the reciprocal dispersive power of the gas in said measurement leg.

62. The apparatus of claim 59 further including means for monitoring the relative precision of said approximate harmonic relationship expressed as said sequence of ratios.

63. The apparatus of claim 62 further including means responsive to said means for monitoring said relative precision of said approximate harmonic relationship for providing a feedback signal to control said means for generating said light beams so that said relative precision of said approximate harmonic relationship is of an order of magnitude less than the dispersive power of the gas times the relative precision required for the measurement of the reciprocal dispersive power of the gas.

64. The apparatus of claim 63 wherein said electronic means further includes means for analyzing said difference phase and said modified heterodyne phase of one of said pair of modified heterodyne signals to determine the reciprocal dispersive power of the gas in said measurement leg.

65. The apparatus of claim 62 further including means responsive to said means for monitoring said relative precision of said approximate harmonic relationship for correcting reciprocal dispersive power of the gas as determined by said electronic means for analyzing and determining said reciprocal dispersive power of the gas.

66. The apparatus of claim 65 wherein said electronic means includes means for analyzing said difference phase and said modified heterodyne phase of one of said pair of modified heterodyne signals to determine the reciprocal dispersive power of the gas in said measurement leg.

67. The apparatus of claim 53 wherein said interferometer means comprises means for generating multiple passes over said measurement leg and said reference leg for said set of phase-shifted, frequency-shifted light beams, the number of multiple passes for a beam of said set of phase-shifted, frequency-shifted light beams being proportional to the wavelength of the beam of said set of phase-shifted, frequency-shifted light beams, the physical lengths of said measurement leg and said reference leg of any beam of said set of phase-shifted, frequency-shifted light beams being substantially the same.

68. The apparatus of claim 67 wherein the magnitude of the phase shifts introduced into each beam of said set of frequency-shifted light beams is proportional to the product of the number of passes over said measurement and reference legs, of the physical lengths of said measurement and reference legs, and the differences in refractivity of the gas in said measurement leg and said predetermined medium in said reference leg, the refractivity of the gas in said measurement leg for each beam of phase-shifted, frequency-shifted light beams being different, one with respect to another, the refractivity of the gas being a function of wavelength.

69. The apparatus of claim 68 wherein said combining means mixes said two different frequency components of each beam of the set of phase-shifted, frequency-shifted light beams to produce mixed optical signals as a set of mixed output beams comprised of at least two mixed output beams, each beam of the set of mixed output beams being derived from one, and only one, beam of the set of phase-shifted, frequency-shifted light beams.

70. The apparatus of claim 69 wherein said means for detecting comprises photodetector means for generating said electrical interference signals as a set of heterodyne signals from the intensities of said set of mixed output beams, said set of heterodyne signals being comprised of at least two heterodyne signals and being characterized by oscillations at heterodyne frequencies related to said frequency differences between said orthogonally polarized components of said beams of said set of frequency-shifted light beams, said set of heterodyne signals being further characterized by a set of heterodyne phases, said heterodyne phases being substantially equal except for differences related to the refractivity of the gas in said measurement leg and the refractivity of the predetermined medium in said reference leg.

71. The apparatus of claim 70 further including electronic means for mixing two of said heterodyne signals, said pair of heterodyne signals, to produce a superheterodyne signal comprised of two sidebands, the sum and difference sidebands, having frequencies, the sum and difference frequencies, equal to the sum and difference of said heterodyne frequencies, respectively, of said pair of heterodyne signals and phases, the sum and difference phases, equal to the sum and difference between said heterodyne phases, respectively, of said pair of heterodyne signals, said difference phase being substantially null except for differences due to the dispersion of the refractivity of gas in said measurement leg and of the predetermined medium in said reference leg of the set of phase-shifted, frequency-shifted light beams.

72. The apparatus of claim 71 wherein the relative precision of said approximate harmonic relationship expressed as said sequence of ratios is of an order of magnitude less than the dispersive power of the gas times the relative precision required for the measurement of the reciprocal dispersive power of the gas.

73. The apparatus of claim 72 wherein said electronic means includes means for analyzing said difference phase and said heterodyne phase of one of said pair of heterodyne signals to determine the reciprocal dispersive power of the gas in said measurement leg.

74. The apparatus of claim 71 further including means for monitoring the relative precision of said approximate harmonic relationship expressed as said sequence of ratios.

75. The apparatus of claim 74 further including means responsive to said means for monitoring said relative precision of said approximate harmonic relationship for providing a feedback signal to control said means for generating said light beams so that said relative precision of said approximate harmonic relationship is of an order of magnitude less than the dispersive power of the gas times the relative precision required for the measurement of the reciprocal dispersive power of the gas.

76. The apparatus of claim 75 wherein said electronic means includes means for analyzing said difference phase and said heterodyne phase of one of said pair of heterodyne signals to determine the reciprocal dispersive power of the gas in said measurement leg.

77. The apparatus of claim 74 further including means responsive to said means for monitoring said relative precision of said approximate harmonic relationship for correcting said reciprocal dispersive power of the gas in said measurement leg as determined by said electronic means for analyzing and determining said reciprocal dispersive power of the gas in said measurement leg.

78. The apparatus of claim 77 wherein said electronic means includes means for analyzing said difference phase and said heterodyne phase of one of said pair of heterodyne signals to determine the reciprocal dispersive power of the gas in said measurement leg.

79. The apparatus of claim 1 wherein said electrical interference signals comprise heterodyne signals containing phase information corresponding to the refractivities of the gas and said apparatus further comprises means for mixing said heterodyne signals to generate at least one superheterodyne signal containing phase information corresponding to the dispersion of the refractivities of the gas.

80. The apparatus of claim 79 further including means for resolving phase ambiguities of the said heterodyne and said superheterodyne signals.

81. An interferometric method for monitoring select intrinsic optical properties of a gas, said interferometric method comprising the steps of:

providing interferometer means comprising a reference leg and a measurement leg, said reference leg being configured and arranged to be occupied by a predetermined medium and said measurement leg being configured and arranged to be occupied by the gas;

generating at least two light beams having different wavelengths;

introducing at least a portion of each of said light beams into said interferometer means so that each beam portion travels through said gas and another portion of at least one of said beams so that said another portion travels through said predetermined medium along predetermined paths and emerge from said interferometer means as exit beams containing information about the respective optical path lengths through said predetermined medium in said reference leg and about the respective optical path lengths through said gas in said measurement leg;

combining said exit beams to produce mixed optical signals containing information corresponding to the phase differences between each of said exit beams from corresponding ones of predetermined paths of said reference and measurement legs; and detecting said mixed optical signals and generating electrical interference signals containing information corresponding to the select intrinsic optical properties of the gas.

82. The interferometric method of claim 81 wherein two of said exit beams corresponding to one of said wavelengths have traveled through said gas and said predetermined medium, respectively, such that, when combined by said means for combining, provide a mixed optical signal containing information about the refractivity of said gas at said one wavelength.

83. The interferometric method of claim 81 wherein said step of introducing further involves introducing said light beams such that portions of each of said light beams travels through said predetermined medium along predetermined paths.

84. The interferometric method of claim 83 further including the step of doubling the frequency of at least one of said exit beams prior to combining said exit beams to produce said mixed optical signals.

85. The interferometric method of claim 83 wherein a first one of said exit beams corresponding to one of said wavelengths has traveled through said gas in said measurement leg, a second one of said exit beams corresponding to the other one of said wavelengths has traveled through said gas in said measurement leg, a third one of said exit beams corresponding to said one wavelength has traveled through said predetermined medium of said reference leg, and a fourth one of said exit beams corresponding to said other wavelength has traveled through said predetermined medium of said reference leg.

86. The interferometric method of claim 85 further including the step of receiving said first, second, third and fourth exit beams and doubling the frequencies of at least two thereof to generate a signals containing information about the dispersion of said gas.

87. The interferometric method of claim 81 wherein the step of introducing at least a portion of each of said light beams into said interferometer means further includes introducing other portions of each of said light beams into said interferometer means such that said other portions are returned as another set of exit beams without traveling along said reference leg and said measurement leg, said another set of said exit beams containing information about the optical path lengths of said interferometric apparatus other than those of said reference and said measurement legs.

88. The interferometric method of claim 87 further including the step of doubling the frequency of at least one of said exit beams and said another set of exit beams prior to combining said exit beams to produce said mixed optical signals.

89. The interferometric method of claim 87 wherein a first one of said exit beams corresponding to one of said wavelengths has traveled through said gas in said measurement leg and a second one of said exit beams corresponding to the other one of said wavelengths has traveled through said gas in said measurement leg.

90. The interferometric method of claim 89 further including the step of receiving said first, second, and said another set of exit beams and doubling the frequency thereof to generate signals containing information about the dispersion of said gas.

91. The interferometric method of claim 81 further including the step of electronically analyzing said interference signals and determining the select intrinsic optical properties of the gas.

92. The interferometric method of claim 81 wherein said step of generating at least two light beams having different wavelengths comprises doubling the frequency of at least one of said light beams having one of said wavelengths to provide the other of said two beams at the other of said wavelengths.

93. The interferometric method of claim 91 wherein said step of electronically analyzing determines the intrinsic optical power, the reciprocal dispersive power, $\Gamma$, of the gas, as:

$$\Gamma = \frac{[n_1(\lambda_1) - 1]}{[n_3(\lambda_3) - n_2(\lambda_2)]},$$

and $\lambda_1$, $\lambda_2$, and $\lambda_3$ wavelengths and $n_1$, $n_2$, and $n_3$ are indices of refraction and wherein the denominator may be replaced by $[n_3(\lambda_3)-n_1(\lambda_1)]$ or $[n_2(\lambda_2)-n_1(\lambda_1)]$.

94. The interferometric apparatus of claim 91 wherein said step of electronically analyzing includes determining the refractivities of the gas corresponding to each light beam wavelength.

95. The interferometric method of claim 91 wherein said step of electronically analyzing determines the intrinsic optical property, the reciprocal dispersive power, $\Gamma$, of the gas as:

$$\Gamma = \frac{[n_i(\lambda_i) - 1]}{[n_{j+1}(\lambda_{j+1}) - 1] - [n_j(\lambda_j) - 1]},$$

where i and j are integers corresponding to wavelengths.

96. The interferometric method of claim 91 wherein said step of electronically analyzing includes determining the intrinsic optical property, the relative refractivities at different beam wavelengths, where said relative refractivities are of the form:

$$\frac{n_{\lambda_i} - 1}{n_{\lambda_j} - 1}$$

where i and j are integers corresponding to wavelengths and are different from one another.

97. The interferometric method of claim 91 further including the step of providing output signals representative of said select intrinsic optical properties of the gas for subsequent downstream applications.

98. The interferometric method of claim 81 wherein said predetermined medium comprises a vacuum.

99. The interferometric method of claim 81 wherein said interferometer means comprises a concentric cell, said concentric cell comprising a closed inner chamber that serves as said reference leg and an outer chamber surrounding said inner chamber that serves as said measurement leg.

100. The interferometric method of claim 99 wherein said inner chamber is substantially evacuated so that said predetermined medium is a vacuum and said outer chamber is opened to the ambient surroundings.

101. The interferometric method of claim 100 wherein said ambient surroundings comprise air.

102. The interferometric method of claim 99 wherein said concentric cell is in form a right circular cylinder with end sections each of which includes wavelength selective mirrors as part of said interferometer means.

103. The interferometric method of claim 102 wherein said step of introducing at least a portion of each of said light beams into said interferometer means includes introducing one of said portions of said light beams corresponding to one wavelength into one of said end sections of said concentric cell and another of said portions of said light beams corresponding to another of said wavelengths into the other one of said end sections of said concentric cell.

104. The interferometric method of claim 81 wherein said step of generating said light beams further includes generating orthogonally polarized components of each of said light beams.

105. The interferometric method of claim 104 further including the step of separating said light beams into pairs of orthogonally polarized components having a common wavelength.

106. The interferometric method of claim 105 further including the step of spatially separating the components of said orthogonally polarized pairs of components for subsequent downstream use in said interferometer means.

107. The interferometric method of claim 105 wherein said wavelengths of said light beams have an approximate harmonic relationship to each other, said approximate harmonic relationship being expressed as a sequence of ratios, each ratio being comprised of a ratio of low order non-zero integers.

108. The interferometric method of claim 107 further including the step of doubling the frequency of at least one of said light beams having one of said wavelengths to provide the other of said two beams at the other of said wavelengths.

109. The interferometric method of claim 107 wherein the relative precision of said approximate harmonic relationship expressed as said sequence of ratios is of an order of magnitude less than the dispersive power of the gas times the relative precision required for the measurement of the reciprocal dispersive power of the gas.

110. The interferometric method of claim 107 further including the step of monitoring the relative precision of said approximate harmonic relationship expressed as said sequence of ratios.

111. The interferometric method of claim 110 further including the step of providing a feedback signal to control said light beams, responsive to said monitoring step, so that said relative precision of said approximate harmonic relationship is of an order of magnitude less than the dispersive power of the gas times the relative precision required for the measurement of the reciprocal dispersive power of the gas.

112. The interferometric method of claim 110 further including the step of correcting said select intrinsic optical properties as determined by said step of electronically analyzing and determining said select intrinsic optical properties.

113. The interferometric method of claim 107 further including the step of introducing a frequency difference between said orthogonally polarized components of each of said light beams to generate a set of frequency-shifted light beams such that no two beams of said set of frequency-shifted light beams have the same frequency difference.

114. The interferometric method of claim 113 further including the step of measuring the approximate harmonic ratio of the wavelengths of the source and providing a signal for correcting the calculations made in determining said select intrinsic optical properties.

115. The interferometric method of claim 113 wherein said electrical interference signals comprise heterodyne signals containing phase information corresponding to the refractivities of the gas and predetermined medium and said method further comprises the step of mixing said heterodyne signals to generate at least one superheterodyne signal containing phase information corresponding to the dispersion of the refractivity of the gas.

116. The interferometric method of claim 115 further including the step of resolving phase ambiguities in said heterodyne and superheterodyne signals.

117. The interferometric method of claim 81 further including the step of spatially separating said light beams prior to introducing said light beams into said interferometer means.

118. The interferometric apparatus of claim 1 further including means for receiving said electrical interference signals and directly extracting therefrom phase information corresponding to the select intrinsic optical properties of the gas.

119. The interferometric method of claim 81 further including the step of receiving said electrical interference signals and directly extracting therefrom phase information corresponding to the select intrinsic optical properties of the gas.

* * * * *